(12) United States Patent
Chakravarty et al.

(10) Patent No.: US 11,332,473 B2
(45) Date of Patent: May 17, 2022

(54) SUBSTITUTED PYRAZOLO[3,4-D]PYRIMIDINES AS WEE1 INHIBITORS

(71) Applicant: NUVATION BIO INC., New York, NY (US)

(72) Inventors: Sarvajit Chakravarty, Edmond, OK (US); Son Minh Pham, San Francisco, CA (US); Jayakanth Kankanala, St. Paul, MN (US); Brahmam Pujala, Greater Noida (IN); Sanjeev Soni, Noida (IN); Puja Jaiswal, Greater Noida (IN); Deepak Palve, Noida (IN); Varun Kumar, Noida (IN)

(73) Assignee: NUVATION BIO INC., New York, NY (US)

( * ) Notice: Subject to any disclaimer, the term of this patent is extended or adjusted under 35 U.S.C. 154(b) by 67 days.

(21) Appl. No.: 16/843,713

(22) Filed: Apr. 8, 2020

(65) Prior Publication Data
US 2020/0325142 A1  Oct. 15, 2020

Related U.S. Application Data

(60) Provisional application No. 62/831,665, filed on Apr. 9, 2019.

(51) Int. Cl.
| A61K 31/519 | (2006.01) |
| C07D 487/04 | (2006.01) |
| A61P 35/04  | (2006.01) |
| A61K 45/06  | (2006.01) |

(52) U.S. Cl.
CPC ............ *C07D 487/04* (2013.01); *A61P 35/04* (2018.01); *A61K 45/06* (2013.01)

(58) Field of Classification Search
CPC ............................ A61K 31/519; C07D 487/04
USPC ........................................ 514/262.1; 544/262
See application file for complete search history.

(56) References Cited

U.S. PATENT DOCUMENTS

| 6,995,153 | B2 | 2/2006 | Seto |
| 7,834,019 | B2 | 11/2010 | Sagara |
| 8,329,711 | B2 | 12/2012 | Furuyama |
| 8,703,779 | B2 | 4/2014 | Petrova |
| 8,791,125 | B2 | 7/2014 | Sagara |
| 9,655,899 | B2 | 5/2017 | Shumway |
| 9,850,247 | B2 | 12/2017 | Harrison |
| 10,807,994 | B2 | 10/2020 | Sarvajit et al. |
| 2006/0069093 | A1 | 3/2006 | Scarborough |
| 2006/0258651 | A1 | 11/2006 | Linschoten |
| 2007/0254892 | A1 | 11/2007 | Sagara |
| 2010/0221211 | A1 | 9/2010 | Furuyama |
| 2013/0102590 | A1 | 4/2013 | Mastracchio et al. |
| 2016/0008361 | A1 | 1/2016 | Shumway |
| 2019/0084985 | A1 | 3/2019 | Reigan |
| 2019/0106427 | A1 | 4/2019 | Chakravarty |
| 2019/0106436 | A1 | 4/2019 | Chakravarty |
| 2019/0248795 | A1 | 8/2019 | Burkamp |

FOREIGN PATENT DOCUMENTS

| EP | 2168966 A1 | 3/2010 |
| WO | 2009054332 A1 | 4/2009 |
| WO | 2010067888 A1 | 6/2010 |
| WO | 2013013031 A1 | 1/2013 |
| WO | 2013059485 A1 | 4/2013 |
| WO | 2013126656 A1 | 8/2013 |
| WO | 2014167347 A1 | 10/2014 |
| WO | 2015019037 A1 | 2/2015 |
| WO | 2015092431 A1 | 6/2015 |
| WO | 2017075629 A2 | 5/2017 |
| WO | 2017075629 A3 | 6/2017 |
| WO | 2018011569 A1 | 1/2018 |
| WO | 2018011570 A1 | 1/2018 |
| WO | 2018056621 A1 | 3/2018 |
| WO | 2018090939 A1 | 5/2018 |
| WO | 2018133829 A1 | 7/2018 |
| WO | 2018162932 A1 | 9/2018 |
| WO | 2018171633 A1 | 9/2018 |
| WO | 2018183891 A1 | 10/2018 |
| WO | 2019011228 A1 | 1/2019 |
| WO | 2019028008 A1 | 2/2019 |

(Continued)

OTHER PUBLICATIONS

Barbosa, R.S.S. et al. (2019). "Sequential Combination of Bortezomid and WEE1 Inhibitor, MK-1775, Induced Apoptosis in Multiple Myeloma Cell Lines," Biochemical and Biophysical Research Communications 8 pgs.

(Continued)

*Primary Examiner* — Douglas M Willis

(74) *Attorney, Agent, or Firm* — Morrison & Foerster LLP

(57) ABSTRACT

This invention provides for substituted pyrazolo[3,4-d]pyrimidine compounds of the Formula (I):

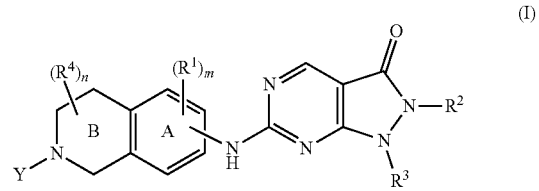

as Wee1 inhibitors. The substituted pyrazolo[3,4-d]pyrimidine compounds may find use as therapeutic agents for the treatment of diseases. The substituted pyrazolo[3,4-d]pyrimidine compounds may also find particular use in oncology.

60 Claims, No Drawings

(56) References Cited

FOREIGN PATENT DOCUMENTS

| WO | 2019037678 A1 | 2/2019 |
|---|---|---|
| WO | 2019074979 A1 | 4/2019 |
| WO | 2019074981 A1 | 4/2019 |
| WO | 2019096322 A1 | 5/2019 |
| WO | 2019134539 A1 | 7/2019 |
| WO | 2019165204 A1 | 8/2019 |
| WO | 2019169065 A2 | 9/2019 |
| WO | 2019173082 A1 | 9/2019 |
| WO | 2019169065 A3 | 4/2020 |
| WO | 2020210377 A1 | 10/2020 |
| WO | 2020210380 A1 | 10/2020 |
| WO | 2020210381 A1 | 10/2020 |
| WO | 2020210383 A1 | 10/2020 |

OTHER PUBLICATIONS

Bridges, K.A. et al. (Sep. 1, 2011; e-pub. Jul. 28, 2011). "MK-1775, a Novel Wee1 Kinase Inhibitor, Radiosensitizes p53-Defective Human Tumor Cells," Clinical Cancer Research 17(17):5638-5648.

Brown, J.S. et al. (Feb. 6, 2018; e-pub. Nov. 9, 2017). "Combining DNA Damaging Therapeutics with Immunotherapy: More Haste, Less Speed," British Journal of Cancer 118(3):312-324.

Bukhari, A.B. et al. (Mar. 2019). "Inhibiting Wee1 and ATR Kinases Produces Tumor-Selective Synthetic Lethality and Suppresses Metastasis," The Journal of Clinical Investigation 129(3):1329-1344.

Chang, Q. et al. (2016; e-pub. Feb. 18, 2016). "Cytokinetic Effects of Wee1 Disruption in Pancreatic Cancer," Cell Cycle 15(4):593-604.

Chen, X. et al. (Dec. 2018; e-pub. Sep. 4, 2018). "Cyclin E Overexpression Sensitizes Triple-Negative Breast Cancer to Wee1 Kinase Inhibition," Clinical Cancer Research 24(24):6594-6610, 44 pages.

Chou, T.-C. (Jan. 15, 2010, e-pub. Jan. 12, 2010). "Drug Combination Studies and Their Synergy Quantification Using the Chou-Talaly Method," Cancer Res. 70(2): 440-446.

Coyne, G.O.S. et al. (Jan. 2018). "Abstract B079: Single Agent AZD 1775, a Wee1 Inhibitor, Shows Activity in BRCA Deficient Patients," Molecular Cancer Therapeutics 17(1 Suppl):B079, 4 pages.

Cuneo, K.C. et al. (Aug. 9, 2019). "Dose Escalation Trial of the Wee1 Inhibitor Adavosertib (AZD1775) in Combination With Gemcitabine and Radiation for Patients With Locally Advanced Pancreatic Cancer," Journal of Clinical Oncology 9 pages.

De Gooijer, M.C. et al. (Jun. 2018; e-pub. Nov. 17, 2017). "ATP-binding Cassette Transporters Limit the Brain Penetration of Wee1 Inhibitors," Invest New Drugs 36(3):380-387.

Do, K. et al. (Oct. 1, 2013, e-pub. Aug. 26, 2013). "Wee1 Kinase as a Target for Cancer Therapy," Cell Cycle 12(19):3159-3164.

Do, K. et al. (Oct. 20, 2015; e-pub. May 11, 2015). "Phase I Study of Single-Agent AZD1775 (MK-1775), a Wee1 Kinase Inhibitor, in Patients With Refractory Solid Tumors," Journal of Clinical Oncology 33(30):3409-3415.

English translation of W02019037678, publ. Feb. 28, 2019, priority date Aug. 24, 2017, pp. 1-34.

Fang, Y. et al. (Jun. 10, 2019). "Sequential Therapy with PARP and WEE1 Inhibitors Minimizes Toxicity while Maintaining Efficacy," Cancer Cell 35:851-867, 25 pages.

Francis, A.M. et al. (Sep. 2017; e-pub. Jun. 15, 2017). "CDK4/6 Inhibitors Sensitize Rb-Positive Sarcoma Cells to Wee1 Kinase Inhibition Through Reversible Cell Cycle Arrest," Molecular Cancer Therapeutics 16(9):1751-1764.

Friedman, J. et al. (2018). "Inhibition of WEE1 Kinase and Cell Cycle Checkpoint Activation Sensitizes Head and Neck Cancers to Natural Killer Cell Therapies," Journal for ImmunoTherapy of Cancer 6:59, 12 pages.

Fu, S. et al. (Sep. 2018; e-pub. Aug. 13, 2018). "Strategic Development of AZD1775, a Wee1 Kinase Inhibitor, for Cancer Therapy," Expert Opinion on Investigational Drugs 27(9):741-751.

Garcia, T.B. et al. (2018; e-pub. Nov. 11, 2017). "Increased Activity of Both CDK1 and CDK2 is Necessary for the Combinatorial Activity of WEE1 Inhibition and Cytarabine," Leukemia Research 64:30-33.

Garcia, T.B. et al. (Oct. 2017; e-pub. Jun. 27, 2017). "A Small Molecule Inhibitor of WEE1, AZD1775, Synergies with Olaparib by Impairing Homologous Recombination and Enhancing DNA Damaga and Apoptosis in Acute Leukemia," Molecular Cancer Therapeutics 16(10):2058-2068.

Garimella, S.V. et al. (Jan. 2012; e-pub. Nov. 23, 2011). "WEE1 Inhibition Sensitizes Basal Breast Cancer Cells to TRAIL-Induced Apoptosis," Molecular Cancer Research 10(1):75-85.

Gavory, G. et al. (Jul. 2016). "Novel, Potent & Selective Inhibitors of Wee1 with Robust Antitumor Activity in Various Cancer Xenograft Models," Poster presented at Proceedings: AACR 107th Annual Meeting 2016; Apr. 16-20, 2016; New Orleans, LA, 76(14):LB-159, 1 page.

Geenen, J.J.J. et al. (Aug. 15, 2017; e-pub. Apr. 25, 2017). "Molecular Pathways: Targeting the Protein Kinase Wee1 in Cancer," Clinical Cancer Research 23(16):OF1-OF5.

Guertin, A.D. et al. (2012). "Unique Functions of CHK1 and WEE1 Underlie Synergistic Anti-Tumor Activity Upon Pharmacologic Inhibition," Cancer Cell International 12:45, 12 pages.

Guertin, A.D. et al. (Aug. 2013; e-pub. May 22, 2013). "Preclinical Evaluation of the WEE1 Inhibitor MK-1775 as Single-Agent Anticancer Therapy," Molecular Cancer Therapeutics 12(8):1442-1452.

Hai, J. et al. (Nov. 15, 2017; e-pub. Aug. 18, 2017). "Synergy of WEE1 and mTOR Inhibition in Mutant KRAS-driven Lung Cancers," Clin Cancer Res 23(22):6993-7005.

Hamilton, D.H. et al. (May 1, 2014; e-pub. Mar. 13, 2014). "WEE1 Inhibition Alleviates Resistance to Immune Attack of Tumor Cells Undergoing Epithelial-Mesenchymal Transition," Cancer Research 74(9):2510-2519.

Hauge, S. et al. (Apr. 2019; e-pub. Apr. 3, 2019). "p21 Limits S Phase DNA Damage Caused by the Wee1 Inhibitor MK1775," Cell Cycle 18(8):834-847.

Hirai, H. et al. (Nov. 2009; e-pub. Nov. 3, 2009). "Small-Molecule Inhibition of Wee1 Kinase by MK-1775 Selectively Sensitizes P53-Deficient Tumor Cells to DNA-Damaging Agents," Molecular Cancer Therapeutics 8(11):2992-3000.

Hsieh, H.-J. et al. (2018). "Systems Biology Approach Reveals a Link Between mTORC1 and G2/M DNA Damage Checkpoint Recovery," Nature Communications 9:3982, 14 pages.

Hu, Y. et al. (2018, e-pub. Dec. 24, 2018). "Pharmacophore Modeling, Multiple Docking, and Molecular Dynamics Studies on Wee1 Kinase Inhibitors," Journal of Biomolecular Structure and Dynamics 14 pages.

International Search Report and Written Opinion dated Aug. 18, 2020 for PCT Application No. PCT/US2020/27297 filed on Apr. 8, 2020, 16 pages.

Invitation to Pay Additional Fees and, Where Applicable, Protest Fee dated Jun. 25, 2020 for PCT Application No. PCT/US2020/27297 filed on Apr. 8, 2020, 2 pages.

Iwai, A. et al. (Oct. 1, 2012; e-pub. Aug. 30, 2012). "Combined Inhibition of Wee1 and Hsp90 Activates Intrinsic Apoptosis in Cancer Cells," Cell Cycle 11(19):3649-3655.

Jin, J. et al. (May 2018). "Combined Inhibition of ATR and WEE1 as a Novel Therapeutic Strategy in Triple-Negative Breast Cancer," Neoplasia 20(5):478-488.

Jin, M.H. et al. (2019). "Therapeutic Co-Targeting of WEE1 and ATM Downregulates PD-L1 Expression in Pancreatic Cancer," Cancer Research and Treatment, 40 pages.

Karakashev, S. et al. (Dec. 19, 2017). "BET Bromodomain Inhibition Synergizes with PARP Inhibitor in Epithelial Ovarian Cancer," Cell Reports 21:3398-3405.

Karnak, D. et al. (2014, e-pub. Aug. 12, 2014). "Combined Inhibition of Wee1 and PARP 1/2 for Radiosensitization in Pancreatic Cancer," Clinical Cancer Research 20(19):5085-5096.

Kausar, T. et al. (Oct. 2015). "Sensitization of Pancreatic Cancers to Gemcitabine Chemoradiation by WEE1 Kinase Inhibition Depends on Homologous Recombination Repair," Neoplasia 17(10):757-766.

(56) References Cited

OTHER PUBLICATIONS

Kaye, S.B. (2016). "DNA Repair Inhibitors in Ovarian Cancer: Current Status and Future Strategies," Presented at Progress and Controversies in Gynecologic Oncology Conference, 37 pages.

Kim, H.-Y et al. (Jun. 23, 2016). "Targeting the WEE1 Kinase as a Molecular Targeted Therapy for Gastric Cancer," Oncotarget 7(31):49902-49916.

Kreahling, J.M. et al. (Jan. 2012). "MK1775, A Selective Wee1 Inhibitor, Shows Single-Agent Antitumor Activity against Sarcoma Cells," Molecular Cancer Therapeutics 11(1):174-182, 15 pages.

Kreahling, J.M. et al. (Mar. 8, 2013). "Wee1 Inhibition by MK-1775 Leads to Tumor Inhibition and Enhances Efficacy of Gemcitabine in Human Sarcomas," PLOS One 8(3):e57523, 8 pages.

Kuzu, O.F. et al. (2017). "Improving Pharmacological Targeting of AKT in Melanoma," Cancer Letters 404:29-36.

Lallo, A. et al. (Oct. 15, 2018 e-pub. Jun. 25, 2018). "The Combination of the PARP Inhibitor Olaparib and the Wee1 Inhibitor AZD1775 as a New Therapeutic Option for Small Cell Lung Cancer," Clinical Cancer Research 24(20):5153-5164, 33 pages.

Lee, J.W. et al. (2019, e-pub. Feb. 12, 2019). "Combined Aurora Kinase A (AURKA) and WEE1 Inhibition Demonstrates Synergistic Antitumor Effect in Squamous Cell Carcinoma of the Head and Neck," Clinical Cancer Research, 42 pages.

Leijen, S. et al. (Dec. 20, 2016; e-pub. Oct. 31, 2016). "Phase II Study of WEE1 Inhibitor AZD1775 Plus Carboplatin in Patients With TP53-Mutated Ovarian Cancer Refractory or Resistant to First-Line Therapy Within 3 Months," Journal of Clinical Oncology 34(36):4354-4361.

Leijen, S. et al. (Dec. 20, 2016; e-pub. Sep. 6, 2016). "Phase I Study Evaluating WEE1 Inhibitor AZD1775 as Monotherapy and in Combination With Gemcitabine, Cisplatin, or Carboplatin in Patients With Advanced Solid Tumors," Journal of Clinical Oncology 34(36):4371-4380.

Lescarbeau, R.S. et al. (Jun. 2016; e-pub. Mar. 23, 2016). "Quantitative Phosphoproteomics Reveals Wee1 Kinase as a Therapeutic Target in a Model of Proneural Glioblastoma," Molecular Cancer Therapeutics 15(6):1332-1343.

Lewis, C.W. et al. (May 13, 2017). "Prolonged Mitotic Arrest Induced by Wee1 Inhibition Sensitizes Breast Cancer Cells to Paclitaxel," Oncotarget 8(43):73705-73722.

Li, J. et al. (Dec. 15, 2017; e-pub. Sep. 19, 2017). "Quantitative and Mechanistic Understanding of AZD1775 Penetration across Human Blood-Brain Barrier in Glioblastoma Patients Using an IVIVE-PBPK Modeling Approach," Clinical Cancer Research 23(24):7454-7466.

Liang, J. et al. (2019, e-pub. Sep. 24, 2019). "Genome-Wide CRISPR-Cas9 Screen Reveals Selective Vulnerability of ATRX-Mutant Cancers to WEE1 Inhibition," AACR Journals, 42 pages.

Liu, D. et al. (2019). "Enhancement of Chemosensitivity by WEE1 Inhibition in EGFR-TKIs Resistant Non-Small Cell Lung Cancer," Biomedicine & Pharmacotherapy 117:109185, 8 pages.

Liu, W. et al. (2019, e-pub. Jun. 13, 2019). "Targeting the WEE1 Kinase Strengthens the Antitumor Activity of Imatinib Via Promoting KIT Autophagic Degradation in Gastrointestingal Stromal Tumors," Gastric Cancer, 13 pages.

Lübbehüsen, C. et al. (2019; e-pub. Apr. 23, 2019). "Characterization of Three Novel H3F3A-mutated Giant Cell Tumor Cell Lines and Targeting of Their Wee1 Pathway," Scientific Reports 9:6458, 10 pages.

Mastracchio, A. et al. (2019). "Investigation of Biaryl Heterocycles as Inhibitors of Wee1 Kinase," Bioorganic & Medicinal Chemistry Letters 29:1481-1486.

Matheson, C.J. et al. (Apr. 15, 2016; e-pub. Jan. 8, 2016). "A WEE1 Inhibitor Analog of AZD1775 Maintains Synergy with Cisplatin and Demonstrates Reduced Single-Agent Cytotoxicity in Medulloblastoma Cells," ACS Chem. Biol. 11(4):921-930, 10 pages.

Matheson, C.J. et al. (Oct. 2016). "Targeting WEE1 Kinase in Cancer," Trends in Pharmacological Sciences 37(10):872-881.

Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.

Mueller, S. et al. (2014; e-pub. Dec. 4, 2013). "Targeting Wee1 for the Treatment of Pediatric High-Grade Gliomas," Neuro-Oncology 16(3):352-360.

Mueller, S. et al. (Oct. 20, 2015). "WEE1 Kinase as a Target for Cancer Therapy," Journal of Clinical Oncology 33(30):3485-3487.

Music, D. et al. (Apr. 2016; e-pub. Jan. 6, 2016). "Expression and Prognostic Value of the WEE1 Kinase in Gliomas," J Neurooncol 127(2):381-399, 9 pages.

Méndez, E. et al. (Jun. 15, 2018; e-pub. Mar. 13, 2018). "A Phase I Clinical Trial of AZD1775 in Combination with Neoadjuvant Weekly Docetaxel and Cisplatin Before Definitive Therapy in Head and Neck Squamous Cell Carcinoma," Clinical Cancer Research 24(12):2740-2748.

O'Dowd, C. et al. (2019). "Antitumor Activity of the Novel Oral Highly Selective Wee1 Inhibitor Debio0123," Abstract #4423, Poster presented at AACR 2019, Atlanta, GA, US, 1 page.

O'Neil, J. et al. (Jun. 2016; e-pub. Mar. 16, 2016). "An Unbiased Oncology Compound Screen to Identify Novel Combination Strategies," Molecular Cancer Therapeutics 15(6):1155-1162.

Palmer, B.D. et al. (2006; e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49(16):4896-4911.

Peer, C.J. et al. (Dec. 15, 2017; e-pub. Oct. 10, 2017). "Jumping the Barrier: Modeling Drug Penetration Across the Blood-Brain Barrier," Clinical Cancer Research 23(24):7437-7439.

Pfister, S.X. et al. (Nov. 9, 2015). "Inhibiting WEE1 Selectively Kills Histone H3K36me3-Deficient Cancers by dNTP Starvation," Cancer Cell 28:557-568.

Pokorny, J.L. et al. (Apr. 15, 2015; e-pub. Jan. 21, 2015). "The Efficacy of the Wee1 Inhibitor MK-1775 Combined with Temozolomide Is Limited by Heterogeneous Distribution across the Blood-Brain Barrier in Glioblastoma," Clinical Cancer Research 21(8):1916-1924.

Rajeshkumar, N.V. et al. (May 1, 2011; e-pub. Mar. 9, 2011). "MK-1775, a Potent Wee1 Inhibitor, Synergizes with Gemcitabine to Achieve Tumor Regressions, Selectively in p53-Deficient Pancreatic Cancer Xenografts," Clinical Cancer Research 17(9):2799-2806.

Restelli, V. et al. (pre-published May 7, 2019). "DNA Damage Response Inhibitor Combinations Exert Synergistic Antitumor Activity in Aggressive B Cell Lymphomas," Molecular Cancer Therapeutics, 25 pages.

Richer, A.L. et al. (Sep. 1, 2017; e-pub. Jun. 26, 2017). "WEE1 Kinase Inhibitor AZD1775 has Pre-Clinical Efficacy in LKB1-Deficient Non-small Cell Lung Cancer," The Journal of Cancer Research 77(17):4663-4672.

Sanai, N. et al. (Aug. 15, 2018; e-pub. May 24, 2018). "Phase 0 Trial of AZD1775 in First-Recurrence Glioblastoma Patients," Clinical Cancer Research 24(16):3820-3828.

Schmidt, M. et al. (Nov. 23, 2017). "Regulation of G2/M Transition by Inhibition of WEE1 and PKMYT1 Kinases," Molecules 22:2045, pp. 1-17.

Serpigo, A.F. et al. (Jun. 13, 2019). "Wee1 Rather Than Plk1 is Inhibited by AZD1775 at Therapeutically Relevant Concentrations," Cancers 11(819), 10 pages.

Steino, A. et al. (Jul. 2018). "Dianhydrogalactitol (VAL-083) has the Potential to Overcome Major Challenges in the Treatment of Diffuse Intrinsic Pontine Glioma (DIPG)," Poster presented at AACR Annual Meeting 2018; Apr. 14-18, 2018; Chicago, IL, 78(13 Supplement), 1 page.

Sun, A. et al. (Apr. 2010). "A Phase Ib Study to Evaluate Induction of pCDC2 in Skin Biopsies from Patients with Solid Tumors Treated with DNA-damaging Chemotherapy," Poster presented at AACR 101st Annual Meeting 2010, Apr. 17-21, 2010, Washington D.C, Merck & Co., Inc., 70(8 Supplement), 1 page.

(56) References Cited

OTHER PUBLICATIONS

Sun, L. et al. (2018; e-pub. Jul. 23, 2018). "WEE1 Kinase Inhibition Reverses G2/M Cell Cycle Checkpoint Activation to Sensitize Cancer Cells to Immunotherapy," OncoImmunology 7(10):e1488359-1-e1488359-14.
Takashima, Y. et al. (e-pub. ahead of print—Jun. 14, 2019). "Bromodomain and Extraterminal Domain Inhibition Synergizes with WEE1WEE1-lnhibitor AZD1775 Effect by Impairing Non Non-Homologous End Joining and Enhancing DNA Damage in Non Non-Small Cell Lung Cancer," Int J Cancer, 34 pages.
Toledo, C.M. et al. (Dec. 22, 2015). "Genome-Wide CRISPR-Cas9 Screens Reveal Loss of Redundancy Between PKMYT1 and WEE1 in Glioblastoma Stem-like Cells," Cell Reports 13:2425-2439.
Tong, Y. et al. (2015, e-pub. Aug. 6, 2014). "Pyrimidine-Based Tricyclic Molecules as Potent and Orally Efficacious Inhibitors of Wee1 Kinase," ACS Med. Chem. Lett. 6:58-62.
Touat, M. et al. (2017; e-pub. Jun. 12, 2017). "Glioblastoma Targeted Therapy: Updated Approaches from Recent Biological Insights," Annals of Oncology 28:1457-1472.
Wang, Y. et al. (Mar. 2004). "Knockdown of Chk1, Wee1 and Myt1 by RNA Interference Abrogates G2 Checkpoint and Induces Apoptosis," Cancer Biology & Therapy 3(3):305-313.
Wichapong, K. et al. (2009, e-pub. Sep. 20, 2008). "Receptor-Based 3D-QSAR Studies of Checkpoint Wee1 Kinase Inhibitors," European Journal of Medicinal Chemistry 44:1383-1395.
Wright, G. et al. (Jul. 21, 2017; e-pub. May 30, 2017). "Dual Targeting of WEE1 and PLK1 by AZD1775 Elicits Single Agent Cellular Anticancer Activity," ACS Chemical Biology 12(7):1883-1892, 18 pages.
Wu, M. et al. (2019). "miR-526b-3p Serves as a Prognostic Factor abd Regulates the Proliferation, Invasion, and Migration of Giloma through Targeting WEE1," Cancer Management and Research 11:3099-3110.
Wu, S. et al. (2018; e-pub. Jul. 7, 2017). "Activation of WEE1 Confers Resistance to PI3K Inhibition in Glioblastoma," Neuro-Oncology 20(1):78-91.
Zhang, M. et al. (2017). "WEE1 inhibition by MK1775 as a Single-Agent Therapy Inhibits Ovarian Cancer Viability," Oneology Letters 14:3580-3586.
Zhang, P. et al. (2019, e-pub. Jul. 21, 2019). "BRD4 Inhibitor AZD5153 Suppresses the Proliferation of Colorectal Cancer Cells and Sensitizes the Anticancer Effect of PARP Inhibitor," Int. J. Biol. Sci. 15(9):1942-1954.
Zhao, W. et al. (2015). "The Role and Mechanism of WEE1 on the Cisplatin Resistance Reversal of the HepG2/DDP Human Hepatic Cancer Cell Line," Oncology Letters 10:3081-3086.
Zhou, L. et al. (Apr. 2015). "A Regimen Combining the Wee1 Inhibitor AZD1775 With HDAC Inhibitors Targets Human Acute Myeloid Leukemia Cells Harboring Various Genetic Mutations," Leukemia 29(4):807-818, 24 pages.
Zhu, J.-Y. et al. (Aug. 9, 2017). "Structural Basis of Wee Kinases Functionality and Inactivation by Diverse Small Molecule Inhibitors," Journal of Medicinal Chemistry 60:7863-7875.
Zupkovitz, G. et al. (Mar. 2010; e-pub. Dec. 22, 2009). "The Cyclin-Dependent Kinase Inhibitor p21 Is a Crucial Target for Histone Deacetylase 1 as a Regulator of Cellular Proliferation," Molecular and Cellular Biology 30(5):1171-1181.
Bhatia, S. et al. (Jul. 2012). "The Challenges Posed by Cancer Heterogeneity," Nature Biotechnology 30(7):604-610.
International Preliminary Report on Patentability, dated Sep. 28, 2021, for PCT Application No. PCT/US2020/027297, filed on Apr. 8, 2020, 7 pages.
Kaiser, J. (Jul. 20, 2012). "Cancer Genetics With an Edge," Science 337:282-284.
Rodriguez, D. (2010). "Know the Most Common Types of Cancer," Everyday Health pp. 1-13.
U.S. Appl. No. 17/594,293, filed Oct. 8, 2021, for Chakravarty et al.
U.S. Appl. No. 17/594,296, filed Oct. 8, 2021, for Chakravarty et al.
U.S. Appl. No. 17/594,298, filed Oct. 8, 2021, for Chakravarty et al.
U.S. Appl. No. 17/594,299, filed Oct. 8, 2021, for Chakravarty et al.
Wistuba, I.I. et al. (Mar. 2011). "Methodological and Practical Challenges for Personalized Cancer Therapies," Nature Rev. Clin. Oncology 8:135-141.

SUBSTITUTED PYRAZOLO[3,4-D]PYRIMIDINES AS WEE1 INHIBITORS

CROSS REFERENCE TO RELATED APPLICATION

This application claims priority to U.S. Provisional Application No. 62/831,665, filed on Apr. 9, 2019, the content of which is incorporated herein by reference in its entirety.

FIELD OF THE INVENTION

This disclosure relates generally to therapeutics engaged in inhibition of the DNA damage checkpoint kinase, Wee1, which potentiates genotoxic chemotherapies by abrogating cell-cycle arrest and proper DNA repair. The invention also provides pharmaceutically acceptable compositions comprising compounds of the present invention and methods of using said compositions in the treatment of diseases associated with this pathway.

BACKGROUND OF THE INVENTION

Wee1 is a tyrosine kinase that phosphorylates and inactivates Cdc2 and is involved in G checkpoint signaling. More particularly, Wee1 is involved in $G_2$-M checkpoint signaling. Because p53 is a key regulator in the G checkpoint, p53-deficient tumors rely only on the G checkpoint after DNA damage. More particularly, because p53 is a key regulator in the $G_1$-S checkpoint, p53-deficient tumors rely only on the $G_2$-M checkpoint after DNA damage. Hence, such tumors are selectively sensitized to DNA-damaging agents by Wee1 inhibition.

Wee1 belongs to a family of protein kinases involved in the terminal phosphorylation and inactivation of cyclin-dependent kinase 1-bound cyclin B, resulting in G cell cycle arrest in response to DNA damage. Wee1 was first identified in fission yeast, where Wee1 deficiency resulted in premature mitotic entry and replication of smaller-sized yeast. It is the major kinase responsible for the inhibitory phosphorylation of the tyrosine.

Before cells undergo mitosis, they progress through a tightly controlled cascade of $G_1$-S, intra-S, and $G_2$-M checkpoints. Wee1 kinase has emerged as a key $G_2$-M checkpoint regulator. This tyrosine kinase negatively regulates entry into mitosis by catalyzing an inhibitory phosphorylation of Cdc2 (the human homolog of cyclin-dependent kinase 1 (CDK1) on tyrosine-15 (Y15). This results in inactivation of the Cdc2/cyclin B complex, which arrests cells in $G_2$-M, allowing for DNA repair. Such inhibition also occurs through Chk1-mediated inhibition of Cdc25 phosphatases, which remove the inhibitory phosphorylation on Cdc2. Thus, entry into mitosis rests on a balance between the opposing activities of Wee1 and Chk1/Cdc25. Wee1 inhibition is thus expected to abrogate $G_2$-M arrest and propel cells into premature mitosis, a hypothesis confirmed by studies documenting that Wee1 inhibition by either small molecule inhibitors or small interference RNA leads to premature entry into mitosis and consequent cell death through mitotic catastrophe or apoptosis. (S. Muller, *J. Clinical. Oncology*, 2015).

Recently, a few classes of Wee1 inhibitors have been disclosed. Among them is a selective inhibitor, AZD-1775 (1, 2-allyl-1-(6-(2-hydroxypropan-2-yl)pyridin-2-yl)-6-((4-(4methylpiperazin-1-yl)phenyl)amino)-1H-pyrazolo[3,4-d] pyrimidin-3(2H)-one). AZD-1775 exhibited antitumor activity in various preclinical studies as a monotherapy or in potentiating chemo- and radiotherapy, and is currently in phase I/II clinical trials.

Wee1 is highly expressed in several cancer types, including hepatocellular carcinoma, breast cancers, cervical cancers, lung cancers, squamous cell carcinoma, diffuse intrinsic pontine glioma (DIPG), glioblastoma, medulloblastoma, leukemia, melanoma, and ovarian cancers. (P. Reigan et al., *Trends in Pharmacol. Sci.*, 2016).

There are few Wee1 inhibitors in clinical development. There is scope to improve Wee1 inhibitor selectivity and the properties of the inhibitors to permit targeting of specific cancer types.

BRIEF SUMMARY OF THE INVENTION

In one aspect, provided is a compound of Formula (I):

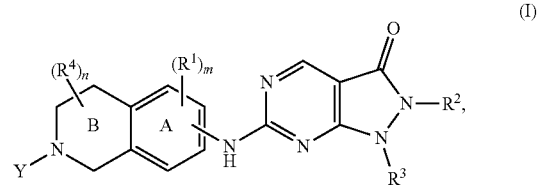

or a salt thereof, wherein Y, $R^1$, $R^2$, $R^3$, $R^4$, m and n are as detailed herein.

In some embodiments, the compound of Formula (I) or a salt thereof, is of the Formula (II) or (III), or a salt thereof as detailed herein.

In another aspect, provided is a method of treating cancer in an individual in need thereof comprising administering to the individual a therapeutically effective amount of a compound as detailed herein, such as a compound of Formula (I), (II) or (III) or a pharmaceutically acceptable salt thereof. Also provided is a method of inhibiting Wee1 in a cell, comprising administering a compound detailed herein, or a salt thereof, to the cell.

In another aspect, provided are pharmaceutical compositions comprising a compound detailed herein and a pharmaceutically acceptable carrier or excipient. Kits comprising a compound detailed herein or a salt thereof are also provided. A compound as detailed herein, or a salt thereof, is also provided for the manufacture of a medicament for the treatment of cancer.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of Formula (I):

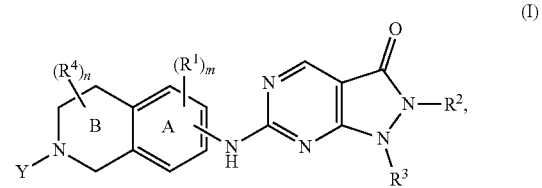

or a salt thereof, wherein:
Y is hydrogen or $R^4$;
m is 0, 1, 2, or 3;
n is 0, 1, 2, 3, or 4;
$R^1$ is independently F, Cl, or methyl;
$R^2$ is $C_1$-$C_6$ alkyl, $C_3$-$C_6$ cycloalkyl or —($C_1$-$C_3$ alkylene)$CF_3$;
$R^3$ is

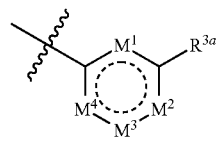

wherein:

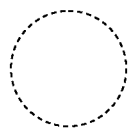

indicates an aromatic ring;
$M^1$ is CH, $CR^{3b}$ or N;
$M^2$ is CH, $CR^{3b}$, N, or absent;
$M^3$ is CH, $CR^{3b}$, N, O, or S;
$M^4$ is CH, $CR^{3b}$, N, O, or S, provided that:
(1) when $M^4$ is O or S and $M^2$ is absent, then $M^3$ is CH, $CR^{3b}$ or N, and
(2) when $M^3$ is O or S and $M^2$ is absent, then $M^4$ is CH, $CR^{3b}$ or N;

$R^{3a}$ is $C_3$-$C_6$ cycloalkyl optionally substituted by $C_1$-$C_6$ haloalkyl or —CN, or $C_1$-$C_6$ alkyl optionally substituted by halogen, —OH or —CN, provided that when $R^{3a}$ is $C_1$-$C_6$ alkyl optionally substituted by halogen, —OH or —CN, then at least one of $M^1$, $M^2$, $M^3$, and $M^4$ is $CR^{3b}$;

$R^{3b}$ is halogen or —CN;

each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)NR$^{17}$R$^{18}$, —CN, —Si($C_1$-$C_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, $C_3$-$C_6$ cycloalkyl, 3- to 6-membered heterocyclyl, —($C_1$-$C_3$ alkylene)CN, —($C_1$-$C_3$ alkylene)OR$^{17}$, —($C_1$-$C_3$ alkylene)NR$^{17}$R$^{18}$, —($C_1$-$C_3$ alkylene)CF$_3$, —($C_1$-$C_3$ alkylene)C(O)R$^{17}$, —($C_1$-$C_3$ alkylene)C(O)NR$^{17}$R$^{18}$, —($C_1$-$C_3$ alkylene)NR$^{17}$C(O)R$^{18}$, —($C_1$-$C_3$ alkylene)S(O)$_2$R$^{17}$, —($C_1$-$C_3$ alkylene)NR$^{17}$S(O)$_2$R$^{18}$, —($C_1$-$C_3$ alkylene)S(O)$_2$NR$^{17}$R$^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —OR$^{19}$, —NR$^{19}$R$^{20}$, or —C(O)R$^{19}$, or two $R^4$, when bound to the same carbon are taken together with the carbon to which they are attached to form a $C_3$-$C_6$ cycloalkyl or 3- to 6-membered heterocyclyl, each is optionally substituted by $R^{19}$;

each $R^{17}$, $R^{18}$, $R^{19}$, and $R^{20}$ is independently hydrogen, $C_3$-$C_6$ cycloalkyl, 3-6 membered heterocyclyl or $C_1$-$C_6$ alkyl, each of which is optionally substituted by halogen, oxo or —OH, or $R^{17}$ and $R^{18}$ are taken together with the atom to which they attached to form a 3-6 membered heterocyclyl optionally substituted by halogen, oxo or —OH.

In some embodiments of a compound of Formula (I), or a salt thereof, the compound is other than the compounds in Table 1X or a salt thereof. In some embodiments of a compound of Formula (I), or a salt thereof, the compound is other than the Compound Nos. 1x-39x in Table 1X or a salt thereof.

TABLE 1X

| | |
|---|---|
| 1x | 1-(6-Cyclopropylpyridin-2-yl)-2-ethyl-6-((1,2,3,4-tetrahydroisoquinolin-7-yl)amino)-1,2-dihydro-3H-pyrazolo[3,4-d]pyrimidin-3-one |
| 2x | 1-(6-Cyclopropylpyridin-2-yl)-2-isopropyl-6-((1,2,3,4-tetrahydroisoquinolin-7-yl)amino)-1,2-dihydro-3H-pyrazolo[3,4-d]pyrimidin-3-one |
| 3x | 1-(6-Cyclopropylpyridin-2-yl)-2-isopropyl-6-((1,2,3,4-tetrahydroisoquinolin-6-yl)amino)-1,2-dihydro-3H-pyrazolo[3,4-d]pyrimidin-3-one |
| 4x | 1-(3-(Tert-butyl)-4-fluorophenyl)-2-isopropyl-6-((1,2,3,4-tetrahydroisoquinolin-6-yl)amino)-1,2-dihydro-3H-pyrazolo[3,4-d]pyrimidin-3-one |
| 5x | 1-(3-Cyclopropyl-4-fluorophenyl)-2-isopropyl-6-((1,2,3,4-tetrahydroisoquinolin-6-yl)amino)-1,2-dihydro-3H-pyrazolo[3,4-d]pyrimidin-3-one |
| 6x | 1-(3-(Tert-butyl)-2-fluorophenyl)-2-isopropyl-6-((1,2,3,4-tetrahydroisoquinolin-6-yl)amino)-1,2-dihydro-3H-pyrazolo[3,4-d]pyrimidin-3-one |
| 7x | 1-(3-Cyclopropyl-2-fluorophenyl)-2-isopropyl-6-((1,2,3,4-tetrahydroisoquinolin-6-yl)amino)-1,2-dihydro-3H-pyrazolo[3,4-d]pyrimidin-3-one |
| 8x | 2-(Tert-butyl)-4-(2-isopropyl-3-oxo-6-((1,2,3,4-tetrahydroisoquinolin-6-yl)amino)-2,3-dihydro-1H-pyrazolo[3,4-d]pyrimidin-1-yl)benzonitrile |
| 9x | 2-(2-Hydroxypropan-2-yl)-4-(2-isopropyl-3-oxo-6-((1,2,3,4-tetrahydroisoquinolin-6-yl)amino)-2,3-dihydro-1H-pyrazolo[3,4-d]pyrimidin-1-yl)benzonitrile |
| 10x | 2-Cyclopropyl-4-(2-isopropyl-3-oxo-6-((1,2,3,4-tetrahydroisoquinolin-6-yl)amino)-2,3-dihydro-1H-pyrazolo[3,4-d]pyrimidin-1-yl)benzonitrile |
| 11x | 2-Cyclopropyl-6-(2-isopropyl-3-oxo-6-((1,2,3,4-tetrahydroisoquinolin-6-yl)amino)-2,3-dihydro-1H-pyrazolo[3,4-d]pyrimidin-1-yl)benzonitrile |
| 12x | 2-(Tert-butyl)-6-(2-isopropyl-3-oxo-6-((1,2,3,4-tetrahydroisoquinolin-6-yl)amino)-2,3-dihydro-1H-pyrazolo[3,4-d]pyrimidin-1-yl)benzonitrile |
| 13x | 1-(3-(Tert-butyl)-4-chloro-2-fluorophenyl)-2-isopropyl-6-((1,2,3,4-tetrahydroisoquinolin-6-yl)amino)-1,2-dihydro-3H-pyrazolo[3,4-d]pyrimidin-3-one |
| 14x | 1-(3-(Tert-butyl)-2,4-difluorophenyl)-2-isopropyl-6-((1,2,3,4-tetrahydroisoquinolin-6-yl)amino)-1,2-dihydro-3H-pyrazolo[3,4-d]pyrimidin-3-one |
| 15x | 1-(2-(Tert-butyl))-3-fluoropyridin-4-yl)-2-isopropyl-6-((1,2,3,4-tetrahydroisoquinolin-6-yl)amino)-1,2-dihydro-3H-pyrazolo[3,4-d]pyrimidin-3-one |
| 16x | 1-(6-(Tert-butyl)-5-fluoropyridin-2-yl)-2-isopropyl-6-((1,2,3,4-tetrahydroisoquinolin-6-yl)amino)-1,2-dihydro-3H-pyrazolo[3,4-d]pyrimidin-3-one |
| 17x | 1-(6-(Tert-butyl)-5-fluoropyridin-2-yl)-2-isopropyl-6-((7-methyl-1,2,3,4-tetrahydroisoquinolin-6-yl)amino)-1,2-dihydro-3H-pyrazolo[3,4-d]pyrimidin-3-one |
| 18x | 1-(2-Cyclopropylpyridin-4-yl)-2-isopropyl-6-((1,2,3,4-tetrahydroisoquinolin-6-yl)amino)-1,2-dihydro-3H-pyrazolo[3,4-d]pyrimidin-3-one |
| 19x | 2-Isopropyl-6-((1,2,3,4-tetrahydroisoquinolin-6-yl)amino)-1-(2-(1-(trifluoromethyl)cyclopropyl)pyridin-4-yl)-1,2-dihydro-3H-pyrazolo[3,4-d]pyrimidin-3-one |
| 20x | 1-(3-(Tert-butyl)-4-fluorophenyl)-2-isopropyl-6-((1,2,3,4-tetrahydroisoquinolin-7-yl)amino)-1,2-dihydro-3H-pyrazolo[3,4-d]pyrimidin-3-one |
| 21x | 1-(3-Cyclopropyl-4-fluorophenyl)-2-isopropyl-6-((1,2,3,4-tetrahydroisoquinolin-7-yl)amino)-1,2-dihydro-3H-pyrazolo[3,4-d]pyrimidin-3-one |
| 22x | 1-(3-(Tert-butyl)-2-fluorophenyl)-2-isopropyl-6-((1,2,3,4-tetrahydroisoquinolin-7-yl)amino)-1,2-dihydro-3H-pyrazolo[3,4-d]pyrimidin-3-one |
| 23x | 1-(3-Cyclopropyl-2-fluorophenyl)-2-isopropyl-6-((1,2,3,4-tetrahydroisoquinolin-7-yl)amino)-1,2-dihydro-3H-pyrazolo[3,4-d]pyrimidin-3-one |
| 24x | 2-(Tert-butyl)-4-(2-isopropyl-3-oxo-6-((1,2,3,4-tetrahydroisoquinolin-7-yl)amino)-2,3-dihydro-1H-pyrazolo[3,4-d]pyrimidin-1-yl)benzonitrile |
| 25x | 2-(2-Hydroxypropan-2-yl)-4-(2-isopropyl-3-oxo-6-((1,2,3,4-tetrahydroisoquinolin-7-yl)amino)-2,3-dihydro-1H-pyrazolo[3,4-d]pyrimidin-1-yl)benzonitrile |
| 26x | 2-Cyclopropyl-4-(2-isopropyl-3-oxo-6-((1,2,3,4-tetrahydroisoquinolin-7-yl)amino)-2,3-dihydro-1H-pyrazolo[3,4-d]pyrimidin-1-yl)benzonitrile |
| 27x | 2-Cyclopropyl-6-(2-isopropyl-3-oxo-6-((1,2,3,4-tetrahydroisoquinolin-7-yl)amino)-2,3-dihydro-1H-pyrazolo[3,4-d]pyrimidin-1-yl)benzonitrile |
| 28x | 2-(Tert-butyl)-6-(2-isopropyl-3-oxo-6-((1,2,3,4-tetrahydroisoquinolin-7-yl)amino)-2,3-dihydro-1H-pyrazolo[3,4-d]pyrimidin-1-yl)benzonitrile |
| 29x | 1-(3-(Tert-butyl)-4-chloro-2-fluorophenyl)-2-isopropyl-6-((1,2,3,4-tetrahydroisoquinolin-7-yl)amino)-1,2-dihydro-3H-pyrazolo[3,4-d]pyrimidin-3-one |
| 30x | 1-(3-(Tert-butyl)-2,4-difluorophenyl)-2-isopropyl-6-((1,2,3,4-tetrahydroisoquinolin-7-yl)amino)-1,2-dihydro-3H-pyrazolo[3,4-d]pyrimidin-3-one |
| 31x | 1-(2-(Tert-butyl)-3-fluoropyridin-4-yl)-2-isopropyl-6-((1,2,3,4-tetrahydroisoquinolin-7-yl)amino)-1,2-dihydro-3H-pyrazolo[3,4-d]pyrimidin-3-one |
| 32x | 1-(6-(Tert-butyl)-5-fluoropyridin-2-yl)-2-isopropyl-6-((1,2,3,4-tetrahydroisoquinolin-7-yl)amino)-1,2-dihydro-3H-pyrazolo[3,4-d]pyrimidin-3-one |
| 33x | 1-(6-(Tert-butyl)-5-fluoropyridin-2-yl)-2-isopropyl-6-((6-methyl-1,2,3,4-tetrahydroisoquinolin-7-yl)amino)-1,2-dihydro-3H-pyrazolo[3,4-d]pyrimidin-3-one |
| 34x | 1-(2-Cyclopropylpyridin-4-yl)-2-isopropyl-6-((1,2,3,4-tetrahydroisoquinolin-7-yl)amino)-1,2-dihydro-3H-pyrazolo[3,4-d]pyrimidin-3-one |

TABLE 1X-continued 35x  2-Isopropyl-6-((1,2,3,4-tetrahydroisoquinolin-7-yl)amino)-1-(2-(1-(trifluoromethyl)cyclopropyl)pyridin-4-yl)-1,2-dihydro-3H-pyrazolo[3,4-d]pyrimidin-3-one
36x  1-(2-(Tert-butyl)-5-fluoropyridin-4-yl)-2-ethyl-6-((1,2,3,4-tetrahydroisoquinolin-7-yl)amino)-1,2-dihydro-3H-pyrazolo[3,4-d]pyrimidin-3-one
37x  1-(6-(Tert-butyl)-3-fluoropyridin-2-yl)-2-ethyl-6-((1,2,3,4-tetrahydroisoquinolin-7-yl)amino)-1,2-dihydro-3H-pyrazolo[3,4-d]pyrimidin-3-one
38x  2-Ethyl-1-(3-fluoro-6-(2-fluoropropan-2-yl)pyridin-2-yl)-6-((1,2,3,4-tetrahydroisoquinolin-7-yl)amino)-1,2-dihydro-3H-pyrazolo[3,4-d]pyrimidin-3-one
39x  1-(2-(Tert-butyl)-5-fluoropyridin-4-yl)-6-((1,2,3,4-tetrahydroisoquinolin-7-yl)amino)-2-(2,2,2-trifluoroethyl)-1,2-dihydro-3H-pyrazolo[3,4-d]pyrimidin-3-one
40x  1-(4-Fluoro-3-(2-hydroxypropan-2-yl)phenyl)-2-isopropyl-6-((1,2,3,4-tetrahydroisoquinolin-6-yl)amino)-1,2-dihydro-3H-pyrazolo[3,4-d]pyrimidin-3-one
41x  1-(4-Fluoro-3-(2-hydroxypropan-2-yl)phenyl)-2-isopropyl-6-((1,2,3,4-tetrahydroisoquinolin-7-yl)amino)-1,2-dihydro-3H-pyrazolo[3,4-d]pyrimidin-3-one
42x  1-(2-(Tert-butyl)-5-fluoropyridin-4-yl)-6-((1,2,3,4-tetrahydroisoquinolin-7-yl)amino)-2-(2,2,2-trifluoroethyl)-1,2-dihydro-3H-pyrazolo[3,4-d]pyrimidin-3-one In some embodiments of a compound of Formula (I), the compound is of Formula (II):

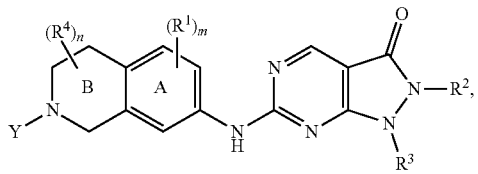

In some embodiments of a compound of Formula (I), the compound is of Formula (III):

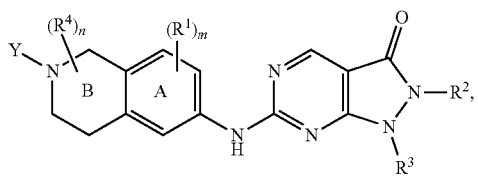

In some embodiments of a compound of Formula (I), $R^2$ is $C_1$-$C_6$ alkyl, such as methyl, ethyl, n-propyl, isopropyl, n-butyl, t-butyl, isobutyl, or sec-butyl. In some embodiments, $R^2$ is isopropyl or ethyl. In some embodiments, $R^2$ is isopropyl. In some embodiments, $R^2$ is ethyl. In some embodiments, $R^2$ is $C_{3-6}$ cycloalkyl, such as cyclopropyl, cyclobutyl, cyclopentyl, or cyclohexyl. In some embodiments, $R^2$ is cyclopropyl. In some embodiments, $R^2$ is —($C_1$-$C_3$ alkylene)$CF_3$. In some embodiments, $R^2$ is —$CH_2CF_3$. In some embodiments, $R^2$ is selected from the group consisting of isopropyl, ethyl, cyclopropyl, and —$CH_2CF_3$.

In some embodiments of a compound of Formula (I), $M^1$ is CH. In some embodiments, $M^1$ is $CR^{3b}$. In some embodiments, $M^1$ is N.

In some embodiments of a compound of Formula (I), $M^2$ is CH. In some embodiments, $M^2$ is $CR^{3b}$. In some embodiments, $M^2$ is N. In some embodiments, $M^2$ is absent.

In some embodiments of a compound of Formula (I), $M^3$ is CH. In some embodiments, $M^3$ is $CR^{3b}$. In some embodiments, $M^3$ is N. In some embodiments, $M^3$ is S. In some embodiments, $M^3$ is O.

In some embodiments of a compound of Formula (I), $M^4$ is CH. In some embodiments, $M^4$ is $CR^{3b}$. In some embodiments, $M^4$ is N. In some embodiments, $M^4$ is S. In some embodiments, $M^4$ is O. In some embodiments, when $M^4$ is O or S and $M^2$ is absent, then $M^3$ is CH, $CR^{3b}$ or N. In some embodiments, when $M^3$ is O or S and $M^2$ is absent, then $M^4$ is CH, $CR^{3b}$ or N.

In some embodiments of a compound of Formula (I), $R^3$ is selected from the group consisting of:

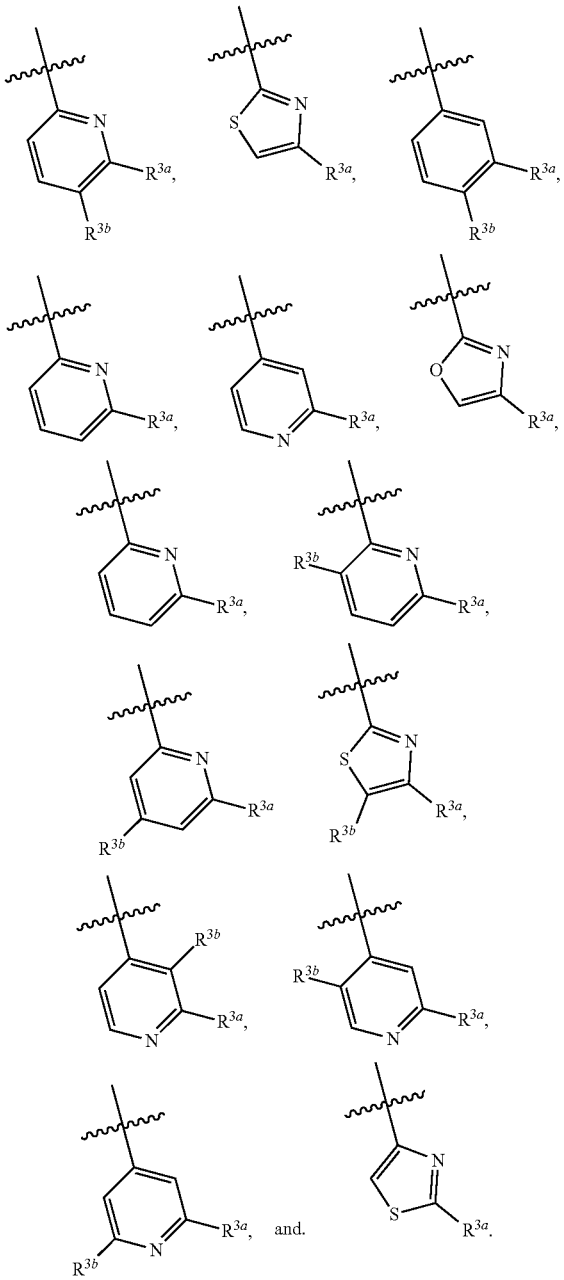

In some embodiments, R³ is
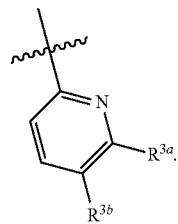
In some embodiments, R³ is
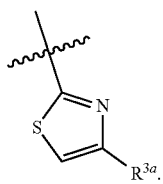
In some embodiments, R³ is
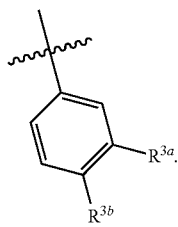
In some embodiments, R³ is
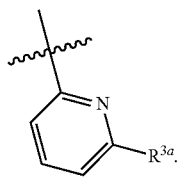
In some embodiments, R³ is
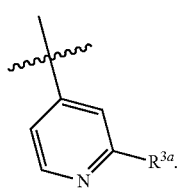
In some embodiments, R³ is
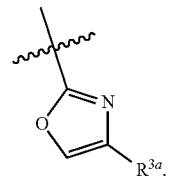
In some embodiments, R³ is
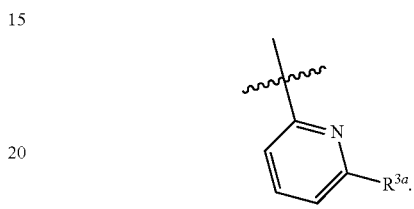
In some embodiments, R³ is
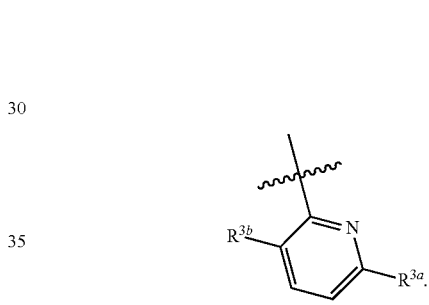
In some embodiments, R³ is
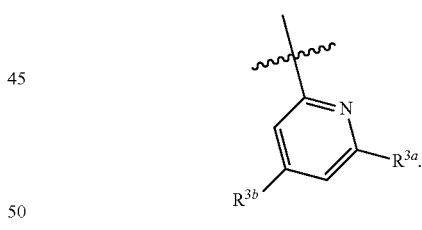
In some embodiments, R³ is
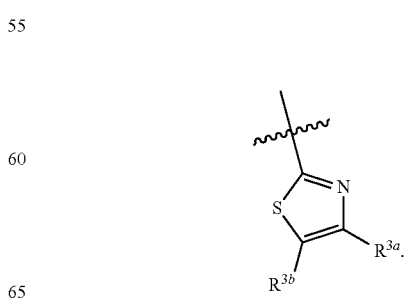

In some embodiments, $R^3$ is

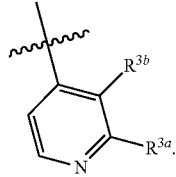

In some embodiments, $R^3$ is

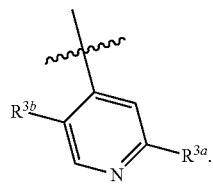

In some embodiments, $R^3$ is

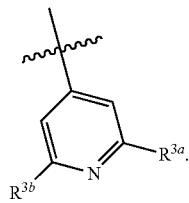

In some embodiments, $R^3$ is

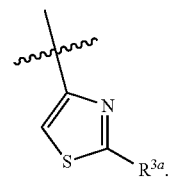

In some embodiments of a compound of Formula (I), $R^{3a}$ is $C_3$-$C_6$ cycloalkyl optionally substituted by $C_1$-$C_6$ haloalkyl or —CN, such as cyclopropyl, cyclobutyl, cyclopentyl, or cyclohexyl, each of which is optionally substituted by $C_1$-$C_6$ haloalkyl or —CN. In some embodiments, $R^{3a}$ is $C_{3-6}$ cycloalkyl which is unsubstituted, such as cyclopropyl, cyclobutyl, cyclopentyl, or cyclohexyl, each of which is unsubstituted. In some embodiments, $R^{3a}$ is $C_3$-$C_6$ cycloalkyl optionally substituted by $C_1$-$C_6$ haloalkyl, such as cyclopropyl, cyclobutyl, cyclopentyl, or cyclohexyl, each of which is optionally substituted by $C_1$-$C_6$ haloalkyl. In some embodiments, $R^{3a}$ is $C_3$-$C_6$ cycloalkyl optionally substituted by —CN, such as cyclopropyl, cyclobutyl, cyclopentyl, or cyclohexyl, each of which is optionally substituted by —CN. In some embodiments, $R^{3a}$ is

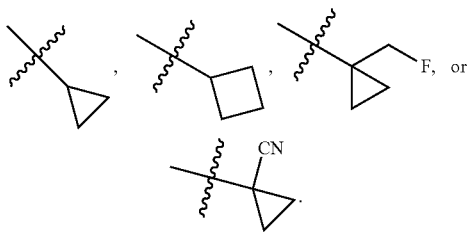

In some embodiments, $R^{3a}$ is

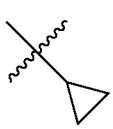

In some embodiments, $R^{3a}$ is

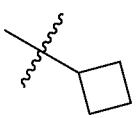

In some embodiments, $R^{3a}$ is

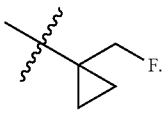 [SMILES: *C1(CF)CC1]

In some embodiments, $R^{3a}$ is

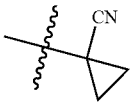

In some embodiments, $R^{3a}$ is $C_1$-$C_6$ alkyl optionally substituted by halogen, —OH or —CN, such as methyl, ethyl, n-propyl, isopropyl, n-butyl, t-butyl, isobutyl, or sec-butyl, each of which is optionally substituted by halogen, —OH or —CN. In some embodiments, $R^{3a}$ is $C_1$-$C_6$ alkyl which is unsubstituted, such as methyl, ethyl, n-propyl, isopropyl, n-butyl, t-butyl, isobutyl, or sec-butyl, each of which is unsubstituted. In some embodiments, $R^{3a}$ is $C_1$-$C_6$ alkyl optionally substituted by halogen, such as methyl, ethyl, n-propyl, isopropyl, n-butyl, t-butyl, isobutyl, or sec-butyl, each of which is optionally substituted by halogen. In some embodiments, $R^{3a}$ is $C_1$-$C_6$ alkyl optionally substituted by —OH, such as methyl, ethyl, n-propyl, isopropyl, n-butyl, t-butyl, isobutyl, or sec-butyl, each of which is optionally substituted by —OH. In some embodiments, $R^{3a}$ is $C_1$-$C_6$ alkyl optionally substituted by —OH, such as methyl, ethyl, n-propyl, isopropyl, n-butyl, t-butyl, isobutyl, or sec-butyl, each of which is optionally substituted by —CN. In some embodiments, $R^{3a}$ is

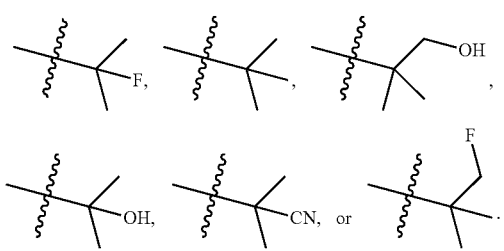

In some embodiments, $R^3$ is

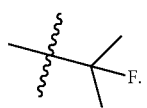 [SMILES: *C(C)(C)F]

In some embodiments, $R^{3a}$ is

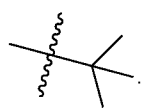 [SMILES: *C(C)(C)C]

In some embodiments, $R^{3a}$ is

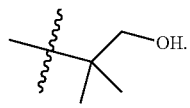

In some embodiments, $R^{3a}$ is

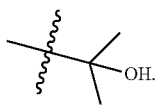

In some embodiments, $R^{3a}$ is

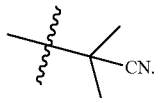 [SMILES: *C(C)(C)C#N]

In some embodiments, $R^{3a}$ is

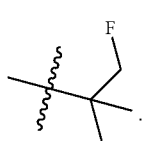 [SMILES: *C(C)(C)CF]

In some embodiments, $R^{3a}$ is

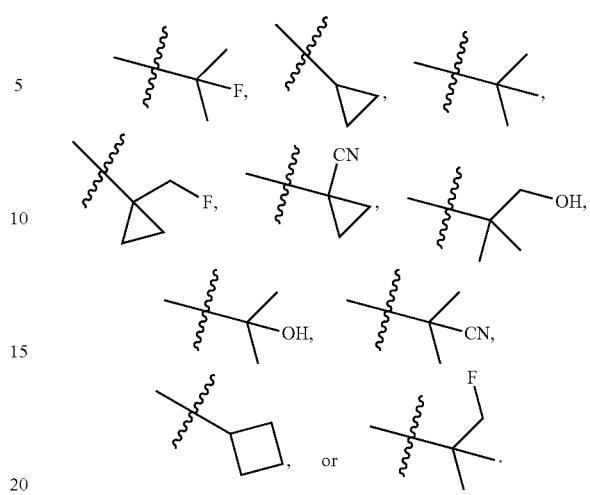

In some embodiments of a compound of Formula (I), $R^{3b}$ is —CN. In some embodiments, $R^{3b}$ is halogen, such as fluoro, chloro, bromo, or iodo. In some embodiments, $R^{3b}$ is fluoro. In some embodiments, $R^{3b}$ is chloro. In some embodiments, $R^{3b}$ is bromo.

In some embodiments of a compound of Formula (I), $R^3$ is selected from the group consisting of:

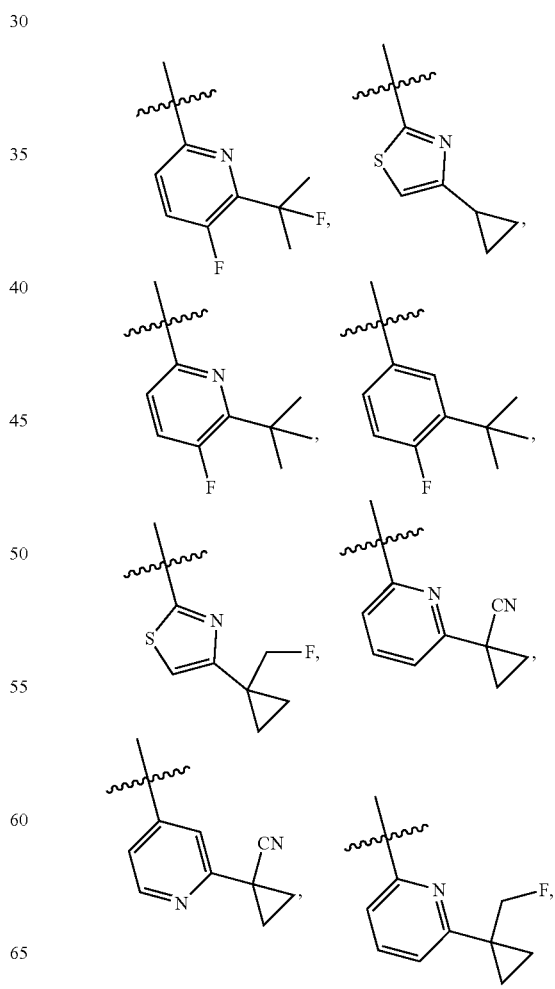

-continued
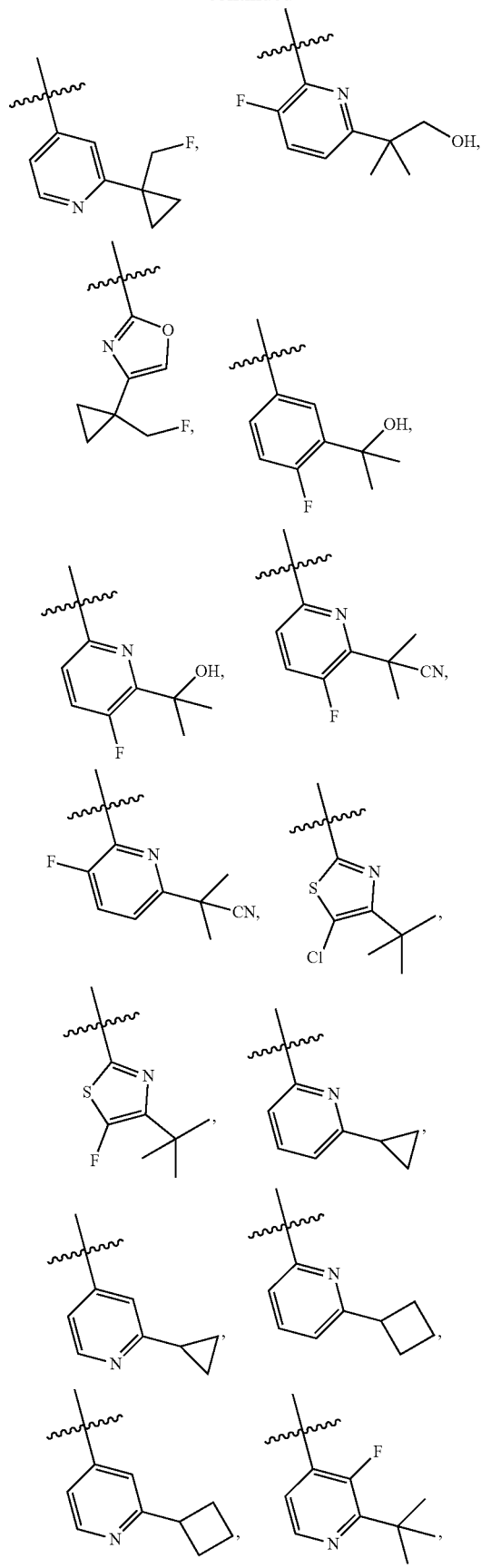
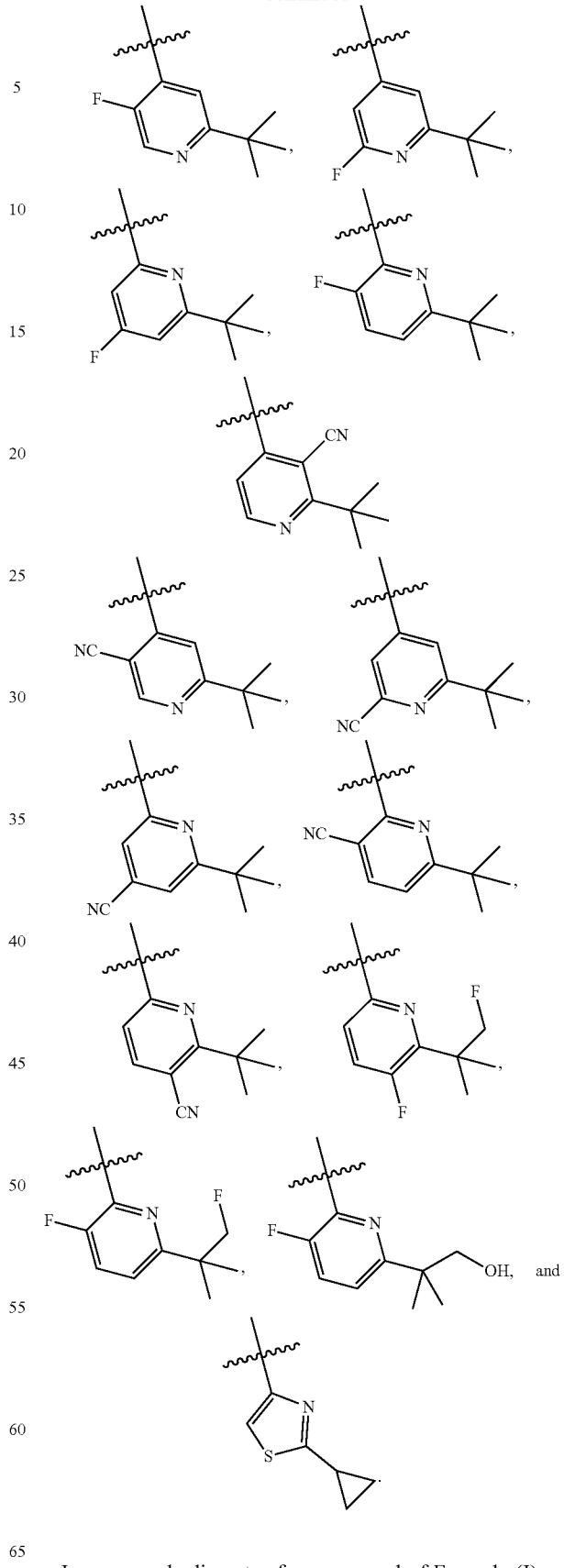
In some embodiments of a compound of Formula (I), m is 0. In some embodiments, m is 1. In some embodiments, m is 2. In some embodiments, m is 3. In some embodiments, m is 0, 1, or 2. In some embodiments, m is 0 or 1.

In some embodiments of a compound of Formula (I), $R^1$ is F. In some embodiments, $R^1$ is Cl. In some embodiments $R^1$ is methyl.

In some embodiments of a compound of Formula (I), n is 0. In some embodiments, n is 1. In some embodiments, n is 2. In some embodiments, n is 3. In some embodiments, n is 4. In some embodiments, n is 0, 1, 2, or 3. In some embodiments, n is 0, 1, or 2. In some embodiments, n is 0 or 1.

In some embodiments of a compound of Formula (I), each $R^4$ is independently $C_1$-$C_6$ alkyl, or two $R^4$, when bound to the same carbon, are taken together with the carbon to which they are attached to form a $C_3$-$C_6$ cycloalkyl. In some embodiments, each $R^4$ is independently $C_1$-$C_6$ alkyl, such as methyl, ethyl, n-propyl, isopropyl, n-butyl, t-butyl, isobutyl, or sec-butyl. In some embodiments, n is 1 and $R^4$ is $C_1$-$C_6$ alkyl. In some embodiments, n is 2 and each $R^4$ is independently $C_1$-$C_6$ alkyl. In some embodiments, n is 2 and each $R^4$ is methyl. In some embodiments, n is 2 and two $R^4$, when bound to the same carbon, are taken together with the carbon to which they are attached to form a $C_3$-$C_6$ cycloalkyl.

In some embodiments of a compound of Formula (I), Y is hydrogen. In some embodiments, Y is $R^4$. In some embodiments, Y is $C_1$-$C_6$ alkyl, $C_2$-$C_6$ alkenyl, $C_2$-$C_6$ alkynyl, $C_3$-$C_6$ cycloalkyl, or 3- to 6-membered heterocyclyl. In some embodiments, Y is $C_1$-$C_6$ alkyl, such as methyl, ethyl, n-propyl, isopropyl, n-butyl, t-butyl, isobutyl, or sec-butyl.

In some embodiments of a compound of Formula (I), ring A, ring B, Y, $R^1$ and $R^4$ together are taken together to form a moiety selected from the group consisting of:

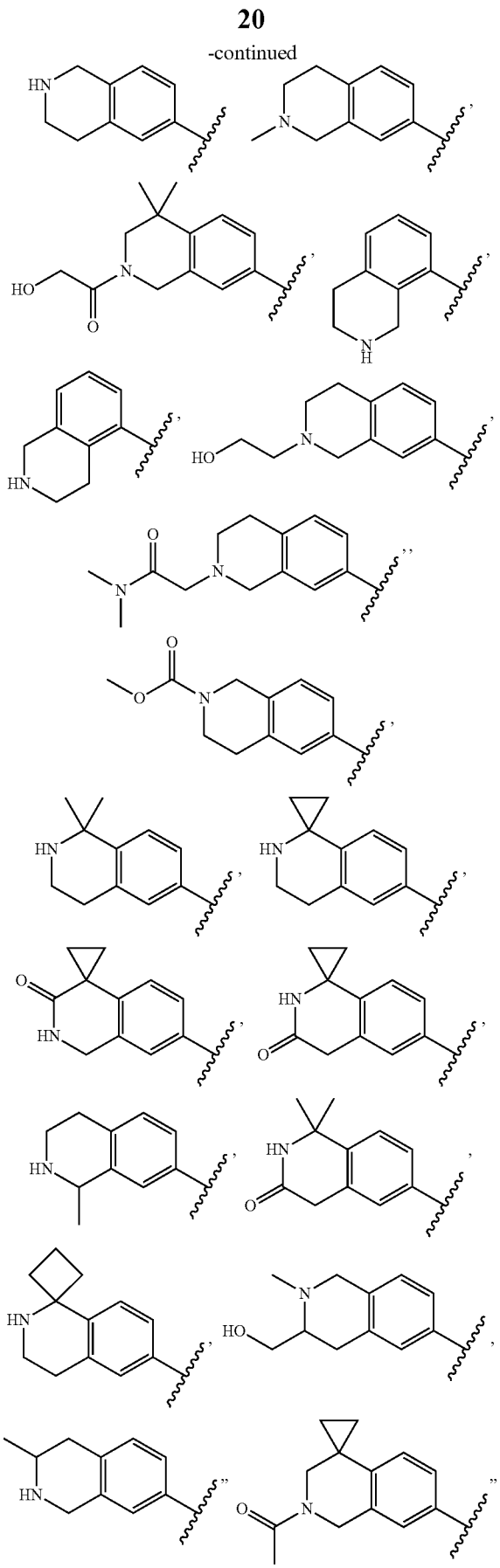

-continued

23
-continued
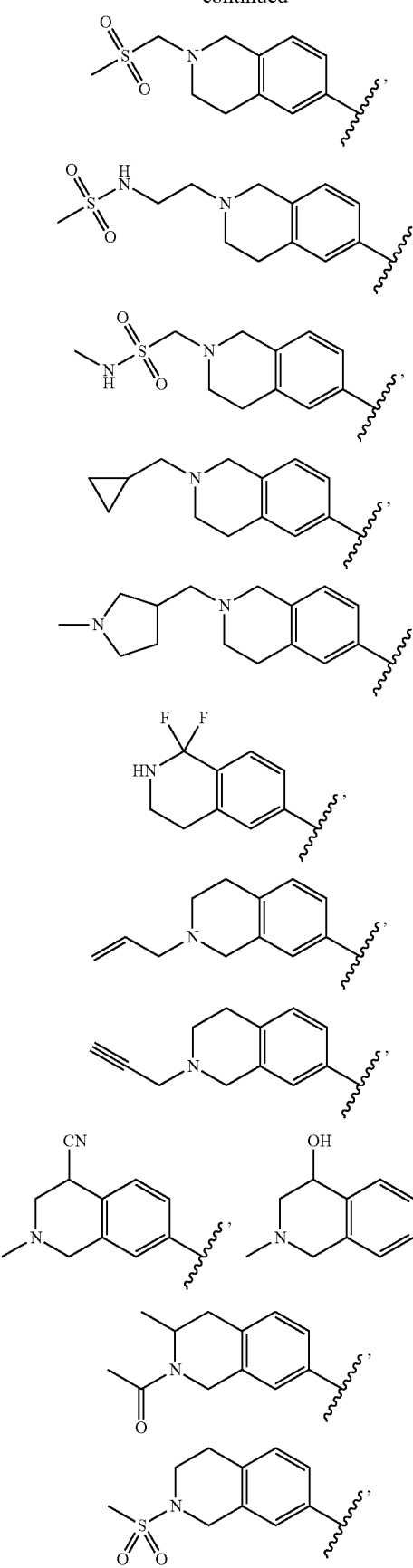
24
-continued
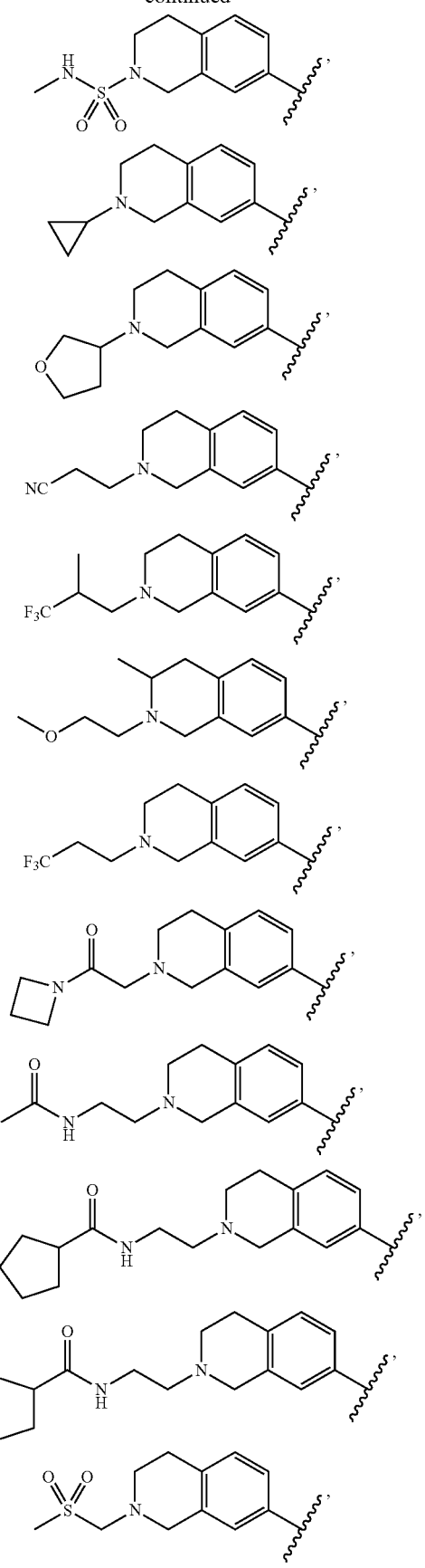

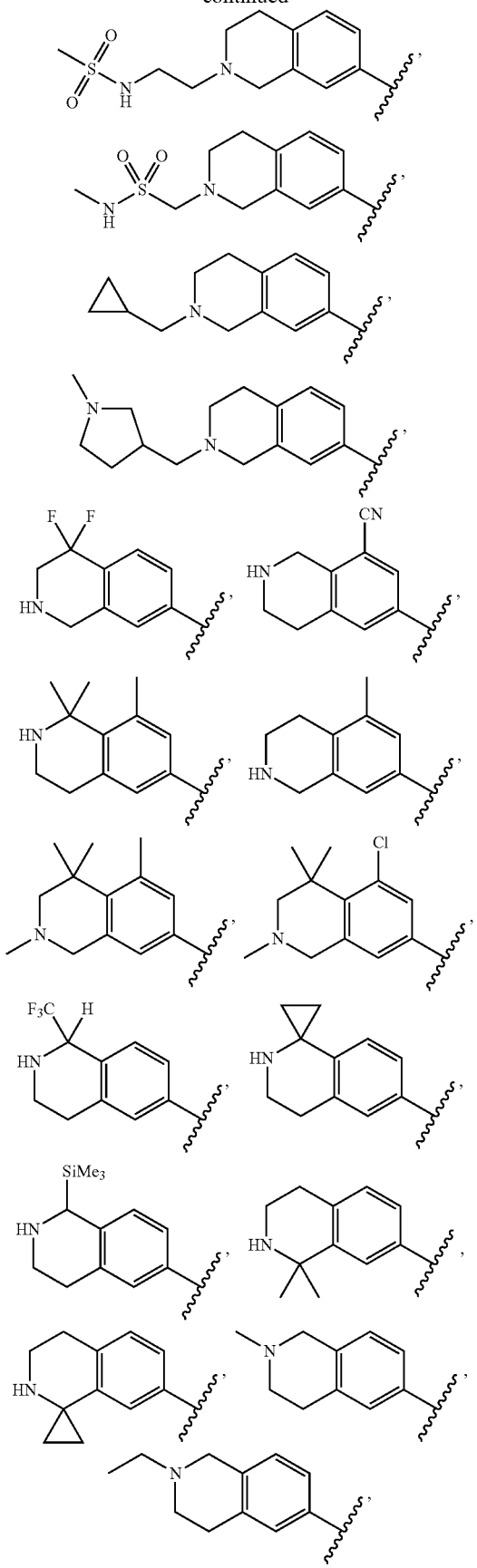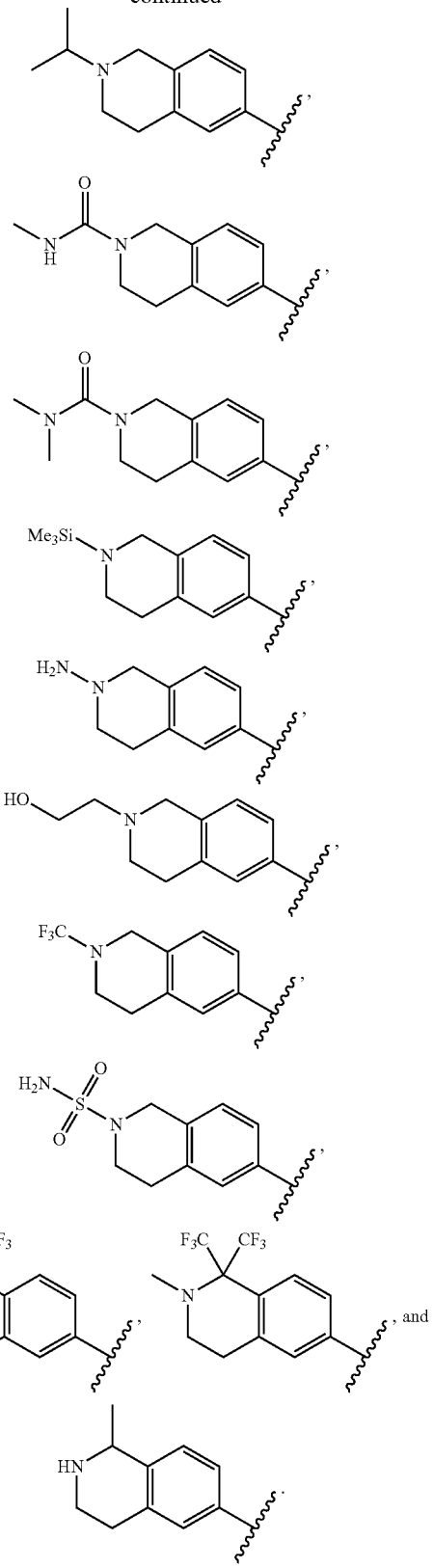
In some embodiments, ring A, ring B, Y, $R^1$ and $R^4$ together are taken together to form a moiety selected from the group consisting of:

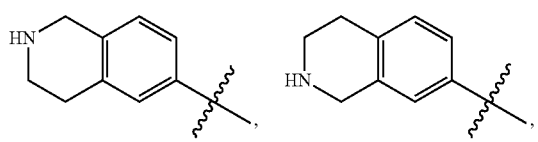

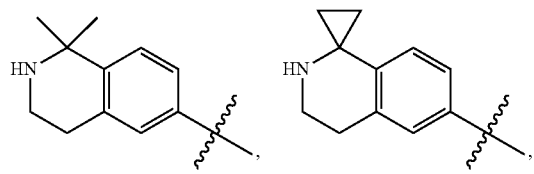

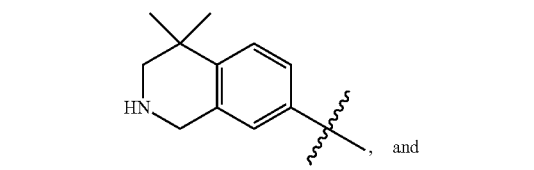, and

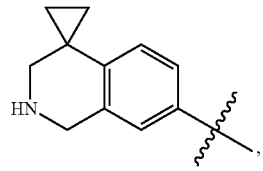

In some embodiments, ring A, ring B, Y, $R^1$ and $R^4$ together are taken together to form

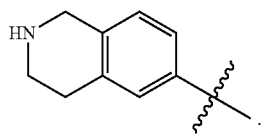 [SMILES: *c1ccc2c(c1)CCNC2]

In some embodiments, ring A, ring B, Y, $R^1$ and $R^4$ together are taken together to form

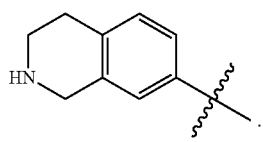 [SMILES: *c1ccc2c(c1)CNCC2]

In some embodiments, ring A, ring B, Y, $R^1$ and $R^4$ together are taken together to form

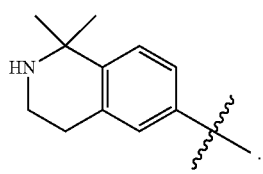 [SMILES: *c1ccc2c(c1)CCNC2(C)C]

In some embodiments, ring A, ring B, Y, $R^1$ and $R^4$ together are taken together to form

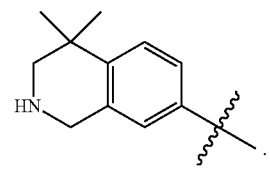

In some embodiments, ring A, ring B, Y, $R^1$ and $R^4$ together are taken together to form

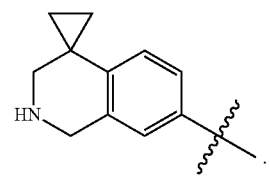

In some embodiments, ring A, ring B, Y, $R^1$ and $R^4$ together are taken together to form

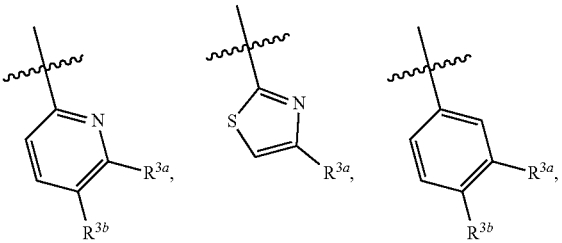

In some embodiments of a compound of Formula (I), the compound has one or more of the following features:
(I) $R^2$ is
(1) $C_1$-$C_6$ alkyl, such as isopropyl or ethyl,
(2) $C_3$-$C_6$ cycloalkyl, such as cyclopropyl, or
(3) —($C_1$-$C_3$ alkylene)$CF_3$, such as —$CH_2CF_3$;
(II) $R^3$ is
(4)

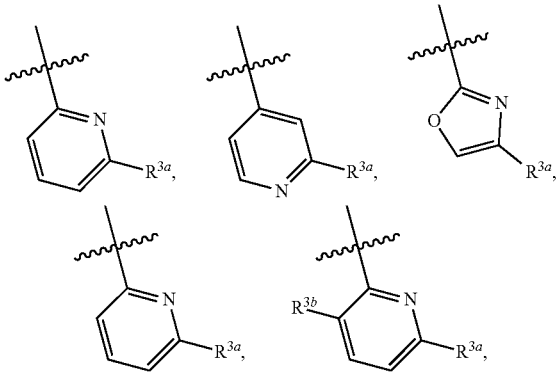

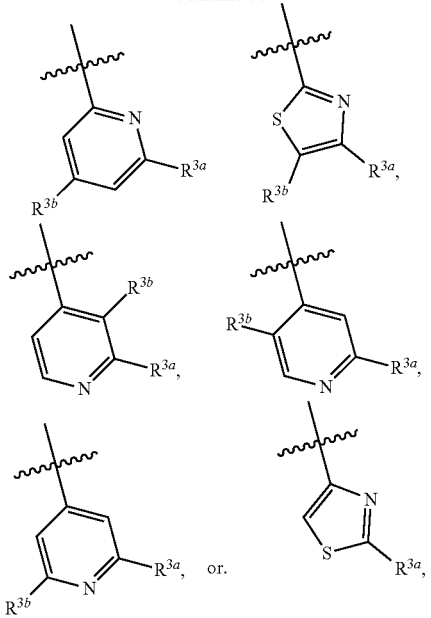
wherein R³ᵃ is C₃-C₆ cycloalkyl optionally substituted by C₁-C₆ haloalkyl or —CN, or C₁-C₆ alkyl optionally substituted by halogen, —OH or —CN, provided that when R³ᵃ is C₁-C₆ alkyl optionally substituted by halogen, —OH or —CN, then at least one of M¹, M², M³, and M⁴ is CR³ᵇ, and R³ᵇ is halogen or —CN, or
(5)
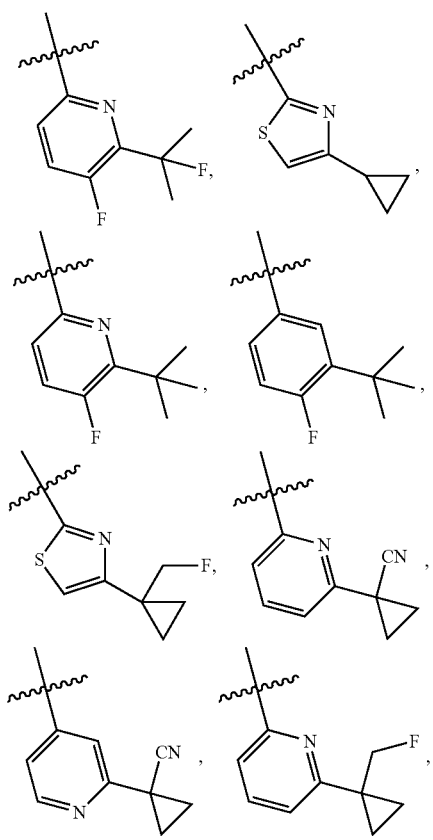
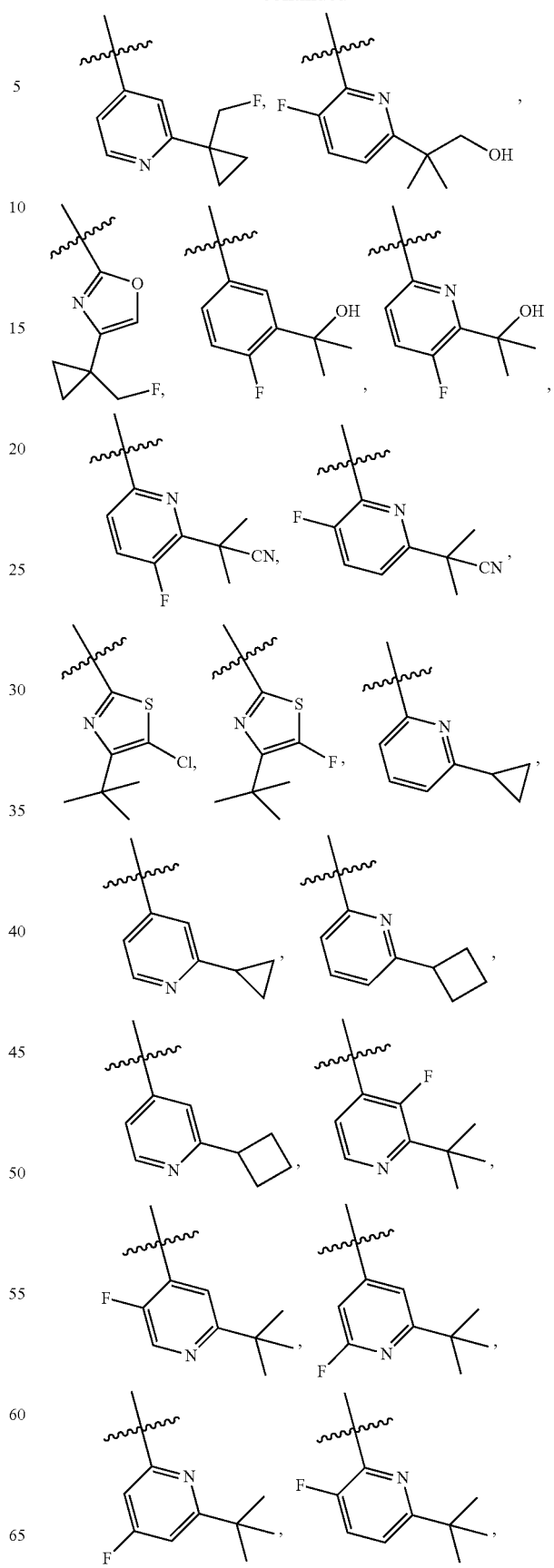

-continued

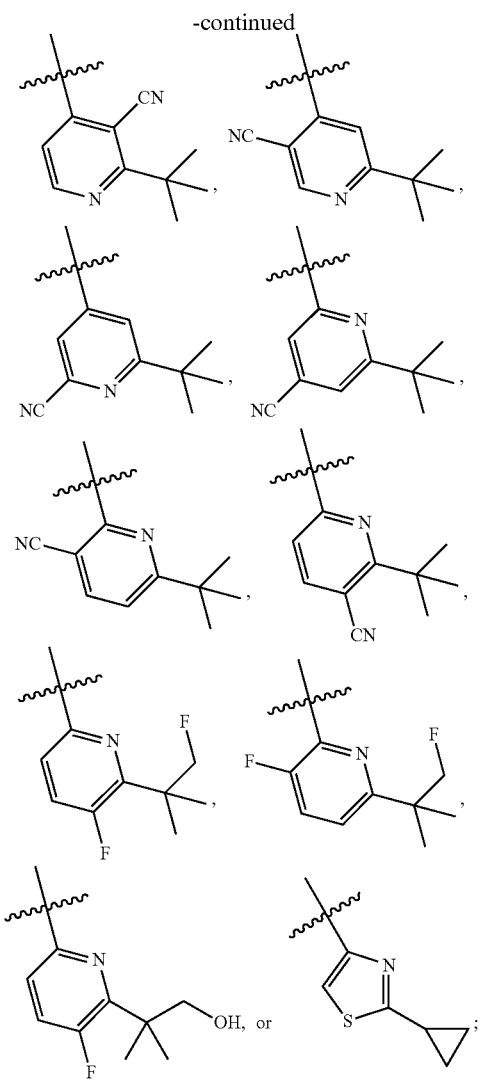

(III) ring A, ring B, $R^1$, and $R^4$ are taken together to form a moiety selected from the group consisting of:

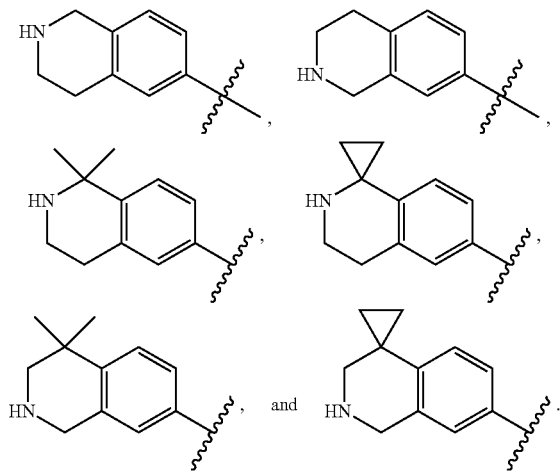

In some embodiments, (1) applies. In some embodiments, (2) applies. In some embodiments, (3) applies. In some embodiments, (4) applies. In some embodiments, (5) applies. In some embodiments, (III) applies. In some embodiments, (I) and (4) apply. In some embodiments, (I) and (5) apply. In some embodiments, (1) and (4) apply. In some embodiments, (1) and (5) apply. In some embodiments, (2) and (4) apply. In some embodiments, (2) and (5) apply. In some embodiments, (3) and (4) apply. In some embodiments, (3) and (5) apply. In some embodiments, (I) and (III) apply. In some embodiments, (1) and (III) apply. In some embodiments, (2) and (III) apply. In some embodiments, (3) and (III) apply. In some embodiments, (4) and (III) apply. In some embodiments, (5) and (III) apply. In some embodiments, (I), (4), and (III) apply. In some embodiments, (I), (5), and (III) apply. In some embodiments, (1), (4), and (III) apply. In some embodiments, (1), (5), and (III) apply. In some embodiments, (2), (4), and (III) apply. In some embodiments, (2), (5), and (III) apply. In some embodiments, (3), (4), and (III) apply. In some embodiments, (3), (5), and (III) apply.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of Formula (I) may be combined with every description, variation, embodiment or aspect of $R^2$, $R^3$, $R^4$, m, n, and Y the same as if each and every combination were specifically and individually listed. It is also understood that all descriptions, variations, embodiments or aspects of Formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as Formula (II) and Formula (III) and are equally described, the same as if each and every description, variation, embodiment or aspect were separately and individually listed for all formulae.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1.

TABLE 1

| Compound No. | Structure |
|---|---|
| 1.1 | 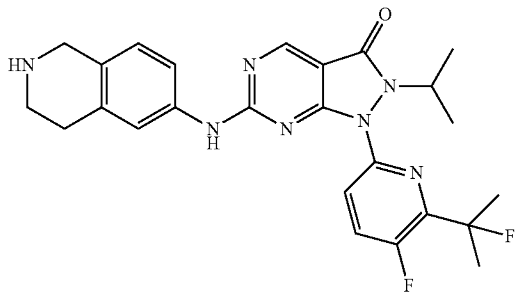 [SMILES: CC(C)n1c(=O)c2cnc(Nc3ccc4c(c3)CCNC4)nc2n1-c1ccc(F)c(C(C)(C)F)n1] |
| 1.2 | 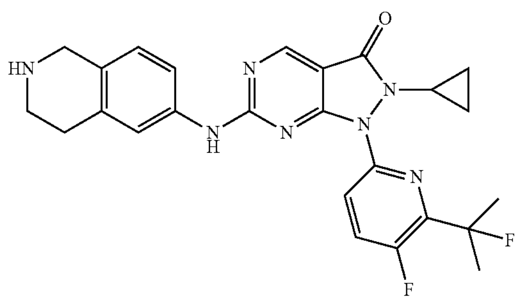 [SMILES: CC(C)(F)c1nc(-n2c3nc(Nc4ccc5c(c4)CCNC5)ncc3c(=O)n2C2CC2)ccc1F] |
| 1.3 | 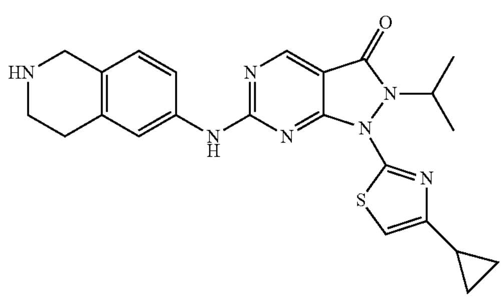 [SMILES: CC(C)n1c(=O)c2cnc(Nc3ccc4c(c3)CCNC4)nc2n1-c1nc(C2CC2)cs1] |
| 1.4 | 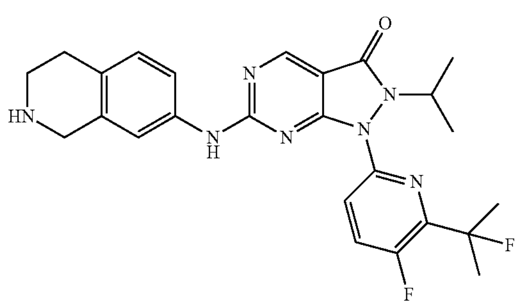 [SMILES: CC(C)n1c(=O)c2cnc(Nc3ccc4c(c3)CNCC4)nc2n1-c1ccc(F)c(C(C)(C)F)n1] |
| 1.5 | 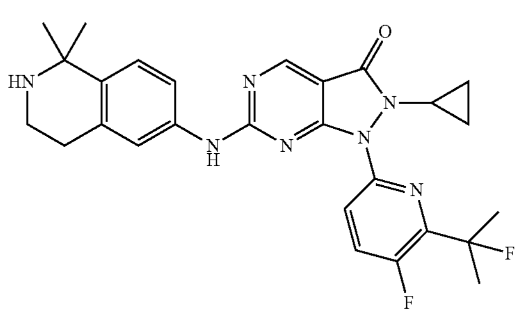 [SMILES: CC(C)(F)c1nc(-n2c3nc(Nc4ccc5c(c4)CCNC5(C)C)ncc3c(=O)n2C2CC2)ccc1F] |

TABLE 1-continued

| Compound No. | Structure |
|---|---|
| 1.6 | 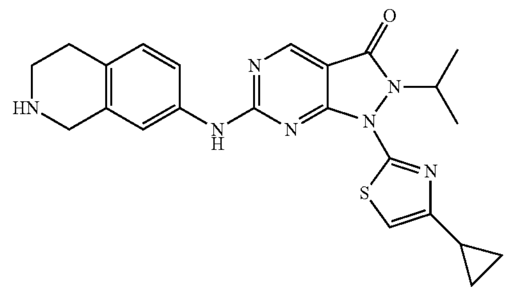 [SMILES: CC(C)n1c(=O)c2cnc(Nc3ccc4c(c3)CNCC4)nc2n1-c1nc(C2CC2)cs1] |
| 1.7 | 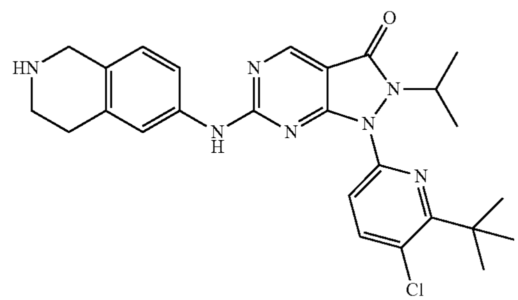 [SMILES: CC(C)n1c(=O)c2cnc(Nc3ccc4c(c3)CCNC4)nc2n1-c1ccc(Cl)c(C(C)(C)C)n1] |
| 1.8 | 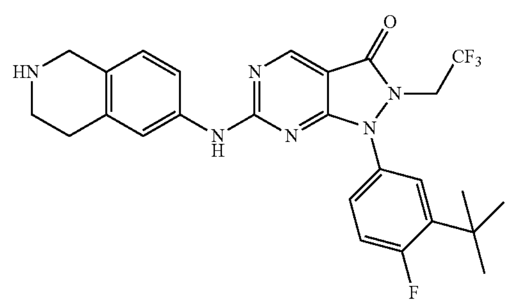 [SMILES: CC(C)(C)c1cc(-n2c3nc(Nc4ccc5c(c4)CCNC5)ncc3c(=O)n2CC(F)(F)F)ccc1F] |
| 1.9 | 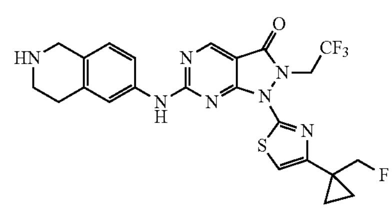 [SMILES: O=c1c2cnc(Nc3ccc4c(c3)CCNC4)nc2n(-c2nc(C3(CF)CC3)cs2)n1CC(F)(F)F] |
| 1.10 | 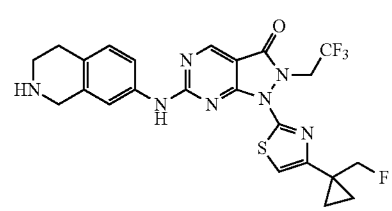 [SMILES: O=c1c2cnc(Nc3ccc4c(c3)CNCC4)nc2n(-c2nc(C3(CF)CC3)cs2)n1CC(F)(F)F] |
| 1.11 | 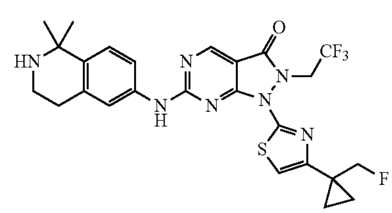 [SMILES: CC1(C)NCCc2cc(Nc3ncc4c(=O)n(CC(F)(F)F)n(-c5nc(C6(CF)CC6)cs5)c4n3)ccc21] |

TABLE 1-continued
| Compound No. | Structure |
|---|---|
| 1.12 | 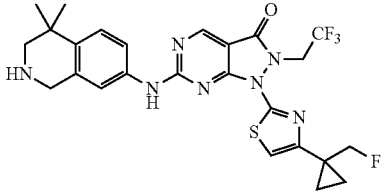 [SMILES: CC1(C)CNCc2cc(Nc3ncc4c(=O)n(CC(F)(F)F)n(-c5nc(C6(CF)CC6)cs5)c4n3)ccc21] |
| 1.13 | 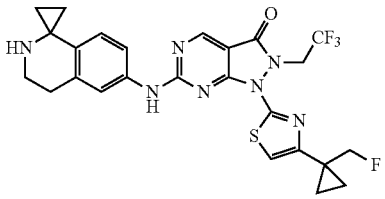 |
| 1.14 | 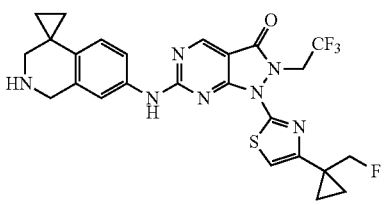 [SMILES: O=c1c2cnc(Nc3ccc4c(c3)CNCC43CC3)nc2n(-c2nc(C3(CF)CC3)cs2)n1CC(F)(F)F] |
| 1.15 | 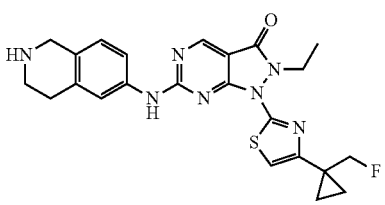 [SMILES: CCn1c(=O)c2cnc(Nc3ccc4c(c3)CCNC4)nc2n1-c1nc(C2(CF)CC2)cs1] |
| 1.16 | 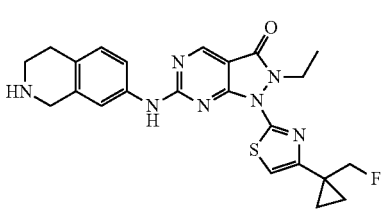 [SMILES: CCn1c(=O)c2cnc(Nc3ccc4c(c3)CNCC4)nc2n1-c1nc(C2(CF)CC2)cs1] |
| 1.17 | 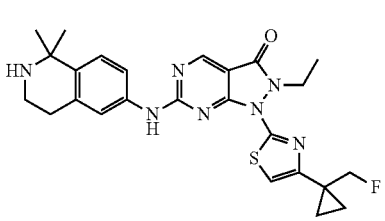 [SMILES: CCn1c(=O)c2cnc(Nc3ccc4c(c3)CCNC4(C)C)nc2n1-c1nc(C2(CF)CC2)cs1] |
| 1.18 | 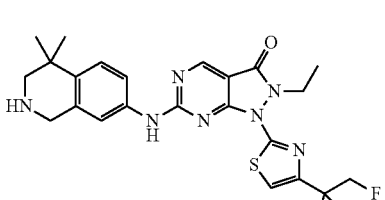 |
| 1.19 | 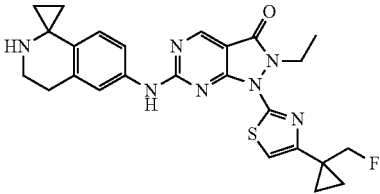 |
| 1.20 | 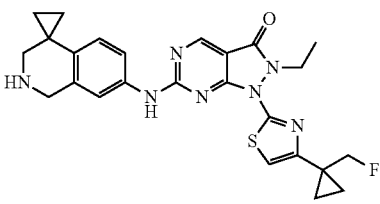 |
| 1.21 | 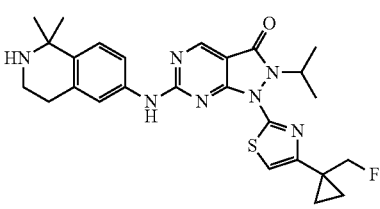 [SMILES: CC(C)n1c(=O)c2cnc(Nc3ccc4c(c3)CCNC4(C)C)nc2n1-c1nc(C2(CF)CC2)cs1] |
| 1.22 | 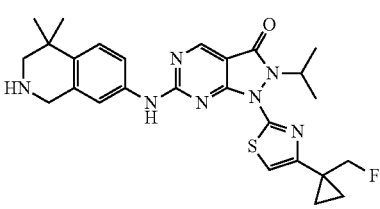 [SMILES: CC(C)n1c(=O)c2cnc(Nc3ccc4c(c3)CNCC4(C)C)nc2n1-c1nc(C2(CF)CC2)cs1] |
| 1.23 | 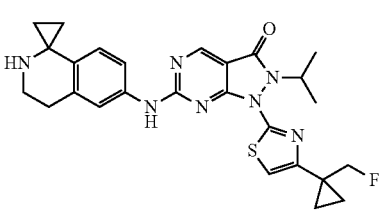 [SMILES: CC(C)n1c(=O)c2cnc(Nc3ccc4c(c3)CCNC43CC3)nc2n1-c1nc(C2(CF)CC2)cs1] |
| 1.24 | 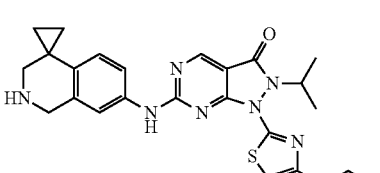 |
| 1.25 | 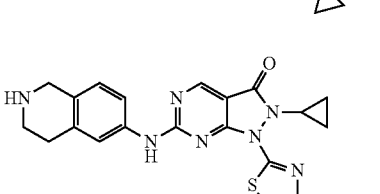 |

TABLE 1-continued

| Compound No. | Structure |
|---|---|
| 1.26 | 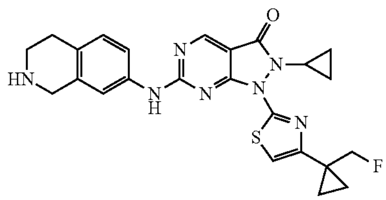 [SMILES: O=c1c2cnc(Nc3ccc4c(c3)CNCC4)nc2n(-c2nc(C3(CF)CC3)cs2)n1C1CC1] |
| 1.27 | 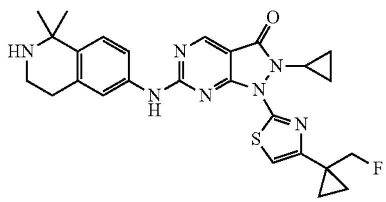 [SMILES: CC1(C)NCCc2cc(Nc3ncc4c(=O)n(C5CC5)n(-c5nc(C6(CF)CC6)cs5)c4n3)ccc21] |
| 1.28 | 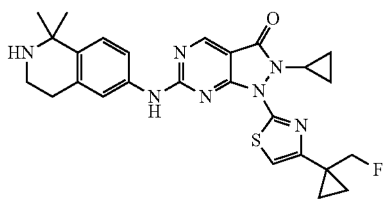 [SMILES: CC1(C)NCCc2cc(Nc3ncc4c(=O)n(C5CC5)n(-c5nc(C6(CF)CC6)cs5)c4n3)ccc21] |
| 1.29 | 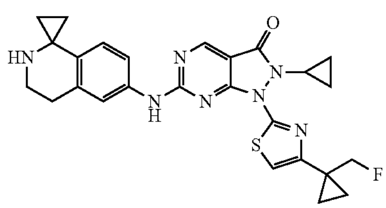 [SMILES: O=c1c2cnc(Nc3ccc4c(c3)CCNC43CC3)nc2n(-c2nc(C3(CF)CC3)cs2)n1C1CC1] |
| 1.30 | 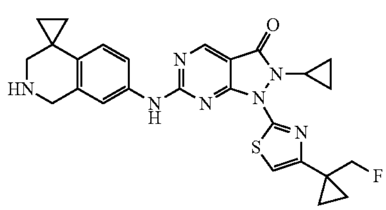 [SMILES: O=c1c2cnc(Nc3ccc4c(c3)CNCC43CC3)nc2n(-c2nc(C3(CF)CC3)cs2)n1C1CC1] |
| 1.31 | 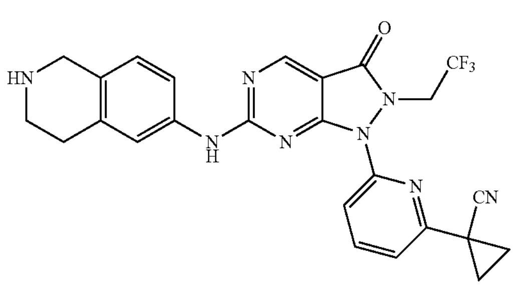 [SMILES: N#CC1(c2cccc(-n3c4nc(Nc5ccc6c(c5)CCNC6)ncc4c(=O)n3CC(F)(F)F)n2)CC1] |
| 1.32 | |
| 1.33 | |
| 1.34 | |
| 1.35 | |
| 1.36 | |

TABLE 1-continued

| Compound No. | Structure |
|---|---|
| 1.37 | 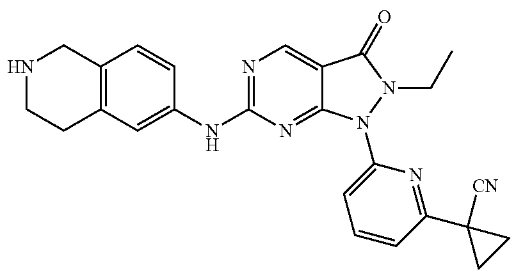 [SMILES: CCn1c(=O)c2cnc(Nc3ccc4c(c3)CCNC4)nc2n1-c1cccc(C2(C#N)CC2)n1] |
| 1.38 | 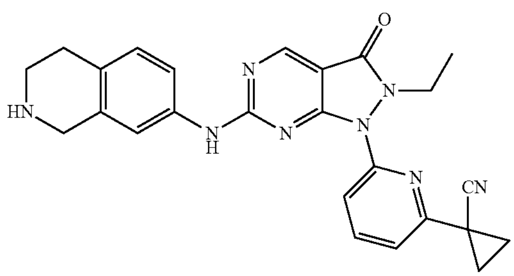 [SMILES: CCn1c(=O)c2cnc(Nc3ccc4c(c3)CNCC4)nc2n1-c1cccc(C2(C#N)CC2)n1] |
| 1.39 | 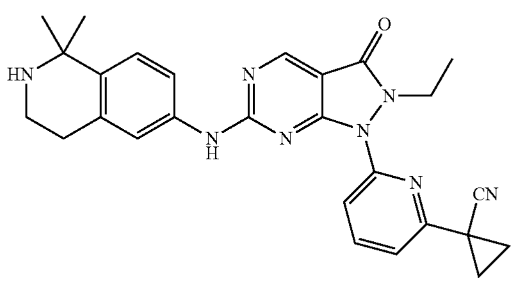 [SMILES: CCn1c(=O)c2cnc(Nc3ccc4c(c3)CCNC4(C)C)nc2n1-c1cccc(C2(C#N)CC2)n1] |
| 1.40 | 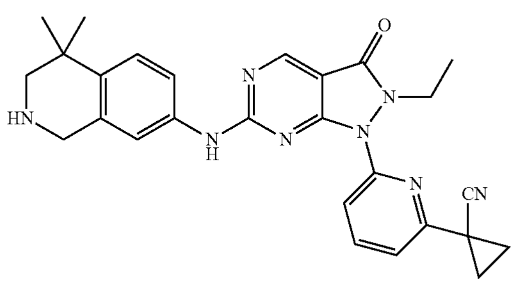 [SMILES: CCn1c(=O)c2cnc(Nc3ccc4c(c3)CNCC4(C)C)nc2n1-c1cccc(C2(C#N)CC2)n1] |
| 1.41 | 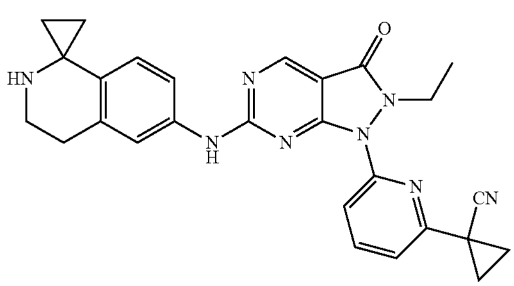 [SMILES: CCn1c(=O)c2cnc(Nc3ccc4c(c3)CCNC43CC3)nc2n1-c1cccc(C2(C#N)CC2)n1] |
| 1.42 | |
| 1.43 | |
| 1.44 | |
| 1.45 | |
| 1.46 | |

TABLE 1-continued

| Compound No. | Structure |
|---|---|
| 1.47 | 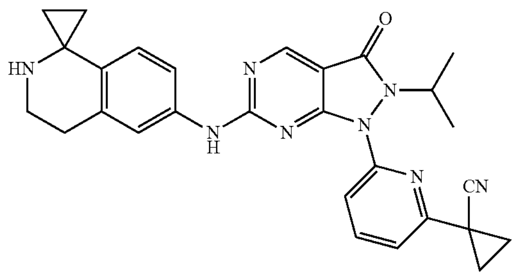 [SMILES: CC(C)n1c(=O)c2cnc(Nc3ccc4c(c3)CCNC43CC3)nc2n1-c1cccc(C2(C#N)CC2)n1] |
| 1.48 | 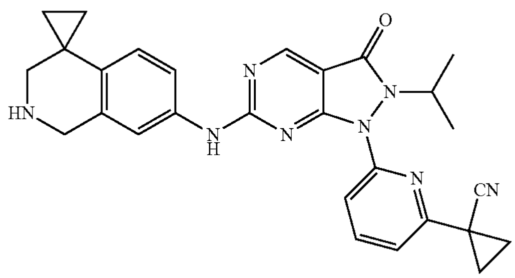 [SMILES: CC(C)n1c(=O)c2cnc(Nc3ccc4c(c3)CNCC43CC3)nc2n1-c1cccc(C2(C#N)CC2)n1] |
| 1.49 | 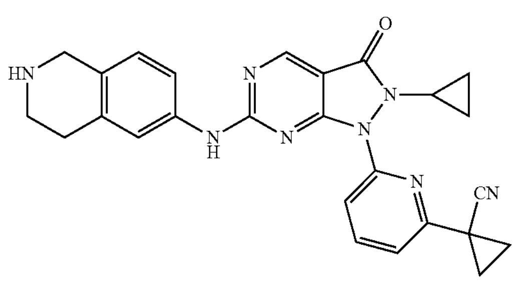 [SMILES: N#CC1(c2cccc(-n3c4nc(Nc5ccc6c(c5)CCNC6)ncc4c(=O)n3C3CC3)n2)CC1] |
| 1.50 | 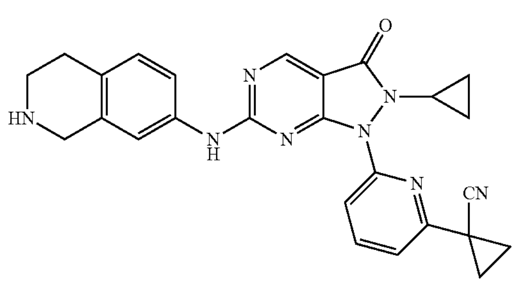 [SMILES: N#CC1(c2cccc(-n3c4nc(Nc5ccc6c(c5)CNCC6)ncc4c(=O)n3C3CC3)n2)CC1] |
| 1.51 | 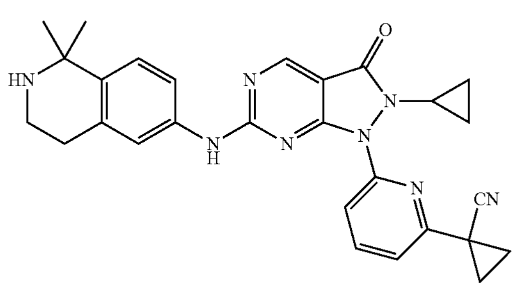 [SMILES: CC1(C)NCCc2cc(Nc3ncc4c(=O)n(C5CC5)n(-c5cccc(C6(C#N)CC6)n5)c4n3)ccc21] |
| 1.52 | 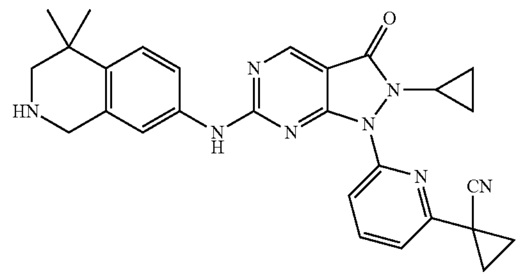 [SMILES: CC1(C)CNCc2cc(Nc3ncc4c(=O)n(C5CC5)n(-c5cccc(C6(C#N)CC6)n5)c4n3)ccc21] |
| 1.53 | 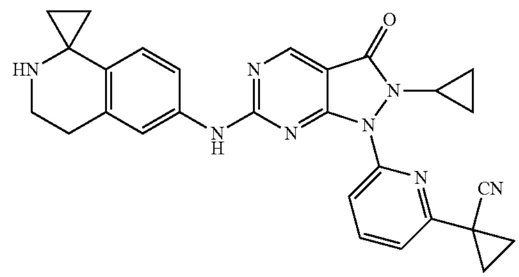 [SMILES: N#CC1(c2cccc(-n3c4nc(Nc5ccc6c(c5)CCNC65CC5)ncc4c(=O)n3C3CC3)n2)CC1] |
| 1.54 | 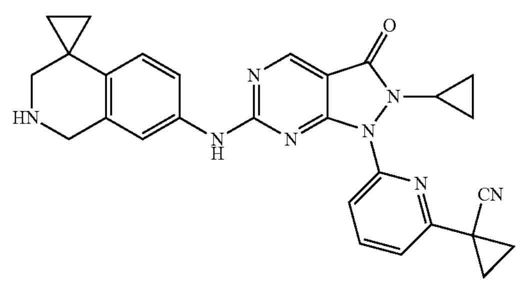 [SMILES: N#CC1(c2cccc(-n3c4nc(Nc5ccc6c(c5)CNCC65CC5)ncc4c(=O)n3C3CC3)n2)CC1] |
| 1.55 | 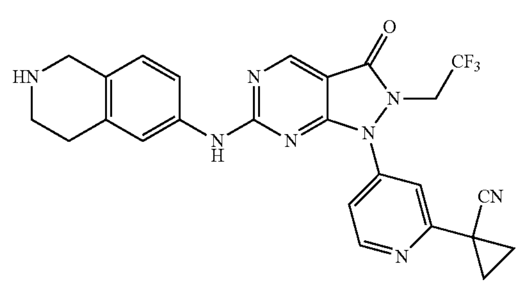 |
| 1.56 | 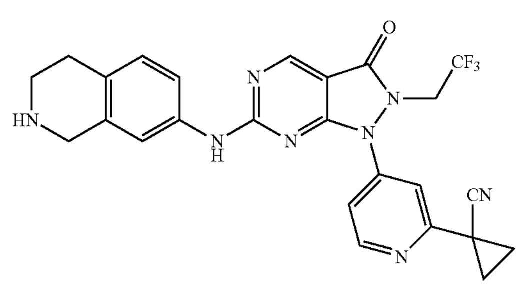 [SMILES: N#CC1(c2cc(-n3c4nc(Nc5ccc6c(c5)CNCC6)ncc4c(=O)n3CC(F)(F)F)ccn2)CC1] |

TABLE 1-continued

| Compound No. | Structure |
|---|---|
| 1.57 | 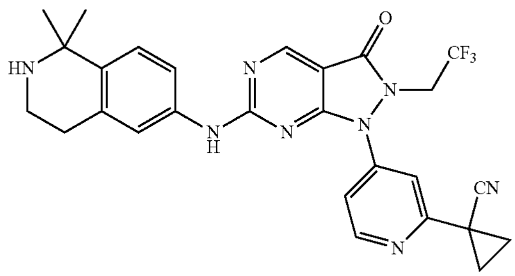 [SMILES: CC1(C)NCCc2cc(Nc3ncc4c(=O)n(CC(F)(F)F)n(-c5ccnc(C6(C#N)CC6)c5)c4n3)ccc21] |
| 1.58 | 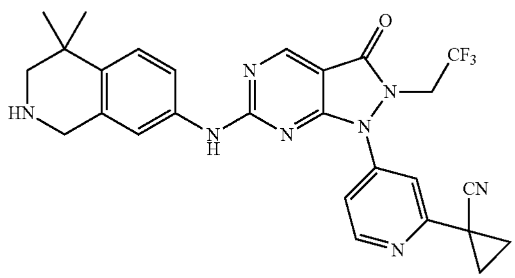 [SMILES: CC1(C)CNCc2cc(Nc3ncc4c(=O)n(CC(F)(F)F)n(-c5ccnc(C6(C#N)CC6)c5)c4n3)ccc21] |
| 1.59 | 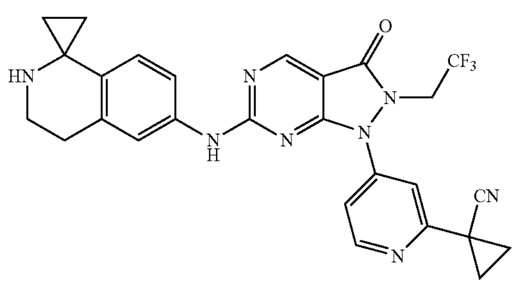 [SMILES: N#CC1(c2cc(-n3c4nc(Nc5ccc6c(c5)CCNC65CC5)ncc4c(=O)n3CC(F)(F)F)ccn2)CC1] |
| 1.60 | 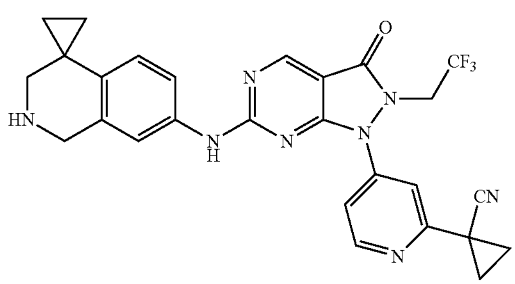 [SMILES: N#CC1(c2cc(-n3c4nc(Nc5ccc6c(c5)CNCC65CC5)ncc4c(=O)n3CC(F)(F)F)ccn2)CC1] |
| 1.61 | 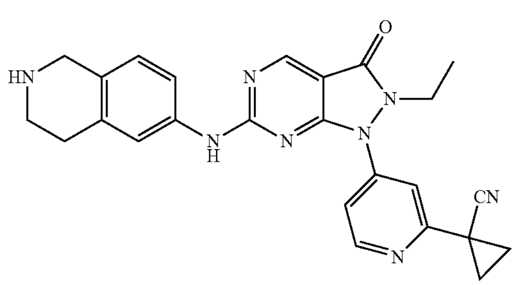 [SMILES: CCn1c(=O)c2cnc(Nc3ccc4c(c3)CCNC4)nc2n1-c1ccnc(C2(C#N)CC2)c1] |
| 1.62 | 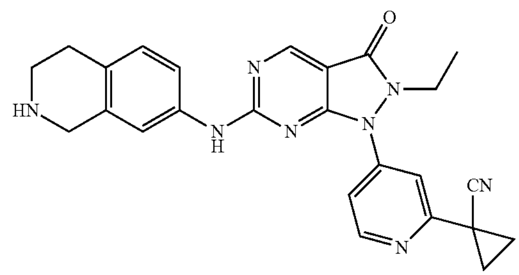 |
| 1.63 | 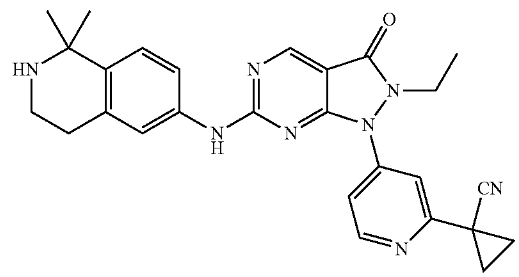 [SMILES: CCn1c(=O)c2cnc(Nc3ccc4c(c3)CCNC4(C)C)nc2n1-c1ccnc(C2(C#N)CC2)c1] |
| 1.64 | 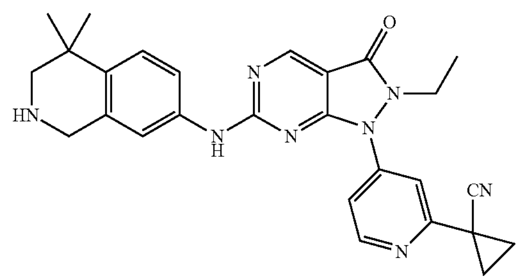 [SMILES: CCn1c(=O)c2cnc(Nc3ccc4c(c3)CNCC4(C)C)nc2n1-c1ccnc(C2(C#N)CC2)c1] |
| 1.65 | 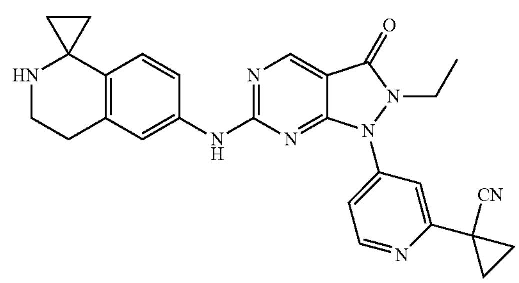 [SMILES: CCn1c(=O)c2cnc(Nc3ccc4c(c3)CCNC43CC3)nc2n1-c1ccnc(C2(C#N)CC2)c1] |
| 1.66 | 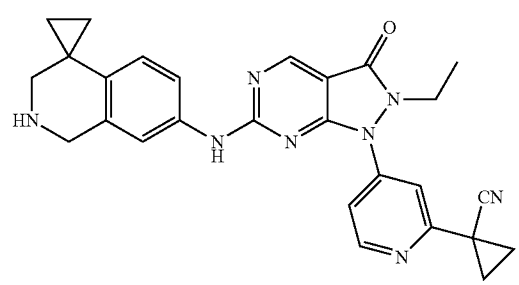 [SMILES: CCn1c(=O)c2cnc(Nc3ccc4c(c3)CNCC43CC3)nc2n1-c1ccnc(C2(C#N)CC2)c1] |

TABLE 1-continued

| Compound No. | Structure |
|---|---|
| 1.67 | 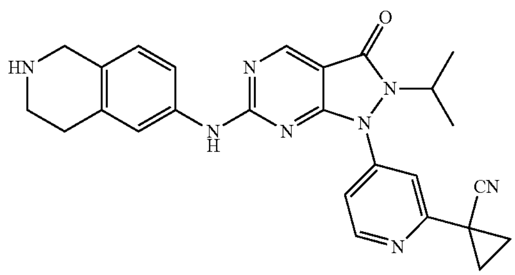 [SMILES: CC(C)n1c(=O)c2cnc(Nc3ccc4c(c3)CCNC4)nc2n1-c1ccnc(C2(C#N)CC2)c1] |
| 1.68 | 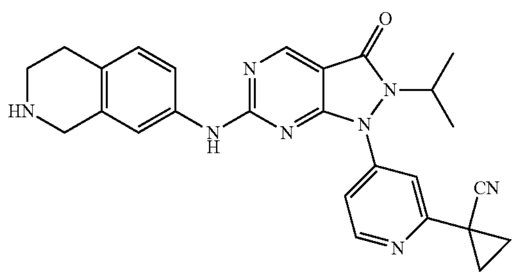 [SMILES: CC(C)n1c(=O)c2cnc(Nc3ccc4c(c3)CNCC4)nc2n1-c1ccnc(C2(C#N)CC2)c1] |
| 1.69 | 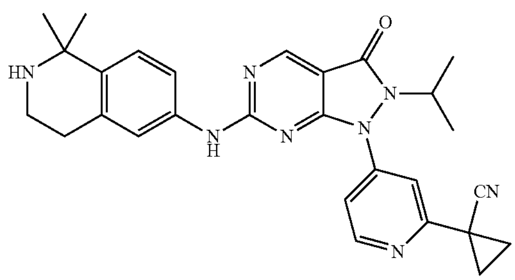 [SMILES: CC(C)n1c(=O)c2cnc(Nc3ccc4c(c3)CCNC4(C)C)nc2n1-c1ccnc(C2(C#N)CC2)c1] |
| 1.70 | 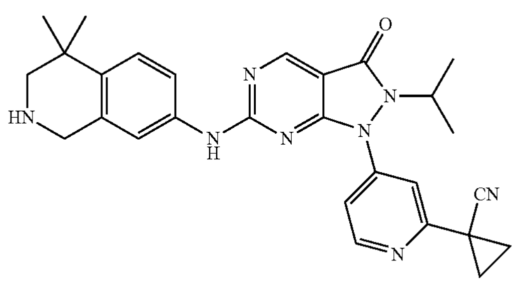 [SMILES: CC(C)n1c(=O)c2cnc(Nc3ccc4c(c3)CNCC4(C)C)nc2n1-c1ccnc(C2(C#N)CC2)c1] |
| 1.71 | 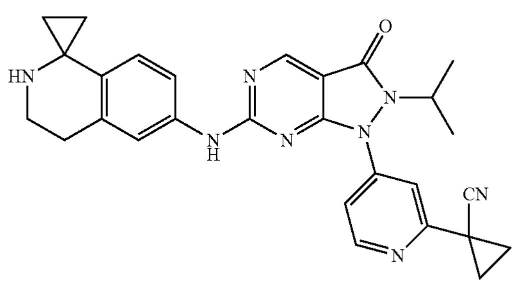 [SMILES: CC(C)n1c(=O)c2cnc(Nc3ccc4c(c3)CCNC43CC3)nc2n1-c1ccnc(C2(C#N)CC2)c1] |
| 1.72 | |
| 1.73 | |
| 1.74 | |
| 1.75 | |
| 1.76 | |

TABLE 1-continued
| Compound No. | Structure |
|---|---|
| 1.77 | 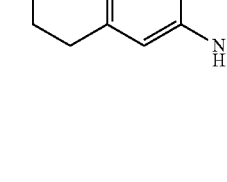 |
| 1.78 | |
| 1.79 | |
| 1.80 | |
| 1.81 | |
| 1.82 | |
| 1.83 | 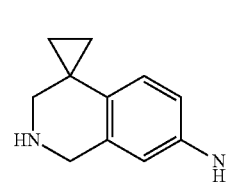 |
| 1.84 | 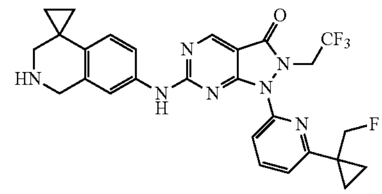 |
| 1.85 | 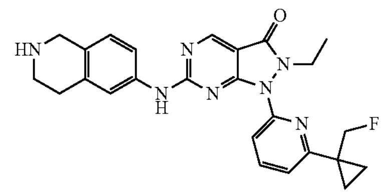 [SMILES: CCn1c(=O)c2cnc(Nc3ccc4c(c3)CCNC4)nc2n1-c1cccc(C2(CF)CC2)n1] |
| 1.86 | 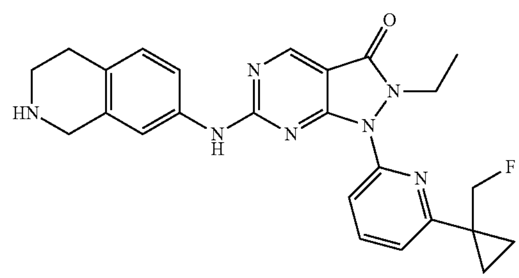 [SMILES: CCn1c(=O)c2cnc(Nc3ccc4c(c3)CNCC4)nc2n1-c1cccc(C2(CF)CC2)n1] |
| 1.87 | 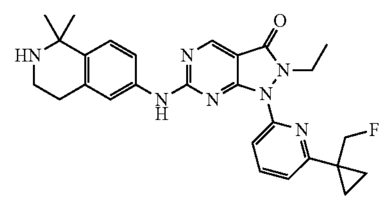 [SMILES: CCn1c(=O)c2cnc(Nc3ccc4c(c3)CCNC4(C)C)nc2n1-c1cccc(C2(CF)CC2)n1] |
| 1.88 | 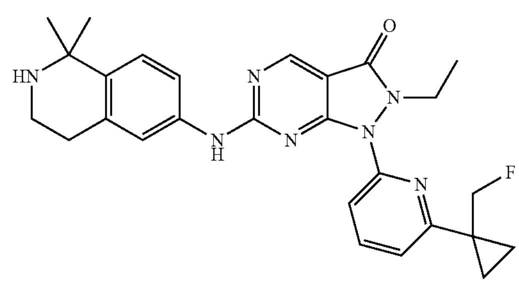 [SMILES: CCn1c(=O)c2cnc(Nc3ccc4c(c3)CCNC4(C)C)nc2n1-c1cccc(C2(CF)CC2)n1] |
| 1.89 | 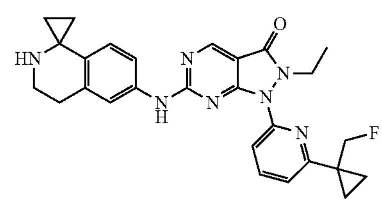 [SMILES: CCn1c(=O)c2cnc(Nc3ccc4c(c3)CCNC43CC3)nc2n1-c1cccc(C2(CF)CC2)n1] |

TABLE 1-continued

| Compound No. | Structure |
|---|---|
| 1.90 | 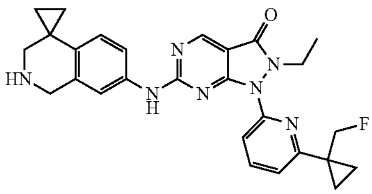 [SMILES: CCn1c(=O)c2cnc(Nc3ccc4c(c3)CNCC43CC3)nc2n1-c1cccc(C2(CF)CC2)n1] |
| 1.91 | 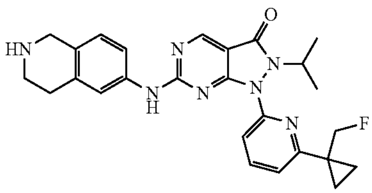 [SMILES: CC(C)n1c(=O)c2cnc(Nc3ccc4c(c3)CCNC4)nc2n1-c1cccc(C2(CF)CC2)n1] |
| 1.92 | 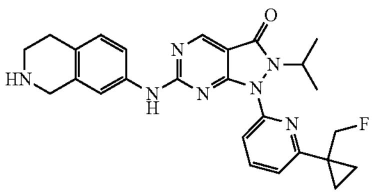 [SMILES: CC(C)n1c(=O)c2cnc(Nc3ccc4c(c3)CNCC4)nc2n1-c1cccc(C2(CF)CC2)n1] |
| 1.93 | 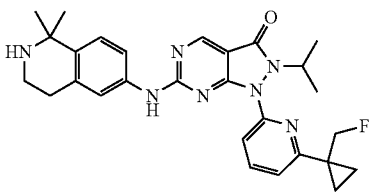 [SMILES: CC(C)n1c(=O)c2cnc(Nc3ccc4c(c3)CCNC4(C)C)nc2n1-c1cccc(C2(CF)CC2)n1] |
| 1.94 | 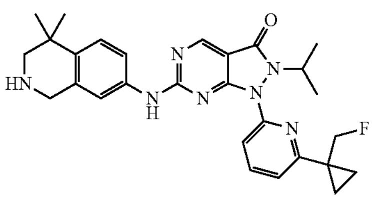 [SMILES: CC(C)n1c(=O)c2cnc(Nc3ccc4c(c3)CNCC4(C)C)nc2n1-c1cccc(C2(CF)CC2)n1] |
| 1.95 | 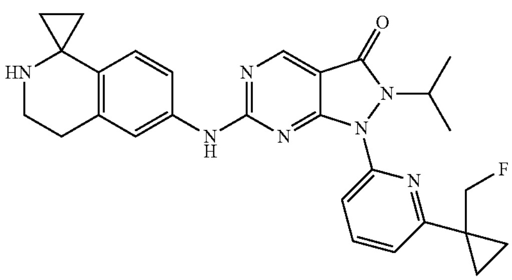 [SMILES: CC(C)n1c(=O)c2cnc(Nc3ccc4c(c3)CCNC43CC3)nc2n1-c1cccc(C2(CF)CC2)n1] |
| 1.96 | 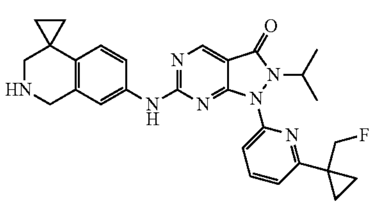 [SMILES: CC(C)n1c(=O)c2cnc(Nc3ccc4c(c3)CNCC43CC3)nc2n1-c1cccc(C2(CF)CC2)n1] |
| 1.97 | |
| 1.98 | |
| 1.99 | |
| 1.100 | |
| 1.101 | |
| 1.102 | |
| 1.103 | |

TABLE 1-continued
| Compound No. | Structure |
|---|---|
| 1.104 | 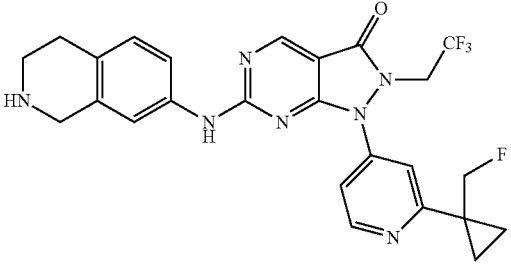 [SMILES: CCn1c(=O)c2cnc(Nc3ccc4c(c3)CNCC4)nc2n1-c1ccnc(C2(CF)CC2)c1] |
| 1.105 | 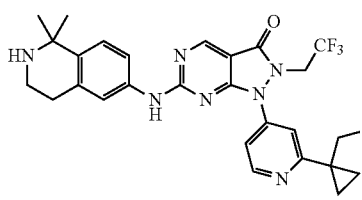 |
| 1.106 | 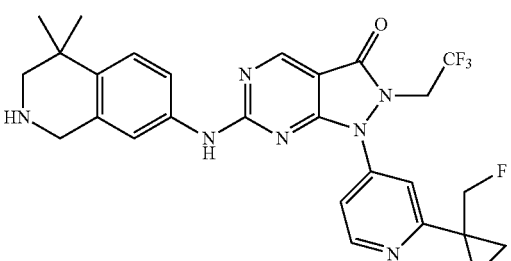 |
| 1.107 | 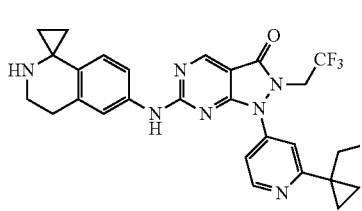 |
| 1.108 | 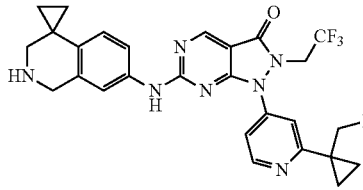 |
| 1.109 | 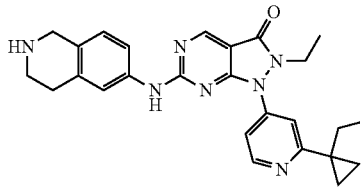 |
| 1.110 | 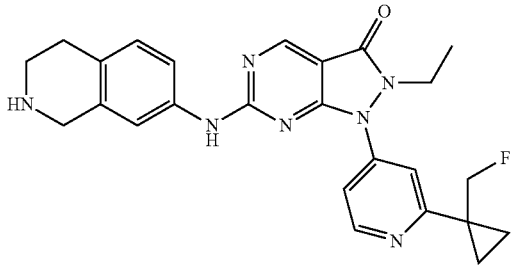 |
| 1.111 | 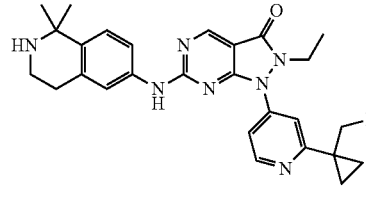 |
| 1.112 | 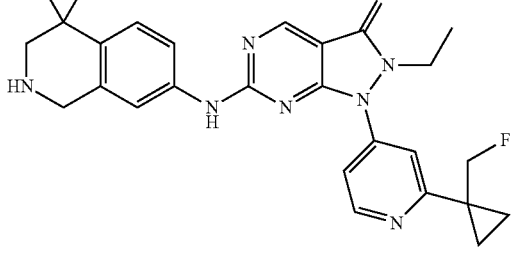 |
| 1.113 | 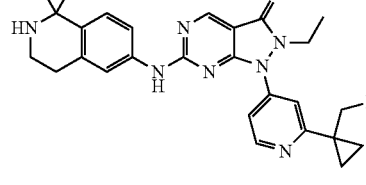 |
| 1.114 | 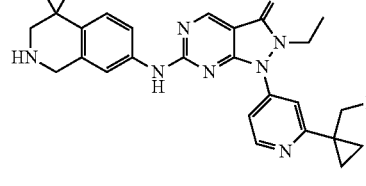 |
| 1.115 | 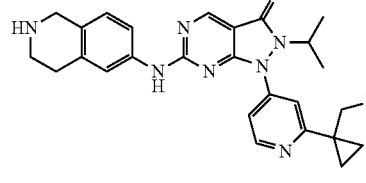 |
| 1.116 | 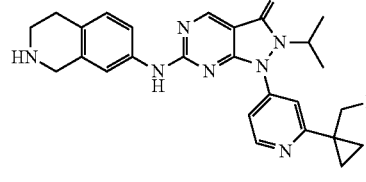 |

TABLE 1-continued
| Compound No. | Structure |
|---|---|
| 1.117 | 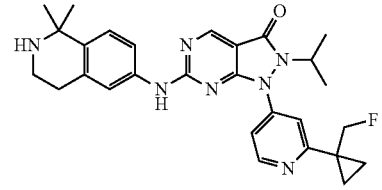 [SMILES: CC(C)n1c(=O)c2cnc(Nc3ccc4c(c3)CCNC4(C)C)nc2n1-c1ccnc(C2(CF)CC2)c1] |
| 1.118 | 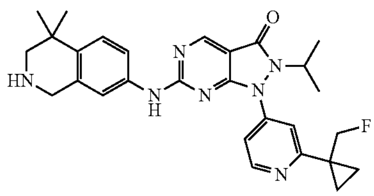 [SMILES: CC(C)n1c(=O)c2cnc(Nc3ccc4c(c3)CNCC4(C)C)nc2n1-c1ccnc(C2(CF)CC2)c1] |
| 1.119 | 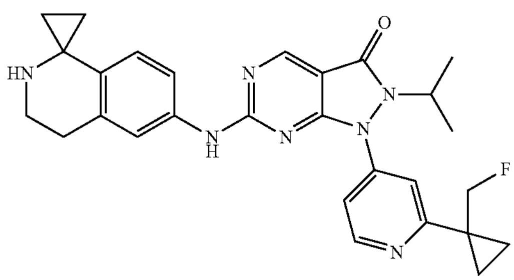 [SMILES: CC(C)n1c(=O)c2cnc(Nc3ccc4c(c3)CCNC43CC3)nc2n1-c1ccnc(C2(CF)CC2)c1] |
| 1.120 | 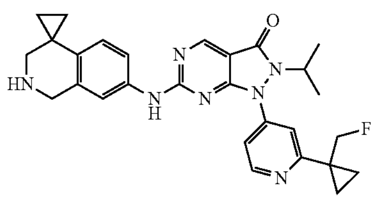 |
| 1.121 | 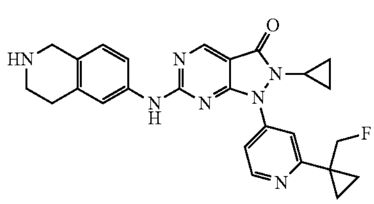 [SMILES: O=c1c2cnc(Nc3ccc4c(c3)CCNC4)nc2n(-c2ccnc(C3(CF)CC3)c2)n1C1CC1] |
| 1.122 | 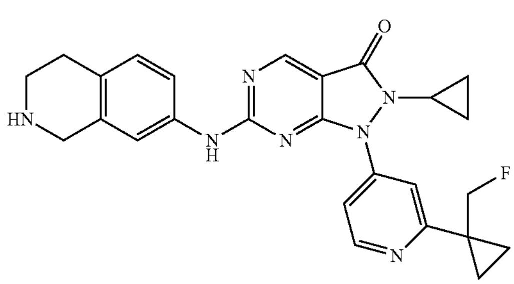 [SMILES: O=c1c2cnc(Nc3ccc4c(c3)CNCC4)nc2n(-c2ccnc(C3(CF)CC3)c2)n1C1CC1] |
| 1.123 | 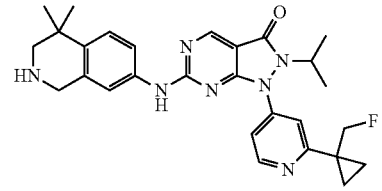 |
| 1.124 | |
| 1.125 | |
| 1.126 | |
| 1.127 | |
| 1.128 | |

TABLE 1-continued

| Compound No. | Structure |
|---|---|
| 1.129 | 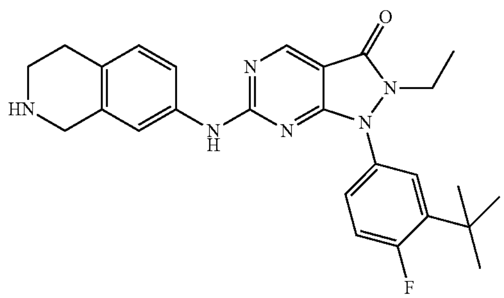 [SMILES: CCn1c(=O)c2cnc(Nc3ccc4c(c3)CNCC4)nc2n1-c1ccc(F)c(C(C)(C)C)c1] |
| 1.130 | 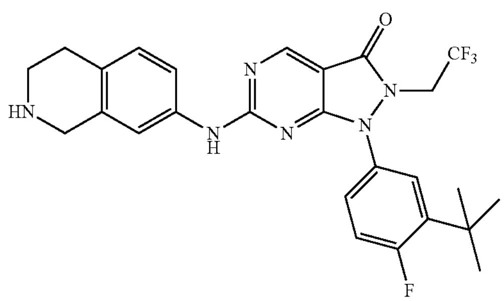 [SMILES: CC(C)(C)c1cc(-n2c3nc(Nc4ccc5c(c4)CNCC5)ncc3c(=O)n2CC(F)(F)F)ccc1F] |
| 1.131 | 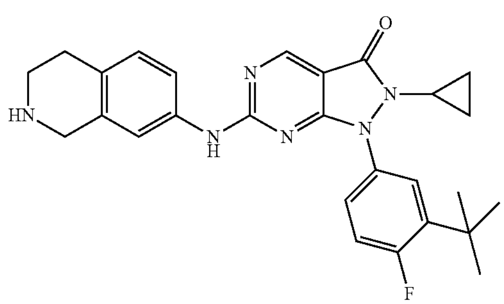 [SMILES: CC(C)(C)c1cc(-n2c3nc(Nc4ccc5c(c4)CNCC5)ncc3c(=O)n2C2CC2)ccc1F] |
| 1.132 | 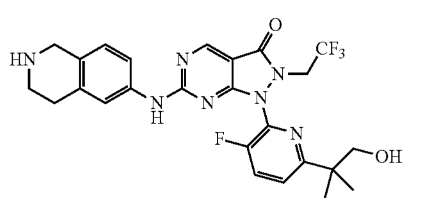 [SMILES: CC(C)(CO)c1ccc(F)c(-n2c3nc(Nc4ccc5c(c4)CCNC5)ncc3c(=O)n2CC(F)(F)F)n1] |
| 1.133 | 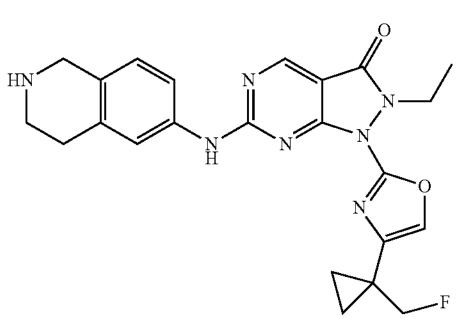 [SMILES: CCn1c(=O)c2cnc(Nc3ccc4c(c3)CCNC4)nc2n1-c1nc(C2(CF)CC2)co1] |
| 1.134 | |
| 1.135 | |
| 1.136 | |
| 1.137 | |
| 1.138 | |

TABLE 1-continued

| Compound No. | Structure |
|---|---|
| 1.139 | 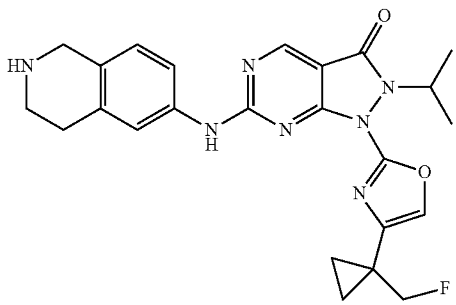 [SMILES: CC(C)n1c(=O)c2cnc(Nc3ccc4c(c3)CCNC4)nc2n1-c1nc(C2(CF)CC2)co1] |
| 1.140 | 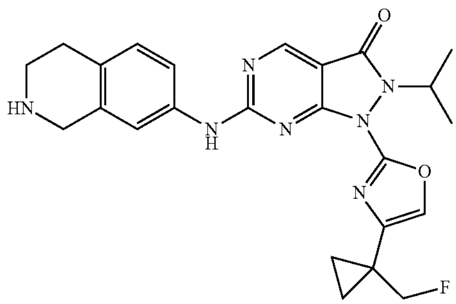 [SMILES: CC(C)n1c(=O)c2cnc(Nc3ccc4c(c3)CNCC4)nc2n1-c1nc(C2(CF)CC2)co1] |
| 1.141 | 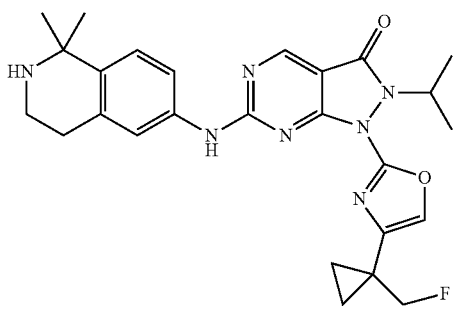 [SMILES: CC(C)n1c(=O)c2cnc(Nc3ccc4c(c3)CCNC4(C)C)nc2n1-c1nc(C2(CF)CC2)co1] |
| 1.142 | 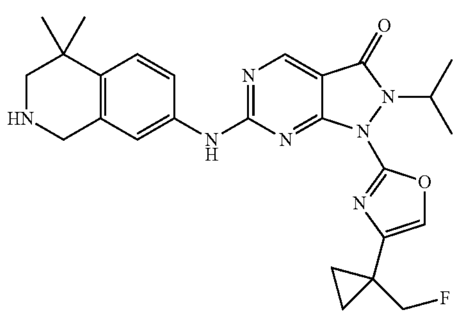 [SMILES: CC(C)n1c(=O)c2cnc(Nc3ccc4c(c3)CNCC4(C)C)nc2n1-c1nc(C2(CF)CC2)co1] |
| 1.143 | 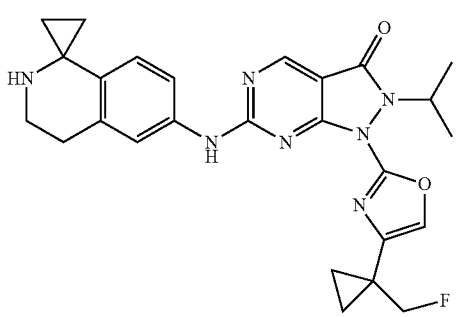 [SMILES: CC(C)n1c(=O)c2cnc(Nc3ccc4c(c3)CCNC43CC3)nc2n1-c1nc(C2(CF)CC2)co1] |
| 1.144 | |
| 1.145 | |
| 1.146 | |
| 1.147 | |
| 1.148 | |

TABLE 1-continued

| Compound No. | Structure |
|---|---|
| 1.149 | 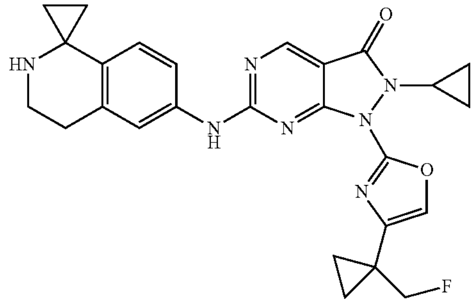 [SMILES: O=c1c2cnc(Nc3ccc4c(c3)CCNC43CC3)nc2n(-c2nc(C3(CF)CC3)co2)n1C1CC1] |
| 1.150 | 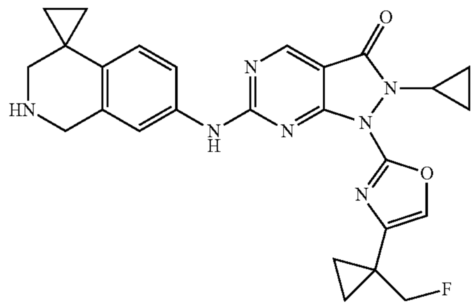 [SMILES: O=c1c2cnc(Nc3ccc4c(c3)CNCC43CC3)nc2n(-c2nc(C3(CF)CC3)co2)n1C1CC1] |
| 1.151 | 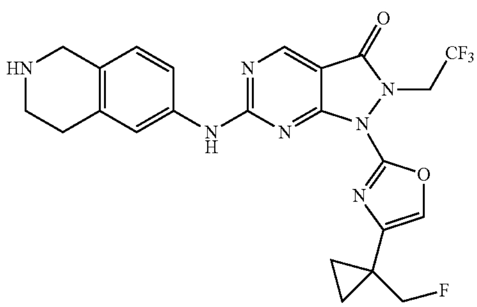 [SMILES: O=c1c2cnc(Nc3ccc4c(c3)CCNC4)nc2n(-c2nc(C3(CF)CC3)co2)n1CC(F)(F)F] |
| 1.152 | 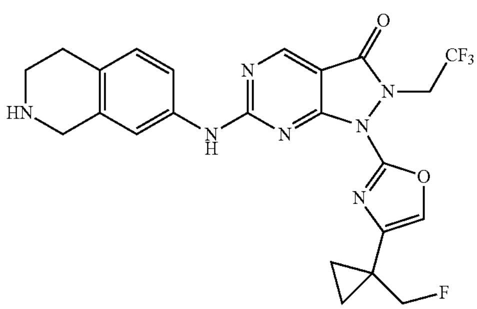 [SMILES: O=c1c2cnc(Nc3ccc4c(c3)CNCC4)nc2n(-c2nc(C3(CF)CC3)co2)n1CC(F)(F)F] |
| 1.153 | 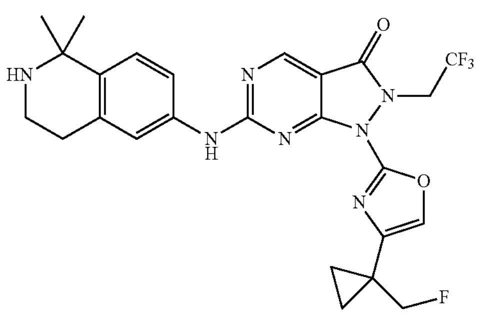 [SMILES: CC1(C)NCCc2cc(Nc3ncc4c(=O)n(CC(F)(F)F)n(-c5nc(C6(CF)CC6)co5)c4n3)ccc21] |
| 1.154 | |
| 1.155 | |
| 1.156 | |
| 1.157 | |
| 1.158 | |

TABLE 1-continued

| Compound No. | Structure |
|---|---|
| 1.159 | 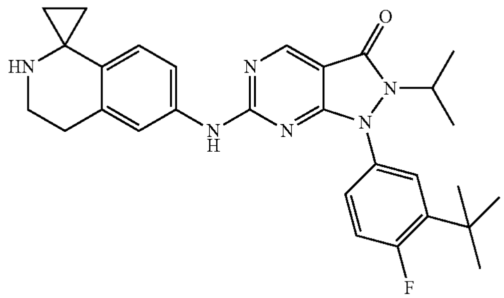 [SMILES: CC(C)n1c(=O)c2cnc(Nc3ccc4c(c3)CCNC43CC3)nc2n1-c1ccc(F)c(C(C)(C)C)c1] |
| 1.160 | 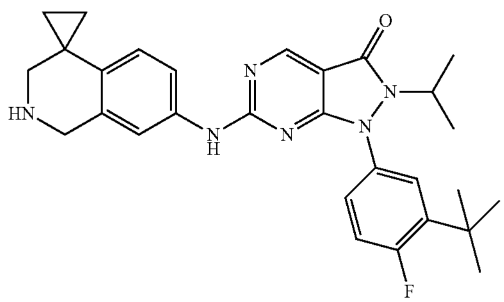 [SMILES: CC(C)n1c(=O)c2cnc(Nc3ccc4c(c3)CNCC43CC3)nc2n1-c1ccc(F)c(C(C)(C)C)c1] |
| 1.161 | 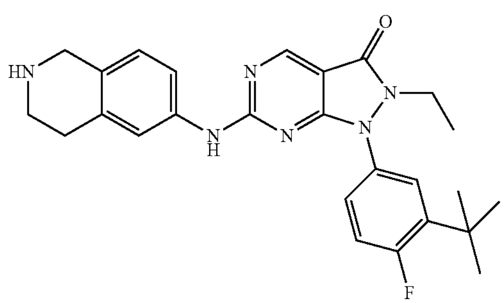 [SMILES: CCn1c(=O)c2cnc(Nc3ccc4c(c3)CCNC4)nc2n1-c1ccc(F)c(C(C)(C)C)c1] |
| 1.162 | 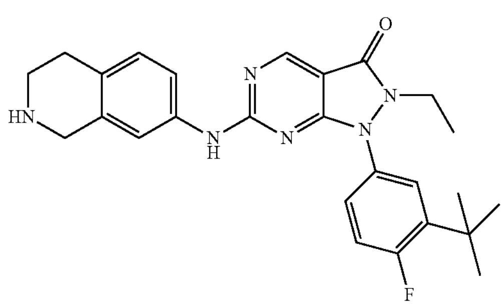 [SMILES: CCn1c(=O)c2cnc(Nc3ccc4c(c3)CNCC4)nc2n1-c1ccc(F)c(C(C)(C)C)c1] |
| 1.163 | 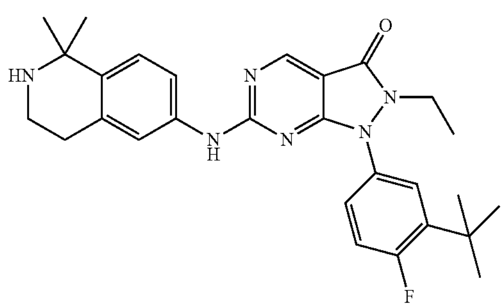 [SMILES: CCn1c(=O)c2cnc(Nc3ccc4c(c3)CCNC4(C)C)nc2n1-c1ccc(F)c(C(C)(C)C)c1] |
| 1.164 | |
| 1.165 | |
| 1.166 | |
| 1.167 | |
| 1.168 | |

TABLE 1-continued
| Compound No. | Structure |
|---|---|
| 1.169 | 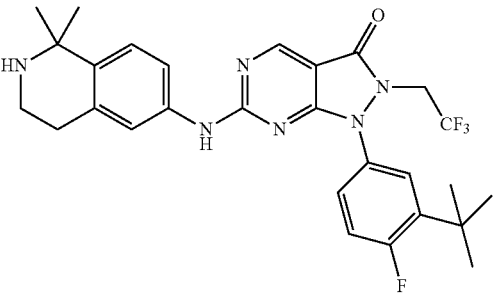 |
| 1.170 | 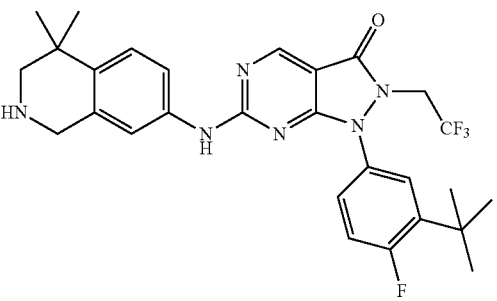 [SMILES: CCn1c(=O)c2cnc(Nc3ccc4c(c3)CNCC4(C)C)nc2n1-c1ccc(F)c(C(C)(C)C)c1] |
| 1.171 | 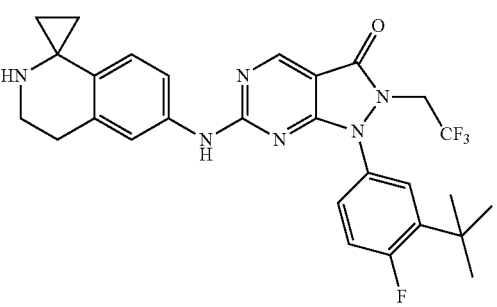 [SMILES: CC(C)(C)c1cc(-n2c3nc(Nc4ccc5c(c4)CCNC54CC4)ncc3c(=O)n2CC(F)(F)F)ccc1F] |
| 1.172 | 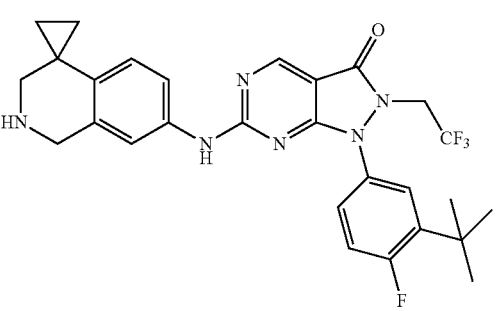 [SMILES: CC(C)(C)c1cc(-n2c3nc(Nc4ccc5c(c4)CNCC54CC4)ncc3c(=O)n2CC(F)(F)F)ccc1F] |
| 1.173 | 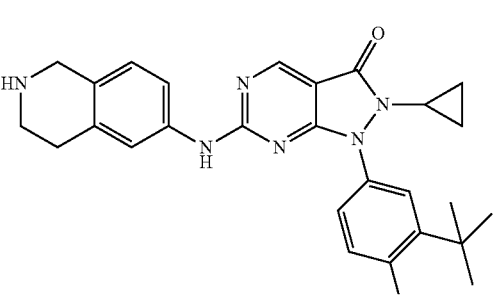 |
| 1.174 | 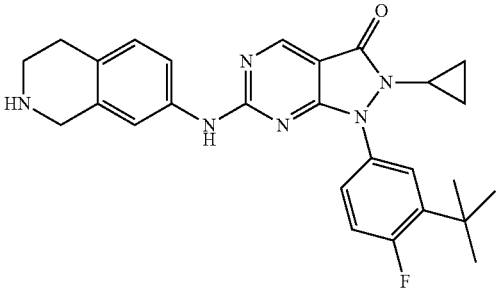 [SMILES: CC(C)(C)c1cc(-n2c3nc(Nc4ccc5c(c4)CNCC5)ncc3c(=O)n2C2CC2)ccc1F] |
| 1.175 | 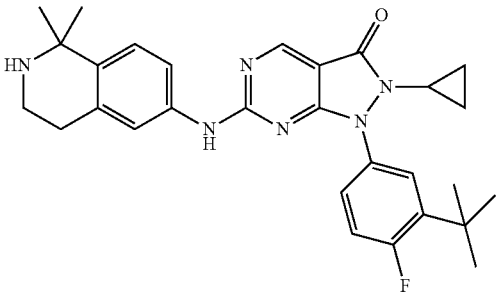 |
| 1.176 | 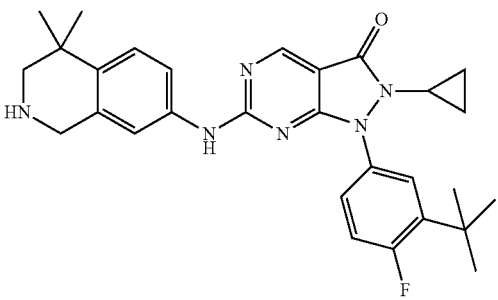 [SMILES: CC(C)(C)c1cc(-n2c3nc(Nc4ccc5c(c4)CNCC5(C)C)ncc3c(=O)n2C2CC2)ccc1F] |
| 1.177 | 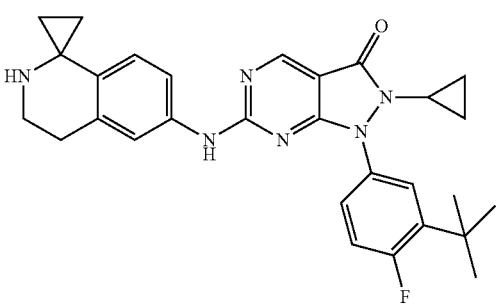 [SMILES: CC(C)(C)c1cc(-n2c3nc(Nc4ccc5c(c4)CCNC54CC4)ncc3c(=O)n2C2CC2)ccc1F] |
| 1.178 | 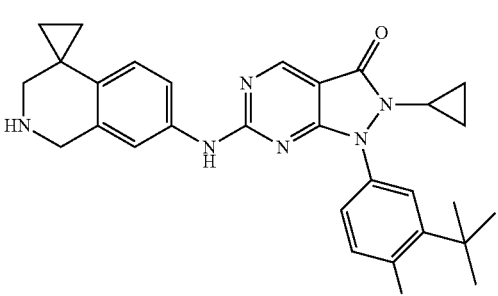 |

TABLE 1-continued

| Compound No. | Structure |
|---|---|
| 1.179 | 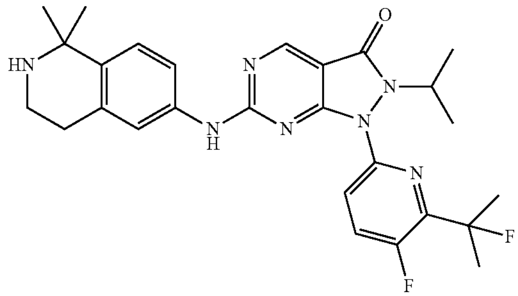 [SMILES: CC(C)n1c(=O)c2cnc(Nc3ccc4c(c3)CCNC4(C)C)nc2n1-c1ccc(F)c(C(C)(C)F)n1] |
| 1.180 | 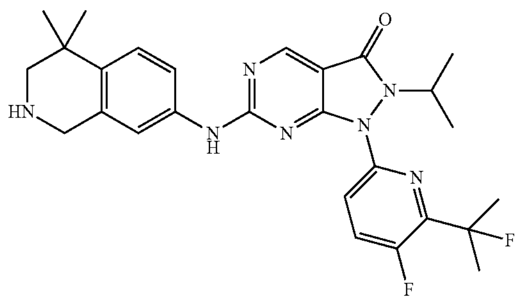 [SMILES: CC(C)n1c(=O)c2cnc(Nc3ccc4c(c3)CNCC4(C)C)nc2n1-c1ccc(F)c(C(C)(C)F)n1] |
| 1.181 | 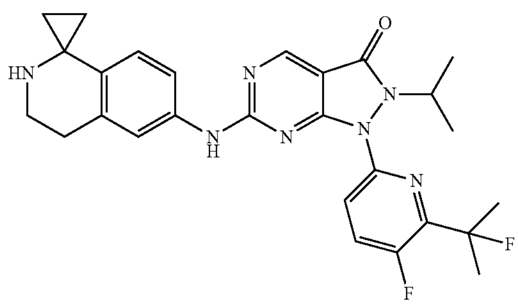 [SMILES: CC(C)n1c(=O)c2cnc(Nc3ccc4c(c3)CCNC43CC3)nc2n1-c1ccc(F)c(C(C)(C)F)n1] |
| 1.182 | 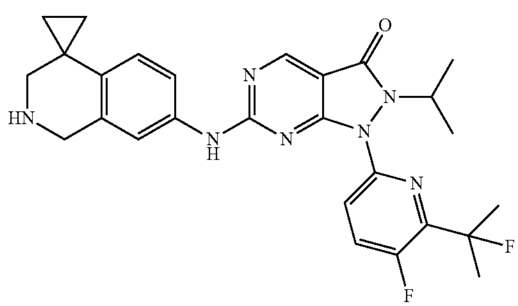 [SMILES: CC(C)n1c(=O)c2cnc(Nc3ccc4c(c3)CNCC43CC3)nc2n1-c1ccc(F)c(C(C)(C)F)n1] |
| 1.183 | 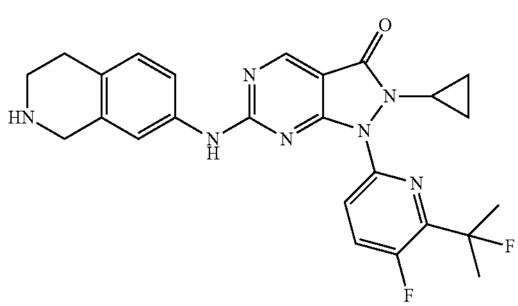 [SMILES: CC(C)(F)c1nc(-n2c3nc(Nc4ccc5c(c4)CNCC5)ncc3c(=O)n2C2CC2)ccc1F] |
| 1.184 | |
| 1.185 | |
| 1.186 | |
| 1.187 | |
| 1.188 | |

TABLE 1-continued

| Compound No. | Structure |
|---|---|
| 1.189 | (structure) |
| 1.190 | (structure) |
| 1.191 | (structure) |
| 1.192 | (structure) |
| 1.193 | (structure) |
| 1.194 | (structure) |
| 1.195 | (structure) |
| 1.196 | (structure) |
| 1.197 | (structure) |
| 1.198 | (structure) |

TABLE 1-continued

| Compound No. | Structure |
|---|---|
| 1.199 | (structure) |
| 1.200 | (structure) |
| 1.201 | (structure) |
| 1.202 | (structure) |
| 1.203 | (structure) |
| 1.204 | (structure) |
| 1.205 | (structure) |
| 1.206 | (structure) |
| 1.207 | (structure) |
| 1.208 | (structure) |

TABLE 1-continued

| Compound No. | Structure |
|---|---|
| 1.209 | 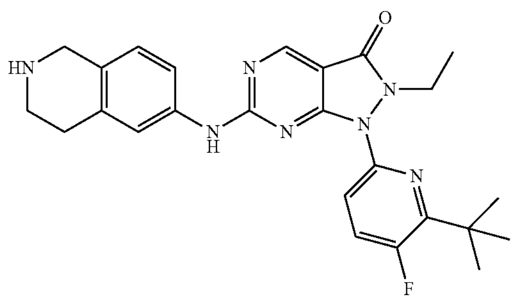 [SMILES: CCn1c(=O)c2cnc(Nc3ccc4c(c3)CCNC4)nc2n1-c1ccc(F)c(C(C)(C)C)n1] |
| 1.210 | 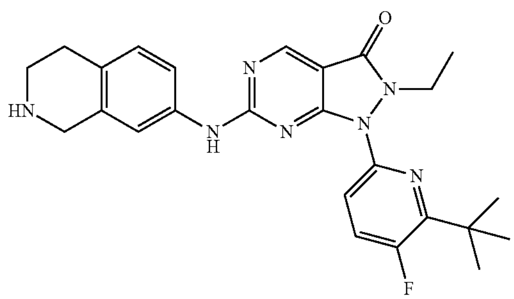 [SMILES: CCn1c(=O)c2cnc(Nc3ccc4c(c3)CNCC4)nc2n1-c1ccc(F)c(C(C)(C)C)n1] |
| 1.211 | 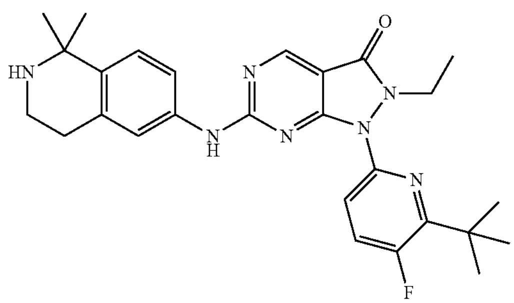 [SMILES: CCn1c(=O)c2cnc(Nc3ccc4c(c3)CCNC4(C)C)nc2n1-c1ccc(F)c(C(C)(C)C)n1] |
| 1.212 | 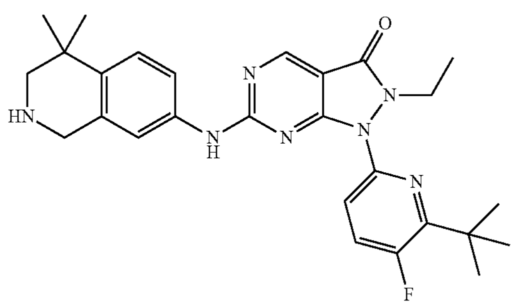 [SMILES: CCn1c(=O)c2cnc(Nc3ccc4c(c3)CNCC4(C)C)nc2n1-c1ccc(F)c(C(C)(C)C)n1] |
| 1.213 | 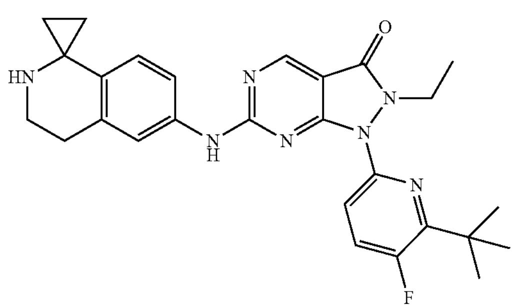 [SMILES: CCn1c(=O)c2cnc(Nc3ccc4c(c3)CCNC43CC3)nc2n1-c1ccc(F)c(C(C)(C)C)n1] |
| 1.214 | 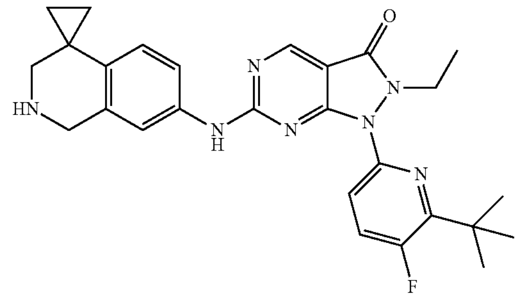 [SMILES: CCn1c(=O)c2cnc(Nc3ccc4c(c3)CNCC43CC3)nc2n1-c1ccc(F)c(C(C)(C)C)n1] |
| 1.215 | 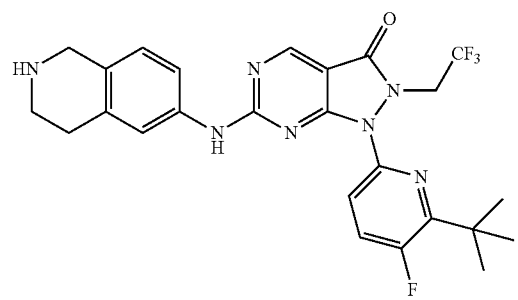 |
| 1.216 | 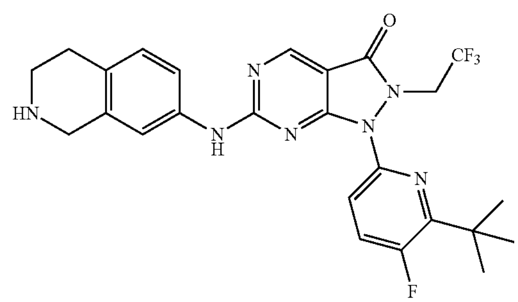 [SMILES: CC(C)(C)c1nc(-n2c3nc(Nc4ccc5c(c4)CNCC5)ncc3c(=O)n2CC(F)(F)F)ccc1F] |
| 1.217 | 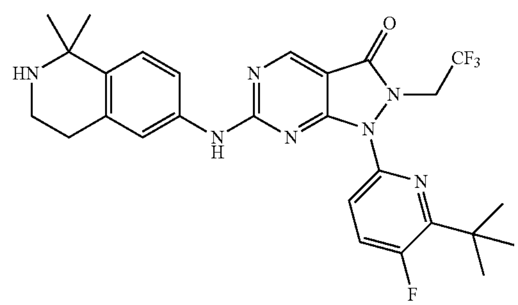 [SMILES: CC(C)(C)c1nc(-n2c3nc(Nc4ccc5c(c4)CCNC5(C)C)ncc3c(=O)n2CC(F)(F)F)ccc1F] |
| 1.218 | 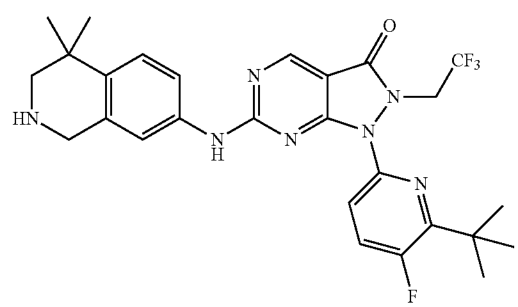 |

TABLE 1-continued
| Compound No. | Structure |
|---|---|
| 1.219 | 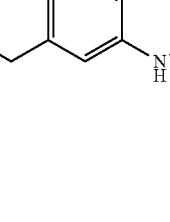 |
| 1.220 | 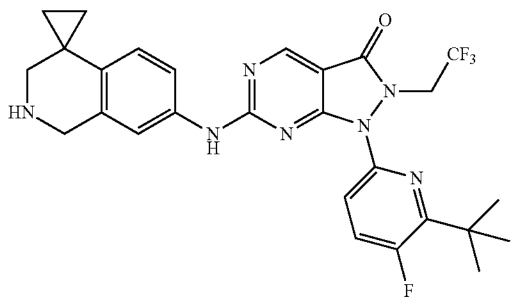 [SMILES: CC(C)(C)c1nc(-n2c3nc(Nc4ccc5c(c4)CNCC54CC4)ncc3c(=O)n2CC(F)(F)F)ccc1F] |
| 1.221 | 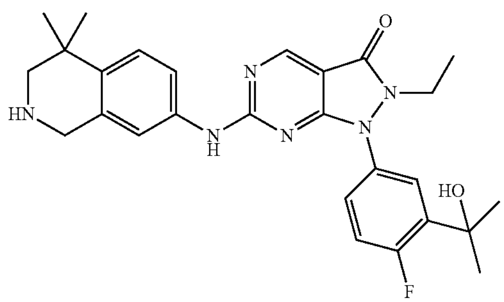 [SMILES: CCn1c(=O)c2cnc(Nc3ccc4c(c3)CNCC4(C)C)nc2n1-c1ccc(F)c(C(C)(C)O)c1] |
| 1.222 | 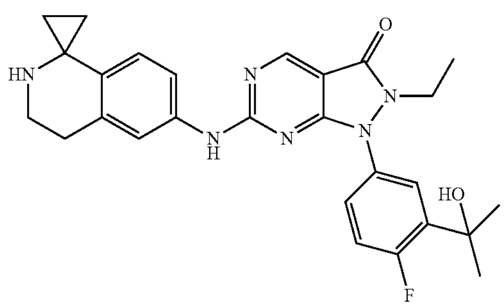 [SMILES: CCn1c(=O)c2cnc(Nc3ccc4c(c3)CCNC43CC3)nc2n1-c1ccc(F)c(C(C)(C)O)c1] |
| 1.223 | 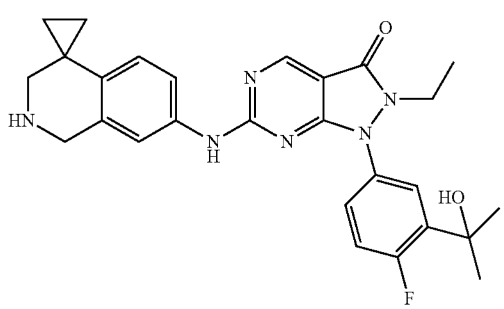 [SMILES: CCn1c(=O)c2cnc(Nc3ccc4c(c3)CNCC43CC3)nc2n1-c1ccc(F)c(C(C)(C)O)c1] |
TABLE 1-continued
| Compound No. | Structure |
|---|---|
| 1.224 | 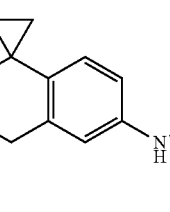 |
| 1.225 | 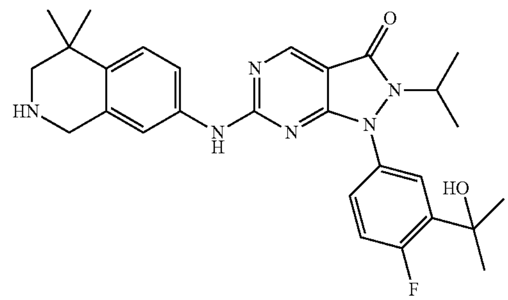 [SMILES: CC(C)n1c(=O)c2cnc(Nc3ccc4c(c3)CNCC4(C)C)nc2n1-c1ccc(F)c(C(C)(C)O)c1] |
| 1.226 | 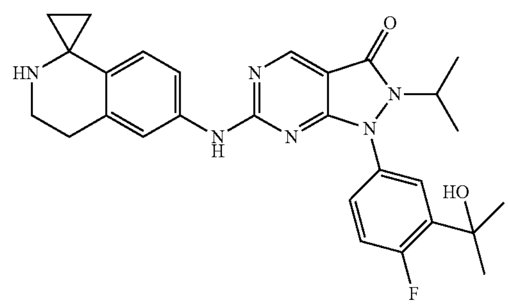 [SMILES: CC(C)n1c(=O)c2cnc(Nc3ccc4c(c3)CCNC43CC3)nc2n1-c1ccc(F)c(C(C)(C)O)c1] |
| 1.227 | 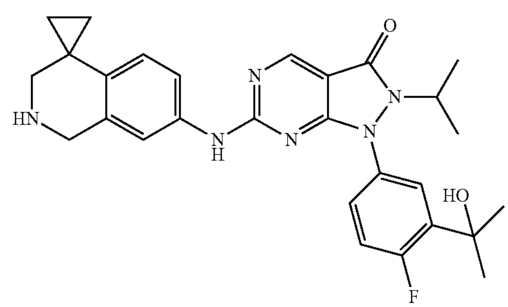 [SMILES: CC(C)n1c(=O)c2cnc(Nc3ccc4c(c3)CNCC43CC3)nc2n1-c1ccc(F)c(C(C)(C)O)c1] |
| 1.228 | 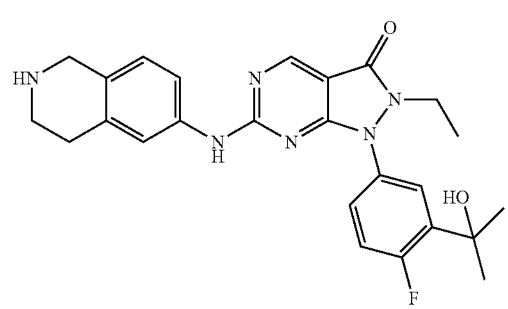 [SMILES: CCn1c(=O)c2cnc(Nc3ccc4c(c3)CCNC4)nc2n1-c1ccc(F)c(C(C)(C)O)c1] |

TABLE 1-continued

| Compound No. | Structure |
|---|---|
| 1.229 | 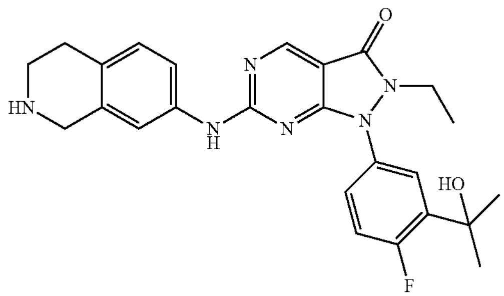 [SMILES: CCn1c(=O)c2cnc(Nc3ccc4c(c3)CNCC4)nc2n1-c1ccc(F)c(C(C)(C)O)c1] |
| 1.230 | 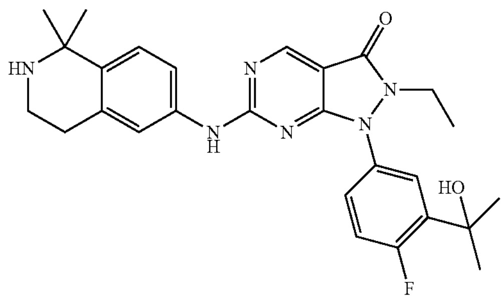 [SMILES: CCn1c(=O)c2cnc(Nc3ccc4c(c3)CCNC4(C)C)nc2n1-c1ccc(F)c(C(C)(C)O)c1] |
| 1.231 | 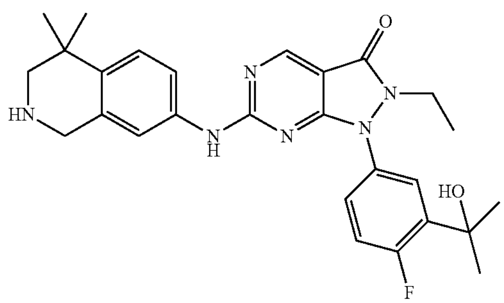 [SMILES: CCn1c(=O)c2cnc(Nc3ccc4c(c3)CNCC4(C)C)nc2n1-c1ccc(F)c(C(C)(C)O)c1] |
| 1.232 | 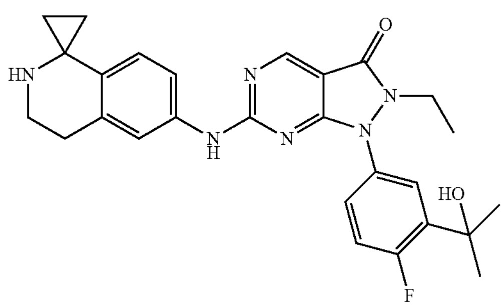 [SMILES: CCn1c(=O)c2cnc(Nc3ccc4c(c3)CCNC43CC3)nc2n1-c1ccc(F)c(C(C)(C)O)c1] |
| 1.233 | 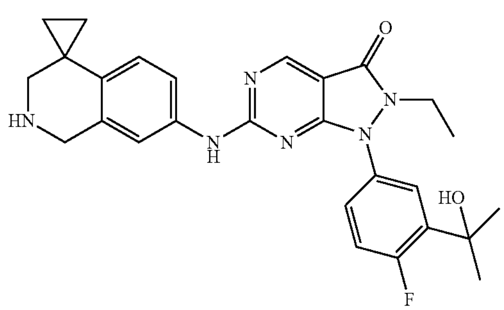 [SMILES: CCn1c(=O)c2cnc(Nc3ccc4c(c3)CNCC43CC3)nc2n1-c1ccc(F)c(C(C)(C)O)c1] |
| 1.234 | |
| 1.235 | |
| 1.236 | |
| 1.237 | |
| 1.238 | |

TABLE 1-continued

| Compound No. | Structure |
|---|---|
| 1.239 | 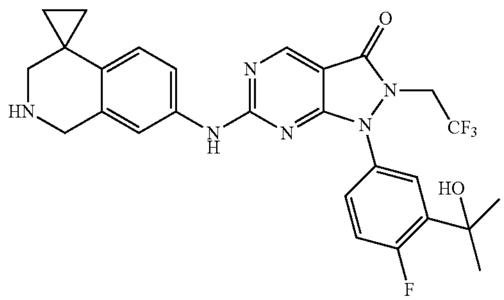 |
| 1.240 | 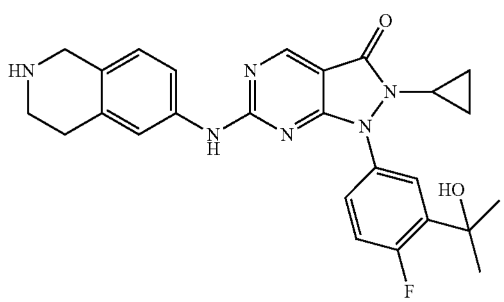 [SMILES: CC(C)(O)c1cc(-n2c3nc(Nc4ccc5c(c4)CCNC5)ncc3c(=O)n2C2CC2)ccc1F] |
| 1.241 | 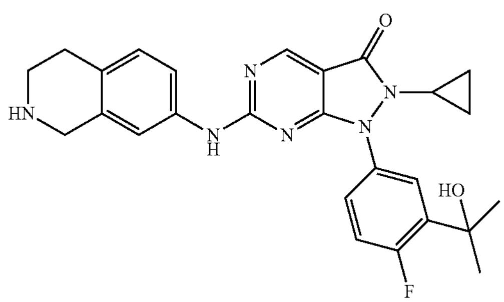 [SMILES: CC(C)(O)c1cc(-n2c3nc(Nc4ccc5c(c4)CNCC5)ncc3c(=O)n2C2CC2)ccc1F] |
| 1.242 | 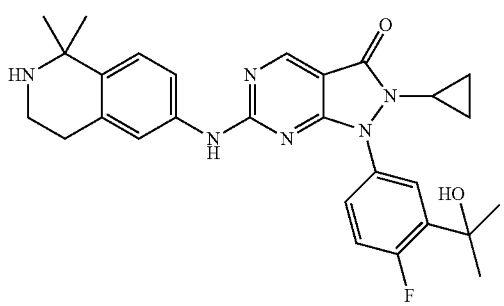 [SMILES: CC(C)(O)c1cc(-n2c3nc(Nc4ccc5c(c4)CCNC5(C)C)ncc3c(=O)n2C2CC2)ccc1F] |
| 1.243 | 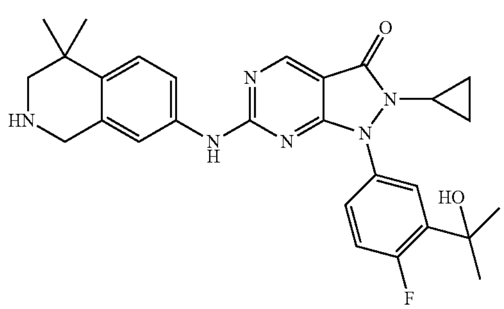 [SMILES: CC(C)(O)c1cc(-n2c3nc(Nc4ccc5c(c4)CNCC54CC4)ncc3c(=O)n2C2CC2)ccc1F] |
| 1.244 | |
| 1.245 | |
| 1.246 | |
| 1.247 | |
| 1.248 | |

TABLE 1-continued

| Compound No. | Structure |
|---|---|
| 1.249 | (structure) |
| 1.250 | (structure) |
| 1.251 | (structure) |
| 1.252 | (structure) |
| 1.253 | (structure) |
| 1.254 | (structure) |
| 1.255 | (structure) |
| 1.256 | (structure) |
| 1.257 | (structure) |
| 1.258 | (structure) |
| 1.259 | (structure) |
| 1.260 | (structure) |
| 1.261 | (structure) |
| 1.262 | (structure) |

TABLE 1-continued

| Compound No. | Structure |
|---|---|
| 1.263 | (structure) |
| 1.264 | (structure) |
| 1.265 | (structure) |
| 1.266 | (structure) |
| 1.267 | (structure) |
| 1.268 | (structure) |
| 1.269 | (structure) |
| 1.270 | (structure) |
| 1.271 | (structure) |
| 1.272 | (structure) |
| 1.273 | (structure) |
| 1.274 | (structure) |
| 1.275 | (structure) |
| 1.276 | (structure) |

TABLE 1-continued

| Compound No. | Structure |
|---|---|
| 1.277 | 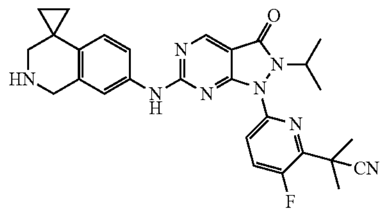 [SMILES: CC(C)n1c(=O)c2cnc(Nc3ccc4c(c3)CNCC43CC3)nc2n1-c1ccc(F)c(C(C)(C)C#N)n1] |
| 1.278 | 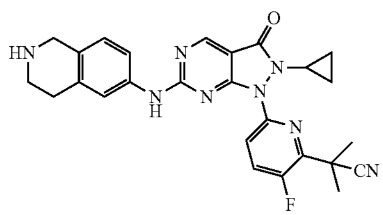 [SMILES: CC(C)(C#N)c1nc(-n2c3nc(Nc4ccc5c(c4)CCNC5)ncc3c(=O)n2C2CC2)ccc1F] |
| 1.279 | 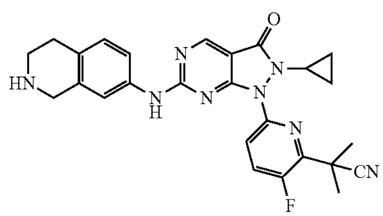 [SMILES: CC(C)(C#N)c1nc(-n2c3nc(Nc4ccc5c(c4)CNCC5)ncc3c(=O)n2C2CC2)ccc1F] |
| 1.280 | 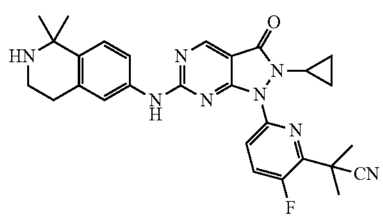 [SMILES: CC(C)(C#N)c1nc(-n2c3nc(Nc4ccc5c(c4)CCNC5(C)C)ncc3c(=O)n2C2CC2)ccc1F] |
| 1.281 | 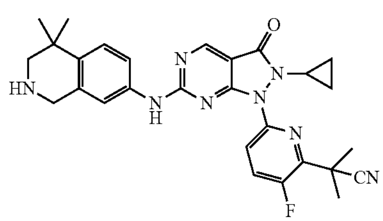 [SMILES: CC(C)(C#N)c1nc(-n2c3nc(Nc4ccc5c(c4)CNCC5(C)C)ncc3c(=O)n2C2CC2)ccc1F] |
| 1.282 | 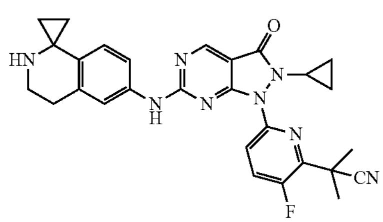 [SMILES: CC(C)(C#N)c1nc(-n2c3nc(Nc4ccc5c(c4)CCNC54CC4)ncc3c(=O)n2C2CC2)ccc1F] |
| 1.283 | 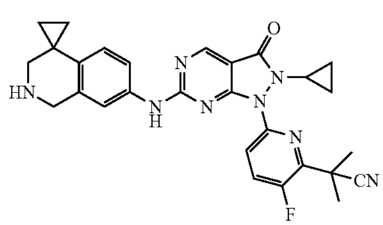 [SMILES: CC(C)(C#N)c1nc(-n2c3nc(Nc4ccc5c(c4)CNCC54CC4)ncc3c(=O)n2C2CC2)ccc1F] |
| 1.284 | |
| 1.285 | |
| 1.286 | |
| 1.287 | |
| 1.288 | |
| 1.289 | |
| 1.290 | |

TABLE 1-continued
| Compound No. | Structure |
|---|---|
| 1.291 | 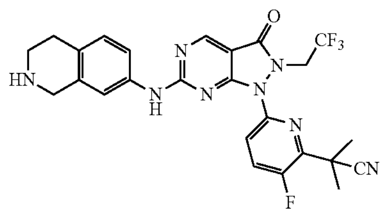 [SMILES: CC(C)(C#N)c1nc(-n2c3nc(Nc4ccc5c(c4)CNCC5)ncc3c(=O)n2CC(F)(F)F)ccc1F] |
| 1.292 | 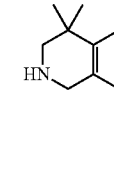 |
| 1.293 | 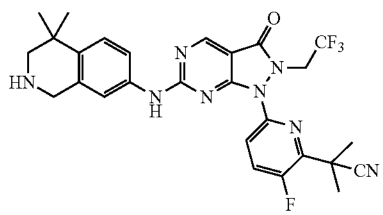 |
| 1.294 | 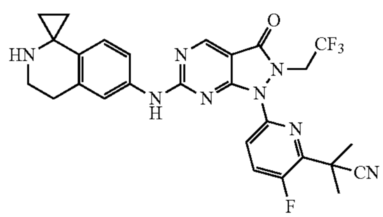 [SMILES: CC(C)(C#N)c1nc(-n2c3nc(Nc4ccc5c(c4)CCNC54CC4)ncc3c(=O)n2CC(F)(F)F)ccc1F] |
| 1.295 | 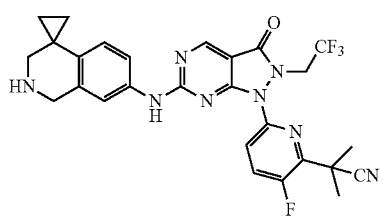 [SMILES: CC(C)(C#N)c1nc(-n2c3nc(Nc4ccc5c(c4)CNCC54CC4)ncc3c(=O)n2CC(F)(F)F)ccc1F] |
| 1.296 | 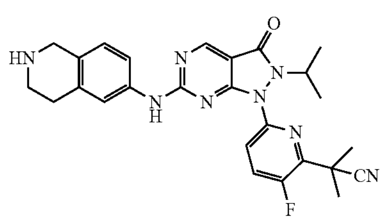 [SMILES: CC(C)n1c(=O)c2cnc(Nc3ccc4c(c3)CCNC4)nc2n1-c1ccc(F)c(C(C)(C)C#N)n1] |
| 1.297 | 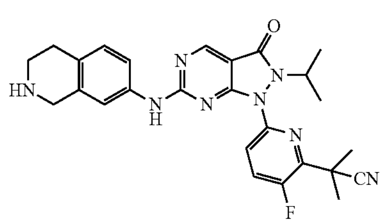 [SMILES: CC(C)n1c(=O)c2cnc(Nc3ccc4c(c3)CNCC4)nc2n1-c1ccc(F)c(C(C)(C)C#N)n1] |
TABLE 1-continued
| Compound No. | Structure |
|---|---|
| 1.298 | |
| 1.299 | |
| 1.300 | |
| 1.301 | |
| 1.302 | |
| 1.303 | |
| 1.304 | |

TABLE 1-continued

| Compound No. | Structure |
|---|---|
| 1.305 | 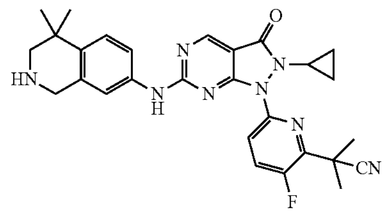 [SMILES: CC(C)(C#N)c1nc(-n2c3nc(Nc4ccc5c(c4)CNCC5(C)C)ncc3c(=O)n2C2CC2)ccc1F] |
| 1.306 | 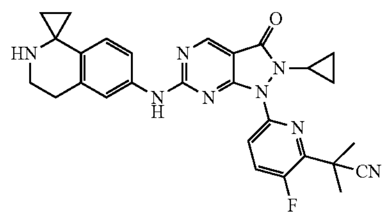 [SMILES: CC(C)(C#N)c1nc(-n2c3nc(Nc4ccc5c(c4)CCNC54CC4)ncc3c(=O)n2C2CC2)ccc1F] |
| 1.307 | 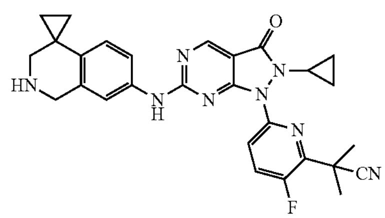 [SMILES: CC(C)(C#N)c1nc(-n2c3nc(Nc4ccc5c(c4)CNCC54CC4)ncc3c(=O)n2C2CC2)ccc1F] |
| 1.308 | 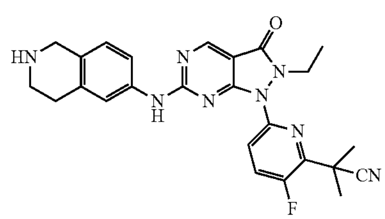 [SMILES: CCn1c(=O)c2cnc(Nc3ccc4c(c3)CCNC4)nc2n1-c1ccc(F)c(C(C)(C)C#N)n1] |
| 1.309 | 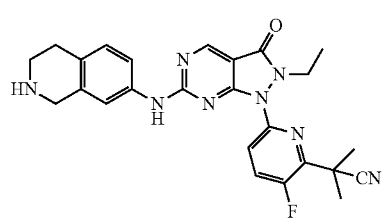 [SMILES: CCn1c(=O)c2cnc(Nc3ccc4c(c3)CNCC4)nc2n1-c1ccc(F)c(C(C)(C)C#N)n1] |
| 1.310 | 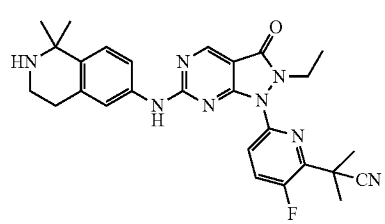 [SMILES: CCn1c(=O)c2cnc(Nc3ccc4c(c3)CCNC4(C)C)nc2n1-c1ccc(F)c(C(C)(C)C#N)n1] |
| 1.311 | 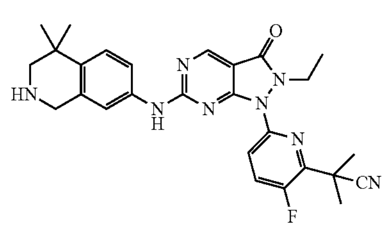 [SMILES: CCn1c(=O)c2cnc(Nc3ccc4c(c3)CNCC4(C)C)nc2n1-c1ccc(F)c(C(C)(C)C#N)n1] |
| 1.312 | |
| 1.313 | |
| 1.314 | |
| 1.315 | |
| 1.316 | |
| 1.317 | |
| 1.318 | |

TABLE 1-continued

| Compound No. | Structure |
|---|---|
| 1.319 | (structure) |
| 1.320 | (structure) |
| 1.321 | (structure) |
| 1.322 | (structure) |
| 1.323 | (structure) |
| 1.324 | (structure) |
| 1.325 | (structure) |
| 1.326 | (structure) |
| 1.327 | (structure) |
| 1.328 | (structure) |
| 1.329 | (structure) |
| 1.330 | (structure) |
| 1.331 | (structure) |
| 1.332 | (structure) |

TABLE 1-continued

| Compound No. | Structure |
|---|---|
| 1.333 | 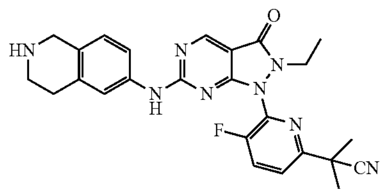 [SMILES: CCn1c(=O)c2cnc(Nc3ccc4c(c3)CCNC4)nc2n1-c1nc(C(C)(C)C#N)ccc1F] |
| 1.334 | 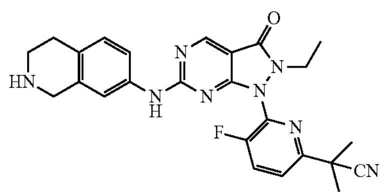 [SMILES: CCn1c(=O)c2cnc(Nc3ccc4c(c3)CNCC4)nc2n1-c1nc(C(C)(C)C#N)ccc1F] |
| 1.335 | 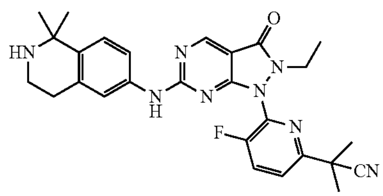 [SMILES: CCn1c(=O)c2cnc(Nc3ccc4c(c3)CCNC4(C)C)nc2n1-c1nc(C(C)(C)C#N)ccc1F] |
| 1.336 | 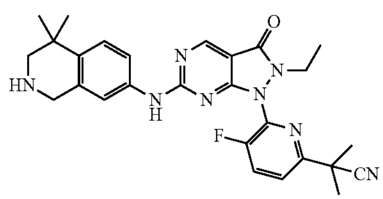 [SMILES: CCn1c(=O)c2cnc(Nc3ccc4c(c3)CNCC4(C)C)nc2n1-c1nc(C(C)(C)C#N)ccc1F] |
| 1.337 | 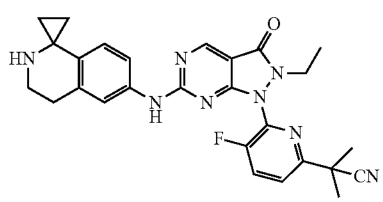 [SMILES: CCn1c(=O)c2cnc(Nc3ccc4c(c3)CCNC43CC3)nc2n1-c1nc(C(C)(C)C#N)ccc1F] |
| 1.338 | 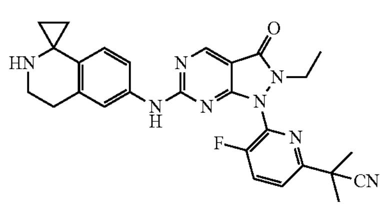 [SMILES: CCn1c(=O)c2cnc(Nc3ccc4c(c3)CCNC43CC3)nc2n1-c1nc(C(C)(C)C#N)ccc1F] |
| 1.339 | 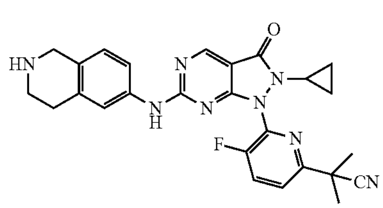 [SMILES: CC(C)(C#N)c1ccc(F)c(-n2c3nc(Nc4ccc5c(c4)CCNC5)ncc3c(=O)n2C2CC2)n1] |
| 1.340 | |
| 1.341 | |
| 1.342 | |
| 1.343 | |
| 1.344 | |
| 1.345 | |

TABLE 1-continued

| Compound No. | Structure |
|---|---|
| 1.346 | (structure) |
| 1.347 | (structure) |
| 1.348 | (structure) |
| 1.349 | (structure) |
| 1.350 | (structure) |
| 1.351 | (structure) |
| 1.352 | (structure) |
| 1.353 | (structure) |
| 1.354 | (structure) |
| 1.355 | (structure) |

TABLE 1-continued
| Compound No. | Structure |
|---|---|
| 1.356 | 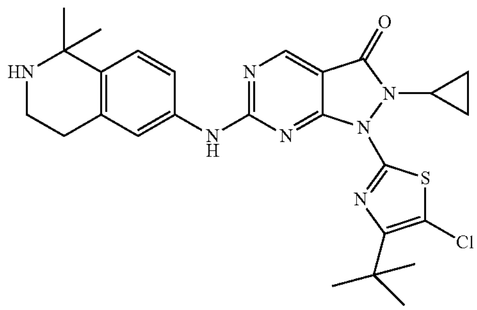 [SMILES: CC(C)(C)c1nc(-n2c3nc(Nc4ccc5c(c4)CCNC5(C)C)ncc3c(=O)n2C2CC2)sc1Cl] |
| 1.357 | 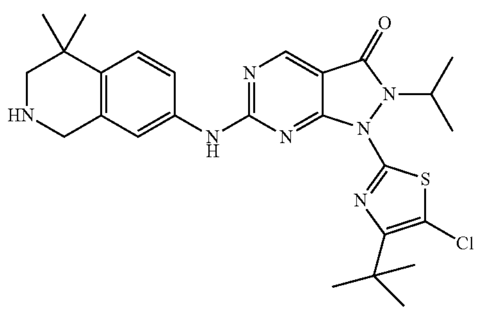 [SMILES: CC(C)n1c(=O)c2cnc(Nc3ccc4c(c3)CNCC4(C)C)nc2n1-c1nc(C(C)(C)C)c(Cl)s1] |
| 1.358 | 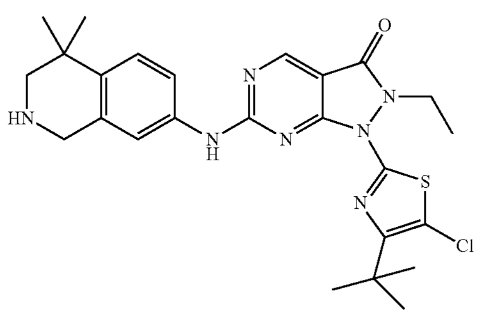 |
| 1.359 | 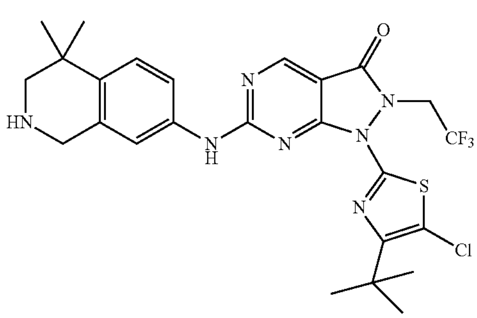 [SMILES: CC(C)(C)c1nc(-n2c3nc(Nc4ccc5c(c4)CNCC5(C)C)ncc3c(=O)n2CC(F)(F)F)sc1Cl] |
| 1.360 | 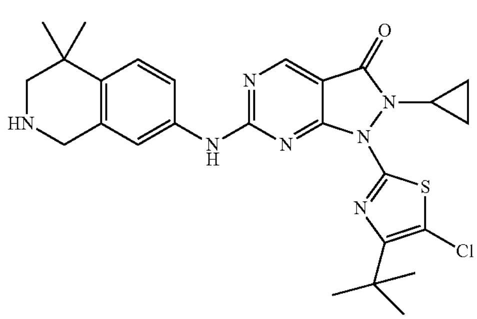 [SMILES: CC(C)(C)c1nc(-n2c3nc(Nc4ccc5c(c4)CNCC5(C)C)ncc3c(=O)n2C2CC2)sc1Cl] |
| 1.361 | 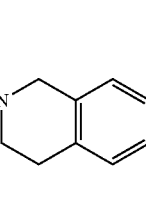 |
| 1.362 | |
| 1.363 | |
| 1.364 | |
| 1.365 | |

TABLE 1-continued
| Compound No. | Structure |
|---|---|
| 1.366 | 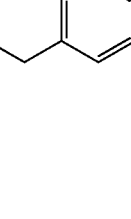 |
| 1.367 | 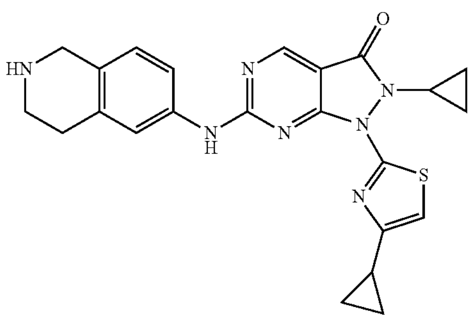 [SMILES: O=c1c2cnc(Nc3ccc4c(c3)CCNC4)nc2n(-c2nc(C3CC3)cs2)n1C1CC1] |
| 1.368 | 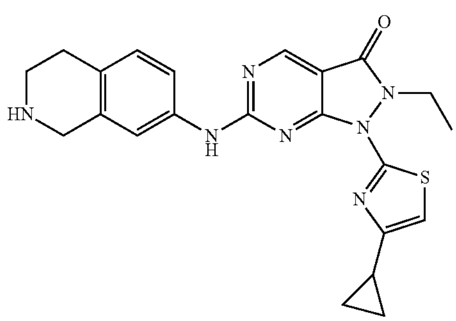 [SMILES: CCn1c(=O)c2cnc(Nc3ccc4c(c3)CNCC4)nc2n1-c1nc(C2CC2)cs1] |
| 1.369 | 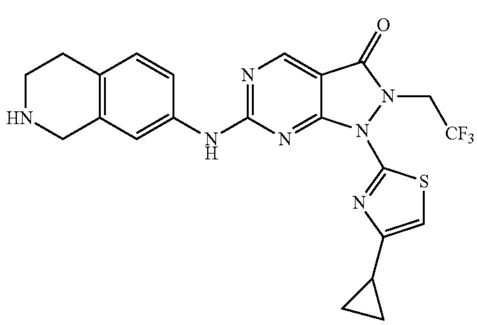 [SMILES: O=c1c2cnc(Nc3ccc4c(c3)CNCC4)nc2n(-c2nc(C3CC3)cs2)n1CC(F)(F)F] |
TABLE 1-continued
| Compound No. | Structure |
|---|---|
| 1.370 | 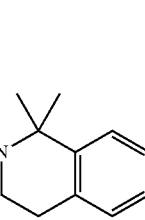 |
| 1.371 | 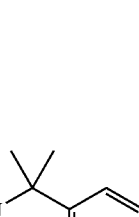 |
| 1.372 | 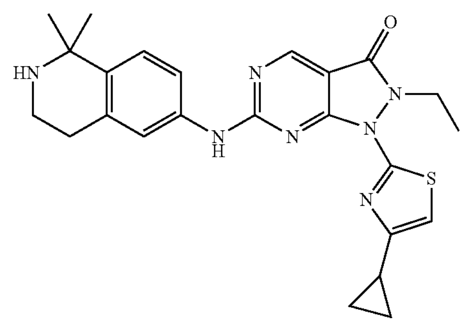 [SMILES: CCn1c(=O)c2cnc(Nc3ccc4c(c3)CCNC4(C)C)nc2n1-c1nc(C2CC2)cs1] |
| 1.373 | 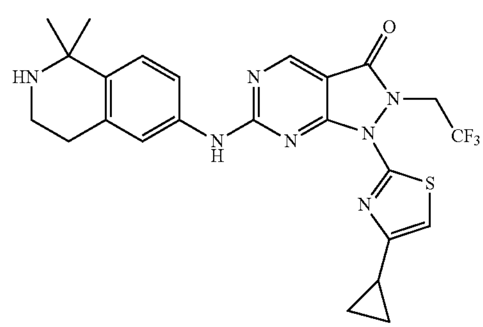 [SMILES: CC1(C)NCCc2cc(Nc3ncc4c(=O)n(CC(F)(F)F)n(-c5nc(C6CC6)cs5)c4n3)ccc21] |

TABLE 1-continued

| Compound No. | Structure |
|---|---|
| 1.374 | |
| 1.375 | |
| 1.376 | |
| 1.377 | |
| 1.378 | 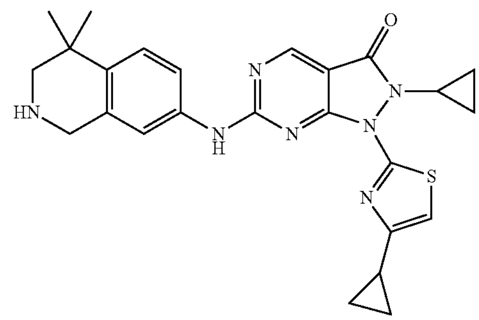 [SMILES: CC1(C)CNCc2cc(Nc3ncc4c(=O)n(C5CC5)n(-c5nc(C6CC6)cs5)c4n3)ccc21] |
| 1.379 | 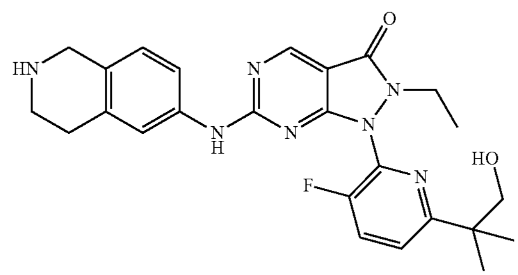 [SMILES: CCn1c(=O)c2cnc(Nc3ccc4c(c3)CCNC4)nc2n1-c1nc(C(C)(C)CO)ccc1F] |
| 1.380 | 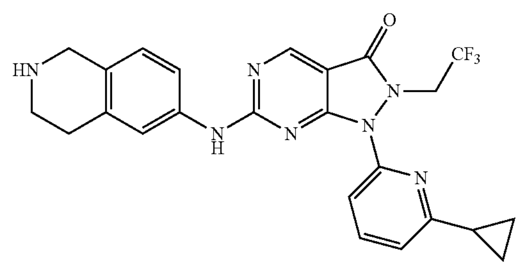 [SMILES: O=c1c2cnc(Nc3ccc4c(c3)CCNC4)nc2n(-c2cccc(C3CC3)n2)n1CC(F)(F)F] |
| 1.381 | 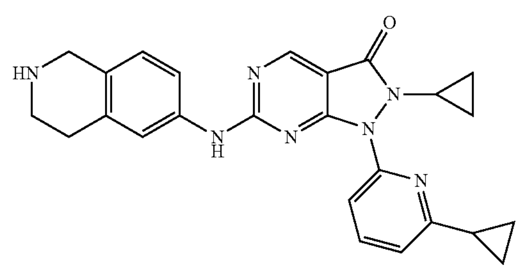 [SMILES: O=c1c2cnc(Nc3ccc4c(c3)CCNC4)nc2n(-c2cccc(C3CC3)n2)n1C1CC1] |
| 1.382 | 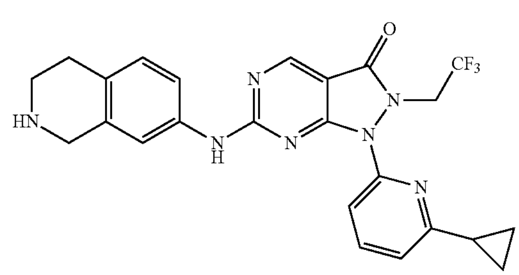 [SMILES: O=c1c2cnc(Nc3ccc4c(c3)CNCC4)nc2n(-c2cccc(C3CC3)n2)n1CC(F)(F)F] |

TABLE 1-continued

| Compound No. | Structure |
|---|---|
| 1.383 | |
| 1.384 | |
| 1.385 | |
| 1.386 | |
| 1.387 | |
| 1.388 | 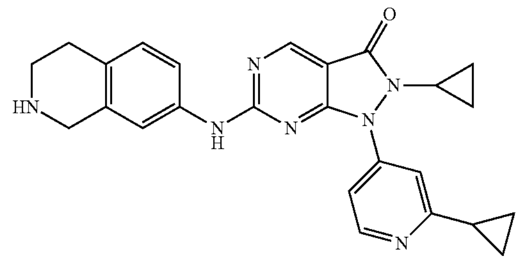 [SMILES: O=c1c2cnc(Nc3ccc4c(c3)CNCC4)nc2n(-c2ccnc(C3CC3)c2)n1C1CC1] |
| 1.389 | 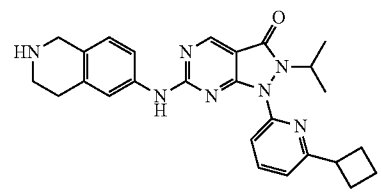 [SMILES: CC(C)n1c(=O)c2cnc(Nc3ccc4c(c3)CCNC4)nc2n1-c1cccc(C2CCC2)n1] |
| 1.390 | 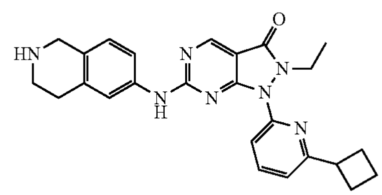 [SMILES: CCn1c(=O)c2cnc(Nc3ccc4c(c3)CCNC4)nc2n1-c1cccc(C2CCC2)n1] |
| 1.391 | 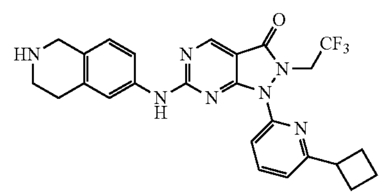 [SMILES: O=c1c2cnc(Nc3ccc4c(c3)CCNC4)nc2n(-c2cccc(C3CCC3)n2)n1CC(F)(F)F] |
| 1.392 | 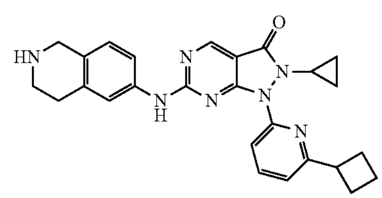 [SMILES: O=c1c2cnc(Nc3ccc4c(c3)CCNC4)nc2n(-c2cccc(C3CCC3)n2)n1C1CC1] |
| 1.393 | 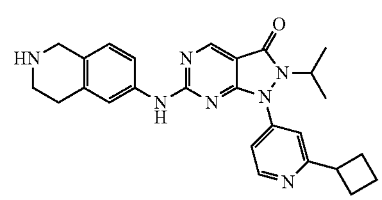 [SMILES: CC(C)n1c(=O)c2cnc(Nc3ccc4c(c3)CCNC4)nc2n1-c1ccnc(C2CCC2)c1] |
| 1.394 | 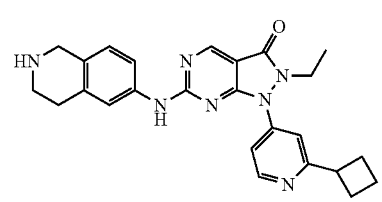 [SMILES: CCn1c(=O)c2cnc(Nc3ccc4c(c3)CCNC4)nc2n1-c1ccnc(C2CCC2)c1] |

TABLE 1-continued

| Compound No. | Structure |
|---|---|
| 1.395 | 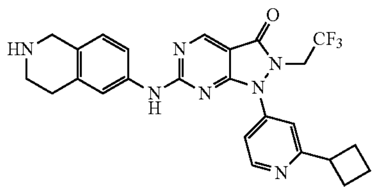 [SMILES: O=c1c2cnc(Nc3ccc4c(c3)CCNC4)nc2n(-c2ccnc(C3CCC3)c2)n1CC(F)(F)F] |
| 1.396 | 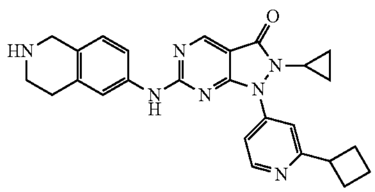 [SMILES: O=c1c2cnc(Nc3ccc4c(c3)CCNC4)nc2n(-c2ccnc(C3CCC3)c2)n1C1CC1] |
| 1.397 | 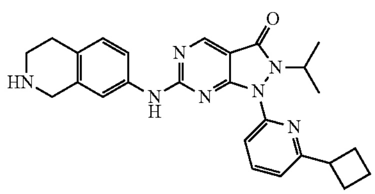 [SMILES: CC(C)n1c(=O)c2cnc(Nc3ccc4c(c3)CNCC4)nc2n1-c1cccc(C2CCC2)n1] |
| 1.398 | 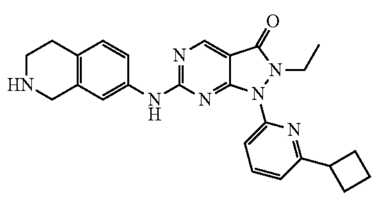 [SMILES: CCn1c(=O)c2cnc(Nc3ccc4c(c3)CNCC4)nc2n1-c1cccc(C2CCC2)n1] |
| 1.399 | 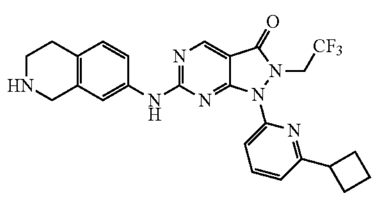 [SMILES: O=c1c2cnc(Nc3ccc4c(c3)CNCC4)nc2n(-c2cccc(C3CCC3)n2)n1CC(F)(F)F] |
| 1.400 | 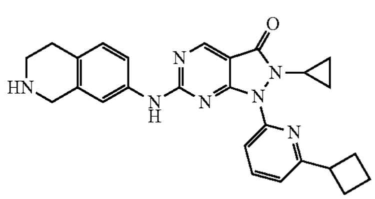 [SMILES: O=c1c2cnc(Nc3ccc4c(c3)CNCC4)nc2n(-c2cccc(C3CCC3)n2)n1C1CC1] |
| 1.401 | 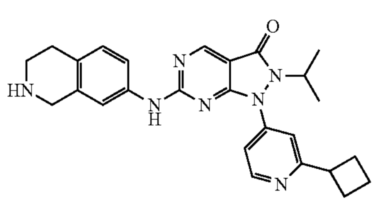 [SMILES: CCn1c(=O)c2cnc(Nc3ccc4c(c3)CNCC4)nc2n1-c1ccnc(C2CCC2)c1] |
| 1.402 | |
| 1.403 | |
| 1.404 | |
| 1.405 | |
| 1.406 | |
| 1.407 | |

TABLE 1-continued
| Compound No. | Structure |
|---|---|
| 1.408 | 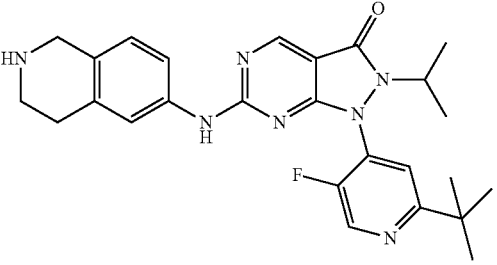 [SMILES: CC(C)n1c(=O)c2cnc(Nc3ccc4c(c3)CCNC4)nc2n1-c1cc(C(C)(C)C)ncc1F] |
| 1.409 | 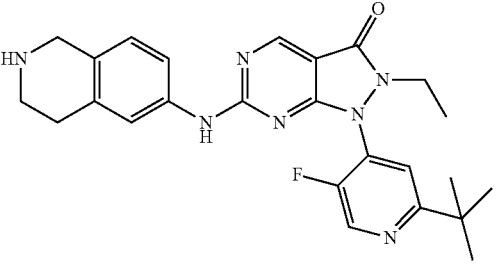 [SMILES: CCn1c(=O)c2cnc(Nc3ccc4c(c3)CCNC4)nc2n1-c1cc(C(C)(C)C)ncc1F] |
| 1.410 | 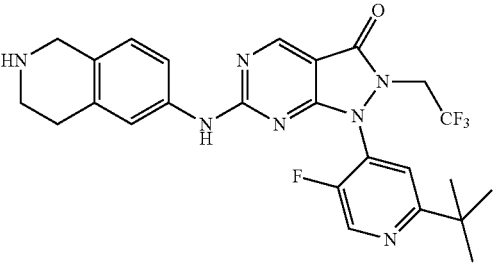 [SMILES: CC(C)(C)c1cc(-n2c3nc(Nc4ccc5c(c4)CCNC5)ncc3c(=O)n2CC(F)(F)F)c(F)cn1] |
| 1.411 | 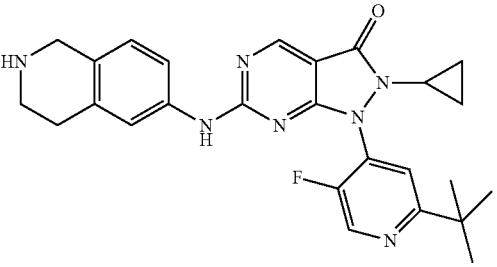 [SMILES: CC(C)(C)c1cc(-n2c3nc(Nc4ccc5c(c4)CCNC5)ncc3c(=O)n2C2CC2)c(F)cn1] |
| 1.412 | 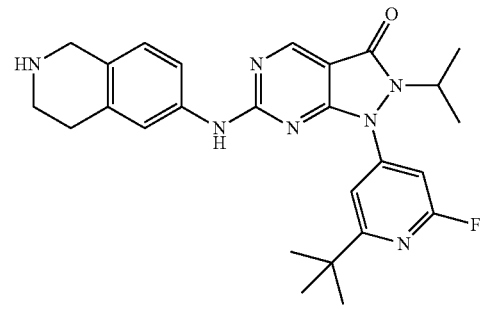 [SMILES: CC(C)n1c(=O)c2cnc(Nc3ccc4c(c3)CCNC4)nc2n1-c1cc(F)nc(C(C)(C)C)c1] |
| 1.413 | 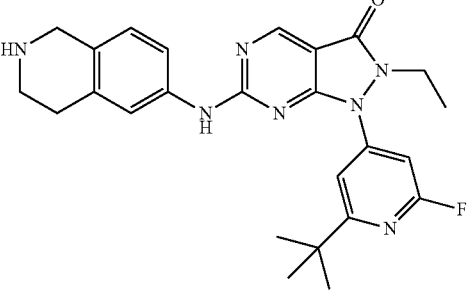 |
| 1.414 | 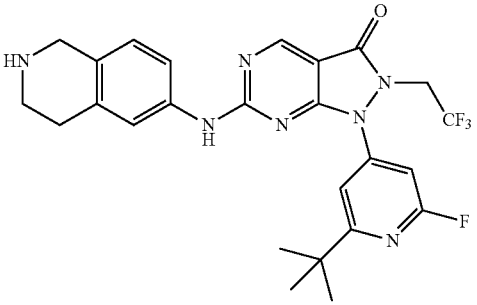 [SMILES: CC(C)(C)c1cc(-n2c3nc(Nc4ccc5c(c4)CCNC5)ncc3c(=O)n2CC(F)(F)F)cc(F)n1] |
| 1.415 | 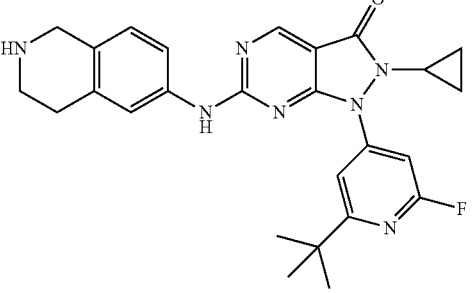 |
| 1.416 | 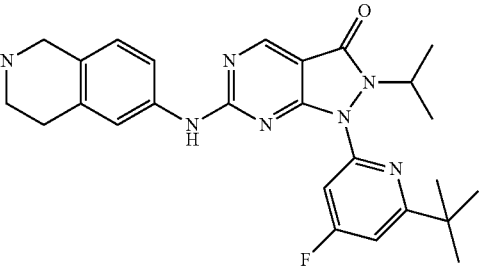 |
| 1.417 | 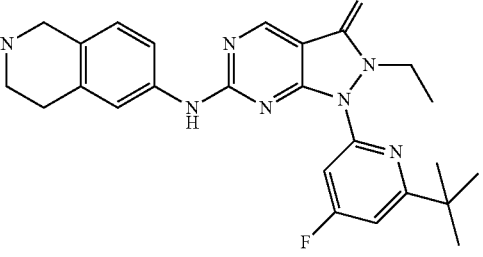 |

TABLE 1-continued

| Compound No. | Structure |
|---|---|
| 1.418 | 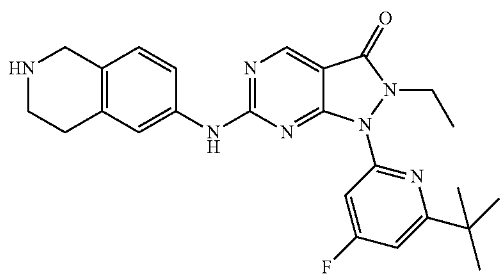 [SMILES: CCn1c(=O)c2cnc(Nc3ccc4c(c3)CCNC4)nc2n1-c1cc(F)cc(C(C)(C)C)n1] |
| 1.419 | 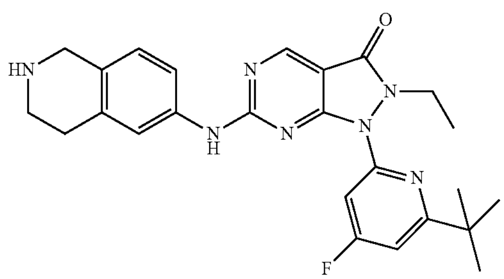 [SMILES: CCn1c(=O)c2cnc(Nc3ccc4c(c3)CCNC4)nc2n1-c1cc(F)cc(C(C)(C)C)n1] |
| 1.420 | 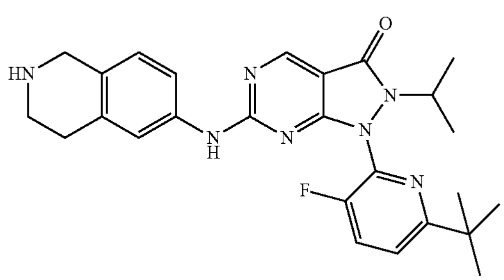 [SMILES: CC(C)n1c(=O)c2cnc(Nc3ccc4c(c3)CCNC4)nc2n1-c1nc(C(C)(C)C)ccc1F] |
| 1.421 | 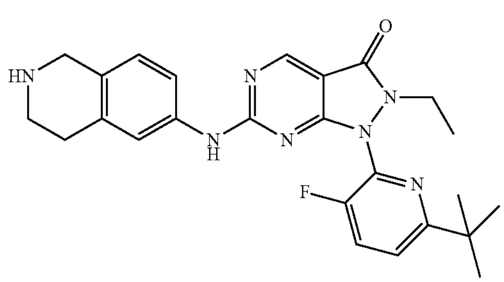 [SMILES: CCn1c(=O)c2cnc(Nc3ccc4c(c3)CCNC4)nc2n1-c1nc(C(C)(C)C)ccc1F] |
| 1.422 | 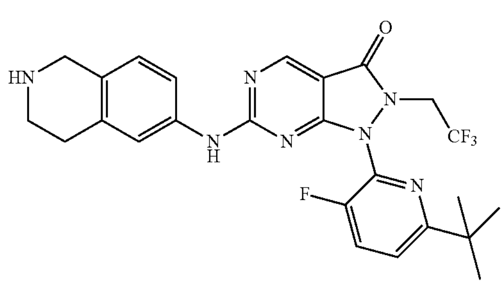 [SMILES: CC(C)(C)c1ccc(F)c(-n2c3nc(Nc4ccc5c(c4)CCNC5)ncc3c(=O)n2CC(F)(F)F)n1] |
| 1.423 | 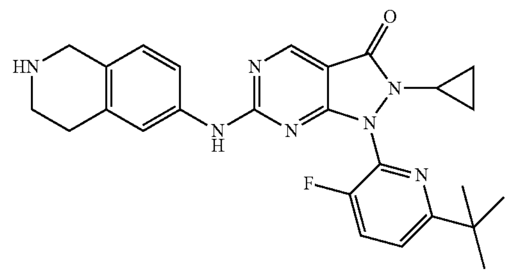 [SMILES: CC(C)(C)c1ccc(F)c(-n2c3nc(Nc4ccc5c(c4)CCNC5)ncc3c(=O)n2C2CC2)n1] |
| 1.424 | 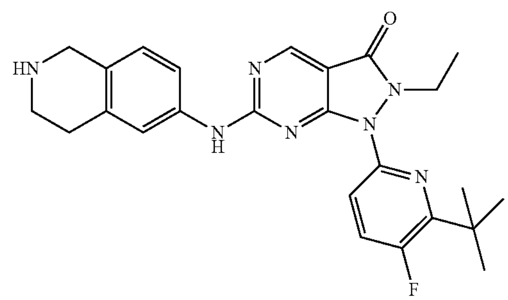 [SMILES: CCn1c(=O)c2cnc(Nc3ccc4c(c3)CCNC4)nc2n1-c1ccc(F)c(C(C)(C)C)n1] |
| 1.425 | 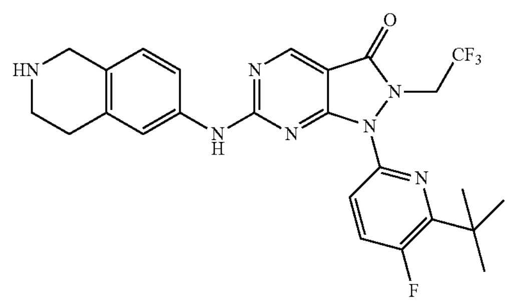 [SMILES: CC(C)(C)c1nc(-n2c3nc(Nc4ccc5c(c4)CCNC5)ncc3c(=O)n2CC(F)(F)F)ccc1F] |
| 1.426 | 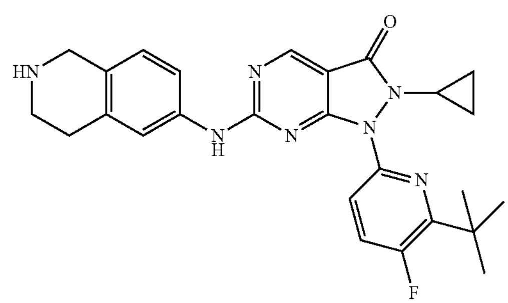 [SMILES: CC(C)(C)c1nc(-n2c3nc(Nc4ccc5c(c4)CCNC5)ncc3c(=O)n2C2CC2)ccc1F] |
| 1.427 | 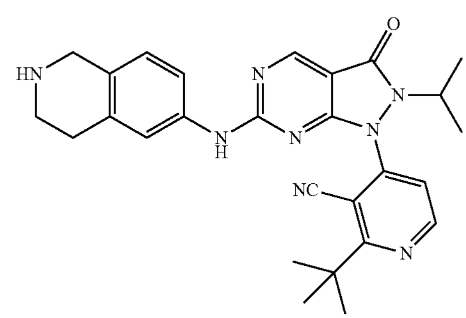 [SMILES: CC(C)n1c(=O)c2cnc(Nc3ccc4c(c3)CCNC4)nc2n1-c1ccnc(C(C)(C)C)c1C#N] |

TABLE 1-continued

| Compound No. | Structure |
|---|---|
| 1.428 | (structure) |
| 1.429 | (structure) |
| 1.430 | (structure) |
| 1.431 | (structure) |
| 1.432 | (structure) |
| 1.433 | (structure) |
| 1.434 | (structure) |
| 1.435 | (structure) |
| 1.436 | (structure) |
| 1.437 | (structure) |

TABLE 1-continued

| Compound No. | Structure |
|---|---|
| 1.438 | 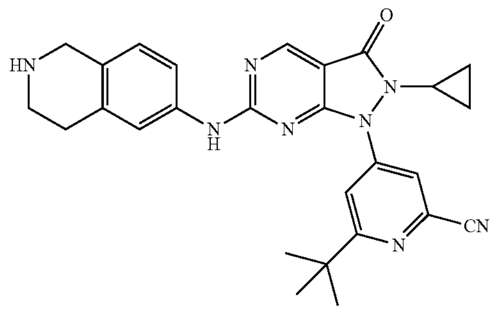 [SMILES: CC(C)(C)c1cc(-n2c3nc(Nc4ccc5c(c4)CCNC5)ncc3c(=O)n2C2CC2)cc(C#N)n1] |
| 1.439 | 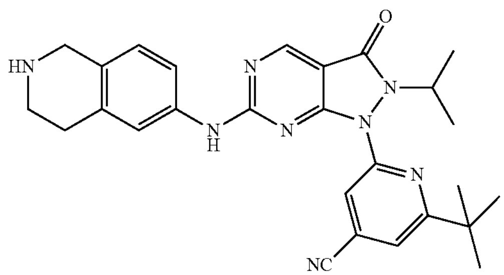 [SMILES: CC(C)n1c(=O)c2cnc(Nc3ccc4c(c3)CCNC4)nc2n1-c1cc(C#N)cc(C(C)(C)C)n1] |
| 1.440 | 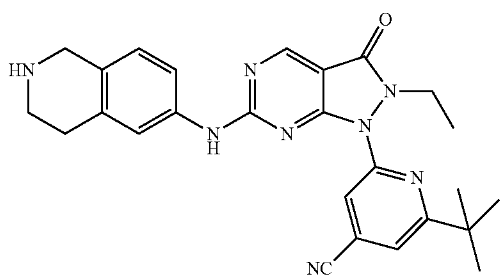 |
| 1.441 | 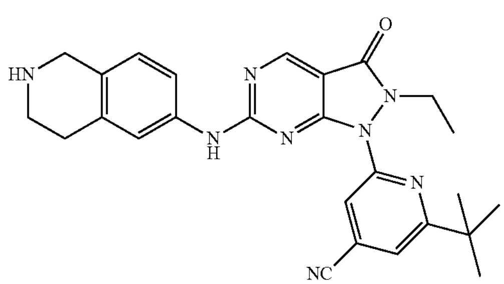 [SMILES: CCn1c(=O)c2cnc(Nc3ccc4c(c3)CCNC4)nc2n1-c1cc(C#N)cc(C(C)(C)C)n1] |
| 1.442 | 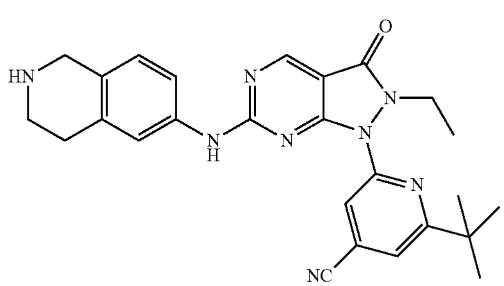 [SMILES: CCn1c(=O)c2cnc(Nc3ccc4c(c3)CCNC4)nc2n1-c1cc(C#N)cc(C(C)(C)C)n1] |
| 1.443 | 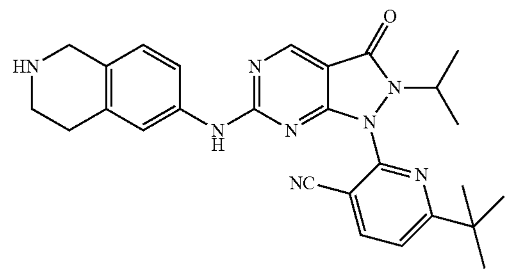 [SMILES: CC(C)n1c(=O)c2cnc(Nc3ccc4c(c3)CCNC4)nc2n1-c1nc(C(C)(C)C)ccc1C#N] |
| 1.444 | 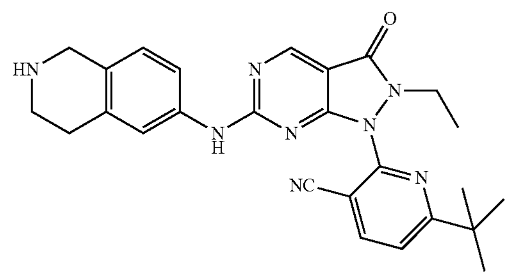 [SMILES: CCn1c(=O)c2cnc(Nc3ccc4c(c3)CCNC4)nc2n1-c1nc(C(C)(C)C)ccc1C#N] |
| 1.445 | 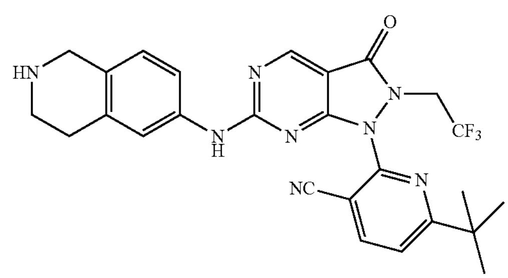 |
| 1.446 | 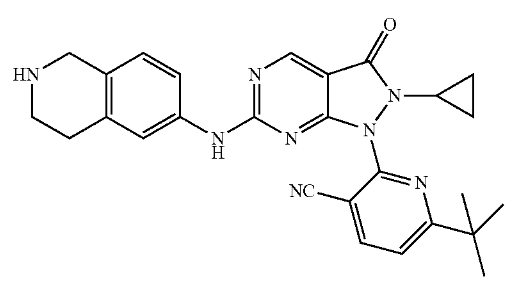 [SMILES: CC(C)(C)c1ccc(C#N)c(-n2c3nc(Nc4ccc5c(c4)CCNC5)ncc3c(=O)n2C2CC2)n1] |
| 1.447 | 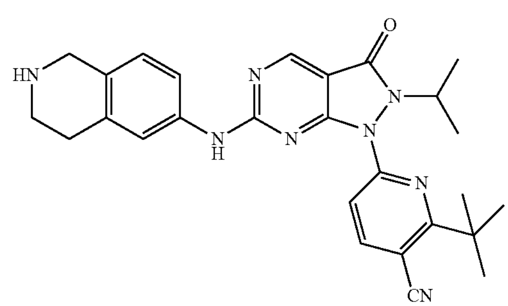 [SMILES: CC(C)n1c(=O)c2cnc(Nc3ccc4c(c3)CCNC4)nc2n1-c1ccc(C#N)c(C(C)(C)C)n1] |

TABLE 1-continued
| Compound No. | Structure |
|---|---|
| 1.448 | 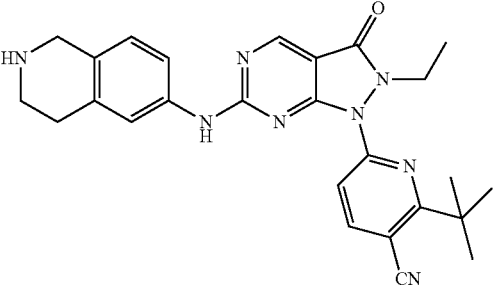 [SMILES: CCn1c(=O)c2cnc(Nc3ccc4c(c3)CCNC4)nc2n1-c1ccc(C#N)c(C(C)(C)C)n1] |
| 1.449 | 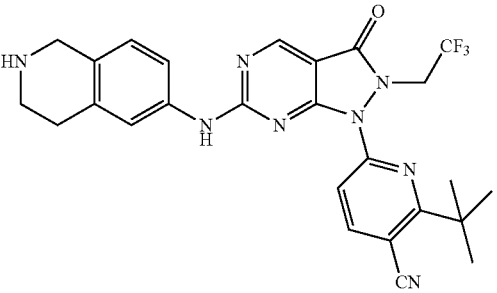 [SMILES: CC(C)(C)c1nc(-n2c3nc(Nc4ccc5c(c4)CCNC5)ncc3c(=O)n2CC(F)(F)F)ccc1C#N] |
| 1.450 | 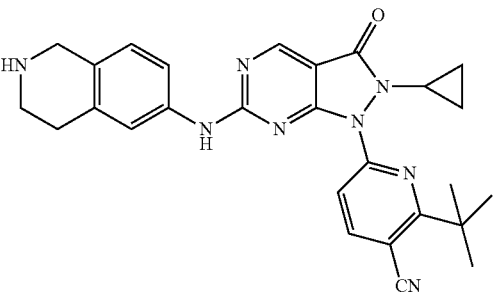 [SMILES: CC(C)(C)c1nc(-n2c3nc(Nc4ccc5c(c4)CCNC5)ncc3c(=O)n2C2CC2)ccc1C#N] |
| 1.451 | 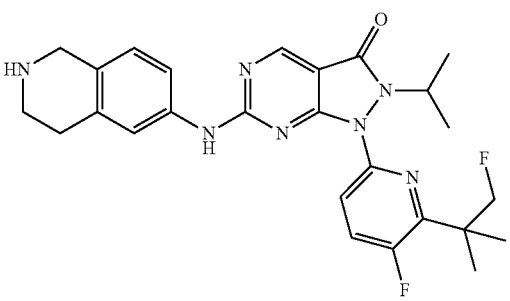 [SMILES: CC(C)n1c(=O)c2cnc(Nc3ccc4c(c3)CCNC4)nc2n1-c1ccc(F)c(C(C)(C)CF)n1] |
| 1.452 | 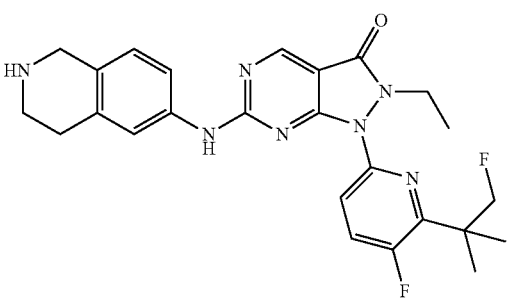 [SMILES: CCn1c(=O)c2cnc(Nc3ccc4c(c3)CCNC4)nc2n1-c1ccc(F)c(C(C)(C)CF)n1] |
| 1.453 | 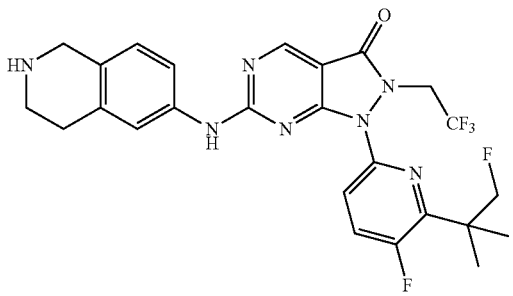 [SMILES: CC(C)(CF)c1nc(-n2c3nc(Nc4ccc5c(c4)CCNC5)ncc3c(=O)n2CC(F)(F)F)ccc1F] |
| 1.454 | 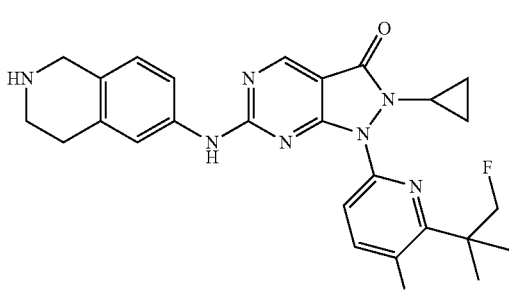 |
| 1.455 | 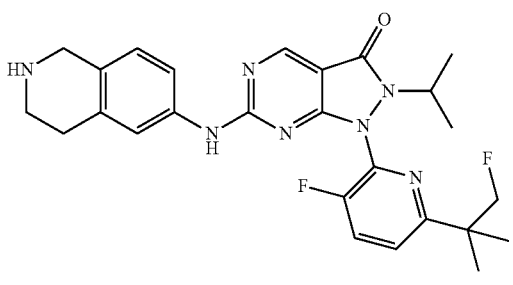 [SMILES: CC(C)n1c(=O)c2cnc(Nc3ccc4c(c3)CCNC4)nc2n1-c1nc(C(C)(C)CF)ccc1F] |
| 1.456 | 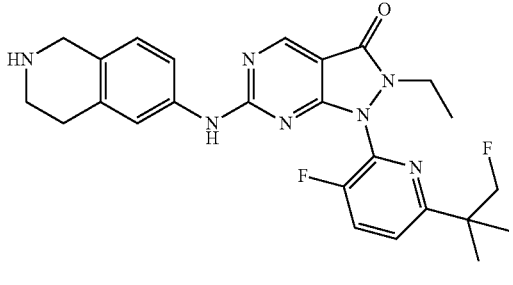 [SMILES: CCn1c(=O)c2cnc(Nc3ccc4c(c3)CCNC4)nc2n1-c1nc(C(C)(C)CF)ccc1F] |
| 1.457 | 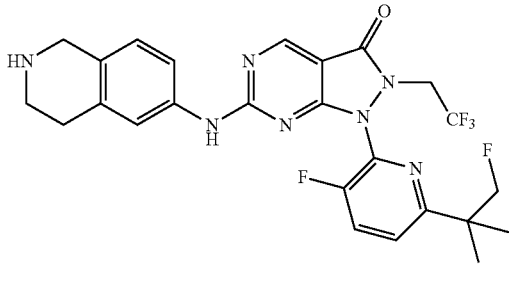 [SMILES: CC(C)(CF)c1ccc(F)c(-n2c3nc(Nc4ccc5c(c4)CCNC5)ncc3c(=O)n2CC(F)(F)F)n1] |

TABLE 1-continued
| Compound No. | Structure |
|---|---|
| 1.458 | 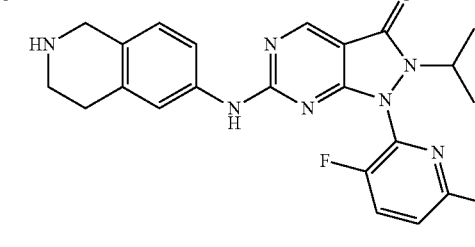 |
| 1.459 | 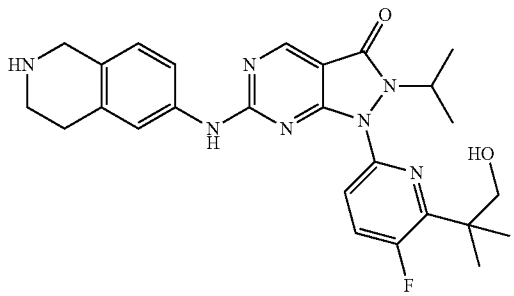 [SMILES: CC(C)n1c(=O)c2cnc(Nc3ccc4c(c3)CCNC4)nc2n1-c1ccc(F)c(C(C)(C)CO)n1] |
| 1.460 | 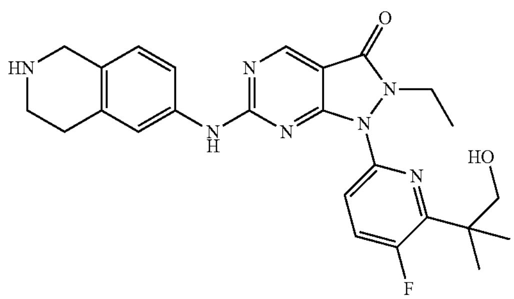 [SMILES: CCn1c(=O)c2cnc(Nc3ccc4c(c3)CCNC4)nc2n1-c1ccc(F)c(C(C)(C)CO)n1] |
| 1.461 | 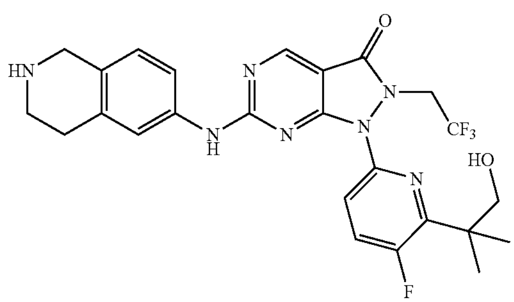 |
| 1.462 | 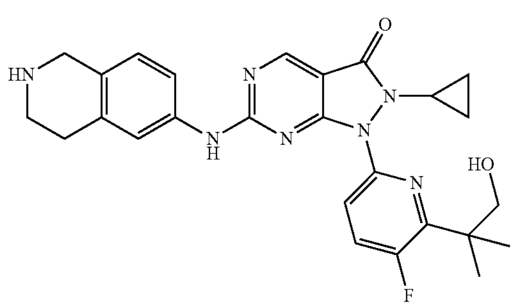 |
| 1.463 | 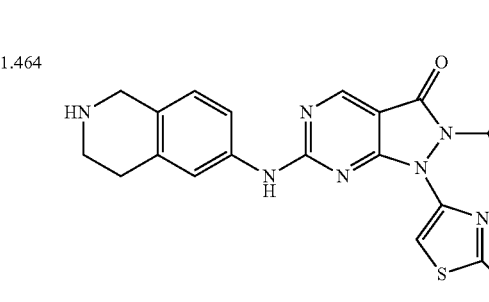 |
| 1.464 | |
| 1.465 | |
| 1.466 | |
| 1.467 | |

TABLE 1-continued

| Compound No. | Structure |
|---|---|
| 1.468 | 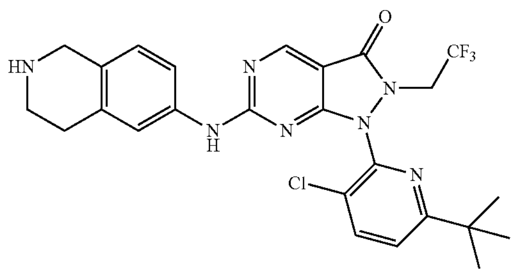 [SMILES: CC(C)(C)c1ccc(Cl)c(-n2c3nc(Nc4ccc5c(c4)CCNC5)ncc3c(=O)n2CC(F)(F)F)n1] |
| 1.469 | 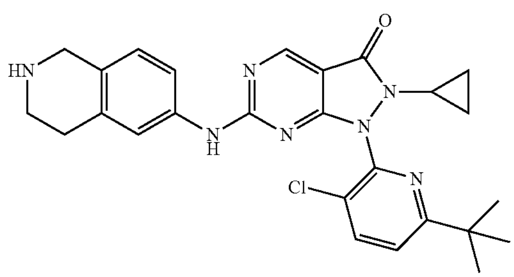 [SMILES: CC(C)(C)c1ccc(Cl)c(-n2c3nc(Nc4ccc5c(c4)CCNC5)ncc3c(=O)n2C2CC2)n1] |
| 1.470 | 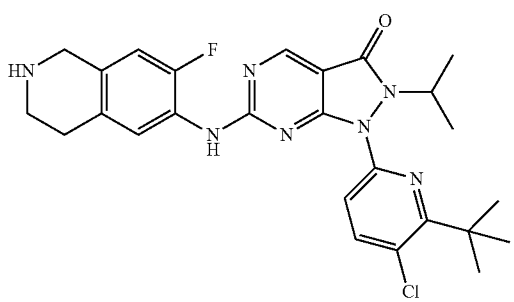 [SMILES: CC(C)n1c(=O)c2cnc(Nc3cc4c(cc3F)CNCC4)nc2n1-c1ccc(Cl)c(C(C)(C)C)n1] |
| 1.471 | 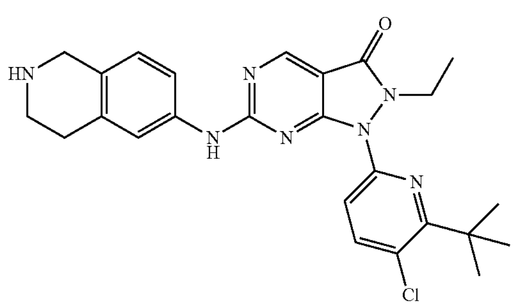 [SMILES: CCn1c(=O)c2cnc(Nc3ccc4c(c3)CCNC4)nc2n1-c1ccc(Cl)c(C(C)(C)C)n1] |
| 1.472 | 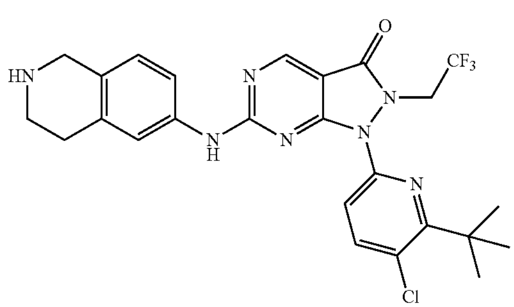 [SMILES: CC(C)(C)c1nc(-n2c3nc(Nc4ccc5c(c4)CCNC5)ncc3c(=O)n2CC(F)(F)F)ccc1Cl] |
| 1.473 | |
| 1.474 | |
| 1.475 | |
| 1.476 | |
| 1.477 | |

TABLE 1-continued
| Compound No. | Structure |
|---|---|
| 1.478 | 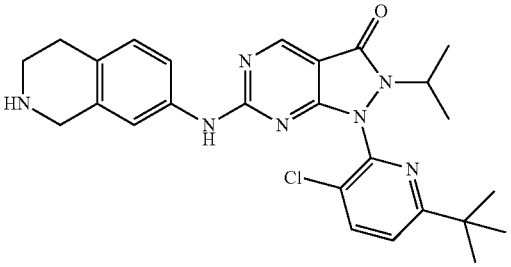 [SMILES: CC(C)n1c(=O)c2cnc(Nc3ccc4c(c3)CNCC4)nc2n1-c1nc(C(C)(C)C)ccc1Cl] |
| 1.479 | 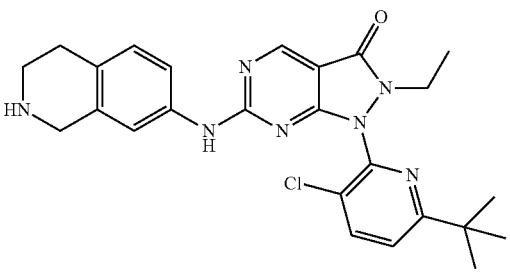 [SMILES: CCn1c(=O)c2cnc(Nc3ccc4c(c3)CNCC4)nc2n1-c1nc(C(C)(C)C)ccc1Cl] |
| 1.480 | 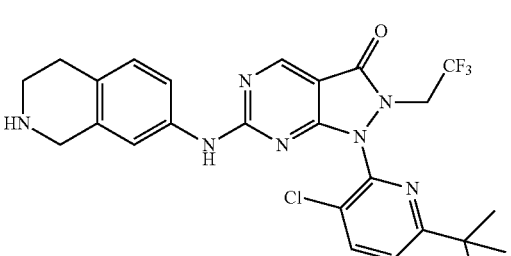 |
| 1.481 | 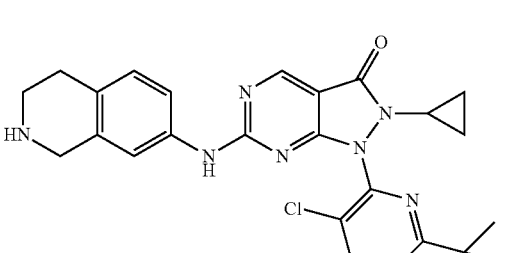 |
| 1.482 | 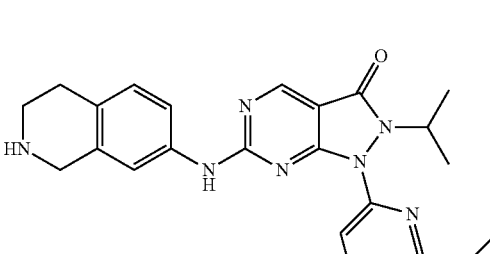 |
TABLE 1-continued
| Compound No. | Structure |
|---|---|
| 1.483 | 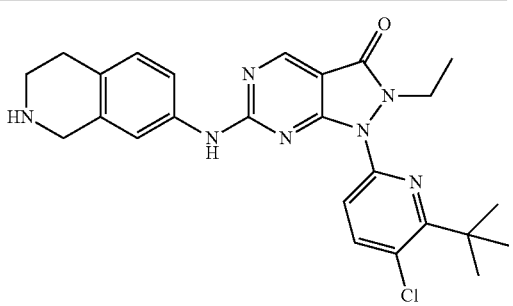 [SMILES: CCn1c(=O)c2cnc(Nc3ccc4c(c3)CNCC4)nc2n1-c1ccc(Cl)c(C(C)(C)C)n1] |
| 1.484 | 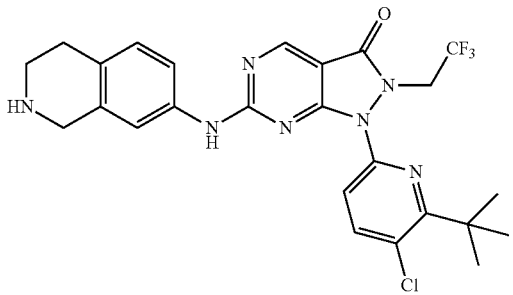 [SMILES: CC(C)(C)c1nc(-n2c3nc(Nc4ccc5c(c4)CNCC5)ncc3c(=O)n2CC(F)(F)F)ccc1Cl] |
| 1.485 | 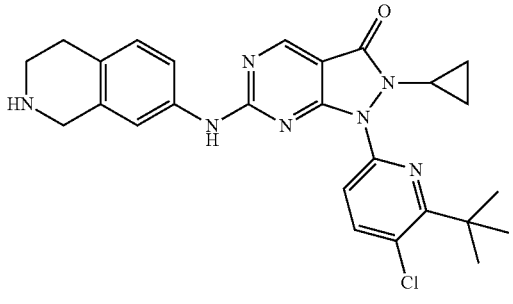 [SMILES: CC(C)(C)c1nc(-n2c3nc(Nc4ccc5c(c4)CNCC5)ncc3c(=O)n2C2CC2)ccc1Cl] |
| 1.486 | 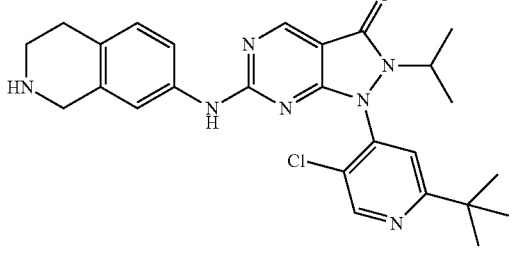 |
| 1.487 | 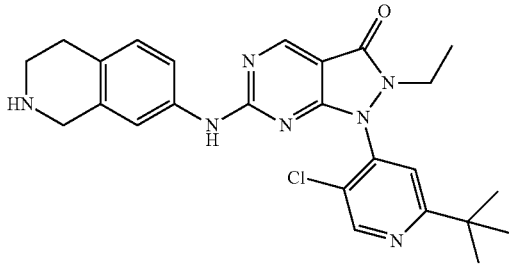 [SMILES: CCn1c(=O)c2cnc(Nc3ccc4c(c3)CNCC4)nc2n1-c1cc(C(C)(C)C)ncc1Cl] |

TABLE 1-continued

| Compound No. | Structure |
|---|---|
| 1.488 | (structure: tetrahydroisoquinoline-NH linked to pyrazolopyrimidinone bearing N-CH2CF3, with chloro-tert-butylpyridyl substituent) |
| 1.489 | (structure: tetrahydroisoquinoline-NH linked to pyrazolopyrimidinone bearing N-cyclopropyl, with chloro-tert-butylpyridyl substituent) |

In some embodiments, provided herein is a compound described in Table 1, or a tautomer thereof, or a salt of any of the foregoing, and uses thereof. In some embodiments, provided herein is a compound described in Table 1 or a pharmaceutically acceptable salt thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described, such as the compounds of Table 1. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C, $^{13}$N, $^{15}$O, $^{17}$O, $^{32}$P, $^{35}$S, $^{18}$F, $^{36}$Cl. Certain isotope labeled compounds (e.g. $^3$H and $^{14}$C) are useful in compound or substrate tissue distribution studies. Incorporation of heavier isotopes such as deuterium ($^2$H) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of Formula (I), (II) or (III) are synthesized according to Scheme 1 to Scheme 5.

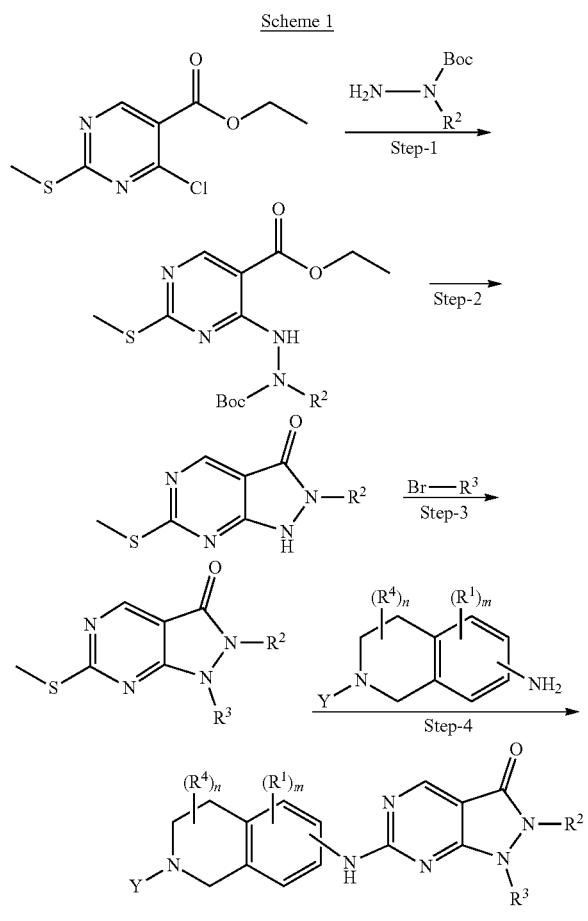

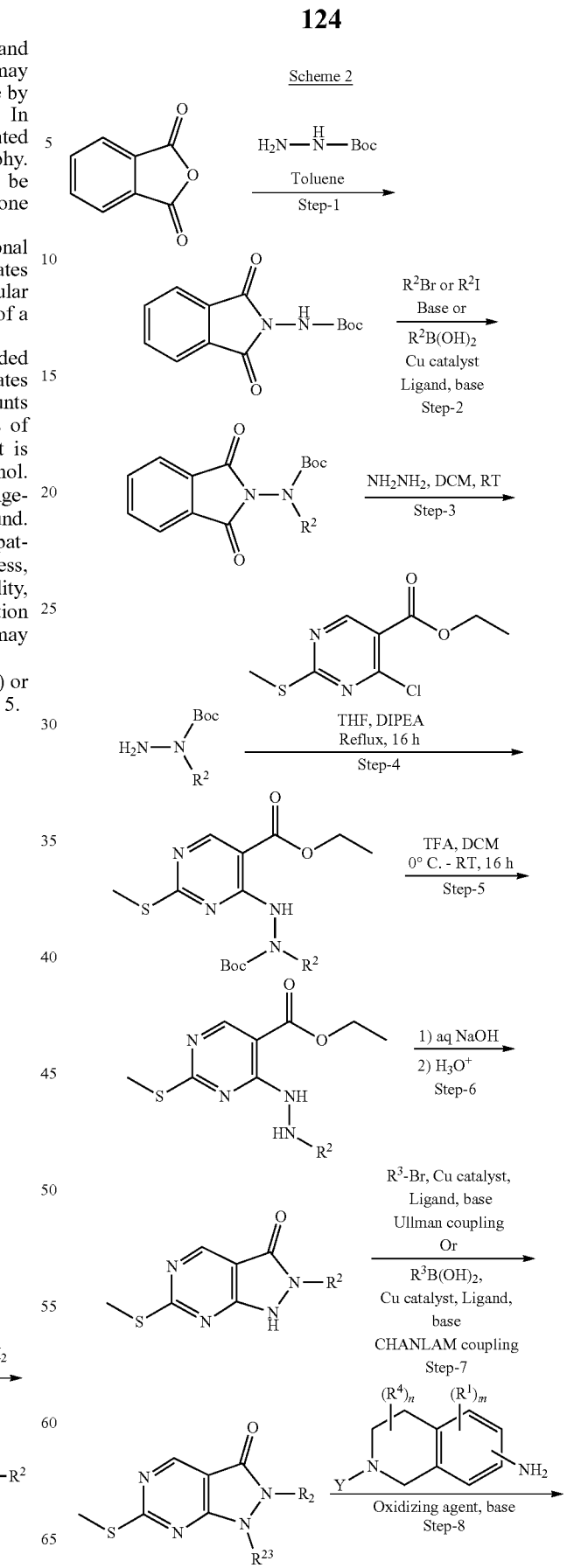

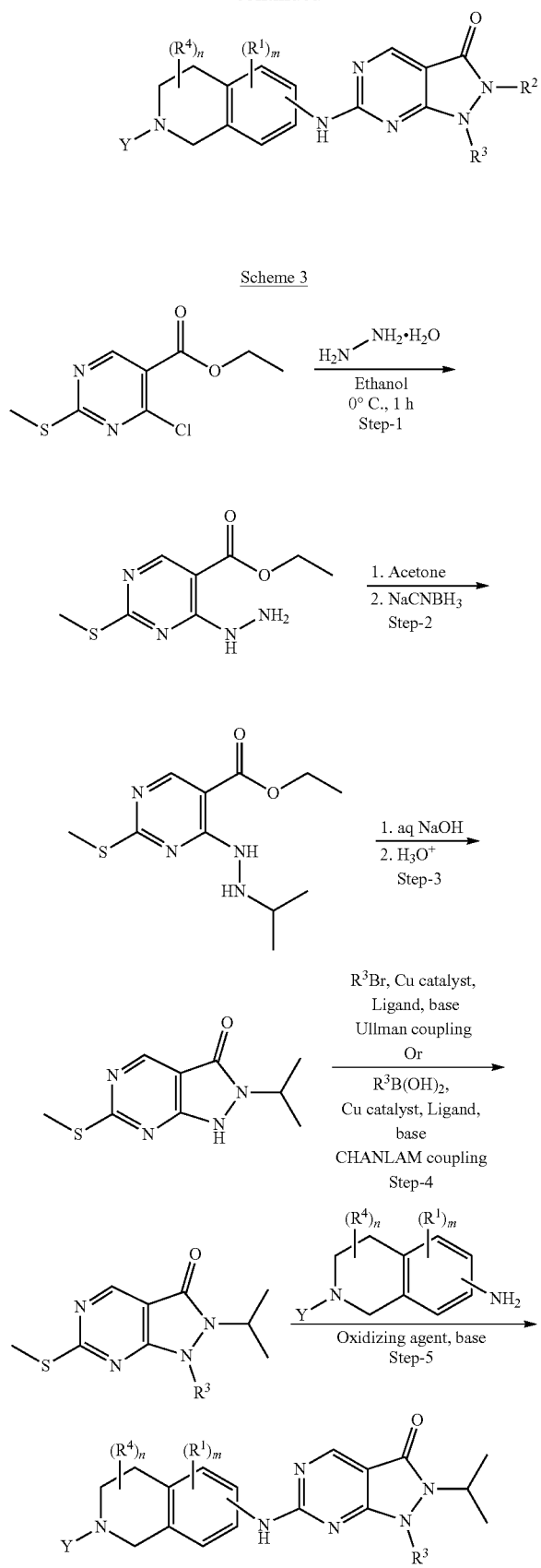

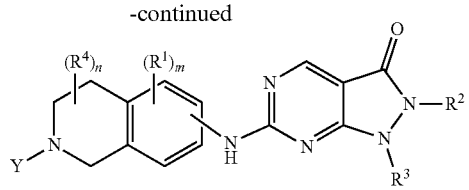

Scheme 5

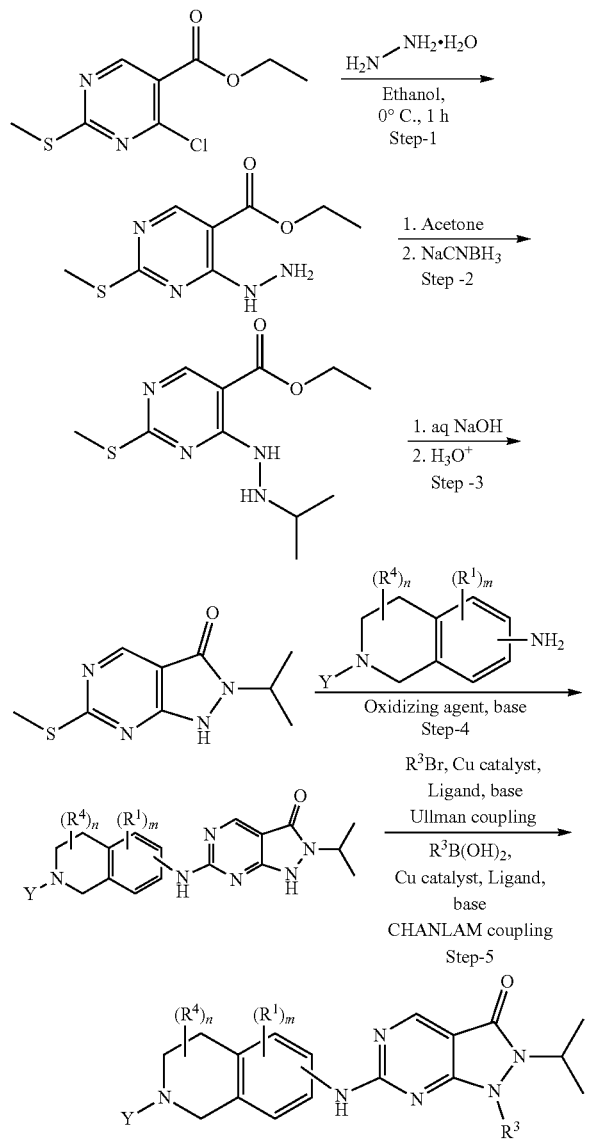

wherein m, n, Y, $R^1$, $R^2$, $R^3$, and $R^4$ are as defined herein for Formula (I). Particular examples are provided in the Example Section below.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of Formula (I), (II) or (III) or any embodiment, variation or aspect thereof (collectively, a compound of Formula (I), (II) or (III) or the present compounds or the compounds detailed or described herein) or a pharmaceutically acceptable salt thereof, to the individual. Further provided herein is a method of treating a proliferative disease in an individual, comprising administering an effective amount of a compound of Formula (I), (II) or (III) or a pharmaceutically acceptable salt thereof, to the individual. Also provided herein is a method of treating cancer in an individual comprising administering an effective amount of a compound of Formula (I), (II) or (III) or a pharmaceutically acceptable salt thereof, to the individual. In some embodiments, the compound is administered to the individual according to a dosage and/or method of administration described herein.

In some embodiments, the cancer in the individual has one or more TP53 gene mutations or expresses mutant p53. In some embodiments, the cancer in the individual that has one or more TP53 gene mutations or expresses mutant p53 is glioblastoma. TP53 is the human gene that encodes p53. In some embodiments, provided herein is a method of treating a cancer in an individual, comprising (a) selecting the individual for treatment based on (i) the presence of one or more mutations of the TP53 gene in the cancer, or (ii) expression of mutant p53 in the cancer, and administering an effective amount of a compound of Formula (I), (II) or (III) or a pharmaceutically acceptable salt thereof, to the individual. In some embodiments, the cancer is assayed for the expression of mutant p53. In some embodiments, the TP53 gene of the cancer is sequenced to detect the one or more mutations. In some embodiments, the TP53 gene is sequenced by biopsying the cancer and sequencing the TP53 gene from the biopsied cancer. In some embodiments, the TP53 gene is sequenced by sequencing circulating-tumor DNA (ctDNA) from the individual.

In some embodiments, provided herein is a method of using a compound of Formula (I), (II) or (III) or any embodiment in the manufacture of a medicament for treatment of a disease. In some embodiments, provided herein is a method of using a compound of Formula (I), (II) or (III) or any embodiment in the manufacture of a medicament for treatment of cancer.

In some embodiments, a compound of Formula (I), (II) or (III) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma, cutaneous T cell lymphoma, Hodgkin's lymphoma, non-Hodgkin's lymphoma, cancer of the adrenal cortex, ACTH-producing tumors, lung cancer, including small cell carcinoma and nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, glioblastoma, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the compounds and compositions described herein suppress $G_2$-M checkpoint in a cell (such as a cancer cell). In some embodiments, the cancer cell is a cancer cell from any of the cancer types described herein. Suppression of the $G_2$-M DNA damage checkpoint results in premature mitosis of the cell, and consequently apoptosis. In some embodiments, provided herein is a method of suppressing the $G_2$-M DNA damage checkpoint in a cell comprising administering an effective amount of a compound of Formula (I), (II) or (III) or a pharmaceutically acceptable salt thereof, to the cell. In some embodiments, the $G_2$-M DNA damage checkpoint is suppressed in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, the $G_2$-M DNA damage checkpoint is suppressed in up to about 99%, up to about 98%, up to about 97%, up to about 96%, up to about 95%, up to about 90%, up to about 85%, or up to about 80% of cells in the cell population.

In some embodiments, provided herein is a method of inducing premature mitosis in a cell comprising administering an effective amount of a compound of Formula (I), (II) or (III) or a pharmaceutically acceptable salt thereof, to the cell. In some embodiments, premature mitosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, premature mitosis is induced in up to about 99%, up to about 98%, up to about 97%, up to about 96%, up to about 95%, up to about 90%, up to about 85%, or up to about 80% of cells in the cell population.

In some embodiments, provided herein is a method of inducing apoptosis in a cell comprising administering an effective amount of a compound of Formula (I), (II) or (III) or a pharmaceutically acceptable salt thereof, to the cell. In some embodiments, apoptosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, apoptosis is induced in up to about 99%, up to about 98%, up to about 97%, up to about 96%, up to about 95%, up to about 90%, up to about 85%, or up to about 80% of cells in the cell population.

In some embodiments, provided herein is a method of inhibiting Wee1 in a cell comprising administering an effective amount of a compound of Formula (I), (II) or (III) or a pharmaceutically acceptable salt thereof, to the cell. In some embodiments, Wee1 is inhibited by about 10% or more, about 20% or more, about 30% or more, about 40% or more, about 50% or more, about 60% or more, about 70% or more, about 75% or more, about 80% or more, about 90% or more, about 95% or more, about 96% or more, about 97% or more, about 98% or more, or about 99% or more. In some embodiments, Wee1 is inhibited up to about 99%, up to about 98%, up to about 97%, up to about 96%, up to about 95%, up to about 90%, up to about 85%, up to about 80%, up to about 70%, or up to about 60%. In some embodiments, the activity of Wee1 is measured according to a kinase assay.

In some embodiments, provided herein is a method of inhibiting Wee1 comprising contacting Wee1 with an effective amount of a compound of Formula (I), (II) or (III) or a pharmaceutically acceptable salt thereof. In some embodiments, a compound of Formula (I), (II) or (III) or a pharmaceutically acceptable salt thereof binds to Wee1 with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, a compound of Formula (I), (II) or (III) or a pharmaceutically acceptable salt thereof binds to Wee1 with an $IC_{50}$ between 0.1 nM and 1 nM, between 1 nM and 5 nM, between 5 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 µM. In some embodiments, the $IC_{50}$ is measured according to a kinase assay. In some embodiments, the $IC_{50}$ is measured according to a cell cytotoxicity assay.

In some embodiments, provided herein is a method of inhibiting the proliferation of a cell, comprising contacting the cell with an effective amount of a compound of Formula (I), (II) or (III) or a pharmaceutically acceptable salt thereof. In some embodiments, a compound of Formula (I), (II) or (III) or a pharmaceutically acceptable salt thereof is effective in inhibiting the proliferation of the cell with an $IC_{50}$ of less than 5 µM, less than 2 µM, less than 1 µM, less than 900 nM, less than 800 nM, less than 700 nM, less than 600 nM, less than 500 nM, less than 400 nM, less than 300 nM, less than 200 nM, less than 100 nM, or less than 50 nM. In some embodiments, a compound of Formula (I), (II) or (III) or a pharmaceutically acceptable salt is effective in inhibiting the proliferation of the cell with an $IC_{50}$ between 10 nM and 20 nM, between 20 nM and 50 nM, between 50 nM and 100 nM, between 100 nM and 500 nM, between 500 nM and 1 µM, between 1 µM and 2 µM, or between 2 µM and 5 µM. In some embodiments, the $IC_{50}$ is measured according to a cell proliferation assay.

Combination Therapy

As provided herein, the presently disclosed compounds or a salt thereof may activate the immune system, for example by inducing apoptosis or suppressing mitosis of cancer cells. Accordingly, the present compounds or a salt thereof may be used in combination with other anti-cancer agents to enhance tumor immunotherapy. In some embodiments, provided herein is a method of treating a disease in an individual comprising administering an effective amount of a compound of Formula (I), (II) or (III) or any embodiment, variation or aspect thereof (collectively, a compound of Formula (I), (II) or (III) or the present compounds or the compounds detailed or described herein) or a pharmaceutically acceptable salt thereof, and an additional therapeutic agent to the individual. In some embodiments, the disease is a proliferative disease such as cancer.

In some embodiments, the additional therapeutic agent is a cancer immunotherapy agent. In some embodiments, the additional therapeutic agent is a chemotherapeutic agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor. In some embodiments, the additional chemotherapeutic agent is a DNA alkylating agent, a platinum-based chemotherapeutic agent, a kinase inhibitor or a DNA damage repair (DDR) pathway inhibitor. In some embodiments, the additional chemotherapeutic agent is a DNA alkylating agent. In some embodiments, the additional chemotherapeutic agent is a platinum-based chemotherapeutic agent. In some embodiments, the additional chemotherapeutic agent is a kinase inhibitor. In some embodiments, the additional chemotherapeutic agent is a DNA damage repair (DDR) pathway inhibitor.

In another aspect, provided herein is a combination therapy for the treatment of a disease, such as cancer. In some embodiments, provided herein is a method of treating a disease in an individual comprising administering an effective amount of a compound of Formula (I), (II) or (III) or any embodiment, variation or aspect thereof (collectively, a compound of Formula (I), (II) or (III) or the present compounds or the compounds detailed or described herein) or a pharmaceutically acceptable salt thereof, in combination with a radiation therapy.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of an additional chemotherapeutic agent. In some embodiments, the chemotherapeutic agent is a kinase inhibitor or an agent that inhibits one or more DNA damage repair (DDR) pathways. In some embodiments, a compound of Formula (I), (II) or (III) or a pharmaceutically acceptable salt thereof is administered prior to, after, or simultaneously co-administered with the additional chemotherapeutic agent. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the additional chemotherapeutic agent.

Examples of chemotherapeutic agents that can be used in combination with a compound of Formula (I), (II) or (III) or a pharmaceutically acceptable salt thereof include DNA-targeted agents, a DNA alkylating agent (such as cyclophosphamide, mechlorethamine, chlorambucil, melphalan, dacarbazine, temozolomide or nitrosoureas), a topoisomerase inhibitor (such as a Topoisomerase I inhibitor (e.g., irinotecan or topotecan) or a Topoisomerase II inhibitor (e.g., etoposide or teniposide)), an anthracycline (such as daunorubicin, doxorubicin, epirubicin, idarubicin, mitoxantrone, or valrubicin), a histone deacetylase inhibitor (such as vorinostat or romidepsin), a bromodomain inhibitor, other epigenetic inhibitors, a taxane (such as paclitaxel or docetaxel), a kinase inhibitor (such as bortezomib, erlotinib, gefitinib, imatinib, vemurafenib, or vismodegib), an anti-angiogenic inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof. In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a kinase inhibitor (such as bortezomib, erlotinib, gefitinib, imatinib, vemurafenib, or vismodegib). In some embodiments, a compound of Formula (I), (II) or (III) or a pharmaceutically acceptable salt thereof is administered prior to, after, or simultaneously co-administered with the kinase inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a DNA damaging agent. In some embodiments, a compound of Formula (I), (II) or (III) or a pharmaceutically acceptable salt thereof is administered prior to, after, or simultaneously co-administered with the DNA damaging agent. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a DNA alkylating agent (such as cyclophosphamide, mechlorethamine, chlorambucil, melphalan, dacarbazine, temozolomide or nitrosoureas). In some embodiments, a compound of Formula (I), (II) or (III) or a pharmaceutically acceptable salt thereof is administered prior to, after, or simultaneously co-administered with the DNA alkylating agent. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, a compound of Formula (I), (II) or (III) or a pharmaceutically acceptable salt thereof is administered prior to, after, or simultaneously co-administered with the topoisomerase inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, a compound of Formula (I), (II) or (III) or a pharmaceutically acceptable salt thereof is administered prior to, after, or simultaneously co-administered with the anthracycline. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a histone deacetylase inhibitor (such as vorinostat or romidepsin). In some embodiments, a compound of Formula (I), (II) or (III) or a pharmaceutically acceptable salt thereof is administered prior to, after, or simultaneously co-administered with the histone deacetylase inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a taxane (such as paclitaxel or docetaxel). In some embodiments, a compound of Formula (I), (II) or (III) or a pharmaceutically acceptable salt thereof is administered prior to, after, or simultaneously co-administered with the taxane. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, a compound of Formula (I), (II) or (III) or a pharmaceutically acceptable salt thereof is administered prior to, after, or simultaneously co-administered with the nucleotide analog or precursor analog. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a platinum-based chemotherapeutic agent (such as cisplatin, carboplatin, or oxaliplatin). In some embodiments, a compound of Formula (I), (II) or (III) or a pharmaceutically acceptable salt thereof is administered prior to, after, or simultaneously co-administered with the platinum-based chemotherapeutic agent. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of pemetrexed. In some embodiments, a compound of Formula (I), (II) or (III) or a pharmaceutically acceptable salt thereof is administered prior to, after, or simultaneously co-administered with the pemetrexed. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a DDR pathway inhibitor. In some embodiments, a compound of Formula (I), (II) or (III) or a pharmaceutically acceptable salt thereof is administered prior to, after, or simultaneously co-administered with the DDR pathway inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of a PARP inhibitor (such as olaparib, rucaparib, niraparib, or talazoparib). In some embodiments, a compound of Formula (I), (II) or (III) or a pharmaceutically acceptable salt thereof is administered prior to, after, or simultaneously co-administered with the PARP inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of an ATM protein inhibitor. In some embodiments, a compound of Formula (I), (II) or (III) or a pharmaceutically acceptable salt thereof is administered prior to, after, or simultaneously co-administered with the ATM protein inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of an ATR protein inhibitor. In some embodiments, a compound of Formula (I), (II) or (III) or a pharmaceutically acceptable salt thereof is administered prior to, after, or simultaneously co-administered with the ATR protein inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, provided herein is a method of treating a disease in an individual comprising (a) administering an effective amount of a compound of Formula (I), (II) or (III) or any embodiment, variation or aspect thereof (collectively, Formula (I), (II) or (III)) or a pharmaceutically acceptable salt thereof, and (b) administering an effective amount of an Chk1 inhibitor. In some embodiments, a compound of Formula (I), (II) or (III) or a pharmaceutically acceptable salt thereof is administered prior to, after, or simultaneously co-administered with the Chk1 inhibitor. In some embodiments, a compound of Formula (I), (II) or (III) or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In another aspect, provided herein is a combination therapy in which a compound of Formula (I), (II) or (III) or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (II) or (III) or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (I), (II) or (III) or a salt thereof and an anti-PD-1 antibody. In another embodiment, the subject is administered a compound of Formula (I), (II) or (III) or a salt thereof and an anti-PD-L1 antibody. In yet another embodiment, the subject is administered a compound of formula (I) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (I), (II) or (III) or a salt thereof and an anti-PD-1 antibody to a subject. In further embodiments, a compound of Formula (I), (II) or (III) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (I), (II) or (III) or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (I), (II) or (III) or a salt thereof and an anti-PD-L1 antibody to a subject. In further embodiments, a compound of Formula (I), (II) or (III) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (II) or (III) or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (II) or (III) or a salt thereof can be administered sequentially, such as anti-CTLA-4 antibody being administered first and a compound of Formula (I), (II) or (III) or a salt thereof second, or a compound of formula Formula (I), (II) or (III) or a salt thereof being administered first and anti-CTLA-4 antibody second. Additionally or alternatively, an anti-PD-1 antibody and a compound of Formula (I), (II) or (III) or a salt thereof can be administered sequentially, such as anti-PD-1 antibody being administered first and a compound of Formula (I), (II) or (III) or a salt thereof second, or a compound of Formula (I), (II) or (III) or a salt thereof being administered first and anti-PD-1 antibody second. Additionally or alternatively, an anti-PD-L1 antibody and a compound of Formula (I), (II) or (III) or a salt thereof can be administered sequentially, such as anti-PD-L1 antibody being administered first and a compound of Formula (I), (II) or (III) or a salt thereof second, or a compound of Formula (I), (II) or (III) or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (I), (II) or (III) or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (I), (II) or (III) or a salt thereof can also be further combined with standard cancer treatments. For example, a compound of Formula (I), (II) or (III) or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of Formula (I), (II) or (III) or a salt thereof include radiation, surgery, or hormone deprivation. Angiogenesis inhibitors can also be combined with a compound of Formula (I), (II) or (III) or a salt thereof. Inhibition of angiogenesis leads to tumor cell death, which can be a source of tumor antigen fed into host antigen presentation pathways.

In another example, a compound of Formula (I), (II) or (III) or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (II) or (III) or a salt thereof. In an exemplary embodiment, a treatment of a hyperproliferative disease (e.g., a cancer tumor) can include an anti-cancer antibody in combination with a compound of Formula (I), (II) or (III) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (II) or (III) or a salt thereof.

In some embodiments, a compound of Formula (I), (II) or (III) or a salt thereof can be combined with an anti-CD73 therapy, such as an anti-CD73 antibody.

In yet further embodiments, a compound of Formula (I), (II) or (III) or a salt thereof is administered in combination with another Wee1 inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Example S-1: Synthesis of 1-(5-fluoro-6-(2-fluoropropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one (Compound No.1.1)

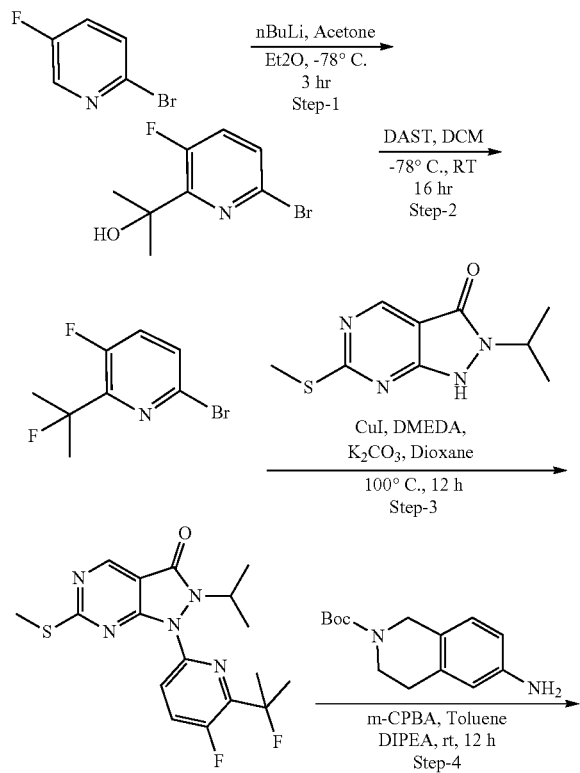

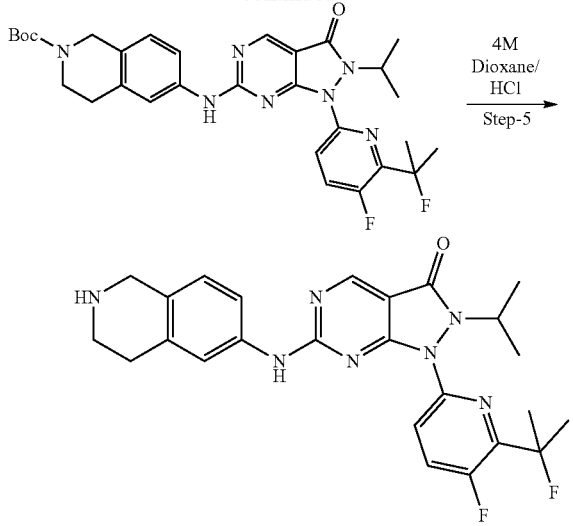

Step-1: Synthesis of 2-(6-bromo-3-fluoropyridin-2-yl)propan-2-ol: To a solution of 2-bromo-5-fluoropyridine (2 g, 11.36 mmol) in diethyl-ether (30 mL) was slowly added n-butyl lithium (2.5 M in hexane, 7.8 mL, 12.49 mmol) at −78° C. under a nitrogen atmosphere. The resulting yellow reaction mixture was stirred at −78° C. for 2 hours and dry acetone (1.0 mL, 13.63 mmol) was added over 30 minutes. Stirring was continued at −78° C. for 1 hour. HCl (2N, 50 mL) was added and the reaction mixture was warmed to 0° C. The pH of the mixture was adjusted to 7 with 2N HCl solution. The reaction mixture was diluted with ethyl acetate and washed with brine, dried over sodium sulfate to afford crude product, which was purified by flash chromatography [silica gel 100-200 mesh; elution 0-50% EtOAc in hexane] to afford the desired product 2-(6-bromo-3-fluoro-pyridin-2-yl)-propan-2-ol (1.5 g, 56.81%) as yellow semi solid. LCMS: 234.1 [M+2]$^+$.

Step-2: Synthesis of 6-bromo-3-fluoro-2-(2-fluoropropan-2-yl)pyridine: To a stirred solution of 2-(6-bromo-3-fluoropyridin-2-yl)propan-2-ol (0.500 g, 2.14 mmol, 1.0 eq) in DCM (10 mL), DAST (0.38 mL, 2.36 mmol, 1.1 eq) was added at −78° C. The reaction mixture was stirred at RT for 12 h. After completion of reaction, the reaction mixture was quenched with saturated sodium bicarbonate solution and was extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-10% EtOAc in hexane] to afford the desired compound, (200 mg, 39.66%) as colorless liquid. LCMS: 236.1 [M+2]$^+$.

Step-3: Synthesis of 1-(5-fluoro-6-(2-fluoropropan-2-yl)pyridin-2-yl)-2-isopropyl-6-(methylthio)-1,2-dihydro-3H-pyrazolo[3,4-d]pyrimidin-3-one: To a stirred solution of 2-isopropyl-6-(methylthio)-1,2-dihydro-3H-pyrazolo[3,4-d]pyrimidin-3-one (224 mg, 1.0 mmol, 1.0 eq) and 6-bromo-3-fluoro-2-(2-fluoropropan-2-yl)pyridine (236 mg, 1.0 mmol, 1.0 eq) in dioxane (10 mL) were added potassium carbonate (276 mg, 2.0 mmol, 2.0 eq) and the resulting mixture was purged with nitrogen for 10 min followed by addition of copper iodide (38 mg, 0.2 mmol, 0.2 eq), and N,N'-dimethylethylenediamine (DMEDA) (0.05 mL, 0.4 mmol, 0.4 eq) and again purged with nitrogen for 10 min, then stirred at 90° C. overnight. After completion of reaction, the reaction mixture was diluted with water and extracted with EtOAc (50 mL×2). Combined organic layer was washed with water (50 mL) and brine solution (50 mL), dried over anhydrous sodium sulphate and concentrated under reduced pressure to afford crude product, which was purified by flash chromatography to afford the desired compound (200 mg, 52.6%) as an off-white solid. LCMS: 380.2 [M+1]+.

Step-4: Synthesis of tert-butyl 6-((1-(5-fluoro-6-(2-fluoropropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(5-fluoro-6-(2-fluoropropan-2-yl)pyridin-2-yl)-2-isopropyl-6-(methylthio)-1,2-dihydro-3H-pyrazolo[3,4-d]pyrimidin-3-one (190 mg, 0.5 mmol, 1.0 eq) in toluene (2.0 mL) was added m-CPBA (245 mg, 1.0 mmol, 2.0 eq) and allowed to stir at RT for 1 h. Tert-butyl 6-amino-3,4-dihydroisoquinoline-2(1H)-carboxylate (149 mg, 0.6 mmol, 1.2 eq) and DIPEA (0.44 mL, 2.5 mmol, 5.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (100 mg, 34.6%) as an off-white solid. LCMS: 580.3 [M+1]+.

Step-5: Synthesis of 1-(5-fluoro-6-(2-fluoropropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one: Tert-butyl 6-((1-(5-fluoro-6-(2-fluoropropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (100 mg, 0.17 mmol, 1.0 eq) was dissolved in dioxane (1.0 mL), followed by dropwise addition of 4.0 M-HCl (1.0 mL) and allowed to stir at RT 2 h. After completion of reaction, solvent was evaporated to give the crude product, which was purified reverse phase chromatography to afford the desired compound (45 mg, 55.5%) as an off-white solid. LCMS: 457.3 [M+1]+; 1H NMR (400 MHz, DMSO-d6, Formate salt): δ 10.24 (br s, 1H) 8.82 (s, 1H) 8.69 (br s, 1H) 8.39 (d, J=7.45 Hz, 1H) 8.28 (br s, 1H) 8.10 (t, J=9.65 Hz, 1H) 7.96 (d, J=8.33 Hz, 2H) 7.55 (br s, 1H) 7.35-7.49 (m, 2H) 7.03 (d, J=8.33 Hz, 1H) 4.11-4.22 (m, 2H) 3.96 (br s, 2H) 3.08-3.17 (m, 2H) 2.79 (br s, 2H) 1.77 (s, 3H) 1.71 (s, 3H) 1.33 (d, J=6.58 Hz, 6H).

Example S-2: Synthesis of 2-cyclopropyl-1-(5-fluoro-6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No.1.2)

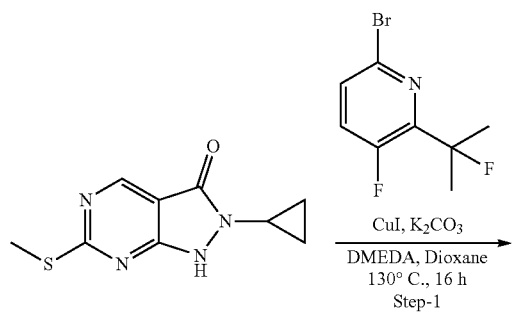

Step-1: Synthesis of 2-cyclopropyl-1-(5-fluoro-6-(2-fluoropropan-2-yl)pyridin-2-yl)-6-(methylthio)-1,2-dihydro-3H-pyrazolo[3,4-d]pyrimidin-3-one: To a stirred solution of 2-cyclopropyl-6-(methylthio)-1,2-dihydro-3H-pyrazolo[3,4-d]pyrimidin-3-one (230 mg, 1.03 mmol, 1.0 eq) and 6-bromo-3-fluoro-2-(2-fluoropropan-2-yl)pyridine (291 mg, 1.24 mmol, 1.2 eq) in dioxane (5 mL) was added potassium carbonate (285 mg, 2.06 mmol, 2.0 eq) and the resulting mixture was purged with nitrogen for 10 min followed by addition of copper iodide (39.4 mg, 0.20 mmol, 0.2 eq), and N,N'-dimethylethylenediamine (DMEDA) (0.04 mL, 0.41 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (180 mg, 48.74%) as yellow semi solid. LCMS: 378.11 [M+1]+.

Step-2: Synthesis of tert-butyl 6-((2-cyclopropyl-1-(5-fluoro-6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate: To a stirred solution of 2-cyclopropyl-1-(5-fluoro-6-(2-fluoropropan-2-yl)pyridin-2-yl)-6-(methylthio)-1,2-dihydro-3H-pyrazolo[3,4-d]pyrimidin-3-one (190 mg, 0.50 mmol, 1.0 eq) in toluene (3.0 mL) was added m-CPBA (174 mg, 1.00 mmol, 2.0 eq) and allowed to stir at RT for 60 minutes. Tert-butyl 6-amino-3,4-dihydroisoquinoline-2(1H)-carboxylate (150 mg, 0.60 mmol, 1.2 eq) and DIPEA (0.4 mL, 0.55 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (130 mg, 44.77%) as light yellow solid. LCMS: 578.3 [M+1]$^+$.

Step-3: Synthesis of 2-cyclopropyl-1-(5-fluoro-6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one dihydrochloride: Tert-butyl 6-((2-cyclopropyl-1-(5-fluoro-6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (130 mg, 0.22 mmol, 1.0 eq) was dissolved in dioxane (2 mL), followed by dropwise addition of 4.0 M-HCl in dioxane (3 mL) and allowed to stir at RT for 2 h. After completion of reaction, the reaction mixture was filtered and dried under reduced pressure; crude product obtained was purified by reverse phase chromatography to afford the desired compound (2 mg, 20.48%) as an off-white solid. LCMS: 478.3 [M+1]$^+$; $^1$H NMR (400 MHz, DMSO-d$_6$, HCl salt): δ 10.17 (br s, 1H) 8.79 (s, 1H) 8.31 (br s, 1H) 8.04-8.18 (m, 2H) 7.96 (dd, 1H) 7.56 (br s, 1H) 7.40 (d, J=7.89 Hz, 1H) 7.02 (d, 1H) 3.91 (br s, 2H) 3.14 (br s, 2H) 3.07 (br s, 2H) 2.75 (br s, 2H) 1.77 (s, 3H) 1.72 (s, 3H).

Example S-3: Synthesis of 1-(5-fluoro-6-(2-fluoropropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (Compound No.1.4)

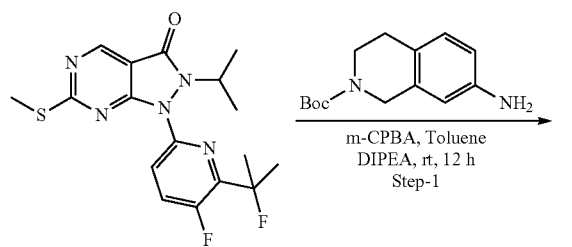

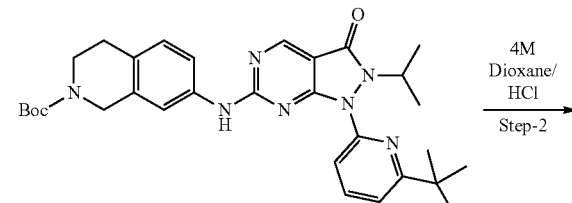

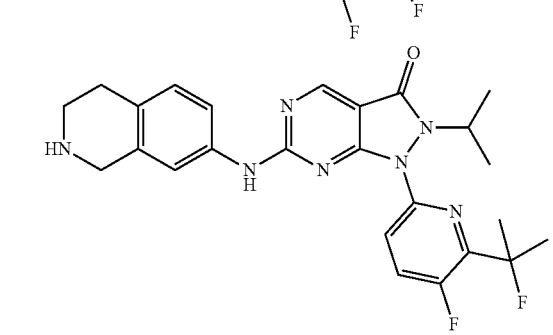

Step-1: Synthesis tert-butyl 7-((1-(5-fluoro-6-(2-fluoropropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(5-fluoro-6-(2-fluoropropan-2-yl)pyridin-2-yl)-2-isopropyl-6-(methylthio)-1,2-dihydro-3H-pyrazolo[3,4-d]pyrimidin-3-one (130 mg, 0.3 mmol, 1.0 eq) in toluene (2.0 mL) was added m-CPBA (148 mg, 0.6 mmol, 2.0 eq) and allowed to stir at RT for 1 h. Tert-butyl 7-amino-3,4-dihydroisoquinoline-2(1H)-carboxylate (149 mg, 0.6 mmol, 1.2 eq) and DIPEA (0.27 mL, 1.5 mmol, 5.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (120 mg, 68.9%) as an off-white solid. LCMS: 580.4 [M+1]$^+$.

Step-2: Synthesis of 1-(5-fluoro-6-(2-fluoropropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one: Tert-butyl 7-((1-(5-fluoro-6-(2-fluoropropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 0.21 mmol, 1.0 eq) was dissolved in dioxane (2.0 mL), followed by dropwise addition of 4.0 M-HCl in dioxane (2.0 mL) and allowed to stir at RT for 1 h. After completion of reaction, solvent was evaporated to give the crude product, which was purified reverse phase chromatography to afford the desired compound (32 mg, 32.0%) as an off-white solid as formate salt. LCMS: 480.5 [M+1]$^+$; $^1$H NMR (400 MHz, DMSO-d$_6$, Formate salt): δ 10.25 (br sbr s, 1H) 8.82 (s, 1H) 8.28 (br s, 1H) 8.05-8.13 (m, 1H) 7.97 (d, J=6.58 Hz, 1H) 7.52 (br sbr s, 1H) 7.38 (d, J=8.33 Hz, 1H) 7.06 (d, J=7.89 Hz, 1H) 4.12-4.19 (m, 2H) 3.96 (br sbr s, 2H) 3.07 (br sbr s, 2H) 2.73 (br sbr s, 2H) 1.77 (s, 3H) 1.71 (s, 3H) 1.34 (d, J=6.58 Hz, 6H).

Example S-4: Synthesis of 1-(2-cyclopropylthiazol-4-yl)-2-isopropyl-6-((1,2,3,4-tetrahydroisoquinolin-6-yl)amino)-1,2-dihydro-3H-pyrazolo[3,4-d]pyrimidin-3-one (Compound No.1.464)

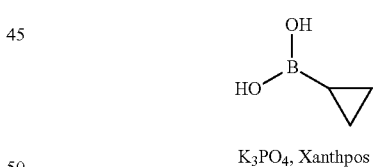

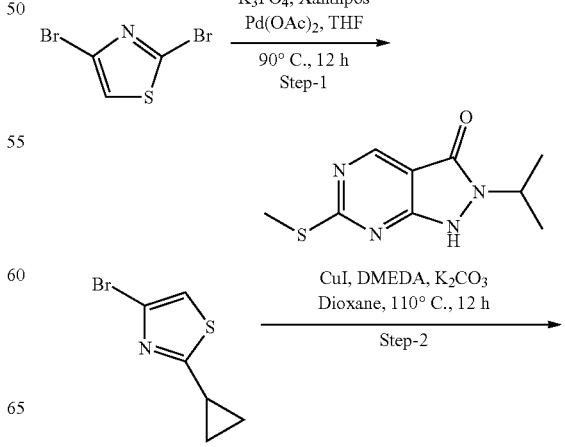

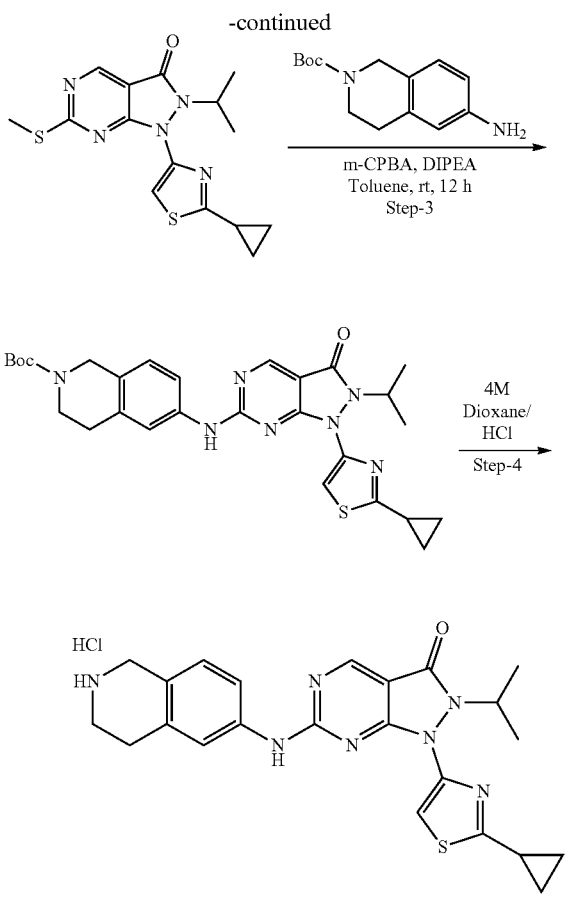

Step-1: Synthesis of 4-bromo-2-cyclopropylthiazole: To a stirred solution of 2,4-dibromothiazole (1.0 g, 4.11 mmol, 1.0 eq) and cyclopropylboronic acid (424 mg, 4.93 mmol, 1.2 eq) in dioxane (12 mL) were added K$_3$PO$_4$ (1.11 g, 8.08 mmol, 2 eq) and the resulting mixture was purged with nitrogen for 10 min, followed by addition of Xanthphos (119 mg, 0.20 mmol, 0.2 eq), and Pd(OAc)$_2$ (46 mg, 0.20 mmol, 0.4 eq) and again purged with nitrogen for 10 min, stirred at 90° C. overnight. After completion of reaction, the reaction mixture was diluted with water and extracted with EtOAc (250 mL×2). The combined organic layers were washed with water (250 mL) and brine solution (250 mL), dried over anhydrous sodium sulphate and concentrated under reduced pressure to afford crude product, which was purified by flash chromatography to afford the desired compound (600 mg, 71.42%) as an off-white solid. LCMS: 204.1 [M+1]$^+$.

Step-2: Synthesis of 1-(2-cyclopropylthiazol-4-yl)-2-isopropyl-6-(methylthio)-1,2-dihydro-3H-pyrazolo[3,4-d]pyrimidin-3-one: To a stirred solution of 2-isopropyl-6-(methylthio)-1,2-dihydro-3H-pyrazolo[3,4-d]pyrimidin-3-one (659 mg, 2.93 mmol, 1.0 eq) and 4-bromo-2-cyclopropylthiazole (600 mg, 2.93 mmol, 1.0 eq) in dioxane (12 mL) were added potassium carbonate (810 mg, 5.86 mmol, 2.0 eq) and the resulting mixture was purged with nitrogen for 10 min, followed by addition of copper iodide (112 mg, 0.58 mmol, 0.2 eq), and N,N'-dimethylethylenediamine (DMEDA) (0.13 mL, 1.17 mmol, 0.4 eq) and again purged with nitrogen for 10 min, then stirred at 90° C. overnight. After completion of reaction, the reaction mixture was diluted with water and extracted with EtOAc (250 mL×2). The combined organic layers were washed with water (250 mL) and brine solution (250 mL), dried over anhydrous sodium sulphate and concentrated under reduced pressure to afford crude product, which was purified by flash chromatography to afford the desired compound (256 mg, 25.07%) as an off-white solid. LCMS: 348.1 [M+1]$^+$.

Step-3: Synthesis of tert-butyl 6-((1-(2-cyclopropylthiazol-4-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirring solution of 1-(2-cyclopropylthiazol-4-yl)-2-isopropyl-6-(methylthio)-1,2-dihydro-3H-pyrazolo[3,4-d]pyrimidin-3-one (128 mg, 0.36 mmol, 1 eq) in toluene (3.0 mL) was added m-CPBA (127 mg, 0.73 mmol, 2.0 eq) and allowed to stir at RT for 1 h. Tert-butyl 6-amino-3,4-dihydroisoquinoline-2(1H)-carboxylate (91 mg, 0.36 mmol, 1.0 eq) and DIPEA (0.25 mL, 1.47 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (86 mg, 42.62%) as an off-white solid. LCMS: 548.3 [M+1]$^+$.

Step-4: Synthesis of 1-(2-cyclopropylthiazol-4-yl)-2-isopropyl-6-(((1,2,3,4-tetrahydroisoquinolin-6-yl)amino)-1,2-dihydro-3H-pyrazolo[3,4-d]pyrimidin-3-one hydrochloride: Tert-butyl 6-((1-(2-cyclopropylthiazol-4-yl)-2-isopropyl-3-oxo-2,3-dihydro-1H-pyrazolo[3,4-d]pyrimidin-6-yl) amino)-3,4-dihydroisoquinoline-2(1H)-carboxylate (86 mg, 0.15 mmol, 1.0 eq) was dissolved in dioxane (1 mL), followed by dropwise addition of 4.0 M-HCl in dioxane (1 mL) and allowed to stir at RT for 1 h. After completion of reaction, the reaction mixture was filtered and dried under reduced pressure to afford the desired compound (30 mg, 39.47%) as an off-white solid. LCMS: 448.3 [M+1]$^+$; $^1$H NMR (400 MHz, DMSO-d$_6$, HCl salt): δ 10.27 (br sbr s, 1H) 9.20 (br sbr s, 2H) 8.84 (s, 1H) 7.90 (s, 1H) 7.67 (br sbr s, 1H) 7.48 (d, J=7.89 Hz, 1H) 7.11 (d, J=8.77 Hz, 1H) 4.28 (dt, J=13.59, 6.80 Hz, 1H) 4.19 (br sbr s, 2H) 3.35 (br sbr s, 2H) 2.92 (br sbr s, 2H) 1.17-1.27 (m, 6H) 1.07-1.17 (m, 2H) 0.88-0.97 (m, 2H).

Example S-5: Synthesis of 1-(2-cyclopropylthiazol-4-yl)-2-isopropyl-6-((1,2,3,4-tetrahydroisoquinolin-7-yl)amino)-1,2-dihydro-3H-pyrazolo[3,4-d]pyrimidin-3-one (Compound No.1.465)

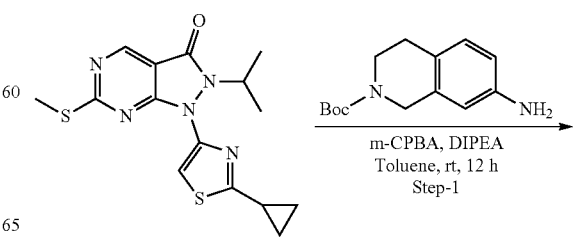

-continued

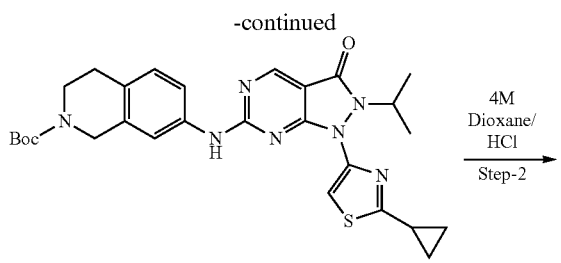

Step-1: Synthesis of tert-butyl 7-((1-(2-cyclopropylthiazol-4-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirring solution of 1-(2-cyclopropylthiazol-4-yl)-2-isopropyl-6-(methylthio)-1,2-dihydro-3H-pyrazolo[3,4-d]pyrimidin-3-one (128 mg, 0.36 mmol, 1 eq) in toluene (3.0 mL) was added m-CPBA (127 mg, 0.73 mmol, 2.0 eq) and allowed to stir at RT for 1 h. Tert-butyl 7-amino-3,4-dihydroisoquinoline-2(1H)-carboxylate (91 mg, 0.36 mmol, 1.0 eq) and DIPEA (0.25 mL, 1.47 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (86 mg, 51.54%) as an off-white solid. LCMS: 548.3 [M+1]$^+$.

Step-2: Synthesis of 1-(2-cyclopropylthiazol-4-yl)-2-isopropyl-6-((1,2,3,4-tetrahydroisoquinolin-7-yl)amino)-1,2-dihydro-3H-pyrazolo[3,4-d]pyrimidin-3-one hydrochloride: Tert-butyl 7-((1-(2-cyclopropylthiazol-4-yl)-2-isopropyl-3-oxo-2,3-dihydro-1H-pyrazolo[3,4-d]pyrimidin-6-yl)amino)-3,4-dihydroisoquinoline-2(1H)-carboxylate (104 mg, 0.18 mmol, 1.0 eq) was dissolved in dioxane (1.5 mL), followed by dropwise addition of 4.0 M-HCl in dioxane (1.5 mL) and allowed to stir at RT for 1 h. After completion of reaction, the reaction mixture was filtered and dried under reduced pressure to afford the desired compound (20 mg, 17.68%) as an off-white solid. LCMS: 448.3 [M+1]$^+$; $^1$H NMR (400 MHz, DMSO-$d_6$, HCl salt): δ 10.28 (br s, 1H) 9.40 (br s, 2H) 8.83 (s, 1H) 7.90 (s, 1H) 7.65 (br., 1H) 7.47 (d, J=7.89 Hz, 1H) 7.12 (d, J=8.77 Hz, 1H) 4.21-4.33 (m, 2H) 4.17 (br s, 2H) 3.33 (br s, 2H) 2.94 (br s, 2H) 1.22 (d, J=7.02 Hz, 6H) 1.16 (dd, J=8.11, 2.41 Hz, 2H) 0.94 (br s, 2H).

Example S-6: Synthesis of 2-cyclopropyl-6-((1,1-dimethyl-1,2,3,4-tetrahydroisoquinolin-6-yl)amino)-1-(5-fluoro-6-(2-fluoropropan-2-yl)pyridin-2-yl)-1,2-dihydro-3H-pyrazolo[3,4-d]pyrimidin-3-one (Compound No.1.5)

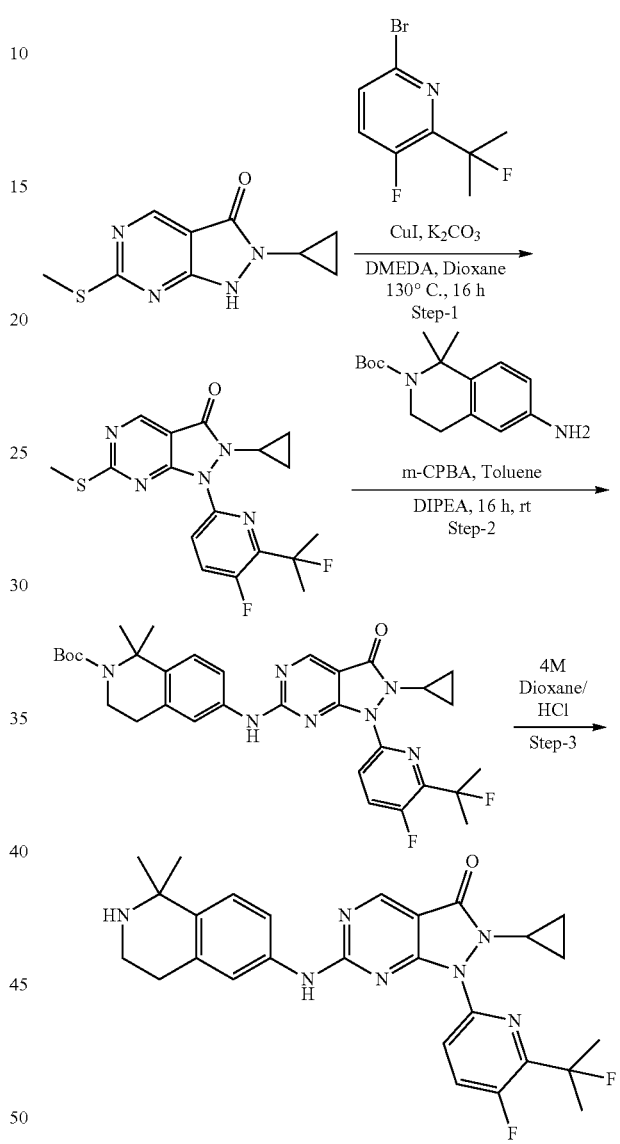

Step-1: Synthesis of 2-cyclopropyl-1-(5-fluoro-6-(2-fluoropropan-2-yl) pyridin-2-yl)-6-(methylthio)-1,2-dihydro-3H-pyrazolo[3,4-d]pyrimidin-3-one: To a stirred solution of (2-cyclopropyl-6-(methylthio)-1,2-dihydro-3H-pyrazolo[3,4-d]pyrimidin-3-one (230 mg, 1.03 mmol, 1.0 eq) and 6-bromo-3-fluoro-2-(2-fluoropropan-2-yl)pyridine (291 mg, 1.24 mmol, 1.2 eq) in dioxane (5 mL) was added potassium carbonate (285 mg, 2.06 mmol, 2.0 eq) and the resulting mixture was purged with nitrogen for 10 min followed by addition of copper iodide (40 mg, 0.26 mmol, 0.2 eq), and N,N'-dimethylethylenediamine (DMEDA) (0.04 mL, 0.413 mmol, 0.4 eq) and again purged with nitrogen for 10 min, stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (190 mg, 48.74%) as yellow semi solid. LCMS: 378.2 [M+1]$^+$.

Step-2: Synthesis of tert-butyl 6-((2-cyclopropyl-1-(5-fluoro-6-(2-fluoropropan-2-yl)pyridin-2-yl)-3-oxo-2,3-dihydro-1H-pyrazolo[3,4-d]pyrimidin-6-yl)amino)-1,1-dimethyl-3,4-dihydroisoquinoline-2(1H)-carboxylate: To a stirred solution of 2-cyclopropyl-1-(5-fluoro-6-(2-fluoropropan-2-yl)pyridin-2-yl)-6-(methylthio)-1,2-dihydro-3H-pyrazolo[3,4-d]pyrimidin-3-one. (190 mg, 0.5 mmol, 1.0 eq) in toluene (3.0 mL) was added m-CPBA (245 mg, 1.0 mmol, 2.0 eq) and allowed to stir at RT for 60 minutes. Tert-butyl 6-amino-1,1-dimethyl-3,4-dihydroisoquinoline-2(1H)-carboxylate (150 mg, 0.6 mmol, 1.2 eq) and DIPEA (0.4 mL, 2.0 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (70 mg, 23.14%) as light yellow solid. LCMS: 606.32 [M+1]$^+$.

Step-3: Synthesis of 2-cyclopropyl-6-((1,1-dimethyl-1,2,3,4-tetrahydroisoquinolin-6-yl)amino)-1-(5-fluoro-6-(2-fluoropropan-2-yl)pyridin-2-yl)-1,2-dihydro-3H-pyrazolo[3,4-d]pyrimidin-3-one: Tert-butyl 6-((2-cyclopropyl-1-(5-fluoro-6-(2-fluoropropan-2-yl)pyridin-2-yl)-3-oxo-2,3-dihydro-1H-pyrazolo[3,4-d]pyrimidin-6-yl)amino)-1,1-dimethyl-3,4-dihydroisoquinoline-2(1H)-carboxylate (70 mg, 0.11 mmol, 1.0 eq) was dissolved in dioxane (1.5 mL), followed by dropwise addition of 4.0 M-HCl in dioxane (4 mL) and allowed to stir at RT for 2 h. After completion of reaction, the reaction mixture was filtered and dried under reduced pressure, crude was given for prep purification to afford the desired compound (2.5 mg, 3.9%) as light yellow solid. LCMS: 506.4 [M+1]$^+$; $^1$H NMR (400 MHz, DMSO-d$_6$, Free base): δ 10.20 (br sbr s, 1H) 8.81 (s, 1H) 8.08-8.20 (m, 2H) 7.98 (d, J=6.58 Hz, 1H) 7.58 (br s, 1H) 7.45 (d, J=8.33 Hz, 1H) 7.30 (d, J=7.89 Hz, 1H) 3.25 (br s, 1H), 3.14 (br s, 2H) 2.86 (br s, 2H) 1.78 (s, 3H) 1.72 (s, 3H) 1.51 (s, 6H) 0.82 (br s, 4H).

Example S-7: Synthesis of 1-(5-fluoro-6-(2-hydroxypropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one (Compound No.1.249)

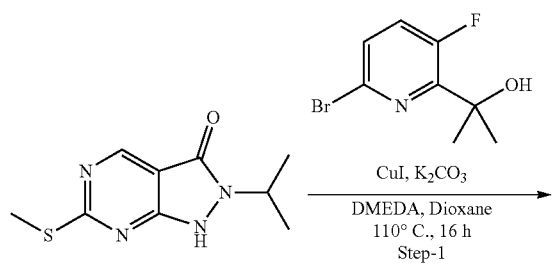

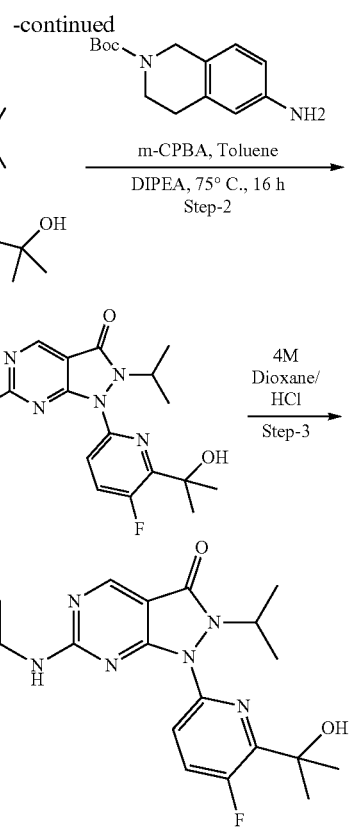

Step-1: Synthesis of 1-(5-fluoro-6-(2-hydroxypropan-2-yl)pyridin-2-yl)-2-isopropyl-6-(methylthio)-1,2-dihydro-3H-pyrazolo[3,4-d]pyrimidin-3-one: To a stirred solution of 2-isopropyl-6-(methylthio)-1,2-dihydro-3H-pyrazolo[3,4-d]pyrimidin-3-one (287 mg, 1.28 mmol, 1.0 eq) and 2-(6-bromo-3-fluoropyridin-2-yl)propan-2-ol (300 mg, 1.28 mmol, 1.0 eq) in dioxane (10 mL) was added potassium carbonate (354.09 mg, 2.56 mmol, 2.0 eq) and the resulting mixture was purged with nitrogen for 10 min, followed by addition of copper iodide (48.8 mg, 0.25 mmol, 0.2 eq), and N,N'-dimethylethylenediamine (DMEDA) (0.05 mL, 0.51 mmol, 0.4 eq) and again purged with nitrogen for 10 min, then stirred at 110° C. overnight. After completion of reaction, the reaction mixture was diluted with water and extracted with EtOAc (50 mL×2). Combined organic layers were washed with water (50 mL) and brine solution (50 mL), dried over anhydrous sodium sulphate and concentrated under reduced pressure to afford crude product, which was purified by flash chromatography to afford the desired compound. LCMS: 378.13 [M+1]$^+$.

Step-2: Synthesis of tert-butyl 6-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(5-fluoro-6-(2-hydroxypropan-2-yl)pyridin-2-yl)-2-isopropyl-6-(methylthio)-1,2-dihydro-3H-pyrazolo[3,4-d]pyrimidin-3-one (275 mg, 0.73 mmol, 1.0 eq) in toluene (3.0 mL) mL was added m-CPBA (251 mg, 1.46 mmol, 2.0 eq) and allowed to stir at RT for 1 h. Tert-butyl 6-amino-3,4-dihydroisoquinoline-2(1H)-carboxylate (199 mg, 0.80 mmol, 1.2 eq) and DIPEA (0.5 mL, 2.92 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound. LCMS: 578.28 [M+1]+.

Step-3: Synthesis of 1-(5-fluoro-6-(2-hydroxypropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one: Tert-butyl 6-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (381 mg, 0.66 mmol, 1.0 eq) was dissolved in dioxane (4 mL), followed by dropwise addition of 4.0 M-HCl (4 mL) and allowed to stir at RT for 1 h. After completion of reaction, the reaction mixture was filtered and dried under reduced pressure to afford the desired compound. LCMS: 478.23 [M+1]+; $^1$H NMR (400 MHz, DMSO-$d_6$): δ 10.20 (br s, 1H) 8.81 (s, 1H) 8.30 (s, 1H) 7.93-8.03 (m, 1H) 7.83 (dd, J=8.33, 2.63 Hz, 1H) 7.56 (br s, 1H) 7.40 (d, J=8.33 Hz, 1H) 7.02 (d, J=8.33 Hz, 1H) 4.17-4.21 (m, 1H) 3.93 (s, 3H) 3.09 (t, J=5.92 Hz, 3H) 2.76 (t, J=5.48 Hz, 2H) 1.52 (s, 6H) 1.32 (d, J=6.58 Hz, 6H).

Example S-8: Synthesis of 1-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)cyclopropane-1-carbonitrile. (Compound No.1.43)

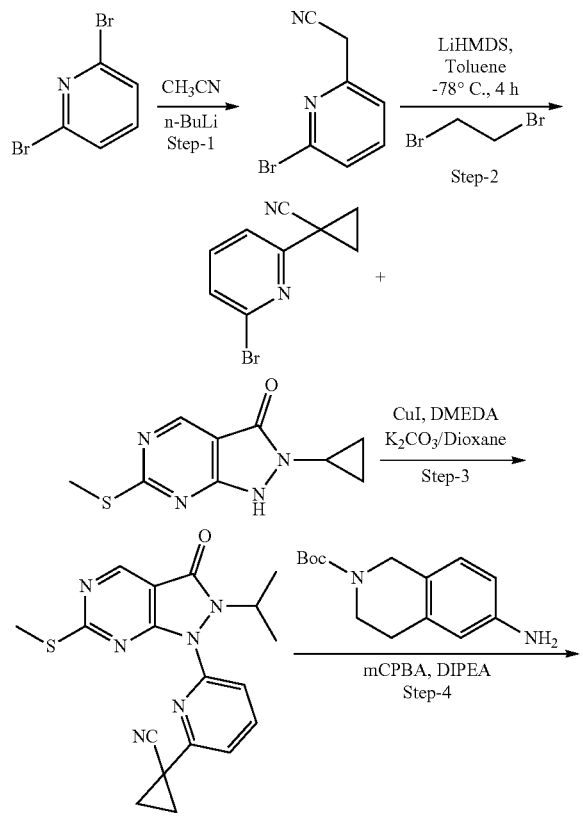

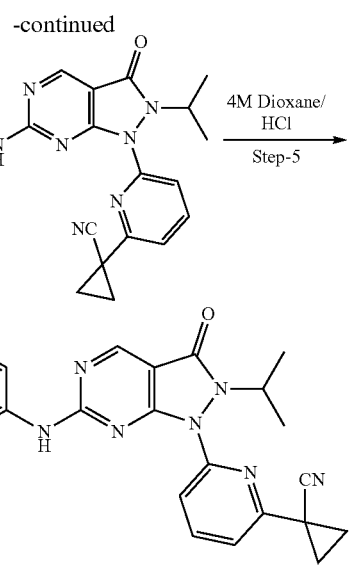

Step-1: Synthesis of 2-(6-bromopyridin-2-yl)acetonitrile: To a stirred solution of MeCN (1.4 mL, 27.4 mmol, 3.6 eq) in THF (30 mL) was added n-BuLi (2.5M in hexane, 10 mL, 25.1 mmol, 3.3 eq) at −78° C. and stirred at −78° C. for 30 min. After stirring for 30 min at −78° C., 2,6-dibromopyridine (1.8 g, 7.6 mmol, 1.0 eq) in THF (10 mL) was added. The reaction mixture was stirred at −78° C. for 45 min. After completion of reaction, the reaction mixture was diluted with water and extracted with EtOAc (50 mL×2). The combined organic layers were washed with water (50 mL) and brine solution (50 mL), dried over anhydrous sodium sulphate and concentrated under reduced pressure to afford crude product, which was purified by flash chromatography [Combiflash, elution-0-30% EtOAc in hexane] to afford the desired compound. LCMS: 197.04 [M+1]+.

Step-2: Synthesis of 1-(6-bromopyridin-2-yl)cyclopropane-1-carbonitrile: To a stirred solution of 2-(6-bromopyridin-2-yl)acetonitrile (2.0 g, 10.15 mmol, 1.0 eq) in THF (30 mL) was added LiHMDS (22.33 mL, 22.33 mmol, 2.2 eq) at −78° C. dropwise under nitrogen atmosphere. After stirring for 30 min at −78° C., dibromoethane (2.0 g, 11.16 mmol, 1.1 eq) was added and the reaction mixture was stirred at RT overnight. After completion of reaction, the reaction mixture was diluted with ammonium chloride (200 mL) and extracted with EtOAc (250 mL×2). The combined organic layers were washed with water (250 mL) and brine solution (250 mL), dried over anhydrous sodium sulphate and concentrated under reduced pressure to afford crude product, which was purified by flash chromatography to afford the desired compound. LCMS: 224.09 [M+1]+.

Step-3: Synthesis of 1-(6-(2-isopropyl-6-(methylthio)-3-oxo-2,3-dihydro-1H-pyrazolo[3,4-d]pyrimidin-1-yl)pyridin-2-yl)cyclopropane-1-carbonitrile: To a stirred solution of 1-(6-bromopyridin-2-yl)cyclopropane-1-carbonitrile (600 mg, 2.67 mmol, 1.0 eq) and (602 mg, 2.67 mmol, 1.0 eq) in dioxane (10 mL) was added potassium carbonate (800 mg, 5.34 mmol, 2.0 eq) and the resulting mixture was purged with nitrogen for 10 min followed by addition of copper iodide (40 mg, 190.4 mmol, 0.2 eq), and N,N'-dimethylethylenediamine (DMEDA) (0.1 mL, 1.06 mmol, 0.4 eq) and again purged with nitrogen for 10 min, then stirred at 100° C. overnight. After completion of reaction, the reaction mixture was diluted with water and extracted with EtOAc (50 mL×2). The combined organic layers were washed with water (50 mL) and brine solution (50 mL), dried over anhydrous sodium sulphate and concentrated under reduced pressure to afford crude product, which was purified by flash chromatography to afford the desired compound. LCMS: 367.2 [M+1]+.

Step-4: Synthesis tert-butyl 6-((1-(6-(1-cyanocyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(6-(2-isopropyl-6-(methylthio)-3-oxo-2,3-dihydro-1H-pyrazolo[3,4-d]pyrimidin-1-yl)pyridin-2-yl)cyclopropane-1-carbonitrile (100 mg, 0.28 mmol, 1.0 eq) in toluene (2.0 mL) was added m-CPBA (98.17 mg, 0.56 mmol, 2.0 eq) and allowed to stir at RT for 1 h. Tert-butyl 6-amino-3,4-dihydroisoquinoline-2(1H)-carboxylate (84 mg, 0.34 mmol, 1.5 eq) and DIPEA (0.2 mL, 1.42 mmol, 5.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-70% EtOAc in hexane] to afford the desired compound. LCMS: 567.3 [M+1]+.

Step-5: Synthesis of 1-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)cyclopropane-1-carbonitrile: Tert-butyl 6-((1-(6-(1-cyanocyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (90 mg, 0.19 mmol, 1.0 eq) was dissolved in dioxane (1 mL), followed by dropwise addition of 4.0 M-HCl (0.5 mL) and allowed to stir at RT for 4 h. After completion of reaction, the reaction mixture was filtered and dried under reduced pressure and purified by reverse phase HPLC to afford the desired compound. LCMS: 467.4 [M+1]+; 1H NMR (400 MHz, DMSO-d6): δ 10.29 (br s, 1H) 8.82 (s, 1H) 8.19 (s, 1H) 8.09-8.16 (m, 1H) 7.84 (d, J=8.33 Hz, 1H) 7.63 (br s, 1H) 7.57 (s, 1H) 7.42 (d, J=8.77 Hz, 1H) 7.06 (s, 1H) 3.98-4.09 (m, 2H) 3.17 (br s, 4H) 2.85 (br s, 2H) 1.82-1.90 (m, 2H) 1.64-1.74 (m, 2H) 1.35 (d, J=6.58 Hz, 6H).

Example S-9: Synthesis of 1-(6-(6-(1,1-dimethyl-1,2,3,4-tetrahydroisoquinolin-6-ylamino)-2-isopropyl-3-oxo-2,3-dihydro-1H-pyrazolo[3,4-d]pyrimidin-1-yl)pyridin-2-yl)cyclopropanecarbonitrile (Compound No.1.45)

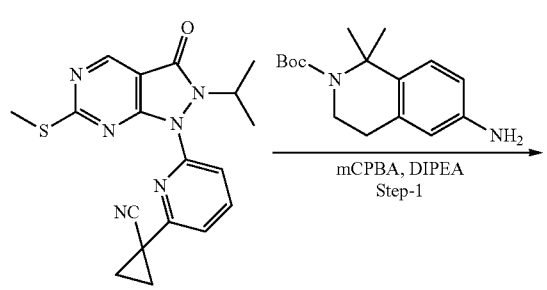

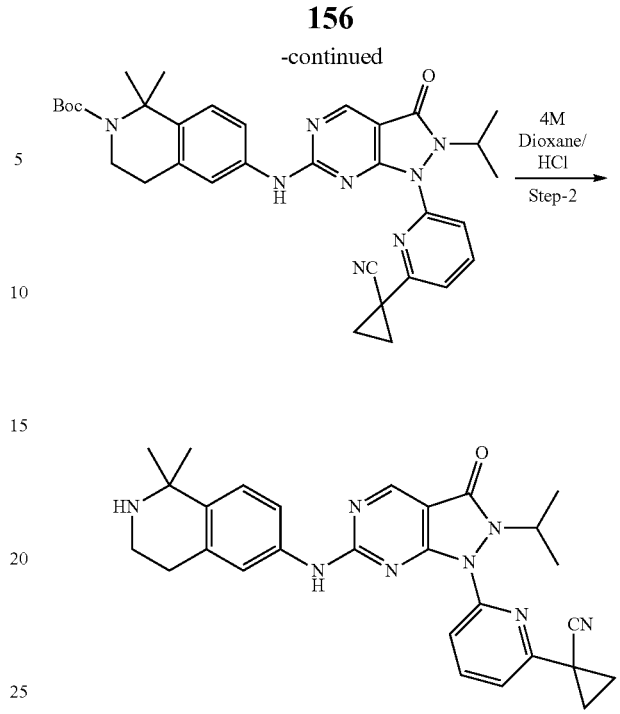

Step-1: Synthesis of tert-butyl 6-(1-(6-(1-cyanocyclopropyl)pyridin-2-yl)-2-isopropyl-3-oxo-2,3-dihydro-1H-pyrazolo[3,4-d]pyrimidin-6-ylamino)-1,1-dimethyl-3,4-dihydroisoquinoline-2(1H)-carboxylate: To a stirred solution of 1-(6-(2-isopropyl-6-(methylthio)-3-oxo-2,3-dihydro-1H-pyrazolo[3,4-d]pyrimidin-1-yl)pyridin-2-yl)cyclopropanecarbonitrile (100 mg, 0.28 mmol, 1.0 eq) in toluene (2.0 mL) was added m-CPBA (138 mg, 0.56 mmol, 2.0 eq) and allowed to stir at RT for 1 h. Tert-butyl 6-amino-1,1-dimethyl-3,4-dihydroisoquinoline-2(1H)-carboxylate (94 mg, 0.34 mmol, 1.1 eq) and DIPEA (0.2 mL, 1.4 mmol, 5.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound. LCMS: 595.4 [M+1]+.

Step-2: Synthesis of 1-(6-(6-(1,1-dimethyl-1,2,3,4-tetrahydroisoquinolin-6-ylamino)-2-isopropyl-3-oxo-2,3-dihydro-1H-pyrazolo[3,4-d]pyrimidin-1-yl)pyridin-2-yl)cyclopropanecarbonitrile: Tert-butyl 6-(1-(6-(1-cyanocyclopropyl)pyridin-2-yl)-2-isopropyl-3-oxo-2,3-dihydro-1H-pyrazolo[3,4-d]pyrimidin-6-ylamino)-1,1-dimethyl-3,4-dihydroisoquinoline-2(1H)-carboxylate (80 mg, 0.13 mmol, 1.0 eq) was dissolved in dioxane (0.8 mL), followed by dropwise addition of 4.0 M-HCl (0.8 mL) and allowed to stir at RT for 1 h. After completion of reaction, the reaction mixture was filtered and purified by reverse phase chromatography of afford the desired compound. LCMS: 495.5 [M+1]++; 1H NMR (400 MHz, DMSO-d6): δ 10.18 (br s, 1H) 8.80 (s, 1H) 8.27 (s, 1H) 8.10-8.13 (m, 1H) 7.83 (d, J=8.33 Hz, 1H) 7.57 (s, 1H) 7.37 (br s, 1H) 7.20 (d, J=8.77 Hz, 1H) 4.09 (d, J=6.58 Hz, 1H) 3.02 (br s, 2H) 2.68 (d, J=9.65 Hz, 2H) 1.85 (d, J=3.51 Hz, 2H) 1.71 (d, J=3.07 Hz, 2H) 1.29-1.44 (m, 12H).

Example S-10: Synthesis of 2 1-(4-(tert-butyl)-5-chlorothiazol-2-yl)-2-isopropyl-6-((1,2,3,4-tetrahydroisoquinolin-7-yl)amino)-1,2-dihydro-3H-pyrazolo[3,4-d]pyrimidin-3-one (Compound No.1.349)

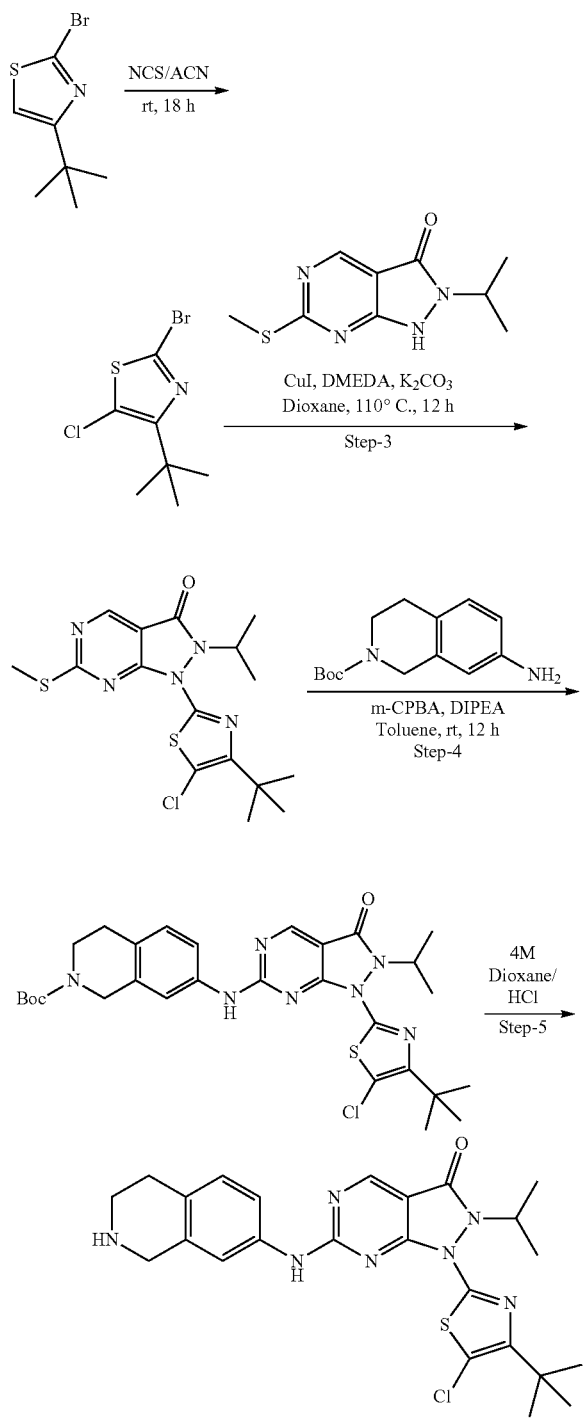

Step-1: Synthesis of 2-bromo-4-(tert-butyl)-5-chlorothiazole: To a stirred solution of 2-bromo-4-(tert-butyl)thiazole (1.21 g, 5.49 mmol, 1.0 eq) in ACN (20 mL), was added NCS (0.80, 6.04 mmol, 1.1 eq). The reaction mixture was stirred at RT for 12 h. After completion of reaction, the reaction mixture was diluted with water (50 mL) and was extracted with EtOAc (50 mL×2). The combined organic layers were washed with water (50 mL) and brine solution (50 mL), dried over anhydrous sodium sulfate and concentrated under reduced pressure to afford crude product, which was purified by flash chromatography to afford the desired compound. LCMS: 254.2 [M+2]$^+$.

Step-2: Synthesis of 1-(4-(tert-butyl)-5-chlorothiazol-2-yl)-2-isopropyl-6-(methylthio)-1,2-dihydro-3H-pyrazolo[3,4-d]pyrimidin-3-one: To a stirred solution of 2-isopropyl-6-(methylthio)-1,2-dihydro-3H-pyrazolo[3,4-d]pyrimidin-3-one (865 mg, 3.85 mmol, 1.0 eq) and 2-bromo-4-(tert-butyl)-5-chlorothiazole (982 mg, 3.85 mmol, 1.0 eq) in dioxane (12 mL) was added potassium carbonate (1.06 g, 7.71 mmol, 2.0 eq) and the resulting mixture was purged with nitrogen for 10 min, followed by addition of copper iodide (146 mg, 0.77 mmol, 0.2 eq), and N,N'-dimethylethylenediamine (DMEDA) (0.16 mL, 1.54 mmol, 0.4 eq) and again purged with nitrogen for 10 min, then stirred at 90° C. overnight. After completion of reaction, the reaction mixture was diluted with water and extracted with EtOAc (50 mL×2). The combined organic layers were washed with water (50 mL) and brine solution (50 mL), dried over anhydrous sodium sulfate and concentrated under reduced pressure to afford crude product, which was purified by flash chromatography to afford the desired product. LCMS: 298.2 [M+1]$^+$.

Step-3: Synthesis of tert-butyl 7-((1-(4-(tert-butyl)-5-chlorothiazol-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(4-(tert-butyl)-5-chlorothiazol-2-yl)-2-isopropyl-6-(methylthio)-1,2-dihydro-3H-pyrazolo[3,4-d]pyrimidin-3-one (32 mg, 0.08 mmol, 1.0 eq) in toluene (2.0 mL) was added m-CPBA (28 mg, 0.16 mmol, 2.0 eq) and allowed to stir at RT for 1 h. Tert-butyl 7-amino-3,4-dihydroisoquinoline-2(1H)-carboxylate (22 mg, 0.31 mmol, 1.1 eq) and Na$_2$CO$_3$ (34 mg, 0.32 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography to afford the desired compound. LCMS: 598.3 [M+1]$^+$.

Step-4: Synthesis of 2 1-(4-(tert-butyl)-5-chlorothiazol-2-yl)-2-isopropyl-6-((1,2,3,4-tetrahydroisoquinolin-7-yl)amino)-1,2-dihydro-3H-pyrazolo[3,4-d]pyrimidin-3-one: Tert-butyl 7-((1-(4-(tert-butyl)-5-chlorothiazol-2-yl)-2-isopropyl-3-oxo-2,3-dihydro-1H-pyrazolo[3,4-d]pyrimidin-6-yl)amino)-3,4-dihydroisoquinoline-2(1H)-carboxylate (25 mg, 0.04 mmol, 1.0 eq) was dissolved in dioxane (0.3 mL), followed by dropwise addition of 4.0 M-HCl (0.3 mL) and allowed to stir at RT for 1 h. After completion of reaction, the reaction mixture was filtered and dried under reduced pressure to afford the desired compound. LCMS: 498.4 [M+1]$^+$; $^1$H NMR (400 MHz, DMSO-d$_6$): δ 10.64 (br s, 1H) 9.31 (br s, 1H) 8.89 (s, 1H) 7.72 (br s, 1H) 7.58 (d, J=8.77 Hz, 1H) 7.23 (d, J=8.33 Hz, 1H) 4.54-4.67 (m, 1H) 4.28 (br s, 2H) 2.99 (t, J=5.92 Hz, 2H) 1.54 (d, J=6.58 Hz, 2H) 1.38-1.49 (m, 15H).

Example S-11: Synthesis of 1-(6-(2-ethyl-3-oxo-6-((1,2,3,4-tetrahydroisoquinolin-6-yl)amino)-2,3-dihydro-1H-pyrazolo[3,4-d]pyrimidin-1-yl)pyridin-2-yl)cyclopropane-1-carbonitrile (Compound No. 1.37)

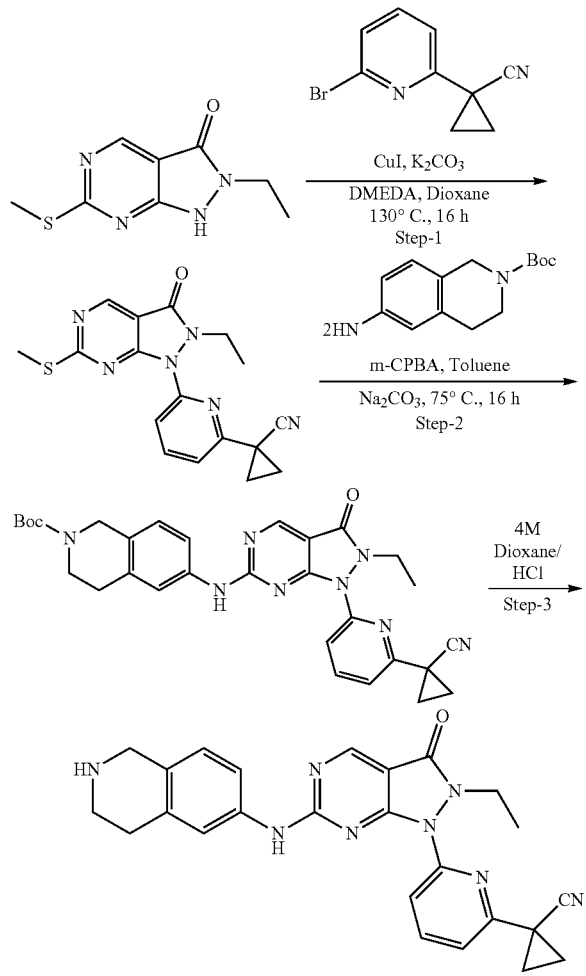

Step-1: Synthesis of 1-(6-(2-ethyl-6-(methylthio)-3-oxo-2,3-dihydro-1H-pyrazolo[3,4-d]pyrimidin-1-yl)pyridin-2-yl)cyclopropane-1-carbonitrile: To a stirred solution of 2-ethyl-6-(methylthio)-1,2-dihydro-3H-pyrazolo[3,4-d]pyrimidin-3-one (200 mg, 0.95 mmol, 1.0 eq) and 1-(6-bromopyridin-2-yl)cyclopropane-1-carbonitrile (212 mg, 0.95 mmol, 1.0 eq) in dioxane (10 mL) was added potassium carbonate (262.9 mg, 2 mmol, 2.0 eq) and the resulting mixture was purged with nitrogen for 10 min followed by addition of copper iodide (36.23 mg, 0.19 mmol, 0.2 eq), and N,N'-dimethylethylenediamine (DMEDA) (0.04 mL, 0.381 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (216 mg, 64.43%) as yellow semi solid. LCMS: 353.13 (M+1)$^+$.

Step-2: Synthesis of tert-butyl 6-((1-(6-(1-cyanocyclopropyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate: To a stirred solution of 1-(6-(2-ethyl-6-(methylthio)-3-oxo-2,3-dihydro-1H-pyrazolo[3,4-d]pyrimidin-1-yl)pyridin-2-yl)cyclopropane-1-carbonitrile (108 mg, 0.31 mmol, 1.0 eq) in toluene (3.0 mL) was added m-CPBA (145.6 mg, 0.61 mmol, 2.0 eq) and allowed to stir at RT for 60 min. Tert-butyl 6-amino-3,4-dihydroisoquinoline-2(1H)-carboxylate (76.10 mg, 0.31 mmol, 1.0 eq) and Na$_2$CO$_3$ (129.7 mg, 1.22 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (121 mg, 71.44%) as light yellow solid. LCMS: 553.26 (M+1)$^+$.

Step-3: Synthesis of 1-(6-(2-ethyl-3-oxo-6-((1,2,3,4-tetrahydroisoquinolin-6-yl)amino)-2,3-dihydro-1H-pyrazolo[3,4-d]pyrimidin-1-yl)pyridin-2-yl)cyclopropane-1-carbonitrile: Tert-butyl 6-((1-(6-(1-cyanocyclopropyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (121 mg, 0.22 mmol, 1.0 eq) was dissolved in dioxane (1 mL), followed by dropwise addition of 4.0 M-HCl in dioxane (1.5 mL) and allowed to stir at RT for 2 h. After completion of reaction, the reaction mixture was filtered and dried under reduced pressure; and crude was purified by reverse phase chromatography to afford the desired compound (10 mg, 10.00%) as an off-white solid. LCMS: 453.21 (M+1)$^+$; $^1$H NMR (400 MHz, DMSO-d$_6$): δ 10.27 (br s, 1H) 8.86 (s, 1H) 8.24 (s, 1H) 8.11 (t, J=7.89 Hz, 1H) 7.91 (d, J=8.33 Hz, 1H) 7.62 (br s, 1H) 7.53 (d, J=7.45 Hz, 1H) 7.39 (br s, 1H) 6.98-7.05 (m, 1H) 3.83-4.05 (m, 4H) 3.10 (br s, 2H) 2.78 (br s, 2H) 1.82-1.96 (m, 2H) 1.61-1.74 (m, 2H) 0.96 (t, J=7.02 Hz, 3H).

Example S-12: Synthesis of 1-(6-(2-ethyl-3-oxo-6-((1,2,3,4-tetrahydroisoquinolin-7-yl)amino)-2,3-dihydro-1H-pyrazolo[3,4-d]pyrimidin-1-yl)pyridin-2-yl)cyclopropane-1-carbonitrile (Compound No. 1.38)

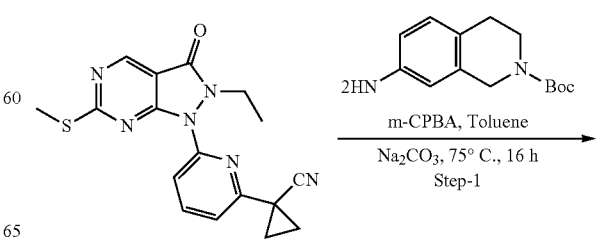

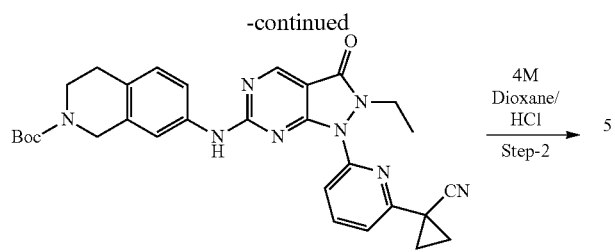

Step-1: Synthesis of tert-butyl 7-((1-(6-(1-cyanocyclopropyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate: To a stirred solution of 2-ethyl-1-(6-(1-methylcyclopropyl)pyridin-2-yl)-6-(methylthio)-1,2-dihydro-3H-pyrazolo[3,4-d]pyrimidin-3-one (108 mg, 0.31 mmol, 1.0 eq) in toluene (3.0 mL) was added m-CPBA (145.6 mg, 0.61 mmol, 2.0 eq) and allowed to stir at RT for 60 minutes. Tert-butyl 7-amino-3,4-dihydroisoquinoline-2(1H)-carboxylate (76.01 mg, 0.31 mmol, 1.0 eq) and Na₂CO₃ (129.7 mg, 1.22 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, (119 mg, 70.2%) as light yellow solid. LCMS: 553.26 (M+1)$^+$.

Step-2: Synthesis of 1-(6-(2-ethyl-3-oxo-6-((1,2,3,4-tetrahydroisoquinolin-7-yl)amino)-2,3-dihydro-1H-pyrazolo[3,4-d]pyrimidin-1-yl)pyridin-2-yl)cyclopropane-1-carbonitrile dihydrochloride: Tert-butyl 7-((1-(6-(1-cyanocyclopropyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (119 mg, 0.21 mmol, 1.0 eq) was dissolved in dioxane (1 mL), followed by dropwise addition of 4.0 M-HCl in dioxane (1.5 mL) and allowed to stir at RT for 2 h. After completion of reaction, the reaction mixture was filtered and dried under reduced pressure and purified product was obtained by reverse phase chromatography (24 mg, 21.2%) as white solid. LCMS: 453.21 (M+1)$^+$; $^1$H NMR (400 MHz, DMSO-d₆): δ 10.39 (br s, 1H) 9.26 (br s, 1H) 8.88 (s, 1H) 8.15 (t, J=7.6 Hz, 1H) 7.93 (d, J=7.8 Hz, 1H) 7.68 (br s, 1H) 7.43-7.56 (m, 2H) 7.20 (d, J=8.3 Hz, 1H) 4.26 (br s, 2H) 3.81-3.98 (m, 2H) 3.38 (d, J=5.7 Hz, 2H) 2.97 (t, J=5.9 Hz, 2H) 1.82-1.92 (m, 2H) 1.65-1.74 (m, 2H) 0.97 (t, J=7.0 Hz, 3H).

Example S-13: Synthesis of 1-(6-(2-isopropyl-3-oxo-6-((1,2,3,4-tetrahydroisoquinolin-7-yl)amino)-2,3-dihydro-1H-pyrazolo[3,4-d]pyrimidin-1-yl)pyridin-2-yl)cyclopropane-1-carbonitrile (Compound No. 1.44)

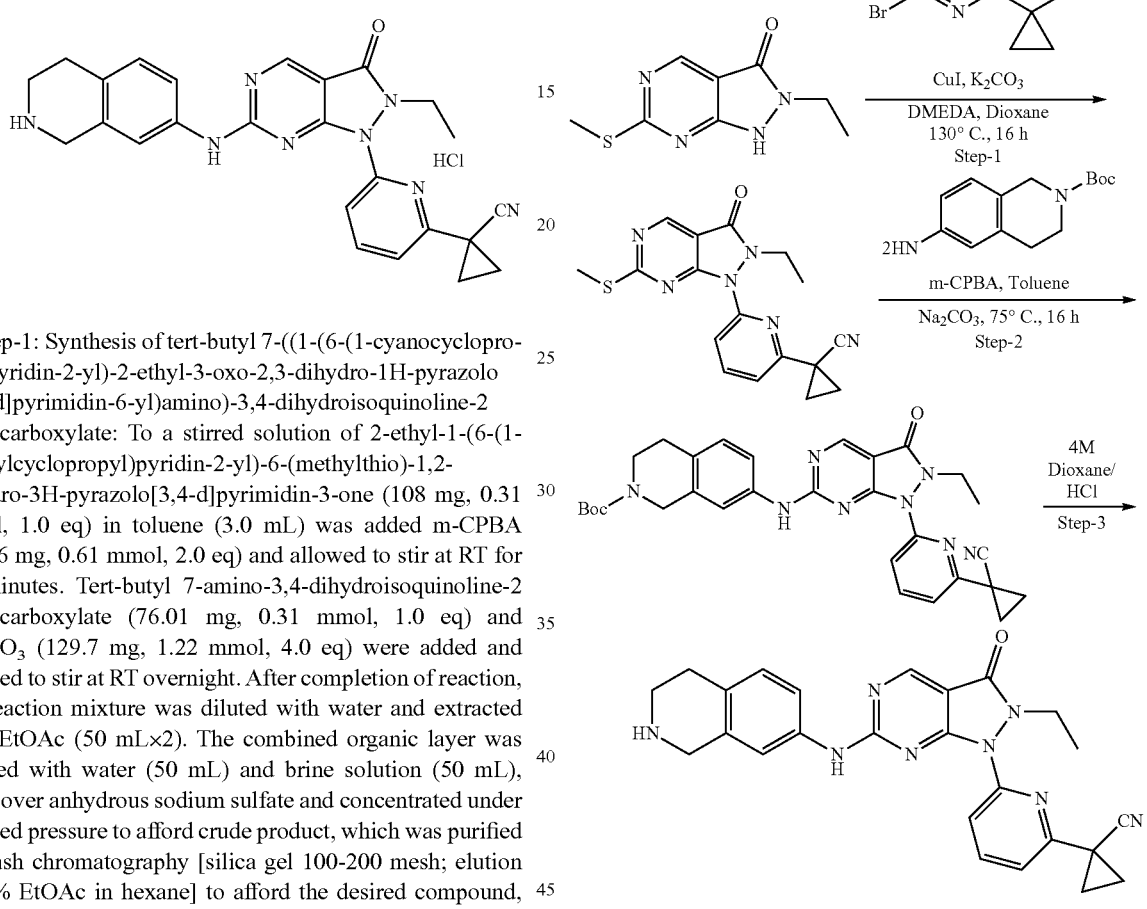

Step-1: Synthesis of 1-(6-(2-isopropyl-6-(methylthio)-3-oxo-2,3-dihydro-1H-pyrazolo[3,4-d]pyrimidin-1-yl)pyridin-2-yl)cyclopropane-1-carbonitrile: To a stirred solution of 2-isopropyl-6-(methylthio)-1,2-dihydro-3H-pyrazolo[3,4-d]pyrimidin-3-one (100 mg, 0.45 mmol, 1.0 eq) and 1-(6-bromopyridin-2-yl)cyclopropane-1-carbonitrile (100 mg, 0.45 mmol, 1.0 eq) in dioxane (6 mL) was added potassium carbonate (123 mg, 0.89 mmol, 2.0 eq) and the resulting mixture was purged with nitrogen for 10 min followed by addition of copper iodide (17 mg, 0.089 mmol, 0.2 eq), and N,N'-dimethylethylenediamine (DMEDA) (0.02 mL, 0.178 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-40% EtOAc in hexane] to afford the desired product (102 mg, 62.4%) as colorless liquid. LCMS: 367.13 (M+1)⁺.

Step-2: Synthesis of tert-butyl 7-((1-(6-(1-cyanocyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(6-(2-isopropyl-6-(methylthio)-3-oxo-2,3-dihydro-1H-pyrazolo[3,4-d]pyrimidin-1-yl)pyridin-2-yl)cyclopropane-1-carbonitrile (102 mg, 0.28 mmol, 1.0 eq) in toluene (3.0 mL) was added m-CPBA (132 mg, 0.56 mmol, 2.0 eq) and allowed to stir at RT for 60 minutes. Tert-butyl 6-amino-3,4-dihydroisoquinoline-2(1H)-carboxylate (75.9 mg, 0.31 mmol, 1.0 eq) and Na₂CO₃ (117.8 mg, 1.11 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (90 mg, 57.0%) as an off-white solid. LCMS: 567.28 (M+1)⁺.

Step-3: Synthesis of 1-(6-(2-isopropyl-3-oxo-6-((1,2,3,4-tetrahydroisoquinolin-7-yl)amino)-2,3-dihydro-1H-pyrazolo[3,4-d]pyrimidin-1-yl)pyridin-2-yl)cyclopropane-1-carbonitrile: Tert-butyl 7-((1-(6-(1-cyanocyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (90 mg, 0.15 mmol, 1.0 eq) was dissolved in dioxane (1 mL), followed by dropwise addition of 4.0 M-HCl in dioxane (2 mL) and allowed to stir at RT for 2 h. After completion of reaction, the reaction mixture was filtered and dried under reduced pressure, purified product was obtained by reverse phase chromatography (40 mg, 46.7%) as an off-white solid. LCMS: −467.22 (M+1)⁺; ¹H NMR (400 MHz, DMSO-d₆): δ 10.35 (br s, 1H) 9.11 (br s, 2H) 8.83 (s, 1H) 8.08-8.20 (m, 1H) 7.87 (s, 1H) 7.65 (br s, 1H) 7.51 (d, J=8.3 Hz, 1H) 7.55 (d, J=7.5 Hz, 1H) 7.19 (d, J=8.7 Hz, 1H) 4.26 (br s, 2H) 4.09 (m, 1H) 3.39 (t, 2H) 2.96 (t, 2H) 1.87 (d, J=3.5 Hz, 2H) 1.71 (d, J=3.1 Hz, 2H) 1.36 (d, J=6.5 Hz, 6H).

Example S-14: Synthesis of 1-(4-(2-isopropyl-3-oxo-6-(1,2,3,4-tetrahydroisoquinolin-6-ylamino)-2,3-dihydro-1H-pyrazolo[3,4-d]pyrimidin-1-yl)pyridin-2-yl)cyclopropanecarbonitrile (Compound No. 1.67)

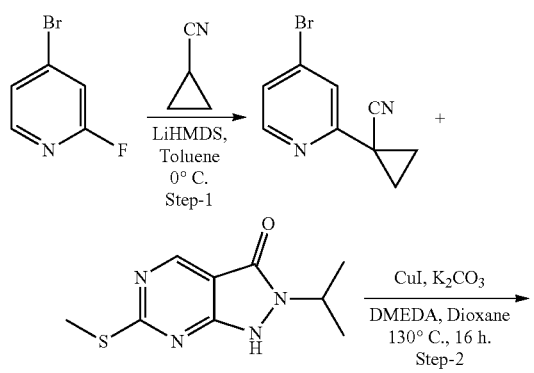

Step-1: Synthesis of 1-(4-bromopyridin-2-yl)cyclopropanecarbonitrile: To a stirred solution of cyclopropanecarbonitrile (1.0 g, 14.5 mmol, 1.0 eq), in toluene (10 mL) was added LiHMDS (16 mL, 15.9 mmol, 1.1 eq), at 0° C. & the reaction mixture was stirred for 1 h. 2-Fluoro-4-bromopyridine in toluene (5 mL) (2.56 g, 14.4 mmol, 1.0 eq) was added dropwise & stirred for 18 h. After completion of reaction, the reaction mixture was diluted with saturated NH₄Cl solution and extracted with diethyl ether (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (2.1 g, 65.0%) as colorless solid. LCMS: 222.9 (M+1)⁺.

Step-2: Synthesis of 1-(4-(2-isopropyl-6-(methylthio)-3-oxo-2,3-dihydro-1H-pyrazolo[3,4-d]pyrimidin-1-yl)pyridin-2-yl)cyclopropanecarbonitrile: To a stirred solution of 2-isopropyl-6-(methylthio)-1,2-dihydro-3H-pyrazolo[3,4-d]pyrimidin-3-one (224 mg, 1.0 mmol, 1.0 eq) and 1-(4-bromopyridin-2-yl)cyclopropanecarbonitrile (223 mg, 1.0 mmol, 1.0 eq) in f dioxane (10 mL) were added potassium carbonate (276 mg, 2.0 mmol, 2.0 eq) and the resulting mixture was purged with nitrogen for 10 min followed by addition of copper iodide (38 mg, 0.2 mmol, 0.2 eq), and N,N'-dimethylethylenediamine (DMEDA) (0.05 mL, 0.4 mmol, 0.4 eq) and again purged with nitrogen for 10 min, then stirred at 90° C. for 48 h. After completion of reaction, the reaction mixture was diluted with water and extracted with EtOAc (50 mL×2). The combined organic layers were washed with water (50 mL) and brine solution (50 mL),

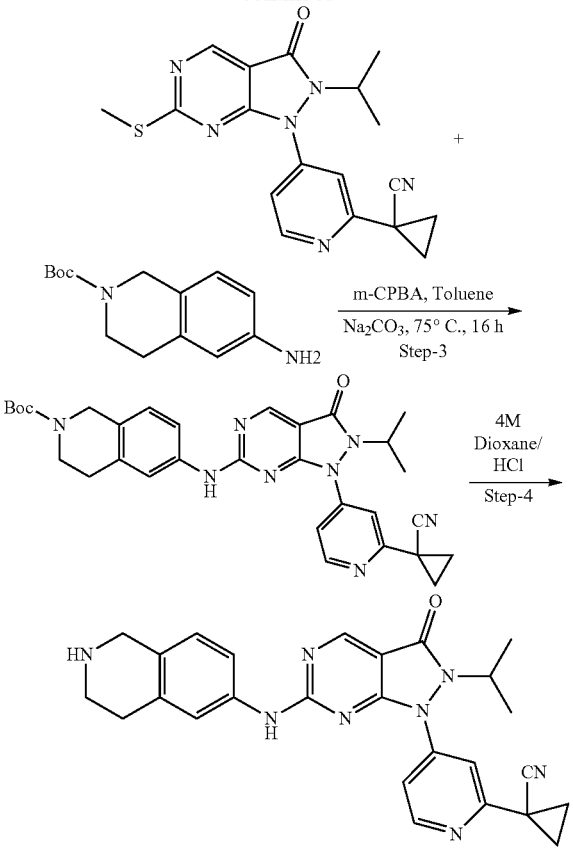

dried over anhydrous sodium sulphate and concentrated under reduced pressure to afford crude product, which was purified by flash chromatography to afford the desired compound (50 mg, 13.6%). LCMS: 367.2 (M+1)⁺

Step-3: Synthesis of tert-butyl 6-(1-(2-(1-cyanocyclopropyl)pyridin-4-yl)-2-isopropyl-3-oxo-2,3-dihydro-1H-pyrazolo[3,4-d]pyrimidin-6-ylamino)-3,4-dihydroisoquinoline-2(1H)-carboxylate: To a stirred solution of 1-(4-(2-isopropyl-6-(methylthio)-3-oxo-2,3-dihydro-1H-pyrazolol[3,4-d]pyrimidin-1-yl)pyridin-2-yl)cyclopropanecarbonitrile (50 mg, 0.14 mmol, 1.0 eq) in toluene (2.0 mL) was added m-CPBA (48 mg, 0.28 mmol, 2.0 eq) and allowed to stir at RT for 1 h. Tert-butyl 6-amino-3,4-dihydroisoquinoline-2(1H)-carboxylate (38 mg, 0.15 mmol, 1.1 eq) and Na$_2$CO$_3$ (58 mg, 0.55 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (40 mg, 51.9%) as an off-white solid. LCMS: 567.4 (M+1)⁺.

Step-4: Synthesis of 1-(4-(2-isopropyl-3-oxo-6-(1,2,3,4-tetrahydroisoquinolin-6-ylamino)-2,3-dihydro-1H-pyrazolo[3,4-d]pyrimidin-1-yl)pyridin-2-yl)cyclopropanecarbonitrile: Tert-butyl 6-(1-(2-(1-cyanocyclopropyl)pyridin-4-yl)-2-isopropyl-3-oxo-2,3-dihydro-1H-pyrazolo[3,4-d]pyrimidin-6-ylamino)-3,4-dihydroisoquinoline-2(1H)-carboxylate (40 mg, 0.07 mmol, 1.0 eq) was dissolved in DCM (5 mL), followed by dropwise addition of Trifluoro acetic acid (0.51 mL) and allowed to stir at RT for 1 h. After completion of reaction, the reaction mixture was dried under reduced pressure and purified product was obtained by reverse phase purification (20 mg, 55.4%) as white solid. LCMS: 467.5 (M+1)⁺; ¹H NMR (400 MHz, DMSO-d$_6$): δ 10.37 (br s, 1H) 8.85 (s, 1H) 8.65 (d, J=5.2 Hz, 1H) 7.56-7.65 (m, 2H) 7.42-7.56 (m, 2H) 7.06 (d, J=8.3 Hz, 1H) 3.87-4.03 (m, 3H) 3.08 (d, J=5.7 Hz, 2H) 2.78 (br s, 2H) 1.84-1.95 (m, 2H) 1.65-1.79 (m, 2H) 1.37 (d, J=7.0 Hz, 6H).

Example S-15: Synthesis of Synthesis of 2-ethyl-1-(6-(1-(fluoromethyl)cyclopropyl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.86)

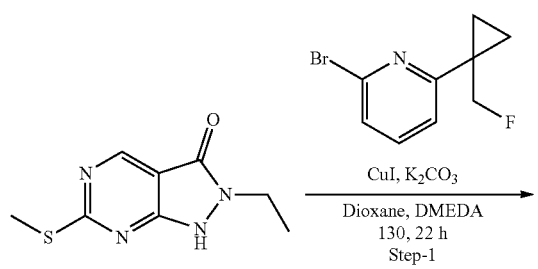

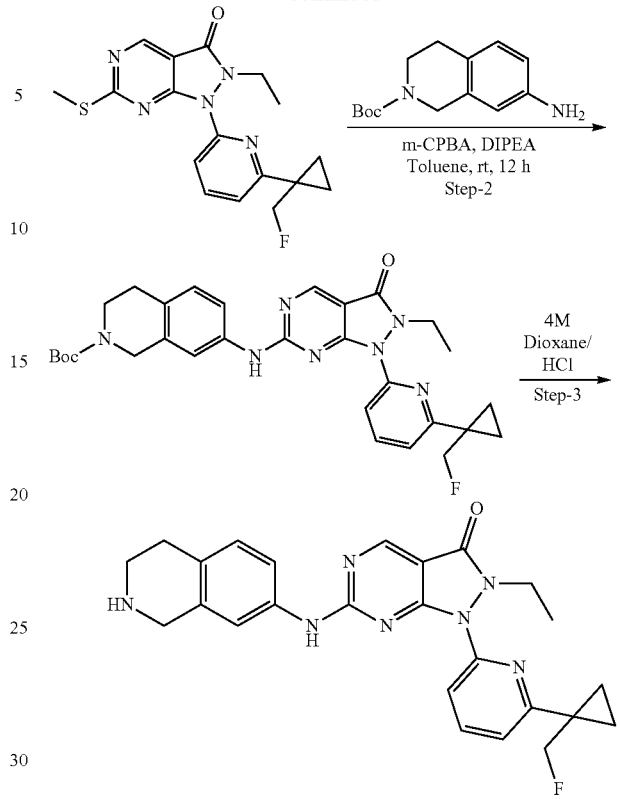

Step-1: Synthesis of 2-ethyl-1-(6-(1-(fluoromethyl)cyclopropyl)pyridin-2-yl)-6-(methylthio)-1,2-dihydro-3H-pyrazolo[3,4-d]pyrimidin-3-one: To a stirred solution of 2-ethyl-6-(methylthio)-1,2-dihydro-3H-pyrazolo[3,4-d]pyrimidin-3-one (172.6 mg, 0.82 mmol, 1.0 eq) and 2-bromo-6-(1-(fluoromethyl)cyclopropyl)pyridine (189.0 mg, 0.82 mmol, 1.0 eq) in dioxane (10 mL) was added potassium carbonate (227 mg, 1.64 mmol, 2.0 eq) and the resulting mixture was purged with nitrogen for 10 min followed by addition of copper iodide (31 mg, 0.16 mmol, 0.2 eq), and N,N'-dimethylethylenediamine (DMEDA) (0.03 mL, 0.33 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (213 mg, 72.8%) as brown semi-solid. LCMS: 360.12 (M+1)⁺.

Step-2: Synthesis tert-butyl 7-((2-ethyl-1-(6-(1-(fluoromethyl)cyclopropyl)pyridin-2-yl)-3-oxo-2,3-dihydro-1H-pyrazolo[3,4-d]pyrimidin-6-yl)amino)-3,4-dihydroisoquinoline-2(1H)-carboxylate: To a stirred solution of 2-ethyl-1-(6-(1-(fluoromethyl)cyclopropyl)pyridin-2-yl)-6-(methylthio)-1,2-dihydro-3H-pyrazolo[3,4-d]pyrimidin-3-one (213 mg, 0.82 mmol, 1.0 eq) in toluene (2.0 mL) was added m-CPBA (405 mg, 1.64 mmol, 2.0 eq) and allowed to stir at RT for 60 minutes. Tert-butyl 7-amino-3,4-dihydroisoquinoline-2(1H)-carboxylate (204 mg, 0.82 mmol, 1.0 eq) and Na$_2$CO$_3$ (348 mg, 3.28 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (60 mg, 18.1%) as light yellow solid. LCMS: 560.27 (M+1)⁺.

Step-3: Synthesis of 2-ethyl-1-(6-(1-(fluoromethyl)cyclopropyl)pyridin-2-yl)-6-((1,2,3,4-tetrahydroisoquinolin-7-yl)amino)-1,2-dihydro-3H-pyrazolo[3,4-d]pyrimidin-3-one: Tert-butyl 7-((2-ethyl-1-(6-(1-(fluoromethyl)cyclopropyl)pyridin-2-yl)-3-oxo-2,3-dihydro-1H-pyrazolo[3,4-d]pyrimidin-6-yl)amino)-3,4-dihydroisoquinoline-2(1H)-carboxylate (60 mg, 0.11 mmol, 1.0 eq) was dissolved in dioxane (1 mL), followed by dropwise addition of 2.0 M-HCl/Dioxane (2.0 mL) and allowed to stir at RT for 2 h. After completion of reaction, the reaction mixture was filtered and dried under reduced pressure and the purified product was obtained by reverse phase chromatography (8 mg, 16.2%) as a white solid. LCMS: 460.22 (M+1)⁺; ¹H NMR (400 MHz, DMSO-$d_6$): δ10.25 (br s, 1H) 8.87 (s, 1H) 8.26 (s, 1H), 8.15 (t, J=7.7 Hz, 1H) 8.00 (d, J=7.9 Hz, 1H) 7.62 (br s, 1H) 7.58 (br s, 1H) 7.51 (d, J=7.5 Hz, 1H) 7.05 (d, J=7.8 Hz, 1H) 3.99-4.12 (m, 2H) 3.92 (s, 2H) 2.97-3.10 (m, 2H) 2.33 (br s, 2H) 2.00 (br s, 2H) 1.81 (d, J=8.7 Hz, 2H) 1.00 (t, J=7.2 Hz, 3H).

Example S-16: Synthesis of 2-ethyl-1-(5-fluoro-6-(2-fluoropropan-2-yl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.91)

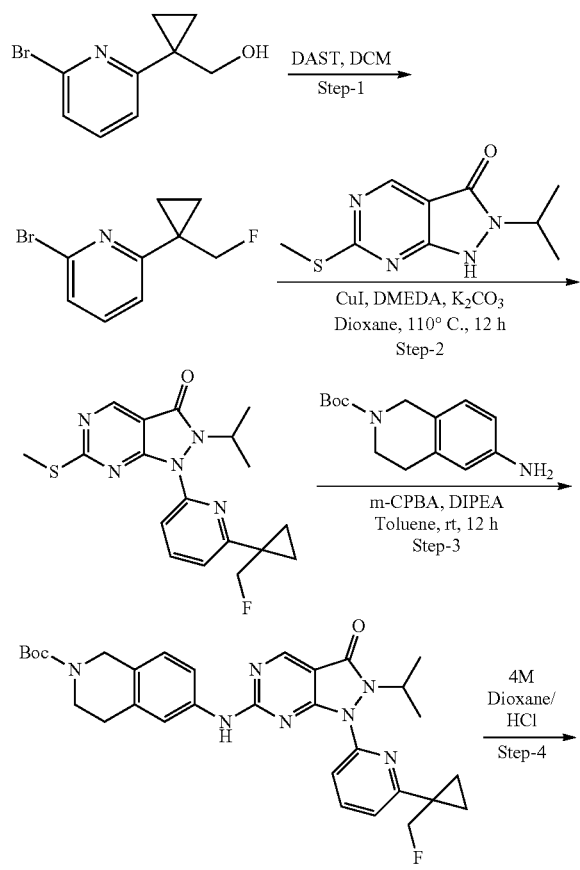

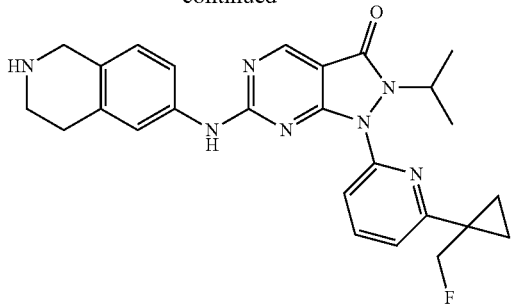

Step-1: Synthesis of 2-bromo-6-(1-(fluoromethyl)cyclopropyl)pyridine: To a stirred solution of (1-(6-bromopyridin-2-yl)cyclopropyl)methanol (1 g, 4.38 mmol, 1.0 eq) in DCM (40 mL) at −78° C. followed by addition of DAST (0.9 mL, 6.57 mmol, 1.5 eq) and allowed to stir at RT overnight. After completion of reaction, the reaction mixture was basified with NaHCO₃ (20 mL) at −78° C. and extracted with DCM (100 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-40% EtOAc in hexane] to afford the desired compound as gummy material. LCMS: 229.99 (M+1)⁺.

Step-2: Synthesis of 1-(6-(1-(fluoromethyl)cyclopropyl)pyridin-2-yl)-2-isopropyl-6-(methylthio)-1,2-dihydro-3H-pyrazolo[3,4-d]pyrimidin-3-one: To a stirred solution of 2-bromo-6-(1-(fluoromethyl)cyclopropyl)pyridine (189 mg, 0.82 mmol, 1.0 eq) and 2-isopropyl-6-(methylthio)-1,2-dihydro-3H-pyrazolo[3,4-d]pyrimidin-3-one (184.23 mg, 0.82 mmol, 1.0 eq) in dioxane (10 mL) was added potassium carbonate (227 mg, 1.64 mmol, 2.0 eq) and the resulting mixture was purged with nitrogen for 10 min followed by addition of copper iodide (31 mg, 0.16 mmol, 0.2 eq), and N,N'-dimethylethylenediamine (DMEDA) (0.03 mL, 0.33 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (133 mg, 43.35%) as brown semi-solid. LCMS: 374.14 (M+1)⁺.

Step-3: Synthesis of tert-butyl 6-((1-(6-(1-(fluoromethyl)cyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(6-(1-(fluoromethyl)cyclopropyl)pyridin-2-yl)-2-isopropyl-6-(methylthio)-1,2-dihydro-3H-pyrazolo[3,4-d]pyrimidin-3-one (133 mg, 0.36 mmol, 1.0 eq) in toluene (2.0 mL) was added m-CPBA (170 mg, 0.712 mmol, 2.0 eq) and allowed to stir at RT for 60 minutes. Tert-butyl 6-amino-3,4-dihydroisoquinoline-2(1H)-carboxylate (88.4 mg, 0.36 mmol, 1.0 eq) and Na₂CO₃ (151 mg, 1.42 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (61 mg, 30.04%) as light yellow solid. LCMS: 574.29 (M+1)+.

Step-4: Synthesis of 1-(6-(1-(fluoromethyl)cyclopropyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one: Tert-butyl 6-((1-(6-(1-(fluoromethyl)cyclopropyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (61 mg, 0.106 mmol, 1.0 eq) was dissolved in dioxane (1 mL) followed by dropwise addition of 2.0 M-HCl in diethylether (2.0 mL) and allowed to stir at RT for 2 h. After completion of reaction, the reaction mixture was filtered and dried under reduced pressure and purified product was obtained by reverse phase chromatography (10 mg, 18.13%) as white solid. LCMS: 474.23 (M+1)+; $^1$H NMR (400 MHz, DMSO-$d_6$): δ 10.24 (br s, 1H) 8.83 (s, 1H) 8.23 (br s, 1H) 8.14 (t, J=8.1 Hz, 1H) 7.91 (d, J=7.8 Hz, 1H) 7.62 (br s, 1H) 7.52 (d, J=7.5 Hz, 1H) 7.40 (d, J=7.8 Hz, 1H) 7.03 (d, J=7.8 Hz, 1H) 4.14-4.27 (m, 1H) 3.96 (br s, 2H) 3.12 (br s, 2H) 2.79 (br s, 2H) 2.67 (br s, 2H) 2.59 (d, J=10.1 Hz, 1H) 2.01 (br s, 2H) 1.81 (dd, J=16.8, 8.1 Hz, 1H) 1.38 (d, J=7.0 Hz, 6H).

Example S-17: Synthesis of 2-ethyl-1-(5-fluoro-6-(2-fluoropropan-2-yl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.188)

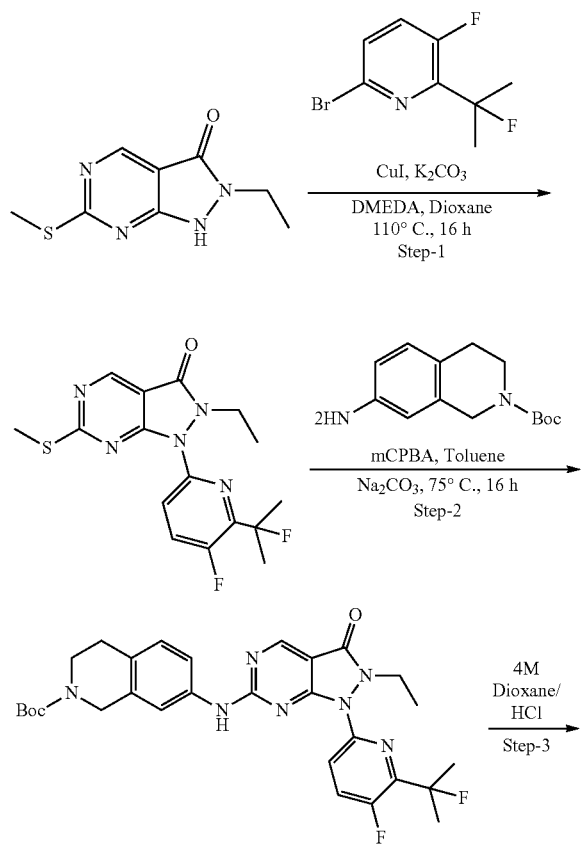

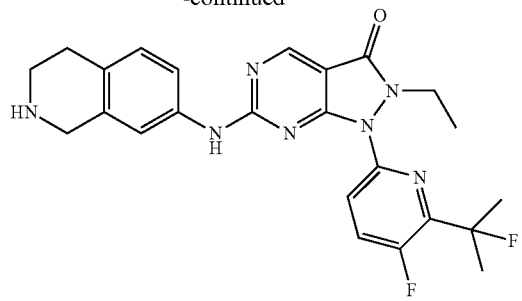

Step-1: Synthesis of 2-ethyl-1-(5-fluoro-6-(2-fluoropropan-2-yl)pyridin-2-yl)-6-(methylthio)-1,2-dihydro-3H-pyrazolo[3,4-d]pyrimidin-3-one: To a stirred solution of 2-ethyl-6-(methylthio)-1,2-dihydro-3H-pyrazolo[3,4-d]pyrimidin-3-one (244 mg, 1.65 mmol, 1.0 eq) and 6-bromo-3-fluoro-2-(2-fluoropropan-2-yl)pyridine (275 mg, 1.65 mmol, 1.0 eq) in dioxane (2.0 mL) was added potassium carbonate (456 mg, 3.3 mmol, 2.0 eq) and the resulting mixture was purged with nitrogen for 10 min followed by addition of copper iodide (62.8 mg, 0.33 mmol, 0.2 eq), and N,N'-dimethylethylenediamine (DMEDA) (0.06 mL, 0.66 mmol, 0.4 eq) and again purged with nitrogen for 10 min, then stirred at 130° C. b overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (234 mg, 55.2%) as yellow semi solid. LCMS: 366.11 (M+1)+.

Step-2: Synthesis of tert-butyl 7-((2-ethyl-1-(5-fluoro-6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate: To a stirred solution of 2-ethyl-1-(5-fluoro-6-(2-fluoropropan-2-yl)pyridin-2-yl)-6-(methylthio)-1,2-dihydro-3H-pyrazolo[3,4-d]pyrimidin-3-one (100 mg, 0.27 mmol, 1.0 eq) in toluene (3.0 mL) was added m-CPBA (130.5 mg, 0.55 mmol, 2.0 eq) and allowed to stir at RT for 60 minutes. Tert-butyl 7-amino-3,4-dihydroisoquinoline-2(1H)-carboxylate (74.7 mg, 0.30 mmol, 1.2 eq) and $Na_2CO_3$ (116.2 mg, 1.09 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (145 mg, 94.2%) as light brown solid. LCMS: 566.26 (M+1)+.

Step-3: Synthesis of 2-ethyl-1-(5-fluoro-6-(2-fluoropropan-2-yl)pyridin-2-yl)-6-((1,2,3,4-tetrahydroisoquinolin-7-yl)amino)-1,2-dihydro-3H-pyrazolo[3,4-d]pyrimidin-3-one: Tert-butyl 7-((2-ethyl-1-(5-fluoro-6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (145 mg, 0.25 mmol, 1.0 eq) was dissolved in dioxane (1 mL), followed by dropwise addition of 4.0 M-HCl in dioxane (1 mL) and allowed to stir at RT for 2 h. After completion of reaction, the reaction mixture was filtered and dried under reduced pressure and the purified product was obtained by reverse phase chromatography (8 mg, 6.7%) as an off-white solid. LCMS 466.21 (M+1)+; $^1$H NMR (400 MHz, DMSO-d$_6$): δ ppm 10.28 (br s, 1H) 8.86 (s, 1H) 7.99-8.18 (m, 2H) 7.56 (br s, 1H) 7.33-7.42 (m, 1H) 7.09 (d, J=8.7 Hz, 1H) 4.00 (br s, 4H) 3.11 (br s, 2H) 2.76 (br s, 2H), 1.78 (s, 3H) 1.72 (s, 3H) 0.98 (t, J=7.2 Hz, 3H).

Example S-18: Synthesis of 1-(5-fluoro-6-(2-hydroxypropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (Compound No. 1.250)

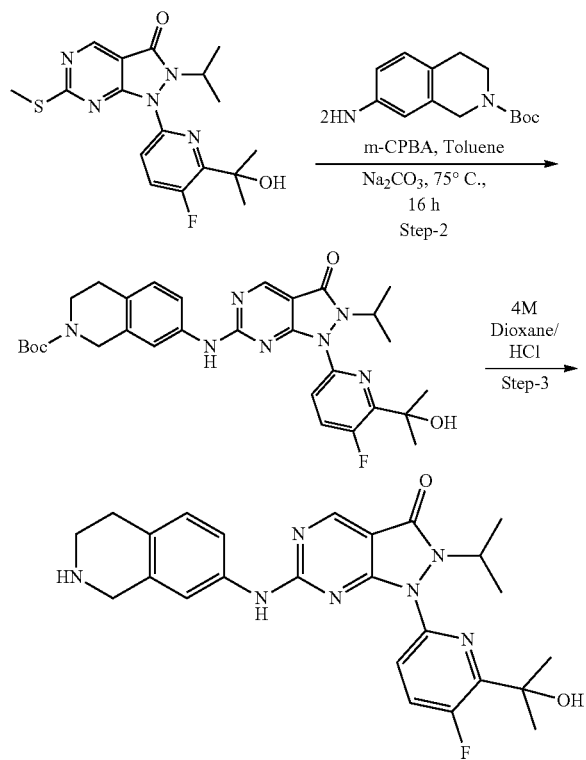

Step-1: Synthesis of tert-butyl 7-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate: To a stirred solution of 1-(5-fluoro-6-(2-hydroxypropan-2-yl)pyridin-2-yl)-2-isopropyl-6-(methylthio)-1,2-dihydro-3H-pyrazolo[3,4-d]pyrimidin-3-one (70 mg, 0.18 mmol, 1.0 eq) in toluene (4.0 mL) was added m-CPBA (88 mg, 0.37 mmol, 2.0 eq) and allowed to stir at RT for 60 minutes. Tert-butyl 7-amino-3,4-dihydroisoquinoline-2(1H)-carboxylate (46 mg, 0.18 mmol, 1.0 eq) and Na$_2$CO$_3$ (78.4 mg, 0.74 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (99 mg, 92.4%) as an off-white solid. LCMS: 578.28 (M+1)+.

Step-2: Synthesis of 1-(5-fluoro-6-(2-hydroxypropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one: Tert-butyl 7-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (99 mg, 0.17 mmol, 1.0 eq) was dissolved in dioxane (1 mL), followed by dropwise addition of 4.0 M-HCl in dioxane (1.5 mL) and allowed to stir at RT for 2 h. After completion of reaction, the reaction mixture was filtered and dried under reduced pressure and purified product was obtained by reverse phase chromatography (51 mg, 51.3%) as white solid. LCMS: 478.25 (M+1)+; $^1$H NMR (400 MHz, DMSO-d$_6$): δ 10.33 (br s, 1H) 9.18 (br s, 2H) 8.84 (s, 1H) 7.96-8.08 (m, 1H) 7.88 (d, J=6.6 Hz, 1H) 7.67 (br s, 1H) 7.48 (d, J=7.5 Hz, 1H) 7.17 (d, J=8.7 Hz, 1H) 4.09-4.33 (m, 4H) 3.37 (br s, 2H) 2.95 (br s, 2H) 1.42-1.58 (m, 6H) 1.33 (d, J=6.6 Hz, 6H).

Example S-19: Synthesis of 2-(5-fluoro-6-(2-isopropyl-3-oxo-6-(1,2,3,4-tetrahydroisoquinolin-6-ylamino)-2,3-dihydro-1H-pyrazolo[3,4-d]pyrimidin-1-yl)pyridin-2-yl)-2-methylpropanenitrile (Compound No. 1.321)

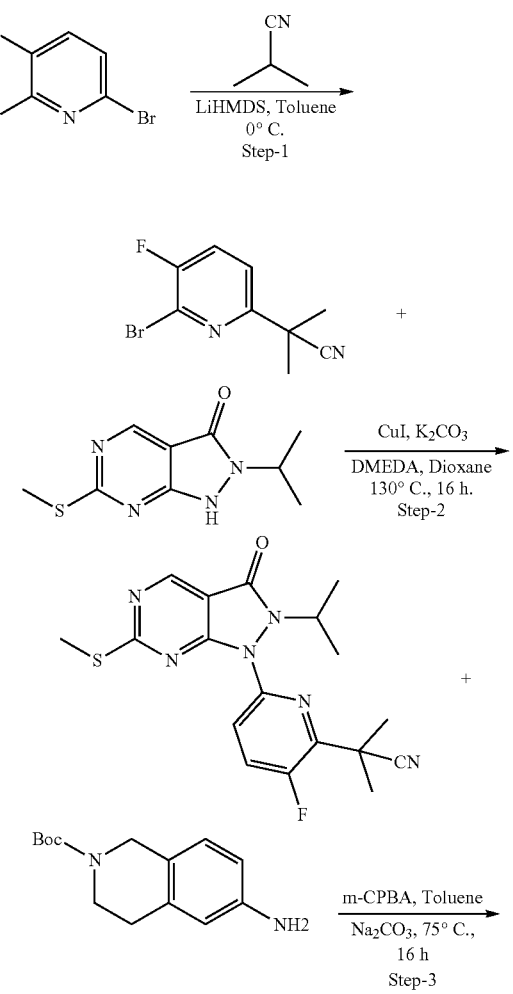

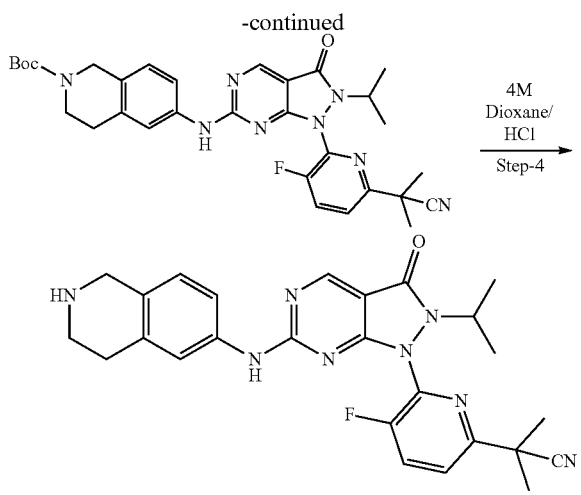

Step-1: Synthesis of 2-(6-bromopyridin-2-yl)-2-cyanopropan-1-ylium: To a stirred solution of isobutyronitrile (1.0 g, 14.46 mmol, 1 eq), in toluene (10 mL) was added LiHMDS (17.4 mL, 17.35 mmol, 1.2 eq), at 0° C. & the reaction mixture was stirred for 1 h. 2, 6-dibromo-3-fluoropyridine in toluene (5 mL), (3.68 g, 14.46 mmol, 1.0 eq) was added dropwise & stirred for 18 h. After completion of reaction, the reaction mixture was diluted with saturated NH$_4$Cl solution and extracted with diethyl ether (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (2.0 g, 57.1%) as colorless liquid. LCMS: 242.9 (M+1)$^+$.

Step-2: Synthesis of 2-(3-fluoro-6-(2-isopropyl-6-(methylthio)-3-oxo-2,3-dihydro-1H-pyrazolo[3,4-d]pyrimidin-1-yl)pyridin-2-yl)-2-methylpropanenitrile: To a stirred solution of 2-isopropyl-6-(methylthio)-1,2-dihydro-3H-pyrazolo[3,4-d]pyrimidin-3-one (224 mg, 1.0 mmol, 1.0 eq) and 2-(6-bromo-5-fluoropyridin-2-yl)-2-methylpropanenitrile (243 mg, 1.0 mmol, 1.0 eq) in dioxane (10 mL) were added potassium carbonate (276 mg, 2.0 mmol, 2.0 eq) and the resulting mixture was purged with nitrogen for 10 min followed by addition of copper iodide (38 mg, 0.2 mmol, 0.2 eq), and N,N'-dimethylethylenediamine (DMEDA) (0.05 mL, 0.4 mmol, 0.4 eq) and again purged with nitrogen for 10 min, then stirred at 90° C. overnight. After completion of reaction, the reaction mixture was diluted with water and extracted with EtOAc (50 mL×2). The combined organic layers were washed with water (50 mL) and brine solution (50 mL), dried over anhydrous sodium sulphate and concentrated under reduced pressure to afford crude product, which was purified by flash chromatography to afford the desired compound (250 mg, 64.7%). LCMS: 387.2 (M+1)$^+$.

Step-3: Synthesis of tert-butyl 6-(1-(6-(2-cyanopropan-2-yl)-3-fluoropyridin-2-yl)-2-isopropyl-3-oxo-2,3-dihydro-1H-pyrazolo[3,4-d]pyrimidin-6-ylamino)-3,4-dihydroisoquinoline-2(1H)-carboxylate: To a 2-(3-fluoro-6-(2-isopropyl-6-(methylthio)-3-oxo-2,3-dihydro-1H-pyrazolo[3,4-d]pyrimidin-1-yl)pyridin-2-yl)-2-methylpropanenitrile (75 mg, 0.19 mmol, 1.0 eq) in toluene (3.0 mL) was added m-CPBA (93 mg, 0.39 mmol, 2.0 eq) and allowed to stir at RT for 1 h. Tert-butyl 6-amino-3,4-dihydroisoquinoline-2 (1H)-carboxylate (51 mg, 0.21 mmol, 1.05 eq) and Na$_2$CO$_3$ (83 mg, 0.78 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (70 mg, 61.9%) as an off-white solid. LCMS: 587.4 (M+1)$^+$.

Step-4: Synthesis of 2-(5-fluoro-6-(2-isopropyl-3-oxo-6-(1,2,3,4-tetrahydroisoquinolin-6-ylamino)-2,3-dihydro-1H-pyrazolo[3,4-d]pyrimidin-1-yl)pyridin-2-yl)-2-methylpropanenitrile: Tert-butyl 6-(1-(6-(2-cyanopropan-2-yl)-3-fluoropyridin-2-yl)-2-isopropyl-3-oxo-2,3-dihydro-1H-pyrazolo[3,4-d]pyrimidin-6-ylamino)-3,4-dihydroisoquinoline-2(1H)-carboxylate (70 mg, 0.12 mmol, 1.0 eq) was dissolved in dioxane (1 mL), followed by dropwise addition of 4.0 M-HCl in dioxane (1 mL) and allowed to stir at RT for 1 h. After completion of reaction, the reaction mixture was filtered and dried under reduced pressure to afford the desired compound (40 mg, 68.9%) as white solid. LCMS: 487.4 (M+1)$^+$; $^1$H NMR (400 MHz, DMSO-d$_6$): δ 10.34 (br s, 1H) 9.31 (br s, 1H) 8.83 (s, 1H) 8.13-8.22 (m, 1H) 8.01 (dd, J=8.7, 3.1 Hz, 1H) 7.59-7.68 (m, 1H) 7.46 (m, J=8.77 Hz, 1H) 7.15 (m, J=8.7 Hz, 1H) 4.09-4.25 (m, 3H) 3.35 (br s, 2H) 2.98 (t, J=5.9 Hz, 2H) 1.73 (s, 6H) 1.34 (d, J=6.5 Hz, 6H).

Example S-20: Synthesis of 2-(5-fluoro-6-(2-isopropyl-3-oxo-6-(1,2,3,4-tetrahydroisoquinolin-7-ylamino)-2,3-dihydro-1H-pyrazolo[3,4-d]pyrimidin-1-yl)pyridin-2-yl)-2-methylpropanenitrile (Compound No. 1.322)

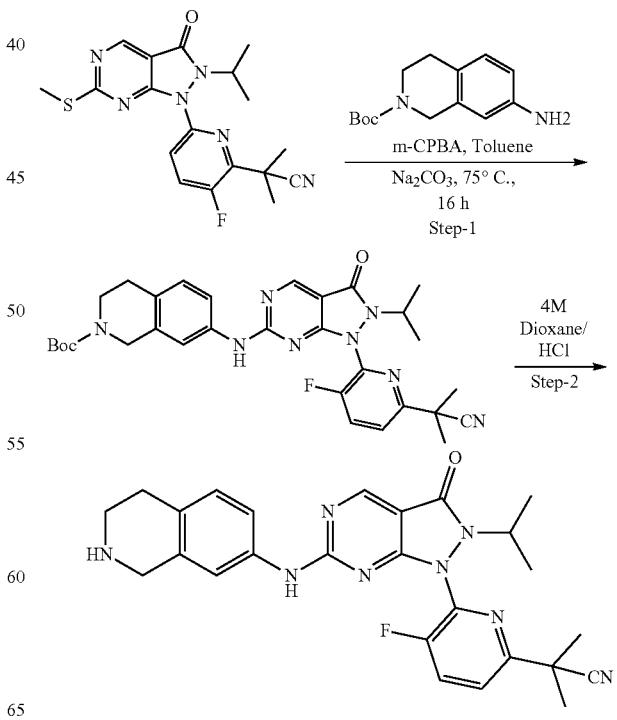

Step-1: Synthesis of tert-butyl 7-(1-(6-(2-cyanopropan-2-yl)-3-fluoropyridin-2-yl)-2-isopropyl-3-oxo-2,3-dihydro-1H-pyrazolo[3,4-d]pyrimidin-6-ylamino)-3,4-dihydroisoquinoline-2(1H)-carboxylate: To a stirred solution of 2-(3-fluoro-6-(2-isopropyl-6-(methylthio)-3-oxo-2,3-dihydro-1H-pyrazolo[3,4-d]pyrimidin-1-yl)pyridin-2-yl)-2-methylpropanenitrile (75 mg, 0.19 mmol, 1.0 eq) in toluene (3.0 mL) was added m-CPBA (93 mg, 0.39 mmol, 2.0 eq) and allowed to stir at RT for 1 h. Tert-butyl 7-amino-3,4-dihydroisoquinoline-2(1H)-carboxylate (51 mg, 0.21 mmol, 1.05 eq) and Na$_2$CO$_3$ (83 mg, 0.78 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (80 mg, 71.4%) as an off-white solid. LCMS: 587.4 (M+1)$^+$.

Step-2: Synthesis of 2-(5-fluoro-6-(2-isopropyl-3-oxo-6-(1,2,3,4-tetrahydroisoquinolin-7-ylamino)-2,3-dihydro-1H-pyrazolo[3,4-d]pyrimidin-1-yl)pyridin-2-yl)-2-methylpropanenitrile: Tert-butyl 7-(1-(6-(2-cyanopropan-2-yl)-3-fluoropyridin-2-yl)-2-isopropyl-3-oxo-2,3-dihydro-1H-pyrazolo[3,4-d]pyrimidin-6-ylamino)-3,4-dihydroisoquinoline-2(1H)-carboxylate (70 mg, 0.12 mmol, 1.0 eq) was dissolved in dioxane (1 mL), followed by dropwise addition of 4.0 M-HCl in dioxane (1 mL) and allowed to stir at RT for 1 h. After completion of reaction, the reaction mixture was filtered and dried under reduced pressure to afford the desired compound (30 mg, 47.3%) as white solid. LCMS: 487.5 (M+1)$^+$; $^1$H NMR (400 MHz, DMSO-d$_6$): δ 10.25 (br s, 1H) 8.82 (s, 1H) 8.27 (br s, 1H) 8.16 (d, J=10.1 Hz, 1H) 8.01 (dd, J=8.7, 3.1 Hz, 1H) 7.50 (br s, 1H) 7.40 (d, J=8.3 Hz, 1H) 7.07 (d, J=8.3 Hz, 1H) 4.18 (dt, J=13.8, 6.6 Hz, 1H) 3.95 (br s, 2H) 3.07 (br s, 2H) 2.73 (br s, 2H) 1.68-1.83 (m, 6H) 1.36 (d, J=6.5 Hz, 6H).

Example S-21: Synthesis of 2-ethyl-1-(5-fluoro-6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.262)

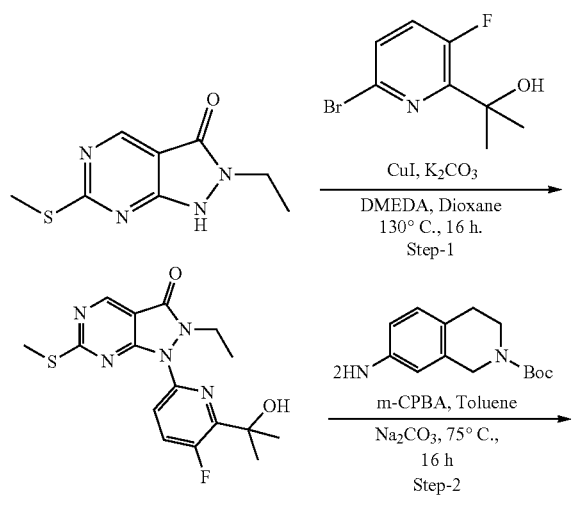

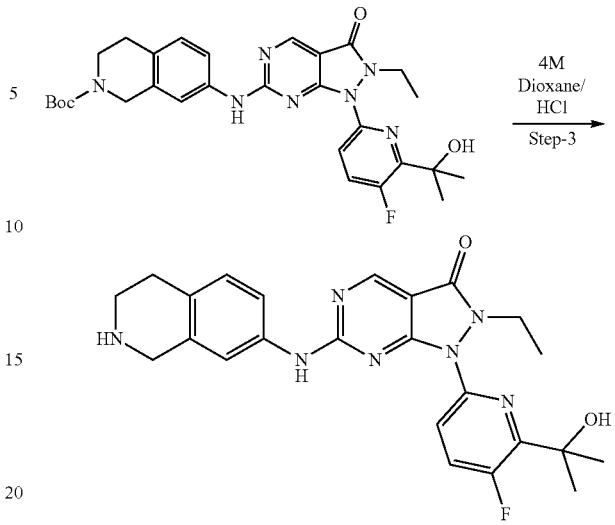

Step-1: Synthesis of 2-ethyl-1-(5-fluoro-6-(2-hydroxypropan-2-yl)pyridin-2-yl)-6-(methylthio)-1,2-dihydro-3H-pyrazolo[3,4-d]pyrimidin-3-one: To a stirred solution of 2-ethyl-6-(methylthio)-1,2-dihydro-3H-pyrazolo[3,4-d]pyrimidin-3-one (359 mg, 1.71 mmol, 1.0 eq) and 2-(6-bromo-3-fluoropyridin-2-yl)propan-2-ol (400 mg, 1.71 mmol, 1.0 eq) in dioxane (10 mL) was added potassium carbonate (472 mg, 3.42 mmol, 2.0 eq) and the resulting mixture was purged with nitrogen for 10 min followed by addition of copper iodide (65 mg, 0.34 mmol, 0.2 eq), and N,N'-dimethylethylenediamine (DMEDA) (0.03 mL, 0.684 mmol, 0.4 eq) and again purged with nitrogen for 10 min, then stirred at 130° C. overnight. After completion of the reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product as brown liquid. LCMS: 364.12 (M+1)$^+$.

Step-2: Synthesis of tert-butyl 7-((2-ethyl-1-(5-fluoro-6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate: To a stirred solution of 2-ethyl-1-(5-fluoro-6-(2-hydroxypropan-2-yl)pyridin-2-yl)-6-(methylthio)-1,2-dihydro-3H-pyrazolo[3,4-d]pyrimidin-3-one (100 mg, 0.27 mmol, 1.0 eq) in toluene (5.0 mL) was added m-CPBA (95 mg, 0.55 mmol, 2.0 eq) and allowed to stir at RT for 60 minutes. Tert-butyl 7-amino-3,4-dihydroisoquinoline-2(1H)-carboxylate (75 mg, 0.30 mmol, 1.2 eq) and Na$_2$CO$_3$ (93 mg, 1.09 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (150 mg, 96.7%) as light brown solid. LCMS: 564.27 (M+1)$^+$.

Step-3: Synthesis of 2-ethyl-1-(5-fluoro-6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one: Tert-butyl 7-((2-ethyl-1-(5-fluoro-6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (150 mg, 0.26 mmol, 1.0 eq) was dissolved in ether (1 mL), followed by dropwise addition of 2.0 M Ether in HCl (10 mL) and allowed to stir at RT for 2 h. After completion of reaction, the reaction mixture was filtered and dried under reduced pressure and the purified product was obtained by reverse phase purification (70 mg, 46.7%) as an off-white solid. LCMS: 464.21 (M+1)$^+$; $^1$H NMR (400 MHz, DMSO-d$_6$): δ 10.33 (br s, 1H) 9.08 (br s, 2H) 8.86 (s, 1H) 7.89-8.09 (m, 2H) 7.70 (br s, 1H) 7.47 (d, J=7.5 Hz, 1H) 7.18 (d, J=8.3 Hz, 1H) 4.26 (br s, 2H) 4.00 (d, J=7.4 Hz, 2H) 3.36 (br s, 3H) 2.94 (br s, 2H) 1.51 (s, 6H) 0.96 (t, J=7.0 Hz, 3H).

Example S-22: Synthesis of 6-((1,1-dimethyl-1,2,3,4-tetrahydroisoquinolin-6-yl)amino)-1-(5-fluoro-6-(2-hydroxypropan-2-yl)pyridin-2-yl)-2-isopropyl-1,2-dihydro-3H-pyrazolo[3,4-d]pyrimidin-3-one (Compound No. 1.251)

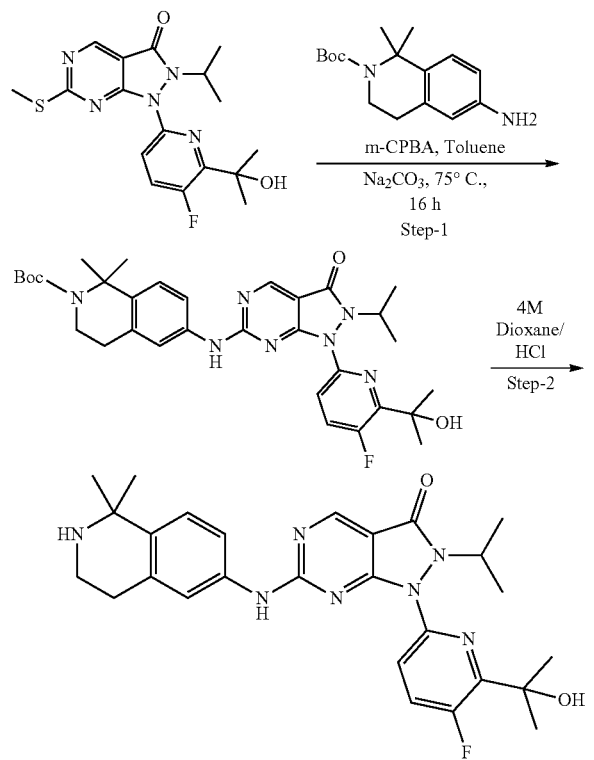

Step-1: Synthesis of tert-butyl 6-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate: To a stirred solution of 1-(5-fluoro-6-(2-hydroxypropan-2-yl)pyridin-2-yl)-2-isopropyl-6-(methylthio)-1,2-dihydro-3H-pyrazolo[3,4-d]pyrimidin-3-one (200 mg, 0.52 mmol, 1.0 eq) in toluene (4.0 mL) was added m-CPBA (231 mg, 1.04 mmol, 2.0 eq) and allowed to stir at RT for 60 minutes. Tert-butyl 6-amino-1,1-dimethyl-3,4-dihydroisoquinoline-2 (1H)-carboxylate (146 mg, 0.52 mmol, 1.0 eq) and Na$_2$CO$_3$ (220 mg, 2.08 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, (120 mg, 37.4%) as an off-white solid. LCMS: 606.28 (M+1)$^+$.

Step-2: Synthesis of 6-((1,1-dimethyl-1,2,3,4-tetrahydroisoquinolin-6-yl)amino)-1-(5-fluoro-6-(2-hydroxypropan-2-yl)pyridin-2-yl)-2-isopropyl-1,2-dihydro-3H-pyrazolo[3,4-d]pyrimidin-3-one: Tert-butyl 6-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (92 mg, 0.15 mmol, 1.0 eq) was dissolved in dioxane (1 mL), followed by dropwise addition of 4.0 M-HCl in dioxane (1.5 mL) and allowed to stir at RT for 2 h. After completion of reaction, the reaction mixture was filtered and dried under reduced pressure and the purified product was obtained by reverse phase purification (21 mg, 27.3%) as white solid. LCMS: 506.6 (M+1)$^+$; $^1$H NMR (400 MHz, DMSO-d$_6$): δ 10.29 (br s, 1H) 8.83 (s, 1H) 8.02 (d, J=10.1 Hz, 1H) 7.86 (d, J=6.1 Hz, 1H) 7.64 (br s, 1H) 7.49 (d, J=8.7 Hz, 1H) 7.33 (d, J=8.7 Hz, 1H) 4.13-4.25 (m, 2H) 3.40 (br s, 2H) 2.98 (br s, 2H) 1.61 (s, 6H) 1.52 (s, 6H) 1.33 (d, J=6.58 Hz, 6H).

Example S-23: Synthesis of 6-((2',3'-dihydro-1'H-spiro[cyclopropane-1,4'-isoquinolin]-7'-yl)amino)-1-(5-fluoro-6-(2-hydroxypropan-2-yl)pyridin-2-yl)-2-isopropyl-1,2-dihydro-3H-pyrazolo[3,4-d]pyrimidin-3-one (Compound No. 1.254)

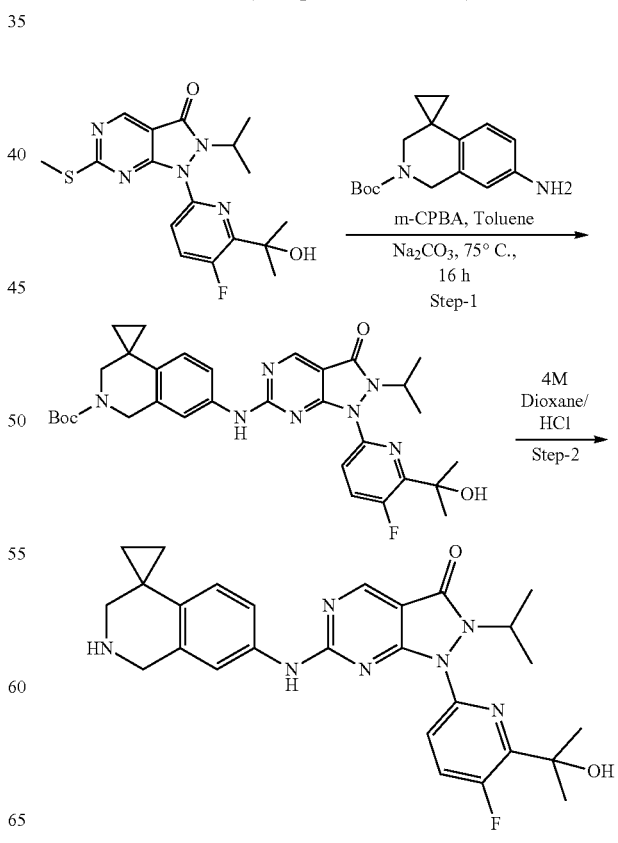

Step-1: Synthesis of tert-butyl 7'-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-1'H-spiro[cyclopropane-1,4'-isoquinoline]-2'(3'H)-carboxylate: To a stirred solution of 1-(5-fluoro-6-(2-hydroxypropan-2-yl)pyridin-2-yl)-2-isopropyl-6-(methylthio)-1,2-dihydro-3H-pyrazolo[3,4-d]pyrimidin-3-one (200 mg, 0.52 mmol, 1.0 eq) in toluene (4.0 mL) was added m-CPBA (249 mg, 1.05 mmol, 2.0 eq) and allowed to stir at RT for 60 minutes. Tert-butyl 7'-amino-1'H-spiro[cyclopropane-1,4'-isoquinoline]-2'(3'H)-carboxylate (146 mg, 0.52 mmol, 1.0 eq) and Na$_2$CO$_3$ (220 mg, 2.08 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound as an off-white solid. LCMS: 604.28 (M+1)$^+$.

Step-2: Synthesis of 6-((2',3'-dihydro-1'H-spiro[cyclopropane-1,4'-isoquinolin]-7'-yl)amino)-1-(5-fluoro-6-(2-hydroxypropan-2-yl)pyridin-2-yl)-2-isopropyl-1,2-dihydro-3H-pyrazolo[3,4-d]pyrimidin-3-one dihydrochloride: Tert-butyl 7'-((1-(5-fluoro-6-(2-hydroxypropan-2-yl)pyridin-2-yl)-2-isopropyl-3-oxo-2,3-dihydro-1H-pyrazolo[3,4-d]pyrimidin-6-yl)amino)-1'H-spiro[cyclopropane-1,4'-isoquinoline]-2'(3'H)-carboxylate (80 mg, 0.13 mmol, 1.0 eq) was dissolved in dioxane (1 mL), followed by dropwise addition of 4.0 M-HCl in dioxane (1.5 mL) and allowed to stir at RT for 2 h. After completion of reaction, the reaction mixture was filtered and dried under reduced pressure and the purified by reverse phase purification to afford the desired compound (34 mg, 44.5%) as white solid. LCMS: 504.58 (M+1)$^+$; $^1$H NMR (400 MHz, DMSO-d$_6$): δ 10.31 (br s, 1H) 9.23 (br s, 2H) 8.73-8.87 (m, 1H), 7.97-8.05 (m, 1H), 7.87 (d, J=8.3 Hz, 1H), 7.65 (br s, 1H), 7.48 (d, J=8.3 Hz, 1H), 6.83 (d, J=8.7 Hz, 1H), 4.36 (br s, 1H) 4.14-4.26 (m, 2H), 3.26 (br s, 2H), 1.52 (s, 6H), 1.33 (d, J=6.5 Hz, 6H), 1.08 (br s, 4H).

Example S-24: Synthesis of 2-ethyl-1-(5-fluoro-6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No. 1.261)

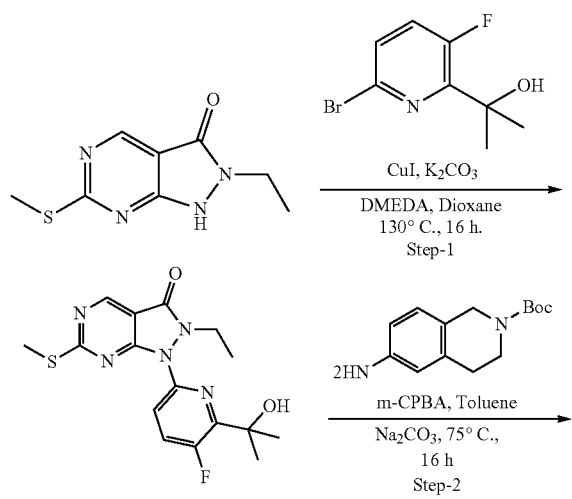

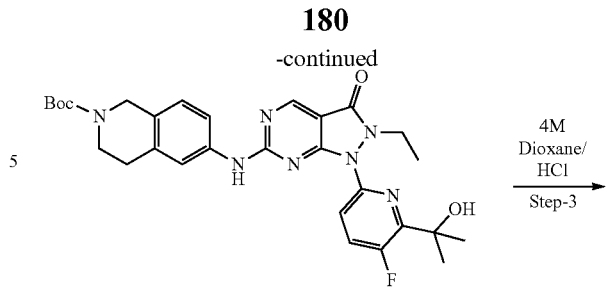

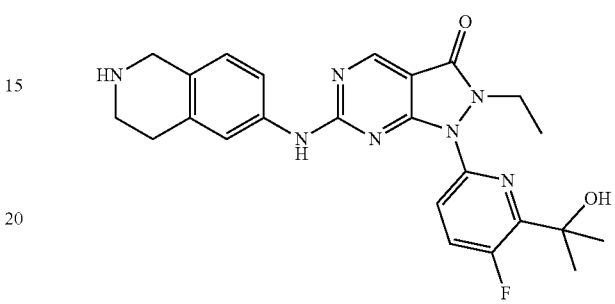

Step-1: Synthesis of 2-ethyl-1-(5-fluoro-6-(2-hydroxypropan-2-yl)pyridin-2-yl)-6-(methylthio)-1,2-dihydro-3H-pyrazolo[3,4-d]pyrimidin-3-one: To a stirred solution of 2-ethyl-6-(methylthio)-1,2-dihydro-3H-pyrazolo[3,4-d]pyrimidin-3-one (500 mg, 2.37 mmol, 1.0 eq) and 2-(6-bromo-3-fluoropyridin-2-yl)propan-2-ol (556.6 mg, 2.37 mmol, 1.0 eq) in dioxane (10 mL) was added potassium carbonate (657.6 mg, 4.75 mmol, 2.0 eq) and the resulting mixture was purged with nitrogen for 10 min followed by addition of copper iodide (90.5 mg, 0.47 mmol, 0.2 eq), and N,N'-dimethylethylenediamine (DMEDA) (0.09 mL, 0.951 mmol, 0.4 eq) and again purged with nitrogen for 10 min, stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product (520 mg, 60.2%) as brown liquid. LCMS: 364.44 (M+1)$^+$.

Step-2: Synthesis of tert-butyl 6-((2-ethyl-1-(5-fluoro-6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate): To a stirred solution of 2-ethyl-1-(5-fluoro-6-(2-hydroxypropan-2-yl)pyridin-2-yl)-6-(methylthio)-1,2-dihydro-3H-pyrazolo[3,4-d]pyrimidin-3-one (250 mg, 0.68 mmol, 1.0 eq) in toluene (5.0 mL) was added m-CPBA (304 mg, 1.37 mmol, 2.0 eq) and allowed to stir at RT for 60 minutes. Tert-butyl 6-amino-3,4-dihydroisoquinoline-2(1H)-carboxylate (170.8 mg, 0.68 mmol, 1.0 eq) and Na$_2$CO$_3$ (291.2 mg, 2.11 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (97 mg, 25.0%) as light brown solid. LCMS: 564.7 (M+1)$^+$.

Step-3: Synthesis of 2-ethyl-1-(5-fluoro-6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one: Tert-butyl 6-((2-ethyl-1-(5-fluoro-6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (90 mg, 0.16 mmol, 1.0 eq) was dissolved in dioxane (1 mL), followed by dropwise addition of 4.0 M dioxane in HCl (10 mL) and allowed to stir at RT for 2 h. After completion of reaction, the reaction mixture was filtered and dried under reduced pressure; purified product was obtained by reverse phase purification (34 mg, 44.6%) as an off-white solid. LCMS: 464.58 (M+1)$^+$; $^1$H NMR (400 MHz, DMSO-d$_6$): δ10.19 (br s, 1H) 8.84 (s, 1H) 7.87-8.06 (m, 2H) 7.51 (br s, 1H) 7.38 (d, J=8.3 Hz, 1H) 7.03 (d, J=8.3 Hz, 1H) 5.25 (s, 1H) 4.01 (d, J=7.0 Hz, 2H) 3.86 (s, 2H) 2.98 (t, J=5.7 Hz, 2H) 2.67 (d, J=5.3 Hz, 2H) 1.41-1.65 (s, 6H) 1.17-1.29 (m, 2H) 0.97 (t, J=7.0 Hz, 3H).

Example S-25: Synthesis of 1-(6-(6-((4,4-dimethyl-1,2,3,4-tetrahydroisoquinolin-7-yl)amino)-2-ethyl-3-oxo-2,3-dihydro-1H-pyrazolo[3,4-d]pyrimidin-1-yl)pyridin-2-yl)cyclopropane-1-carbonitrile
(Compound No. 1.40)

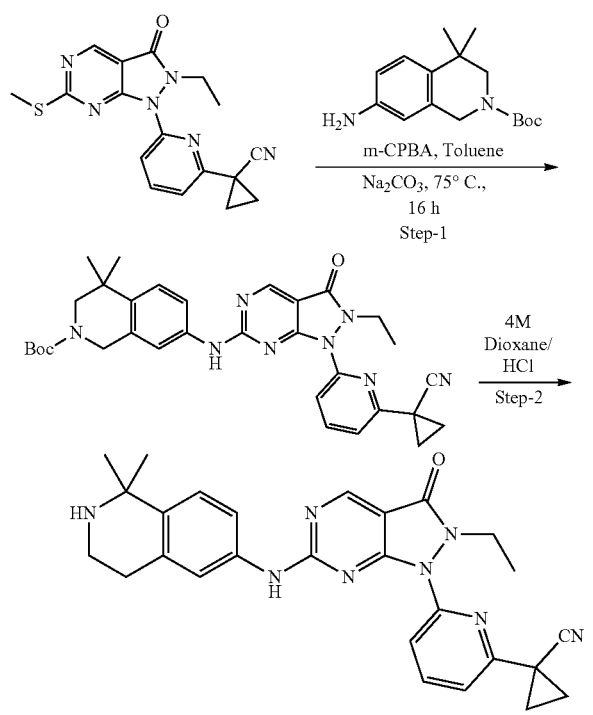

Step-1: Synthesis of tert-butyl 7-((1-(6-(1-cyanocyclopropyl)pyridin-2-yl)-2-ethyl-3-oxo-2,3-dihydro-1H-pyrazolo[3,4-d]pyrimidin-6-yl)amino)-4,4-dimethyl-3,4-dihydroisoquinoline-2(1H)-carboxylate: To a stirred solution of 1-(6-(2-ethyl-6-(methylthio)-3-oxo-2,3-dihydro-1H-pyrazolo[3,4-d]pyrimidin-1-yl)pyridin-2-yl)cyclopropane-1-carbonitrile (100 mg, 0.28 mmol, 1.0 eq) in toluene (3.0 mL) was added m-CPBA (134 mg, 0.56 mmol, 2.0 eq) and allowed to stir at RT for 1 h. Tert-butyl 7-amino-4,4-dimethyl-3,4-dihydroisoquinoline-2(1H)-carboxylate (78 mg, 0.28 mmol, 1.0 eq) and Na$_2$CO$_3$ (120 mg, 1.132 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound (51 mg, 30.9%) as light yellow solid. LCMS: 581.29 (M+1)$^+$.

Step-2: Synthesis of 1-(6-(6-((4,4-dimethyl-1,2,3,4-tetrahydroisoquinolin-7-yl)amino)-2-ethyl-3-oxo-2,3-dihydro-1H-pyrazolo[3,4-d]pyrimidin-1-yl)pyridin-2-yl)cyclopropane-1-carbonitrile: Tert-butyl 7-((1-(6-(1-cyanocyclopropyl)pyridin-2-yl)-2-ethyl-3-oxo-2,3-dihydro-1H-pyrazolo[3,4-d]pyrimidin-6-yl)amino)-4,4-dimethyl-3,4-dihydroisoquinoline-2(1H)-carboxylate (51 mg, 0.087 mmol, 1.0 eq) was dissolved in dioxane (1 mL), followed by dropwise addition of 4.0 M-HCl in dioxane (1 mL) and allowed to stir at RT for 2 h. After completion of reaction, the reaction mixture was filtered and dried under reduced pressure, crude was given for prep purification to afford the desired compound (22 mg, 45.2%) as white solid. LCMS: 481.24 (M+1)$^+$; $^1$H NMR (400 MHz, DMSO-d$_6$): δ 10.36 (br s, 1H) 9.11 (br s, 2H) 8.88 (s, 1H) 8.14 (t, J=7.7 Hz, 1H) 7.93 (d, J=7.8 Hz, 1H) 7.63 (br s, 1H) 7.49-7.60 (m, 1H) 7.45 (d, J=8.7 Hz, 1H) 4.26 (br s, 2H) 3.98 (m, J=7.45 Hz, 2H) 3.24 (br s, 2H) 1.81-1.91 (m, 2H) 1.63-1.75 (m, 2H) 1.35 (s, 6H) 0.97 (t, J=7.02 Hz, 3H).

Example S-26: Synthesis of 1-(6-(3-oxo-6-(1,2,3,4-tetrahydroisoquinolin-7-ylamino)-2-(2,2,2-trifluoroethyl)-2,3-dihydro-1H-pyrazolo[3,4-d]pyrimidin-1-yl)pyridin-2-yl)cyclopropanecarbonitrile
(Compound No. 1.32)

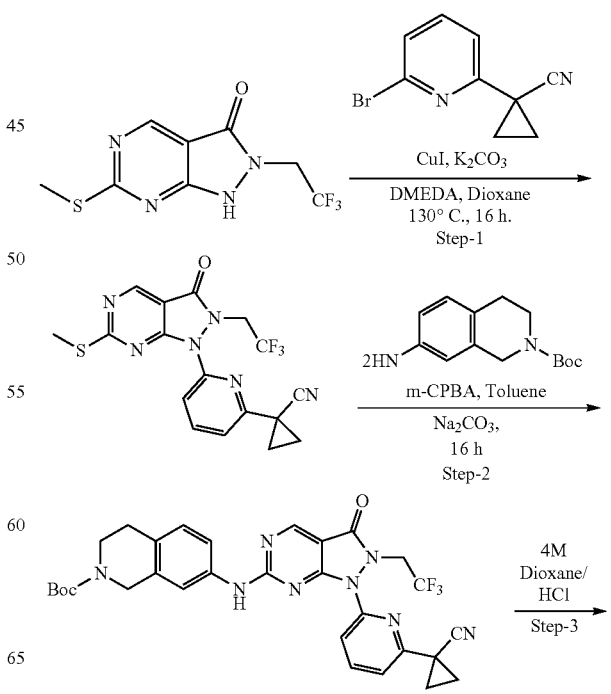

-continued

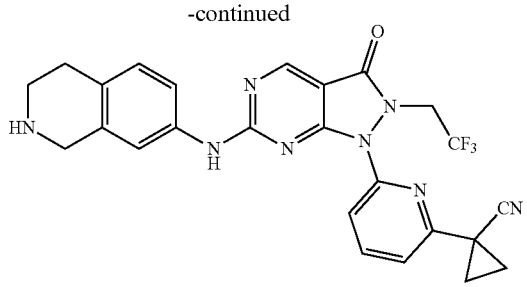

Step-1: Synthesis of 1-(6-(6-(methylthio)-3-oxo-2-(2,2,2-trifluoroethyl)-2,3-dihydro-1H-pyrazolo[3,4-d]pyrimidin-1-yl)pyridin-2-yl)cyclopropanecarbonitrile: To a stirred solution of 6-(methylthio)-2-(2,2,2-trifluoroethyl)-1H-pyrazolo[3,4-d]pyrimidin-3(2H)-one (264 mg, 1.0 mmol, 1.0 eq) and 1-(6-bromopyridin-2-yl)cyclopropane-1-carbonitrile (245 mg, 1.1 mmol, 1.0 eq) in dioxane (10 mL) was added potassium carbonate (276 mg, 2.0 mmol, 2.0 eq) and the resulting mixture was purged with nitrogen for 10 min followed by addition of copper iodide (38 mg, 0.2 mmol, 0.2 eq), and N,N'-dimethylethylenediamine (DMEDA) (0.05 mL, 0.4 mmol, 0.4 eq) and again purged with nitrogen for 10 min, then stirred at 130° C. overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product, (220 mg, 54.2%) as light brown solid. LCMS: 407.3 (M+1)$^+$.

Step-2: Synthesis of tert-butyl 7-(1-(6-(1-cyanocyclopropyl)pyridin-2-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate: To a stirred solution of 1-(6-(6-(methylthio)-3-oxo-2-(2,2,2-trifluoroethyl)-2,3-dihydro-1H-pyrazolo[3,4-d]pyrimidin-1-yl)pyridin-2-yl)cyclopropanecarbonitrile (102 mg, 0.25 mmol, 1.0 eq) in toluene (2.0 mL) was added m-CPBA (122 mg, 0.5 mmol, 2.0 eq) and allowed to stir at RT for 60 minutes. Tert-butyl 7-amino-3,4-dihydroisoquinoline-2(1H)-carboxylate (75 mg, 0.31 mmol, 1.2 eq) and Na$_2$CO$_3$ (106 mg, 1.0 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, (100 mg, 72%) as off-white solid. LCMS: 607.4 (M+1)$^+$.

Step-3: Synthesis of 1-(6-(3-oxo-6-(1,2,3,4-tetrahydroisoquinolin-7-ylamino)-2-(2,2,2-trifluoroethyl)-2,3-dihydro-1H-pyrazolo[3,4-d]pyrimidin-1-yl)pyridin-2-yl)cyclopropanecarbonitrile: Tert-butyl 7-(1-(6-(1-cyanocyclopropyl)pyridin-2-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate (100 mg, 0.18 mmol, 1.0 eq) was dissolved in dioxane (1 mL), followed by dropwise addition of 4.0 M-HCl in dioxane (1 mL) and allowed to stir at RT for 4 h. After completion of reaction, the reaction mixture was filtered, dried under reduced pressure and triturated with diethyl ether to give white solid. To this solid was added aq. NaHCO$_3$ (10 mL) and product was extracted in to DCM. Organic layer was dried over anhydrous sodium sulfate and concentrated under reduced pressure to afford the desired product as an off-white solid (20 mg, 22%). LCMS: 507.2 (M+1)$^+$; $^1$H NMR (400 MHz, DMSO-d$_6$): δ10.43 (br s, 1H) 8.95 (s, 1H) 8.11 (t, J=7.8 Hz, 1H) 7.91 (br s, 1H) 7.53 (d, J=7.8 Hz, 2H) 7.33 (br s, 1H) 7.04 (d, J=8.3 Hz, 1H) 4.91 (d, J=8.7 Hz, 2H) 3.85 (br s, 2H) 2.96 (d, J=6.1 Hz, 2H) 2.67 (d, J=1.75 Hz, 2H) 1.79-1.89 (m, 2H) 1.63-1.76 (m, 2H).

Example S-27: Synthesis of 1-(6-(6-(1,1-dimethyl-1,2,3,4-tetrahydroisoquinolin-6-ylamino)-2-ethyl-3-oxo-2,3-dihydro-1H-pyrazolo[3,4-d]pyrimidin-1-yl)pyridin-2-yl)cyclopropanecarbonitrile (Compound No. 1.39)

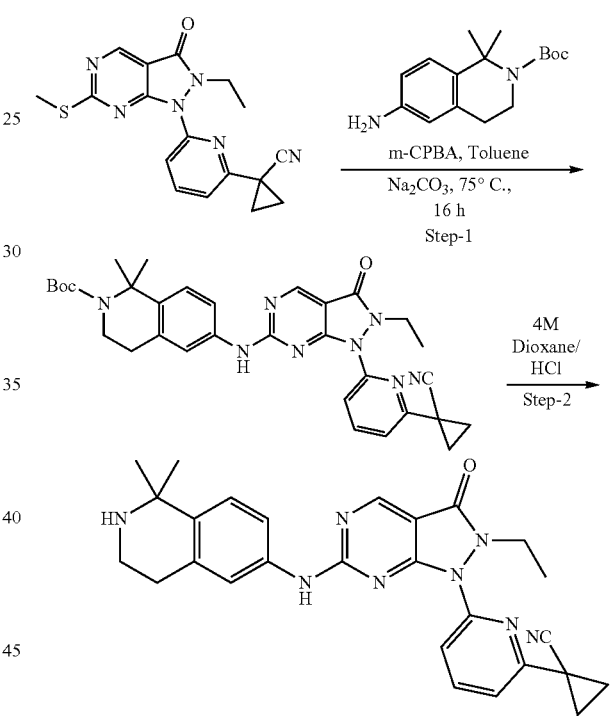

Step-1: Synthesis of tert-butyl 6-(1-(6-(1-cyanocyclopropyl)pyridin-2-yl)-2-ethyl-3-oxo-2,3-dihydro-1H-pyrazolo[3,4-d]pyrimidin-6-ylamino)-1,1-dimethyl-3,4-dihydroisoquinoline-2(1H)-carboxylate: To a stirred solution of 1-(6-(2-ethyl-6-(methylthio)-3-oxo-2,3-dihydro-1H-pyrazolo[3,4-d]pyrimidin-1-yl)pyridin-2-yl)cyclopropanecarbonitrile (125 mg, 0.35 mmol, 1.0 eq) in toluene (2.0 mL) was added m-CPBA (172 mg, 0.7 mmol, 2.0 eq) and allowed to stir at RT for 60 minutes. Tert-butyl 6-amino-1,1-dimethyl-3,4-dihydroisoquinoline-2(1H)-carboxylate (107 mg, 0.39 mmol, 1.1 eq) and Na$_2$CO$_3$ (149 mg, 1.4 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh;

elution 0-50% EtOAc in hexane] to afford the desired compound, (110 mg, 54.2%) as light yellow solid. LCMS: 581.2 (M+1)⁺.

Step-2: Synthesis of 1-(6-(6-(1,1-dimethyl-1,2,3,4-tetrahydroisoquinolin-6-ylamino)-2-ethyl-3-oxo-2,3-dihydro-1H-pyrazolo[3,4-d]pyrimidin-1-yl)pyridin-2-yl)cyclopropanecarbonitrile: Tert-butyl 6-(1-(6-(1-cyanocyclopropyl)pyridin-2-yl)-2-ethyl-3-oxo-2,3-dihydro-1H-pyrazolo[3,4-d]pyrimidin-6-ylamino)-1,1-dimethyl-3,4-dihydroisoquinoline-2(1H)-carboxylate (110 mg, 0.19 mmol, 1.0 eq) was dissolved in dioxane (2 mL), followed by dropwise addition of 4.0 M-HCl in dioxane (2 mL) and allowed to stir at RT for 2 h. After completion of reaction, solvent was evaporated, triturated with diethyl ether (3×5 mL) and dried to give the desired compound (76 mg, 83.3%) as an off-white solid. LCMS: 481.5 (M+1)⁺; ¹H NMR (400 MHz, DMSO-d₆): δ10.34 (br s, 1H) 9.62 (br s, 2H) 8.77-8.94 (s, 1H) 8.17 (t, J=7.8 Hz, 1H) 7.91 (d, J=7.8 Hz, 1H) 7.68 (br s, 1H) 7.45-7.56 (m, 2H) 7.36 (d, J=8.7 Hz, 1H) 3.98 (q, J=6.8 Hz, 2H) 3.40 (br s, 2H) 3.04 (t, J=6.1 Hz, 2H) 1.81-1.93 (m, 2H) 1.58-1.77 (m, 8H) 0.97 (t, J=7.0 Hz, 3H).

Example S-28: Synthesis of 1-(6-(6-(2',3'-dihydro-1¹H-spiro[cyclopropane-1,4'-isoquinoline]-7'-ylamino)-2-ethyl-3-oxo-2,3-dihydro-1H-pyrazolo[3,4-d]pyrimidin-1-yl)pyridin-2-yl)cyclopropanecarbonitrile (Compound No. 1.42)

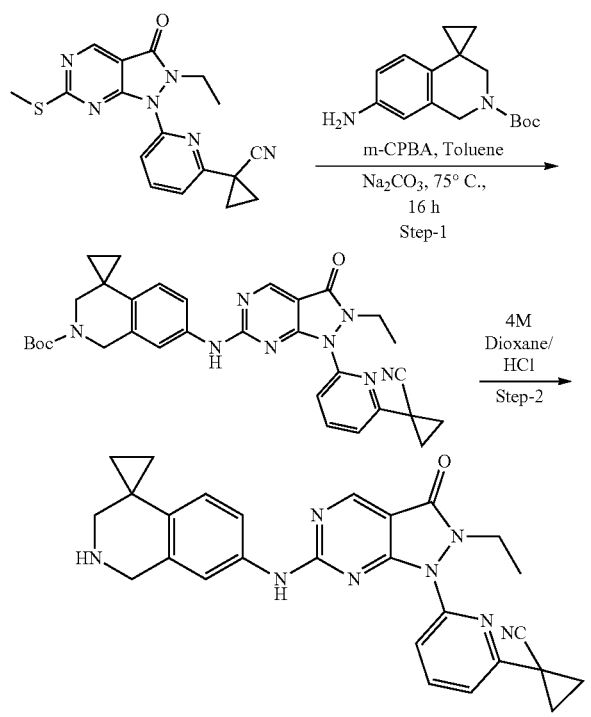

Step-1: Synthesis of tert-butyl 7'-(1-(6-(1-cyanocyclopropyl)pyridin-2-yl)-2-ethyl-3-oxo-2,3-dihydro-1H-pyrazolo[3,4-d]pyrimidin-6-ylamino)-1'H-spiro[cyclopropane-1,4'-isoquinoline]-2'(3'H)-carboxylate: To a stirred solution of 1-(6-(2-ethyl-6-(methylthio)-3-oxo-2,3-dihydro-1H-pyrazolo[3,4-d]pyrimidin-1-yl)pyridin-2-yl)cyclopropanecarbonitrile (125 mg, 0.35 mmol, 1.0 eq) in toluene (2.0 mL) was added m-CPBA (172 mg, 0.7 mmol, 2.0 eq) and allowed to stir at RT for 60 minutes. Tert-butyl 7'-amino-1'H-spiro[cyclopropane-1,4'-isoquinoline]-2'(3'H)-carboxylate (106 mg, 0.39 mmol, 1.1 eq) and Na₂CO₃ (149 mg, 1.4 mmol, 4.0 eq) were added and allowed to stir at RT overnight. After completion of reaction, the reaction mixture was diluted with water and extracted with EtOAc (50 mL×2). The combined organic layer was washed with water (50 mL) and brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, (90 mg, 44.6%) as light yellow solid. LCMS: 579.2 (M+1)⁺.

Step-2: Synthesis of 1-(6-(6-(2',3'-dihydro-1'H-spiro[cyclopropane-1,4'-isoquinoline]-7'-ylamino)-2-ethyl-3-oxo-2,3-dihydro-1H-pyrazolo[3,4-d]pyrimidin-1-yl)pyridin-2-yl)cyclopropanecarbonitrile: Tert-butyl 7'-(1-(6-(1-cyanocyclopropyl)pyridin-2-yl)-2-ethyl-3-oxo-2,3-dihydro-1H-pyrazolo[3,4-d]pyrimidin-6-ylamino)-1'H-spiro[cyclopropane-1,4'-isoquinoline]-2'(3'H)-carboxylate (90 mg, 0.16 mmol, 1.0 eq) was dissolved in dioxane (1 mL), followed by dropwise addition of 4.0 M-HCl in dioxane (1 mL) and allowed to stir at RT for 4 h. After completion of reaction, triturated with diethyl ether (3×5 mL) and dried to give the desired compound (31 mg, 40.5%) as an off-white solid. LCMS: 479.5 (M+1)⁺; ¹H NMR (400 MHz, DMSO-d₆): δ10.34 (br s, 1H) 9.36 (br s, 2H) 8.88 (s, 1H) 8.16 (t, J=7.9 Hz, 1H) 7.92 (d, J=7.9 Hz, 1H) 7.67 (br s, 1H) 7.45-7.56 (m, 2H) 6.84 (d, J=8.7 Hz, 1H) 4.37 (br s, 2H) 3.89-4.03 (m, 2H) 3.26 (br s, 2H) 1.77-1.92 (m, 2H) 1.60-1.76 (m, 2H) 1.09 (d, J=4.4 Hz, 4H) 0.97 (t, J=6.8 Hz, 3H).

Example S-29: Synthesis of 1-(4-(6-((1,1-dimethyl-1,2,3,4-tetrahydroisoquinolin-6-yl)amino)-2-ethyl-3-oxo-2,3-dihydro-1H-pyrazolo[3,4-d]pyrimidin-1-yl)pyridin-2-yl)cyclopropane-1-carbonitrile (Compound No. 1.63)

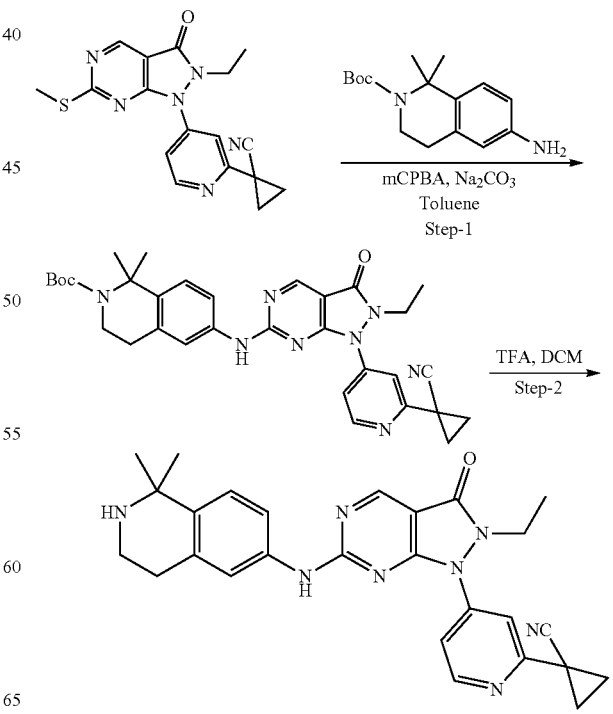

Step-1: Synthesis of tert-butyl 6-((1-(2-(1-cyanocyclopropyl)pyridin-4-yl)-2-ethyl-3-oxo-2,3-dihydro-1H-pyrazolo[3,4-d]pyrimidin-6-yl)amino)-1,1-dimethyl-3,4-dihydroisoquinoline-2(1H)-carboxylate: To a stirred solution of 1-(4-(2-ethyl-6-(methylthio)-3-oxo-2,3-dihydro-1H-pyrazolo[3,4-d]pyrimidin-1-yl)pyridin-2-yl)cyclopropane-1-carbonitrile (100 mg, 0.28 mmol, 1.0 eq) in toluene (3 mL) was added m-CPBA (126 mg, 0.56 mmol, 2.0 eq) and allowed to stir at RT for 60 minutes. tert-butyl 6-amino-1,1-dimethyl-3,4-dihydroisoquinoline-2(1H)-carboxylate (78.4 mg, 0.28 mol, 1.0 eq) and Na$_2$CO$_3$ (120 mg, 1.13 mmol, 4.0 eq) were added and allowed to stir at RT for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the titled compound (70 mg, 42.5%). LCMS: 581.69 (M+1)$^+$.

Step-2: Synthesis of 1-(4-(6-(((1,1-dimethyl-1,2,3,4-tetrahydroisoquinolin-6-yl)amino)-2-ethyl-3-oxo-2,3-dihydro-1H-pyrazolo[3,4-d]pyrimidin-1-yl)pyridin-2-yl)cyclopropane-1-carbonitrile: tert-butyl 6-((1-(2-(1-cyanocyclopropyl)pyridin-4-yl)-2-ethyl-3-oxo-2,3-dihydro-1H-pyrazolo[3,4-d]pyrimidin-6-yl)amino)-1,1-dimethyl-3,4-dihydroisoquinoline-2(1H)-carboxylate (70 mg, 0.12 mmol, 1.0 eq) was dissolved in dichloromethane (1 mL), followed by dropwise addition of TFA (0.5 mL) and allowed to stir at rt for 1 h. After completion of reaction, the reaction mixture was filtered and dried under reduced pressure and triturated with diethyl ether to afford the titled compound (4 mg, 6.3%). LCMS: 481.58 (M+1)$^+$; $^1$H NMR (400 MHz, DMSO-d$_6$): δ10.43 (br s, 1H) 8.84-8.95 (m, 1H) 8.69 (d, J=5.2 Hz, 1H) 7.48-7.67 (m, 4H) 7.37 (d, J=8.7 Hz, 1H) 3.70-3.86 (m, 2H) 3.39 (br s, 2H), 2.97 (br s, 2H) 1.70-1.95 (m, 4H), 1.61 (s, 6H), 0.98 (t, J=7.2 Hz, 3H).

Example S-30: Synthesis of 2-(6-(6-(1,1-dimethyl-1,2,3,4-tetrahydroisoquinolin-6-ylamino)-2-ethyl-3-oxo-2,3-dihydro-1H-pyrazolo[3,4-d]pyrimidin-1-yl)-5-fluoropyridin-2-yl)-2-methylpropanenitrile
(Compound No. 1.335)

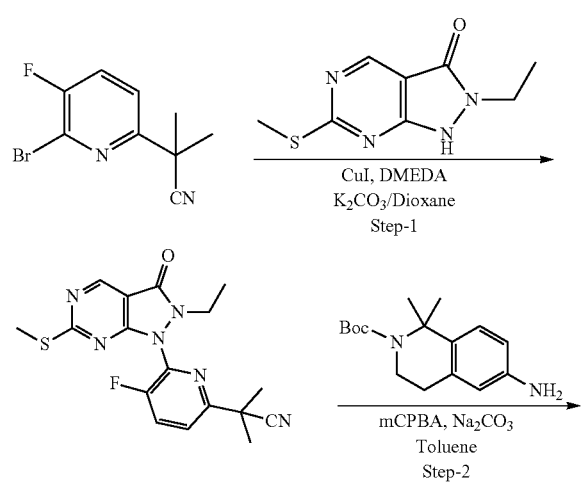

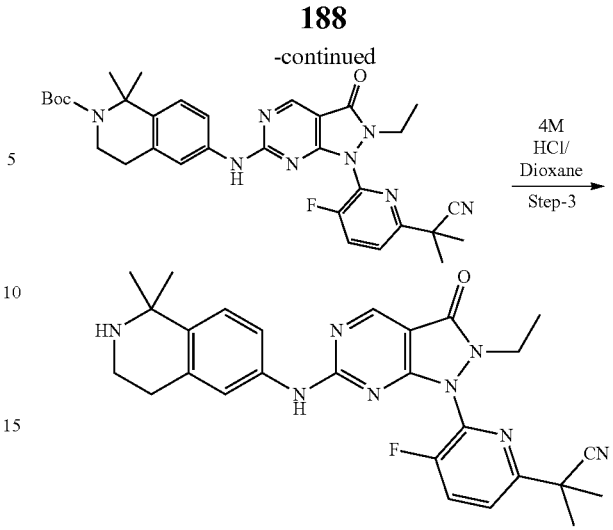

Step-1: Synthesis of 2-(6-(2-ethyl-6-(methylthio)-3-oxo-2,3-dihydro-1H-pyrazolo[3,4-d]pyrimidin-1-yl)-5-fluoropyridin-2-yl)-2-methylpropanenitrile: To a stirred solution of 2-(6-bromo-5-fluoropyridin-2-yl)-2-methylpropanenitrile (300 mg, 1.23 mmol, 1.0 eq) and 2-ethyl-6-(methylthio)-1,2-dihydro-3H-pyrazolo[3,4-d]pyrimidin-3-one (259 mg, 1.23 mmol, 1.0 eq) in (10 mL) of dioxane were added Potassium carbonate (341.2 mg, 2.46 mmol, 2.0 eq) and the resulting mixture was purged with nitrogen for 10 min followed by addition of copper iodide (47 mg, 0.24 mmol, 0.2 eq), and N,N'-dimethylethylenediamine (DMEDA) (0.05 mL, 0.49 mmol, 0.4 eq) and again purged with nitrogen for 10 min, stirred at 90° C. for overnight. After completion of reaction, the reaction mixture was diluted with water and extracted with EtOAc (50 mL×2). The combined organic layers were washed with water (50 mL) brine solution (50 mL), dried over anhydrous sodium sulphate and concentrated under reduced pressure to afford crude product, which was purified by flash chromatography to afford the titled compound (106 mg, 23.1%). LCMS: 372.4 (M+1)$^+$.

Step-2: Synthesis of tert-butyl 6-((1-(6-(2-cyanopropan-2-yl)-3-fluoropyridin-2-yl)-2-ethyl-3-oxo-2,3-dihydro-1H-pyrazolo[3,4-d]pyrimidin-6-yl)amino)-1,1-dimethyl-3,4-dihydroisoquinoline-2(1H)-carboxylate: To a stirred solution of 2-(6-(2-ethyl-6-(methylthio)-3-oxo-2,3-dihydro-1H-pyrazolo[3,4-d]pyrimidin-1-yl)-5-fluoropyridin-2-yl)-2-methylpropanenitrile (106 mg, 0.28 mmol, 1.0 eq) in (3.0 mL) of toluene was added m-CPBA (126.4 mg, 0.56 mmol, 2.0 eq) and allowed to stir at RT for 1 h. tert-butyl 6-amino-1,1-dimethyl-3,4-dihydroisoquinoline-2(1H)-carboxylate (79 mg, 0.28 mmol, 1.05 eq) and Na$_2$CO$_3$ (120 mg, 1.13 mmol, 4.0 eq) were added and allowed to stir at RT for overnight. After completion of reaction, the reaction mixture was diluted with water (50 mL) and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] afford the titled compound (40 mg, 23.4%). LCMS: 600.7 (M+1)$^+$.

Step-3: Synthesis of 2-(6-(6-(1,1-dimethyl-1,2,3,4-tetrahydroisoquinolin-6-ylamino)-2-ethyl-3-oxo-2,3-dihydro-1H-pyrazolo[3,4-d]pyrimidin-1-yl)-5-fluoropyridin-2-yl)-2-methylpropanenitrile: tert-butyl 6-((1-(6-(2-cyanopropan-2-yl)-3-fluoropyridin-2-yl)-2-ethyl-3-oxo-2,3-dihydro-1H- pyrazolo[3,4-d]pyrimidin-6-yl)amino)-1,1-dimethyl-3,4-dihydroisoquinoline-2(1H)-carboxylate (40 mg, 0.06 mmol, 1.0 eq) was dissolved in dioxane (1 mL), followed by dropwise addition of 4.0 M HCl in dioxane (1 mL) and allowed to stir at RT for 1 h. After completion of reaction, the reaction mixture was filtered and dried under reduced pressure to afford the titled compound (22 mg, 60.5%). LCMS: 501.5 (M+1)$^+$; $^1$H NMR (400 MHz, DMSO-d$_6$): δ10.24 (br s, 1H) 8.87 (s, 1H) 8.26 (br s, 1H) 8.13-8.24 (m, 2H) 8.09 (d, J=6.1 Hz, 1H) 7.51 (br s, 1H) 7.45 (d, J=8.3 Hz, 1H) 7.27 (d, J=8.7 Hz, 1H) 3.95-4.09 (m, 2H) 3.10 (br s, 2H) 2.77 (br s, 2H) 1.76 (s, 6H) 1.43 (s, 6H) 0.98 (t, J=7.0 Hz, 3H).

The compounds disclosed therein are prepared according to the experimental details exemplified in Examples S1-S30 and Scheme 1 to Scheme 5, using the appropriate starting materials and reagents.

BIOLOGICAL EXAMPLES

Example B1. WEE1 IC$_{50}$ Determination

IC$_{50}$ values of compounds against WEE1 kinase enzyme were determined by LanthaScreen™ Terbium Labeled TR-FRET assay. Kinase assays were performed in 1X kinase buffer (#PV6135, Invitrogen, Life Technologies Grand Island, N.Y.) where total reaction volume was 10 μL in low-volume 384-well plates (#4511, Corning). Serially diluted compounds (3-fold) were incubated with WEE1 Enzyme (1 nM) (#PR7373A, Invitrogen, Life Technologies, Grand Island, N.Y.) for 10 min; a mixture of ATP (10 μM) (#A1852, Sigma, St. Louis, Mo.) and fluorescent-PolyGT substrate (200 nM) (#PV3610, Invitrogen, Life Technologies Grand Island, N.Y.) was added and incubated in dark at room temperature for 1 h. After 1 h, 10 μL stop solution containing Terbium labeled antibody (4 nM) (#PV3529, Invitrogen, Life Technologies Grand Island, N.Y.) and EDTA (#E5134, Sigma, St. Louis, Mo.) (20 mM) in TR-FRET dilution buffer (#PV3574, Invitrogen, Life Technologies Grand Island, N.Y.) was added. Readings were taken in a Synergy Neo Plate reader (BioTek, Winooski, Vt.) at single excitation of 340 nm and dual emission at 495 nm and 520 nm respectively.

The % activity of test samples was calculated as (Sample–Min)*100/(Max–Min). [Max: DMSO control, complete reaction with enzyme & DMSO and Min: No enzyme & DMSO]. Percent inhibition (100-% activity) was fitted to the "four-parameter logistic model" in XLfit for determination of IC$_{50}$ values. The results are shown in Table 2.

TABLE 2

| Compound No. | Wee1 IC$_{50}$ (μM) |
| --- | --- |
| 1.1 | 0.006 |
| 1.2 | 0.036 |
| 1.4 | 0.013 |
| 1.5 | 0.005 |
| 1.32 | 0.008 |
| 1.37 | 0.013 |
| 1.38 | 0.004 |
| 1.39 | 0.001 |
| 1.40 | 0.004 |
| 1.42 | 0.001 |
| 1.43 | 0.009 |
| 1.44 | 0.003 |
| 1.45 | 0.010 |
| 1.63 | 0.018 |
| 1.67 | 0.015 |

TABLE 2-continued

| Compound No. | Wee1 IC$_{50}$ (μM) |
| --- | --- |
| 1.86 | 0.002 |
| 1.91 | 0.003 |
| 1.188 | 0.027 |
| 1.249 | 0.016 |
| 1.250 | 0.008 |
| 1.251 | 0.007 |
| 1.254 | 0.140 |
| 1.261 | 0.009 |
| 1.262 | 0.008 |
| 1.321 | 0.013 |
| 1.322 | 0.007 |
| 1.335 | 0.005 |
| 1.349 | 0.384 |
| 1.464 | 0.049 |
| 1.465 | 0.045 |

Example B2. PKMYT1 IC$_{50}$ Determination

Inhibition of PKMYT1 kinase activity by test compounds was measured by the HotSpot Kinase Assay at Reaction Biology Corporation (Malvern, Pa.). Briefly, Myelin Basic Protein substrate was prepared in Reaction Buffer (20 mM Hepes (pH 7.5), 10 mM MgCl$_2$, 1 mM EGTA, 0.01% Brij35, 0.02 mg/mL BSA, 0.1 mM Na$_3$VO$_4$, 2 mM DTT, 1% DMSO). PKMYT1 kinase was delivered into the substrate solution and gently mixed. Test compounds in 100% DMSO were added into the kinase reaction mixture by Acoustic technology (Echo550; nanoliter range) and incubated for 20 min at room temperature. $^{33}$P-ATP was delivered into the reaction mixture to initiate the reaction. Reactions were carried out at 10 μM ATP. After a 2 hour incubation at room temperature, kinase activity was detected by P81 filter-binding method. Compounds were tested in 10-dose IC$_{50}$ mode with a 3-fold serial dilution. A nonlinear regression model with a sigmoidal dose response and variable slope within GraphPad Prism (GraphPad Software, San Diego, Calif.) was used to calculate the IC$_{50}$ value of individual test compounds. The results are shown in Table 3.

TABLE 3

| Compound No. | PKMYT1 IC$_{50}$ (μM) |
| --- | --- |
| 1.1 | 6.57 |
| 1.2 | 10.2 |
| 1.4 | 17.8 |
| 1.5 | 5.5 |
| 1.32 | 0.767 |
| 1.37 | 0.691 |
| 1.38 | 0.223 |
| 1.40 | 0.121 |
| 1.43 | 5.63 |
| 1.44 | 1.17 |
| 1.45 | 1.54 |
| 1.67 | 2.9 |
| 1.86 | 4.2 |
| 1.91 | 6.92 |
| 1.188 | 2.24 |
| 1.249 | 20.1 |
| 1.250 | 13.5 |
| 1.251 | 6.69 |
| 1.254 | 3.56 |
| 1.261 | 4.54 |
| 1.262 | 16.8 |
| 1.321 | 11.2 |
| 1.322 | 7.49 |
| 1.349 | 19.9 |
| 1.464 | 28.8 |
| 1.465 | >30 |

Example B3. Determination of Potency of Compounds in Cytotoxicity Assay in A427 Cell Line A427 (HTB-53; ATCC), a lung epithelial cell line, was seeded in medium (MEM, 41090101; Gibco) at a cell count of 1500 cells per 100 μL per well in a 96 well edge plate (167425; ThermoFisher). Cells were allowed to grow at 37° C. for 24 hr in 5% $CO_2$ environment (culture conditions) in a Nuaire incubator (humidified). Serially diluted test compounds (100 μL) within the desired testing concentration ranges were added to the culture plate and the cells were further incubated in culture conditions for 72 hr. The experiment was terminated at the designated incubation time by replacing the medium with 100 μL of 1 mM of resazurin (R7017; Sigma) prepared in culture medium, and the plates were further incubated in culture conditions for 4-6 hr. Fluorescence was recorded using a multimodal plate reader (Biotek Synergy Neo) at an excitation wavelength of 535 nm and emission wavelength of 590 nm to obtain relative fluorescence units. Data were analysed as follows: the background fluorescence (blank containing only medium) value was subtracted from each reading and normalized with the vehicle control (DMSO treated cells) to obtain percent survival/proliferation. Percent survival was subtracted from 100 to get the percent inhibition of proliferation which was used to calculate $IC_{50}$ values. Potency of compounds in other cell lines (such as A549, AsPc-1, Panc 10.05, A172, U-87MG) may be determined in an analogous manner. The results are shown in Table 4.

TABLE 4

| Compound No. | A427 $IC_{50}$ (μM) |
| --- | --- |
| 1.1 | 3.740 |
| 1.2 | 3.410 |
| 1.4 | 1.410 |
| 1.5 | 7.599 |
| 1.32 | 0.870 |
| 1.37 | 0.660 |
| 1.38 | 0.401 |
| 1.39 | 0.510 |
| 1.40 | 0.440 |
| 1.42 | 0.255 |
| 1.43 | 1.478 |
| 1.44 | 0.892 |
| 1.45 | 2.179 |
| 1.63 | 17.160 |
| 1.67 | 2.575 |
| 1.86 | 0.685 |
| 1.91 | 0.565 |
| 1.188 | 2.171 |
| 1.249 | 0.592 |
| 1.250 | 2.690 |
| 1.251 | 12.355 |
| 1.254 | 0.765 |
| 1.261 | 0.900 |
| 1.262 | 1.455 |
| 1.321 | 3.537 |
| 1.322 | 2.281 |
| 1.335 | 4.733 |
| 1.349 | 0.490 |
| 1.464 | 24.621 |
| 1.465 | >30 |

Example B4. Determination of Potency of Compounds in Cell Proliferation Assay in Selected Cancer Cell Lines and Cellular PD Effects The effects of test compounds are studied in additional cell lines with various histotypes, such as LoVo colorectal adenocarcinoma, NCI-H460 large-cell lung carcinoma, HCT-116 colorectal carcinoma, and A2780 ovarian cancer cells. The cancer cells are harvested during the logarithmic growth period and counted. Cell concentrations are adjusted to the appropriate number with suitable medium, and 90 μL cell suspensions are added to 96-well plates. After cells are seeded, the plates are shaken gently to distribute cells evenly and incubated at 37° C., 5% $CO_2$ on day 1.

Cells are treated with test compounds at 9 concentrations within a desired concentration range (e.g. 1.5 nM-10 μM) on day 2 by series diluting the test compound stock solution (10 mM in DMSO) with culture medium. Cell viability is assessed by Cell Titer-Glo® as recommended by Promega (Cat. No.: G7572, Promega) typically 72 h post-treatment.

Cell viability data are plotted using GraphPad Prism (version 5, GraphPad Software, Inc., San Diego, Calif.). In addition, a nonlinear regression model with a sigmoidal dose response and variable slope within GraphPad Prism is used to calculate the $IC_{50}$ value of individual test compounds.

Test compounds may be studied in the same and/or other cancer cell lines with varying sensitivities to reported Wee1 inhibiting compounds using similar proliferation methods with possible variations in cell seeding densities and/or incubation durations.

Example B5. Determination of Potency of Compounds by Assay of Cellular PD Effects Phospho-CDC2 and γ-H2AX are two clinically relevant biomarkers associated with Wee1 inhibition. CDC2Y15 phosphorylation in cells was reported to be abolished by Wee1 inhibitors (Gavory G et. al., Almac Discovery, AACR poster, 2016). γ-H2AX, a DNA double-strand break marker, was upregulated by Wee1 treatment in Wee1 sensitive cell lines (Guertin A D et al., Molecular Cancer Therapeutics, 2013). The effects of selected test compounds on pCDC2 and γ-H2AX are assessed in selected cancer cell lines post 24 or 48 hr treatment using Western blotting methods with selective antibodies (Guertin A D et al., Molecular Cancer Therapeutics, 2013).

Changes in the levels of phospho-CDC2 following treatment of cells with test compounds were assessed by enzyme-linked immunosorbent assay (ELISA). A427 cells or AsPC-1 cells were plated in 6-well plates and cultured for 24 hr to approximately 80-90% confluency. Medium was replaced, and the cells were treated with the vehicle control or the test compound at several different concentrations. After incubation of treated cells in cell culture conditions for a specified time (e.g., 24 hr), cells were rinsed with ice-cold PBS and lysed in 1× cell lysis buffer containing protease inhibitors and phosphatase inhibitors. The cells were scraped from the plate with a cell scraper after a brief incubation on ice and transferred to a centrifuge tube, and then subjected to three freeze-thaw cycles in liquid nitrogen and a 37° C. water bath for further lysis. The lysates were centrifuged to pellet cell debris (using, for example, a 10 min centrifugation of 2000× g at 4° C.) and the supernatants transferred to fresh tubes on ice. The protein concentrations of the samples were estimated by the Bradford method or equivalent. The ELISA was carried out with the PathScan® Phospho-CDC2 (Tyr15) Sandwich ELISA Kit (Cat. #7176, Cell Signaling Technology, Danvers, Mass.) according to the manufacturer's instructions. Results are shown in Table 5.

TABLE 5

| Compound No. | A427 phospho-CDC2 IC$_{50}$ (μM) | AsPC-1 phospho-CDC2 IC$_{50}$ (μM) |
|---|---|---|
| 1.1 | 0.339 | ND |
| 1.2 | 0.952 | ND |
| 1.4 | 0.414 | ND |
| 1.38 | 0.176 | ND |
| 1.43 | 0.320 | ND |
| 1.45 | 0.066 | 0.285 |
| 1.249 | 0.230 | ND |

ND: Not Determined

Changes in the levels of phospho-CDC2 are alternatively or additionally analyzed by Western blotting of the samples using a primary antibody to phospho-CDC2 such as phospho-CDC2 (Tyr15) (10A11) rabbit mAb (Cat. #4539, Cell Signaling Technology) or rabbit polyclonal anti-CDK1 (phospho Y15) antibody (Cat. #ab47594, Abcam, Cambridge, United Kingdom).

Example B6. Evaluation of Test Compound in Mouse Xenograft Models

To examine the in vivo antitumor activity of test compound (as a single agent and in combination with other agents such as gemcitabine, nab-paclitaxel and temozomide), tumor growth experiments are performed in a cell line xenograft model and/or a PDX model. The cell line is chosen based on the in vitro studies described above. The PDX model to be used is established from a tumor taken directly from a patient with, for example, pancreatic ductal adenocarcinoma (PDAC) or glioblastoma.

Cells or tumor chucks are implanted subcutaneously into the flanks of nude mice and allowed to grow until the tumor size reaches 200 mm$^3$. Tumors are measured using a caliper and tumor volumes calculated using the formula: Tumor volume=(a×b$^2$/2) where 'b' is the smallest diameter and 'a' is the largest diameter. Once the established tumors reach approximately 200 mm$^3$, the mice are then stratified into treatment groups. The treatment groups are, for example: vehicle control, gemcitabine+nab-paclitaxel, test compound alone, gemcitabine+nab-paclitaxel+test compound at 10 mice per group. The treatment groups are alternatively, for example: vehicle control, temozolomide, test compound alone, temozolomide+test compound. The exact treatment groups, drug dose, and dosing schedule are determined specifically for each study according to standard practice. Tumor growth is monitored, and volume recorded at regular intervals. When the individual tumor of each mouse reaches an approximate end-point (tumor volume>1,500 mm$^3$), the mouse is sacrificed with regulated CO$_2$. The tumor growth inhibition (TGI) is calculated by comparing the control group's tumor measurements with the other study groups once the predetermined endpoint is reached in the control group. Alternatively, cells are implanted orthotopically and overall survival is measured.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:
1. A compound of Formula (I):

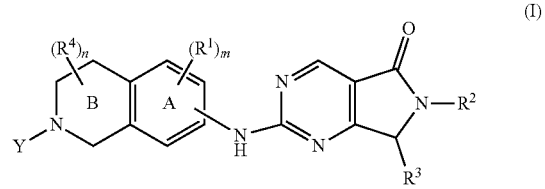

or a stereoisomer or tautomer thereof, or a pharmaceutically acceptable salt of any of the foregoing,
wherein:
Y is H or R$^4$;
each R$^1$ is independently F, Cl, or CH$_3$;
R$^2$ is (C$_1$-C$_3$ alkylene)-CF$_3$, C$_1$-C$_6$ alkyl, or C$_3$-C$_6$ cycloalkyl;
R$^3$ is:

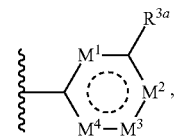

wherein:
M$^1$ is N;
M$^2$ is absent, CH, CR$^{3b}$, or N;
M$^3$ is CH, CR$^{3b}$, N, O, or S;
M$^4$ is CH, CR$^{3b}$, N, O, or S;
R$^{3a}$ is C$_3$-C$_6$ cycloalkyl, wherein the C$_3$-C$_6$ cycloalkyl is substituted by one or more substituents independently selected from the group consisting of CN and C$_1$-C$_6$ haloalkyl;
each R$^{3b}$ is independently halogen or CN; and

is an aromatic ring;
each R$^4$ is independently halogen, CN, (C$_1$-C$_3$ alkylene)-CN, (C$_1$-C$_3$ alkylene)-CF$_3$, (C$_1$-C$_3$ alkylene)-C(O)R$^{17}$, (C$_1$-C$_3$ alkylene)-C(O)NR$^{17}$R$^{18}$, (C$_1$-C$_3$ alkylene)-NR$^{17}$R$^{18}$, (C$_1$-C$_3$ alkylene)-NR$^{17}$C(O)R$^{18}$, (C$_1$-C$_3$ alkylene)-NR$^{17}$S(O)$_2$R$^{18}$, (C$_1$-C$_3$ alkylene)-OR$^{17}$, (C$_1$-C$_3$ alkylene)-S(O)$_2$R$^{17}$, (C$_1$-C$_3$ alkylene)-S(O)$_2$NR$^{17}$R$^{18}$, (C$_1$-C$_3$ alkylene)-(C$_3$-C$_6$ cycloalkyl), (C$_1$-C$_3$ alkylene)-(3- to 6-membered heterocyclyl), C$_1$-C$_6$ alkyl, C$_2$-C$_6$ alkenyl, C$_2$-C$_6$ alkynyl, C(O)R$^{17}$, C(O)NR$^{17}$R$^{18}$, C(O)OR$^{17}$, NR$^{17}$R$^{18}$, NR$^{17}$C(O)R$^{18}$, NR$^{17}$S(O)$_2$R$^{18}$, OR$^{17}$, OC(O)NR$^{17}$R$^{18}$, =O, S(O)$_2$R$^{17}$, S(O)$_2$NR$^{17}$R$^{18}$, Si(C$_1$-C$_6$ alkyl)$_3$, C$_3$-C$_6$ cycloalkyl, or 3- to 6-membered heterocyclyl, wherein each R$^4$ is optionally and independently substituted by one or more substituents independently selected from the group consisting of halogen, C(O)R$^{19}$, NR$^{19}$R$^{20}$, OR$^{19}$, and =O; or
any two geminal R$^4$, together with the carbon atom to which they are attached, independently form a C$_3$-C$_6$ cycloalkyl or 3- to 6-membered heterocyclyl, wherein each C$_3$-C$_6$ cycloalkyl and 3- to 6-membered heterocyclyl is optionally and independently substituted by one or more independently selected $R^{19}$ substituents;

each $R^{17}$ is independently H, $C_1$-$C_6$ alkyl, $C_3$-$C_6$ cycloalkyl, or 3- to 6-membered heterocyclyl, wherein each $C_1$-$C_6$ alkyl, $C_3$-$C_6$ cycloalkyl, and 3- to 6-membered heterocyclyl is optionally and independently substituted by one or more substituents independently selected from the group consisting of halogen, OH, and =O;

each $R^{18}$ is independently H, $C_1$-$C_6$ alkyl, $C_3$-$C_6$ cycloalkyl, or 3- to 6-membered heterocyclyl, wherein each $C_1$-$C_6$ alkyl, $C_3$-$C_6$ cycloalkyl, and 3- to 6-membered heterocyclyl is optionally and independently substituted by one or more substituents independently selected from the group consisting of halogen, OH, and =O; or each $R^{17}$ and $R^{18}$, together with the atom(s) to which they are attached, independently form a 3- to 6-membered heterocyclyl, wherein each 3- to 6-membered heterocyclyl is optionally and independently substituted by one or more substituents independently selected from the group consisting of halogen, OH, and =O;

each $R^{19}$ is independently H, $C_1$-$C_6$ alkyl, $C_3$-$C_6$ cycloalkyl, or 3- to 6-membered heterocyclyl, wherein each $C_1$-$C_6$ alkyl, $C_3$-$C_6$ cycloalkyl, and 3- to 6-membered heterocyclyl is optionally and independently substituted by one or more substituents independently selected from the group consisting of halogen, OH, and =O;

each $R^{20}$ is independently H, $C_1$-$C_6$ alkyl, $C_3$-$C_6$ cycloalkyl, or 3- to 6-membered heterocyclyl, wherein each $C_1$-$C_6$ alkyl, $C_3$-$C_6$ cycloalkyl, and 3- to 6-membered heterocyclyl is optionally and independently substituted by one or more substituents independently selected from the group consisting of halogen, OH, and =O;

m is 0, 1, 2, or 3; and n is 0, 1, 2, 3, or 4;

with the provisos that:

(1) when $M^2$ is absent and $M^4$ is O or S, then $M^3$ is CH, $CR^{3b}$, or N; and (2) when $M^2$ is absent and $M^3$ is O or S, then $M^4$ is CH, $CR^{3b}$, or N.

2. The compound of claim 1, wherein the compound is of Formula (II):

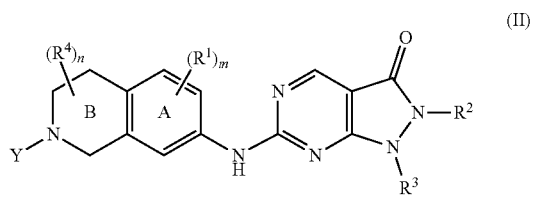

or a stereoisomer or tautomer thereof, or a pharmaceutically acceptable salt of any of the foregoing.

3. The compound of claim 1, wherein the compound is of Formula (III):

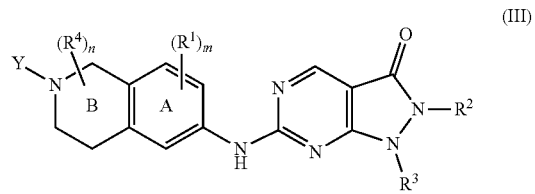

or a stereoisomer or tautomer thereof, or a pharmaceutically acceptable salt of any of the foregoing.

4. The compound of claim 1, or a stereoisomer or tautomer thereof, or a pharmaceutically acceptable salt of any of the foregoing, wherein Y is H.

5. The compound of claim 1, or a stereoisomer or tautomer thereof, or a pharmaceutically acceptable salt of any of the foregoing, wherein $R^2$ is ($C_1$-$C_3$ alkylene)-$CF_3$.

6. The compound of claim 5, or a stereoisomer or tautomer thereof, or a pharmaceutically acceptable salt of any of the foregoing, wherein $R^2$ is $CH_2CF_3$.

7. The compound of claim 1, or a stereoisomer or tautomer thereof, or a pharmaceutically acceptable salt of any of the foregoing, wherein $R^2$ is $C_1$-$C_6$ alkyl.

8. The compound of claim 7, or a stereoisomer or tautomer thereof, or a pharmaceutically acceptable salt of any of the foregoing, wherein $R^2$ is $CH_2CH_3$ or $CH(CH_3)_2$.

9. The compound of claim 1, or a stereoisomer or tautomer thereof, or a pharmaceutically acceptable salt of any of the foregoing, wherein $R^2$ is $C_3$-$C_6$ cycloalkyl.

10. The compound of claim 9, or a stereoisomer or tautomer thereof, or a pharmaceutically acceptable salt of any of the foregoing, wherein $R^2$ is cyclopropyl.

11. The compound of claim 1, or a stereoisomer or tautomer thereof, or a pharmaceutically acceptable salt of any of the foregoing, wherein $R^3$ is:

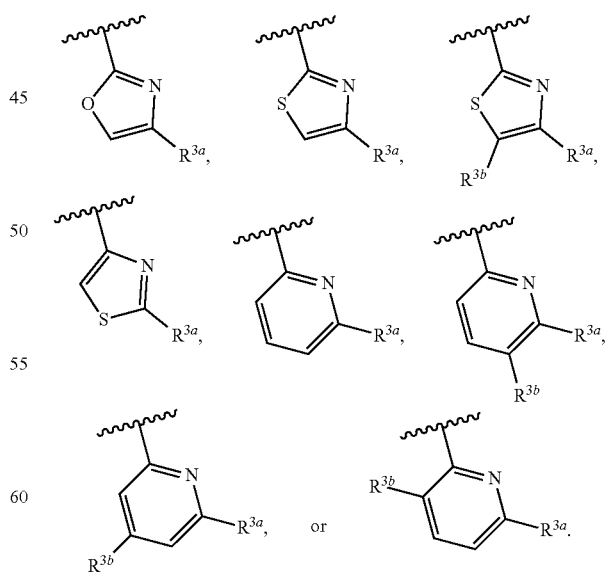

12. The compound of claim 1, or a stereoisomer or tautomer thereof, or a pharmaceutically acceptable salt of any of the foregoing, wherein $R^{3a}$ is $C_3$-$C_6$ cycloalkyl, wherein the $C_3$-$C_6$ cycloalkyl is substituted by one or more independently selected $C_1$-$C_6$ haloalkyl substituents.

13. The compound of claim 1, or a stereoisomer or tautomer thereof, or a pharmaceutically acceptable salt of any of the foregoing, wherein $R^{3a}$ is $C_3$-$C_6$ cycloalkyl, wherein the $C_3$-$C_6$ cycloalkyl is substituted by one or more CN substituents.

14. The compound of claim 1, or a stereoisomer or tautomer thereof, or a pharmaceutically acceptable salt of any of the foregoing, wherein $R^{3a}$ is:

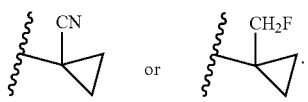

15. The compound of claim 1, or a stereoisomer or tautomer thereof, or a pharmaceutically acceptable salt of any of the foregoing, wherein each $R^{3b}$ is independently halogen.

16. The compound of claim 1, or a stereoisomer or tautomer thereof, or a pharmaceutically acceptable salt of any of the foregoing, wherein each $R^{3b}$ is independently CN.

17. The compound of claim 1, or a stereoisomer or tautomer thereof, or a pharmaceutically acceptable salt of any of the foregoing, wherein $R^3$ is:

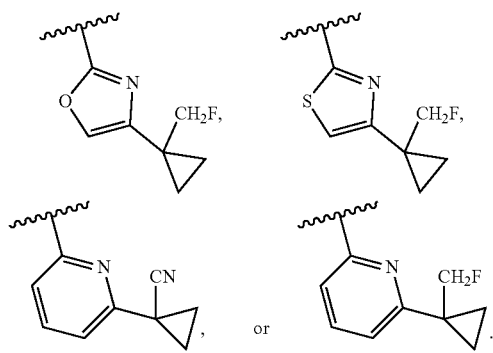

18. The compound of claim 1, or a stereoisomer or tautomer thereof, or a pharmaceutically acceptable salt of any of the foregoing, wherein:
each $R^4$ is independently $C_1$-$C_6$ alkyl; or
any two geminal $R^4$, together with the carbon atom to which they are attached, independently form a $C_3$-$C_6$ cycloalkyl.

19. The compound of claim 1, or a stereoisomer or tautomer thereof, or a pharmaceutically acceptable salt of any of the foregoing, wherein m is 0.

20. The compound of claim 1, or a stereoisomer or tautomer thereof, or a pharmaceutically acceptable salt of any of the foregoing, wherein m is 1.

21. The compound of claim 1, or a stereoisomer or tautomer thereof, or a pharmaceutically acceptable salt of any of the foregoing, wherein n is 0.

22. The compound of claim 1, or a stereoisomer or tautomer thereof, or a pharmaceutically acceptable salt of any of the foregoing, wherein n is 1.

23. The compound of claim 1, or a stereoisomer or tautomer thereof, or a pharmaceutically acceptable salt of any of the foregoing, wherein n is 2.

24. The compound of claim 1, or a stereoisomer or tautomer thereof, or a pharmaceutically acceptable salt of any of the foregoing, wherein

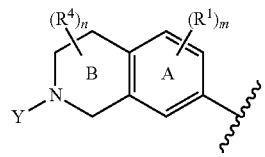

is:

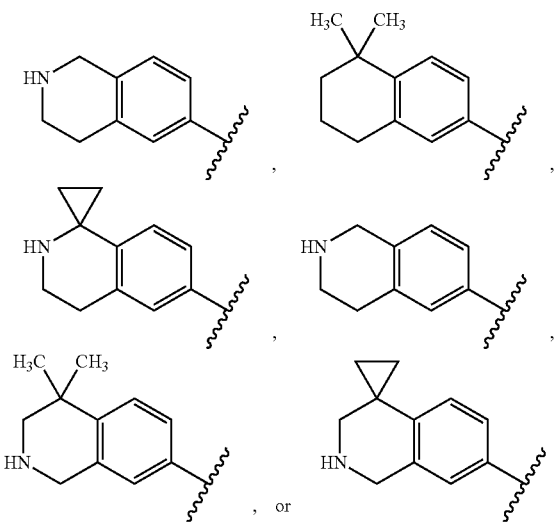

25. The compound of claim 1, wherein the compound is:

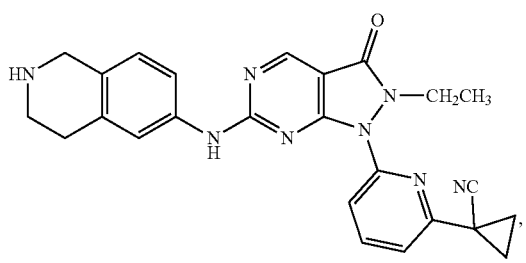 [SMILES: CCn1c(=O)c2cnc(Nc3ccc4c(c3)CCNC4)nc2n1-c1cccc(C2(C#N)CC2)n1]

or a pharmaceutically acceptable salt thereof.

26. The compound of claim 25, wherein the compound is:

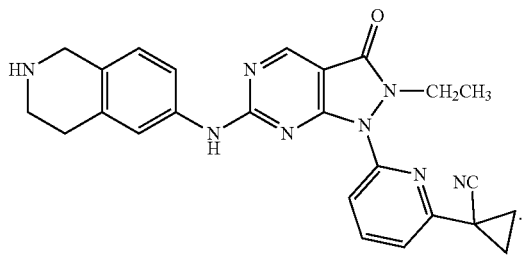 [SMILES: CCn1c(=O)c2cnc(Nc3ccc4c(c3)CCNC4)nc2n1-c1cccc(C2(C#N)CC2)n1]

27. The compound of claim 1, wherein the compound is:

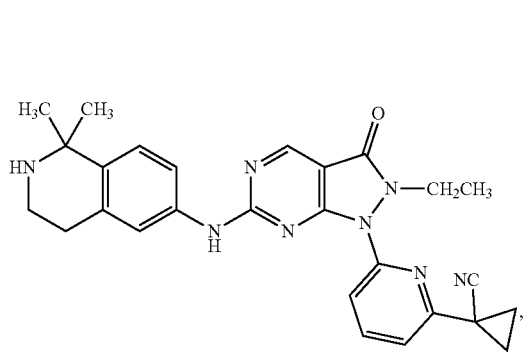 [SMILES: CCn1c(=O)c2cnc(Nc3ccc4c(c3)CCNC4(C)C)nc2n1-c1cccc(C2(C#N)CC2)n1]

or a pharmaceutically acceptable salt thereof.

28. The compound of claim 27, wherein the compound is:

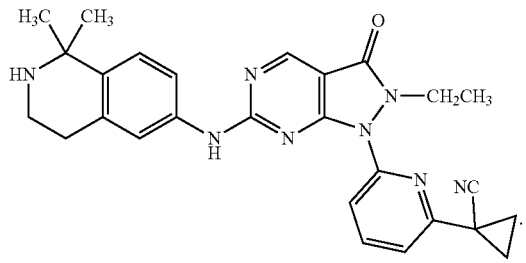 [SMILES: CCn1c(=O)c2cnc(Nc3ccc4c(c3)CCNC4(C)C)nc2n1-c1cccc(C2(C#N)CC2)n1]

29. The compound of claim 1, wherein the compound is:

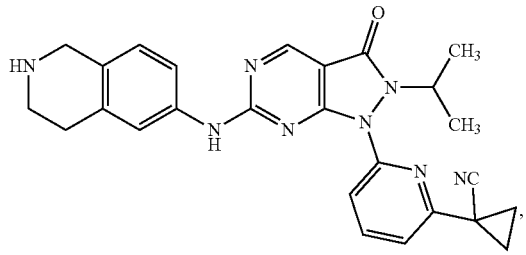 [SMILES: CC(C)n1c(=O)c2cnc(Nc3ccc4c(c3)CCNC4)nc2n1-c1cccc(C2(C#N)CC2)n1]

or a pharmaceutically acceptable salt thereof.

30. The compound of claim 29, wherein the compound is:

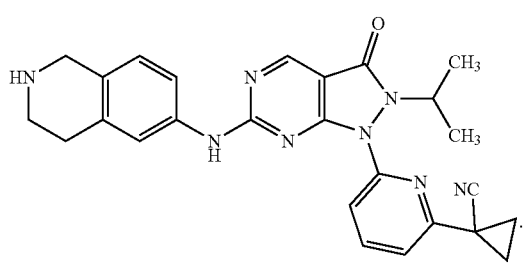 [SMILES: CC(C)n1c(=O)c2cnc(Nc3ccc4c(c3)CCNC4)nc2n1-c1cccc(C2(C#N)CC2)n1]

31. The compound of claim 1, wherein the compound is:

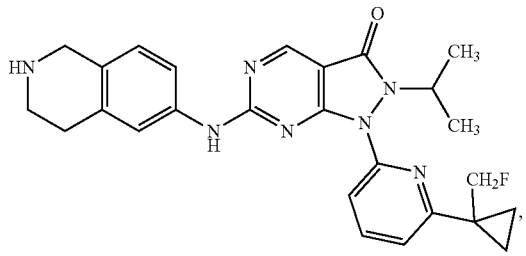

or a pharmaceutically acceptable salt thereof.

32. The compound of claim 31, wherein the compound is:

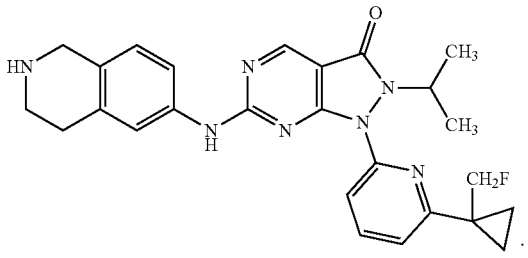

33. The compound of claim 1, wherein the compound is:

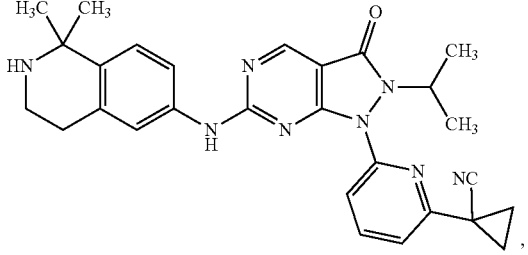 [SMILES: CC(C)n1c(=O)c2cnc(Nc3ccc4c(c3)CCNC4(C)C)nc2n1-c1cccc(C2(C#N)CC2)n1]

or a pharmaceutically acceptable salt thereof.

34. The compound of claim 33, wherein the compound is:

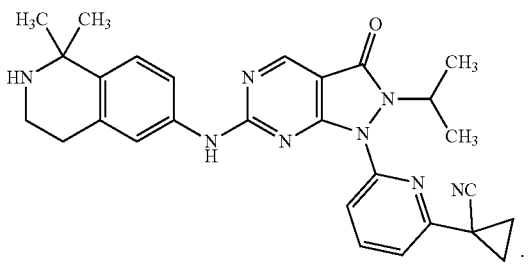 [SMILES: CC(C)n1c(=O)c2cnc(Nc3ccc4c(c3)CCNC4(C)C)nc2n1-c1cccc(C2(C#N)CC2)n1]

35. The compound of claim 1, wherein the compound is:

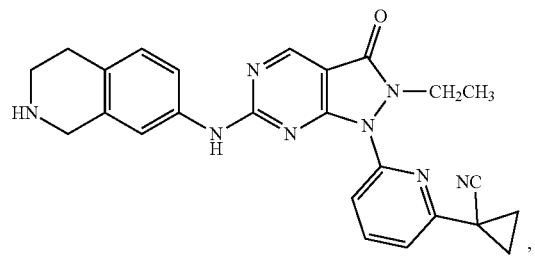 [SMILES: CCn1c(=O)c2cnc(Nc3ccc4c(c3)CNCC4)nc2n1-c1cccc(C2(C#N)CC2)n1]

or a pharmaceutically acceptable salt thereof.

36. The compound of claim 35, wherein the compound is:

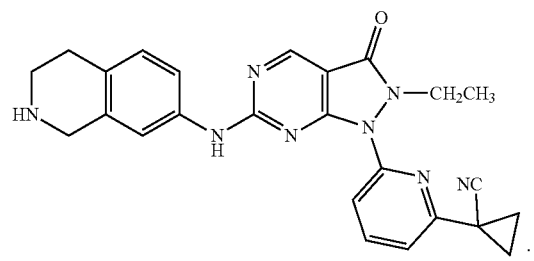

37. The compound of claim 1, wherein the compound is:

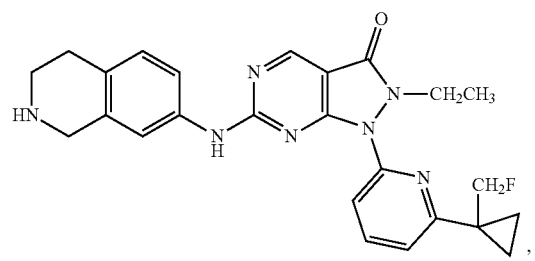

or a pharmaceutically acceptable salt thereof.

38. The compound of claim 37, wherein the compound is:

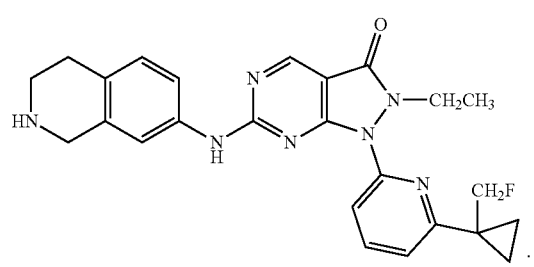

39. The compound of claim 1, wherein the compound is:

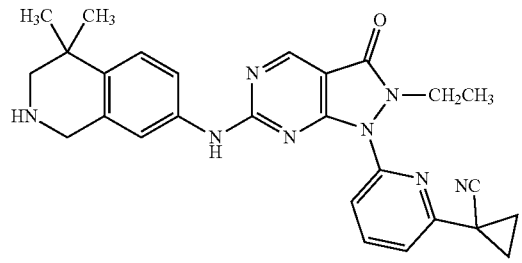

or a pharmaceutically acceptable salt thereof.

40. The compound of claim 39, wherein the compound is:

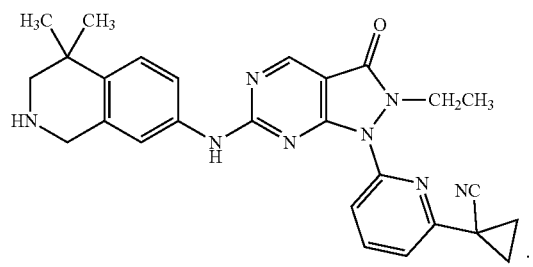 [SMILES: CCn1c(=O)c2cnc(Nc3ccc4c(c3)CNCC4(C)C)nc2n1-c1cccc(C2(C#N)CC2)n1]

41. The compound of claim 1, wherein the compound is:

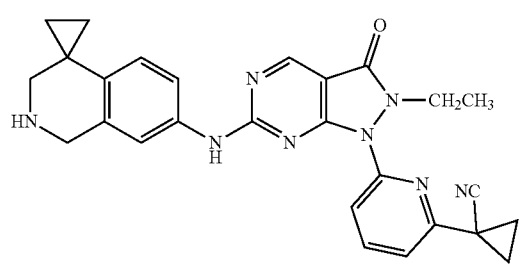

or a pharmaceutically acceptable salt thereof.

42. The compound of claim 41, wherein the compound is:

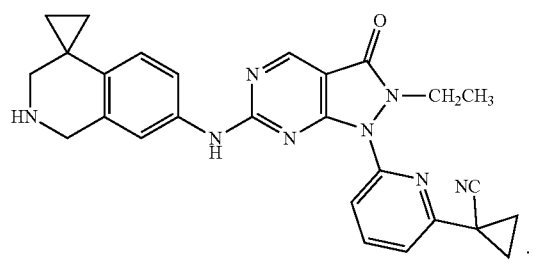 [SMILES: CCn1c(=O)c2cnc(Nc3ccc4c(c3)CNCC43CC3)nc2n1-c1cccc(C2(C#N)CC2)n1]

43. The compound of claim 1, wherein the compound is:

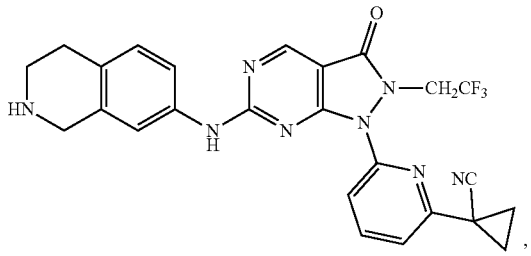

or a pharmaceutically acceptable salt thereof.

44. The compound of claim 43, wherein the compound is:

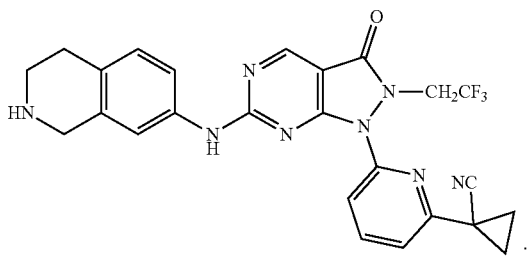

45. The compound of claim 1, wherein the compound is:

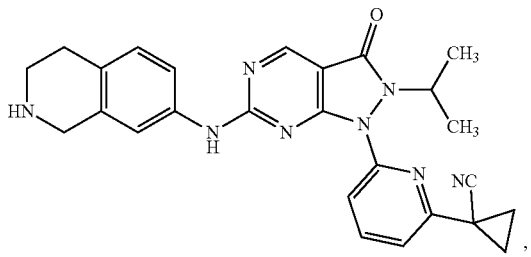 [SMILES: CC(C)n1c(=O)c2cnc(Nc3ccc4c(c3)CNCC4)nc2n1-c1cccc(C2(C#N)CC2)n1]

or a pharmaceutically acceptable salt thereof.

46. The compound of claim 45, wherein the compound is:

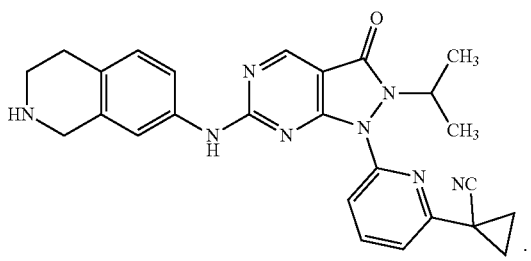 [SMILES: CC(C)n1c(=O)c2cnc(Nc3ccc4c(c3)CNCC4)nc2n1-c1cccc(C2(C#N)CC2)n1]

47. A pharmaceutical composition comprising a pharmaceutically acceptable carrier and a compound of claim 1, or a stereoisomer or tautomer thereof, or a pharmaceutically acceptable salt of any of the foregoing.

48. A kit comprising a compound of claim 1, or a stereoisomer or tautomer thereof, or a pharmaceutically acceptable salt of any of the foregoing.

49. A method for inducing premature mitosis in a cell, wherein the method comprises contacting the cell with a compound of claim 1, or a stereoisomer or tautomer thereof, or a pharmaceutically acceptable salt of any of the foregoing.

50. A method for inducing apoptosis in a cell, wherein the method comprises contacting the cell with a compound of claim 1, or a stereoisomer or tautomer thereof, or a pharmaceutically acceptable salt of any of the foregoing.

51. A method for suppressing a $G_2$-M deoxyribonucleic acid damage checkpoint in a cell, wherein the method comprises contacting the cell with a compound of claim 1, or a stereoisomer or tautomer thereof, or a pharmaceutically acceptable salt of any of the foregoing.

52. A method for inhibiting Wee1 activity in a cell, wherein the method comprises contacting the cell with a compound of claim 1, or a stereoisomer or tautomer thereof, or a pharmaceutically acceptable salt of any of the foregoing.

53. A method for treating a cancer in an individual in need thereof, wherein the method comprises administering to the individual a therapeutically effective amount of a compound of claim 1, or a stereoisomer or tautomer thereof, or a pharmaceutically acceptable salt of any of the foregoing.

54. The method of claim 53, wherein the cancer comprises a mutant tumor protein p53 gene.

55. The method of claim 53, wherein the method further comprises:
   (i) selecting the individual for treatment based on the presence of one or more mutations in the tumor protein p53 gene in the cancer; or
   (ii) selecting the individual for treatment based on expression of the mutant tumor protein p53 gene in the cancer.

56. The method of claim 53, wherein the method further comprises administering to the individual a therapeutically effective amount of an additional therapeutic agent.

57. The method of claim 56, wherein the additional therapeutic agent is selected from the group consisting of a cancer immunotherapy agent and a chemotherapeutic agent.

58. The method of claim 56, wherein the additional therapeutic agent is selected from the group consisting of a deoxyribonucleic acid alkylating agent, a deoxyribonucleic acid damage repair pathway inhibitor, a kinase inhibitor, and a platinum-based chemotherapeutic agent.

59. The method of claim 53, wherein the method further comprises administering to the individual a therapeutically effective amount of a radiation therapy.

60. A compound selected from the group consisting of:

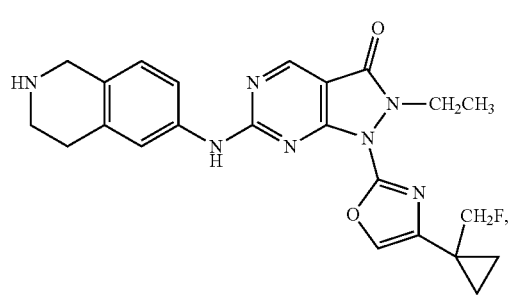

-continued
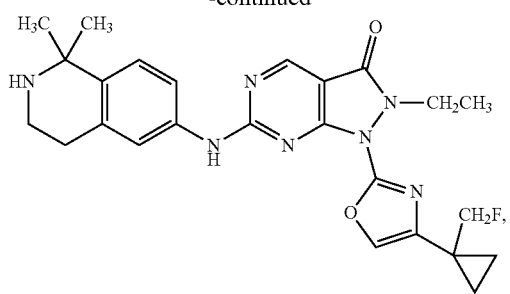
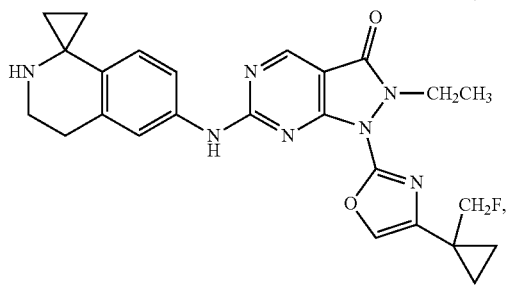
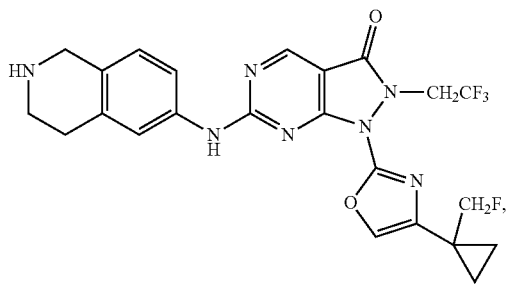
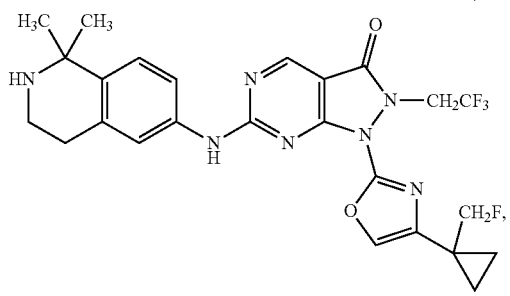
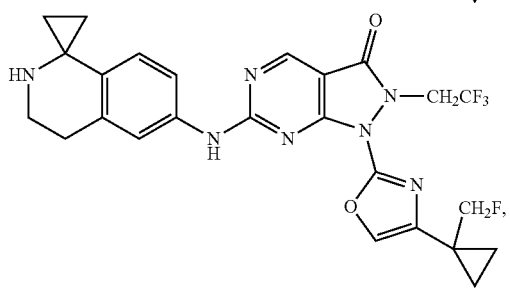
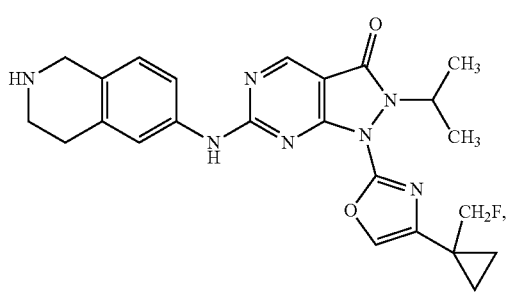
-continued
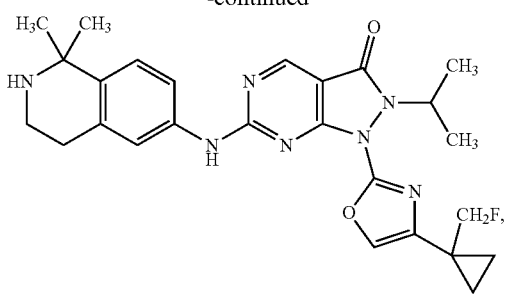
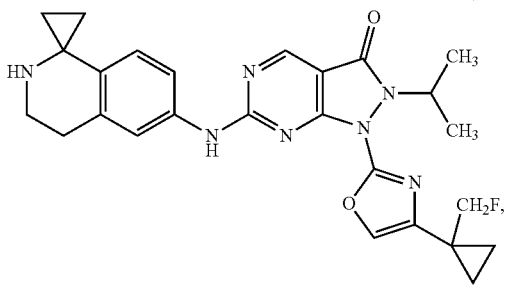
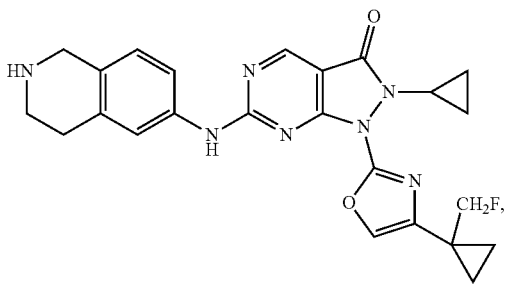
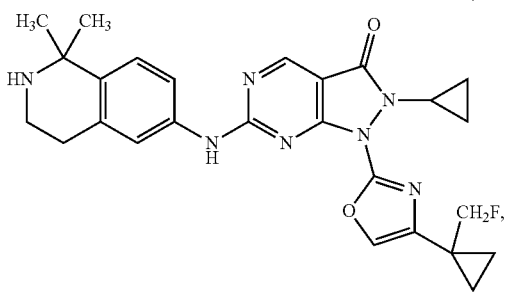
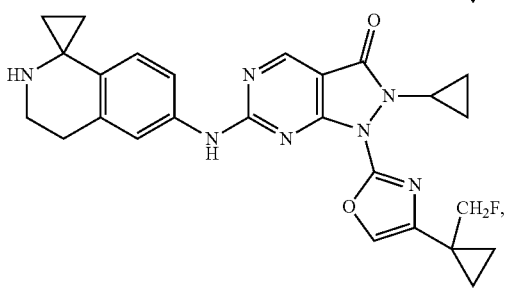
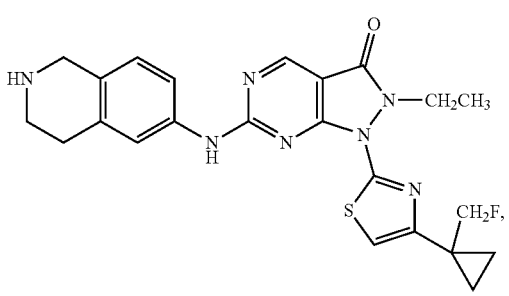

207
-continued
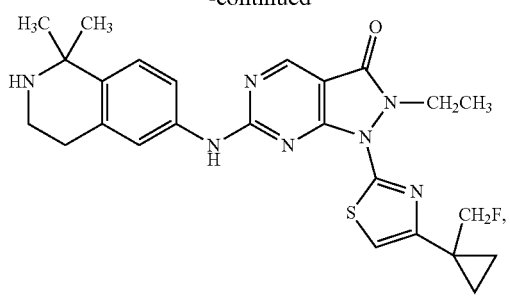
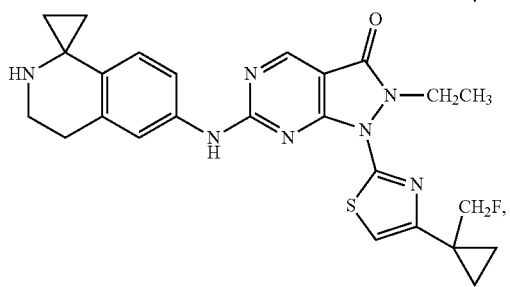
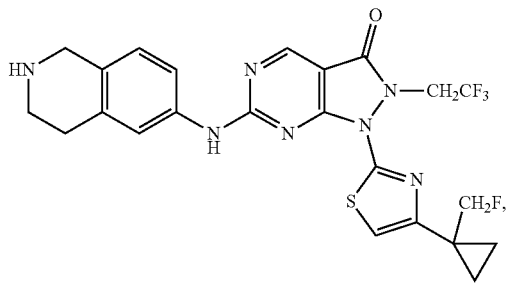
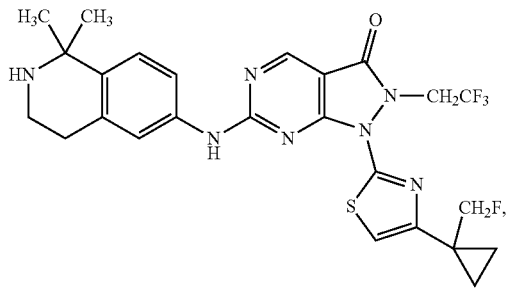
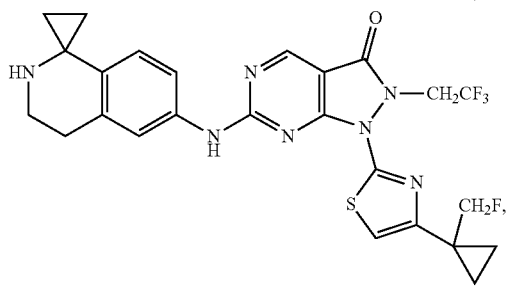
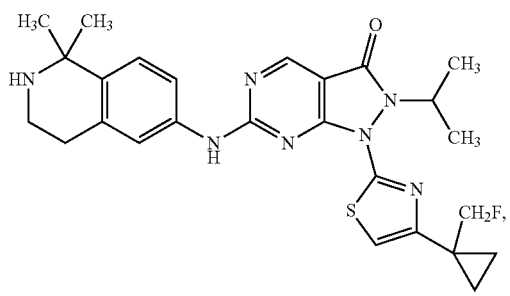
208
-continued
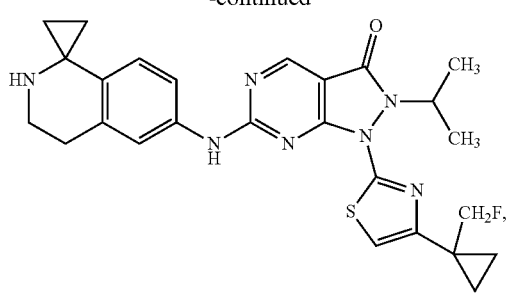
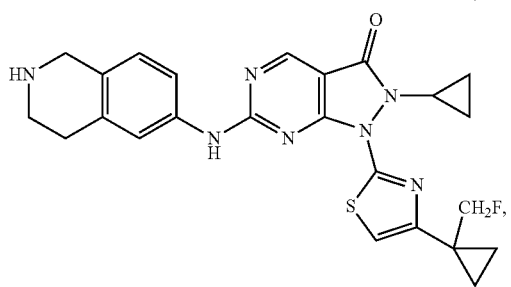
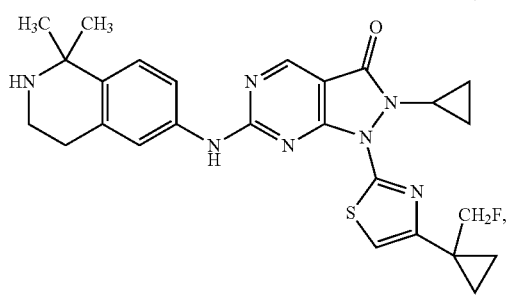
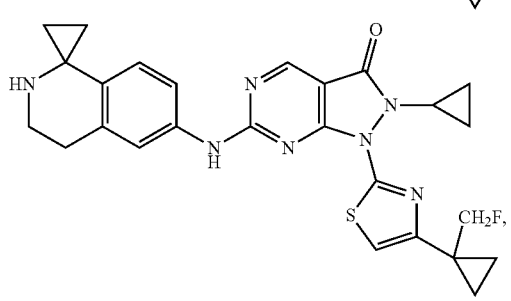
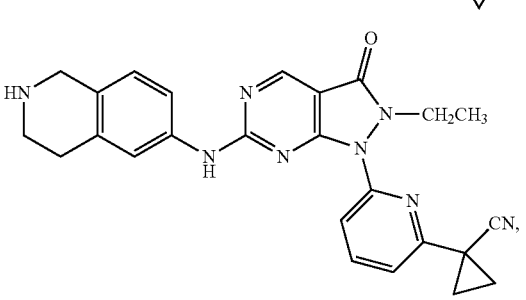
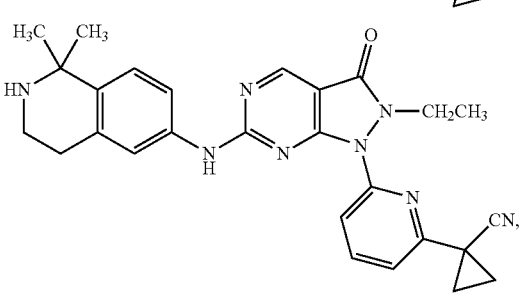

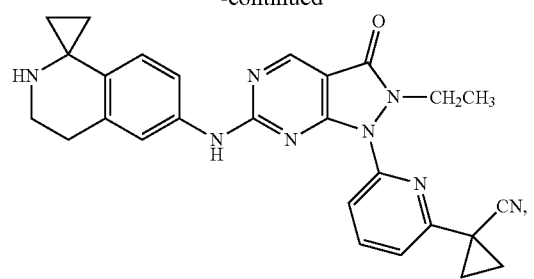
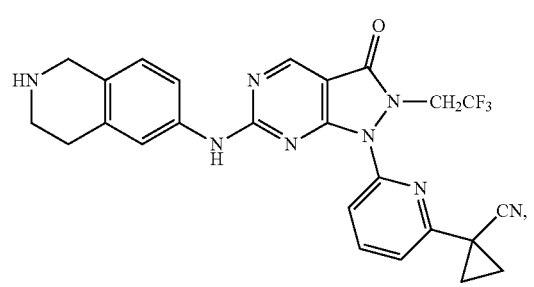
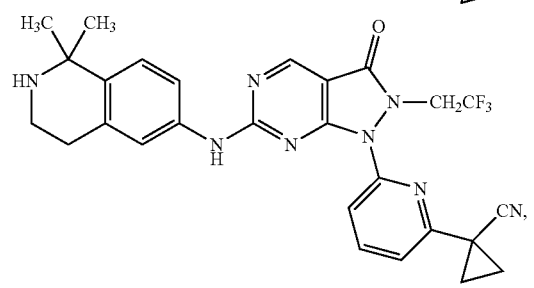
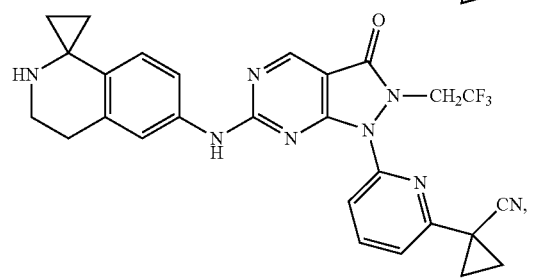
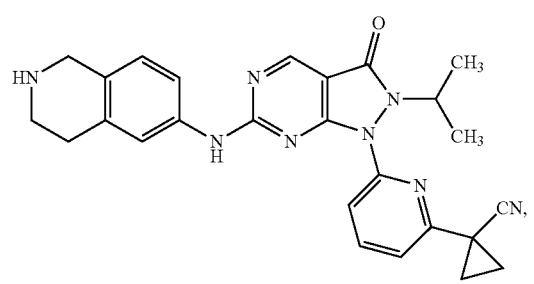
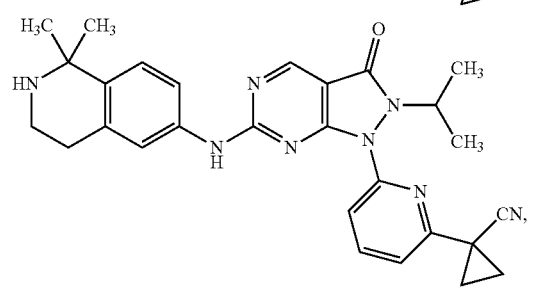
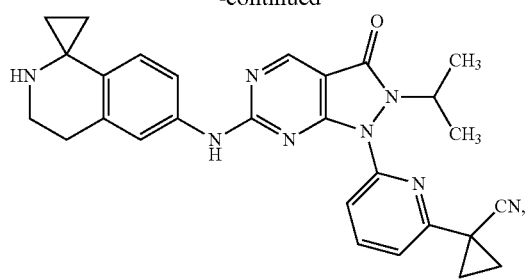
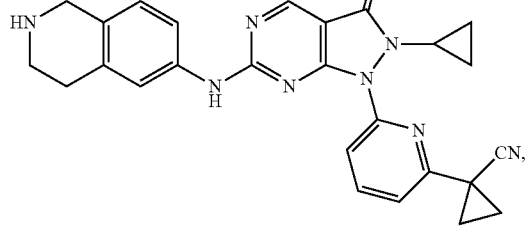
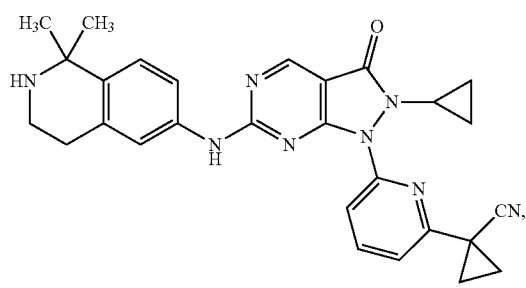
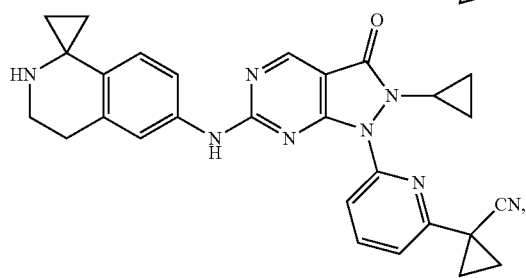
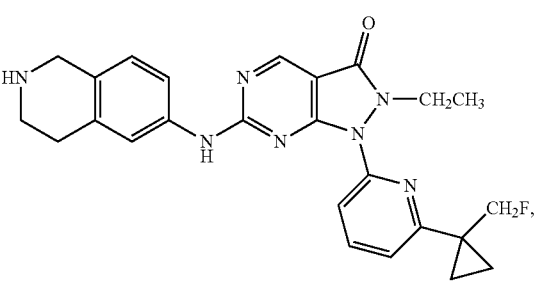
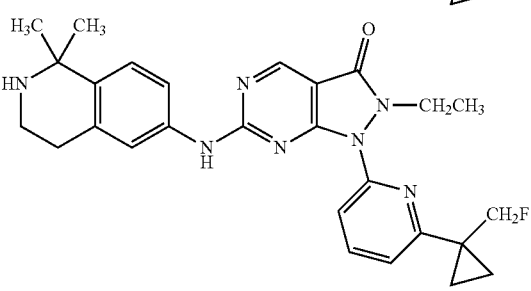

211
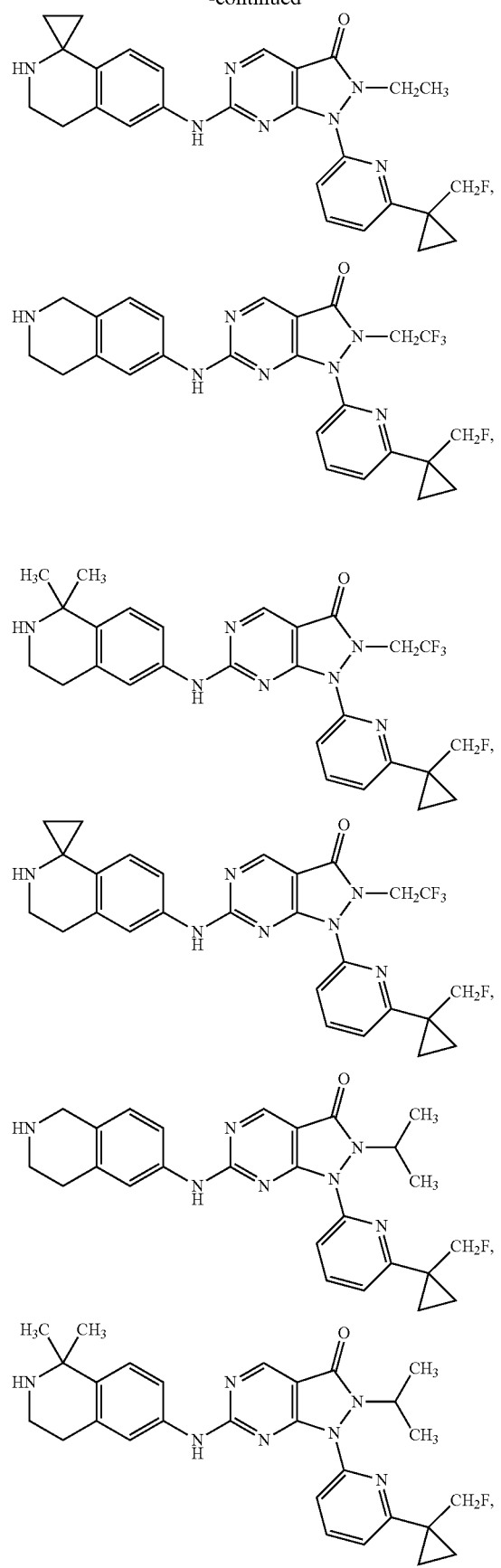
212
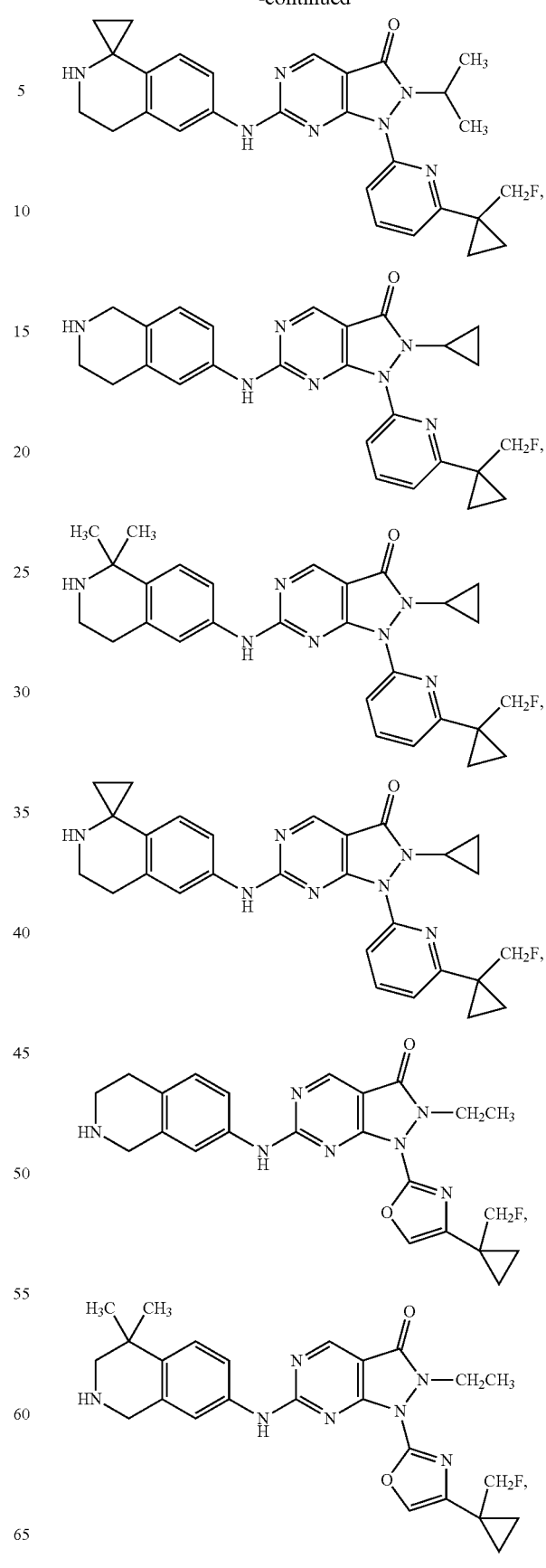

213
-continued
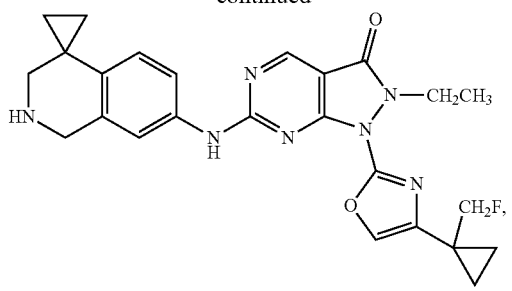
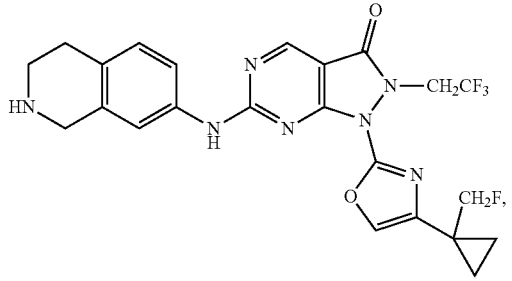
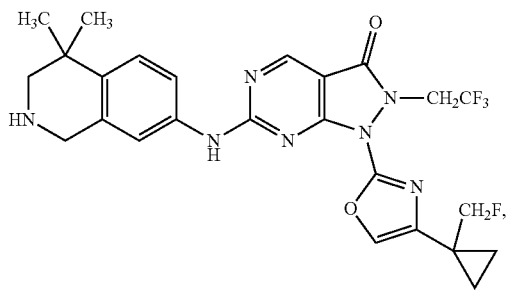
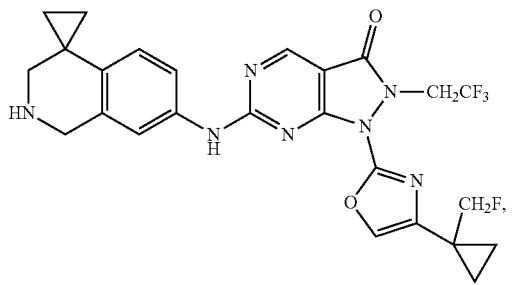
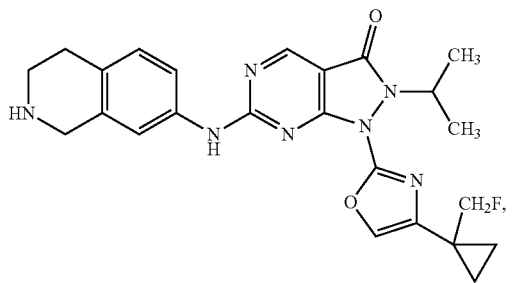
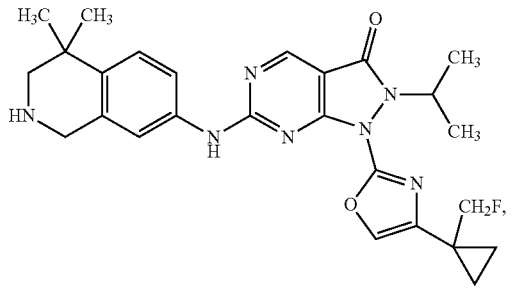
214
-continued
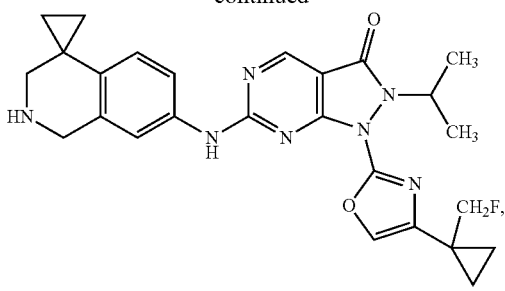
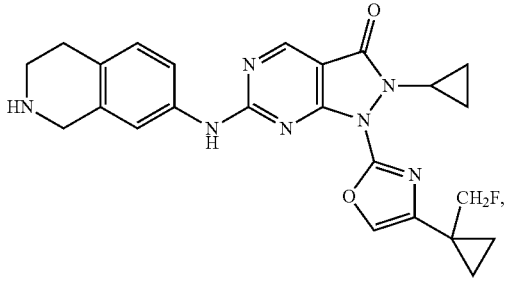
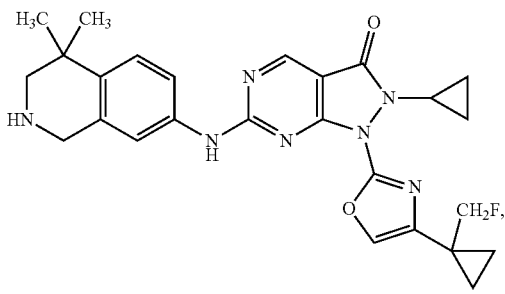
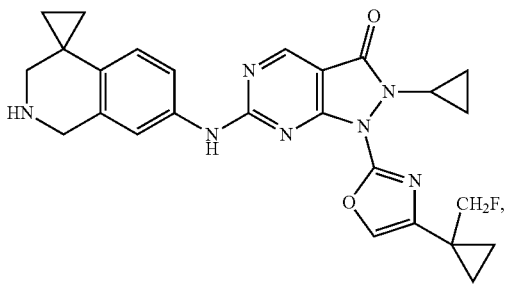
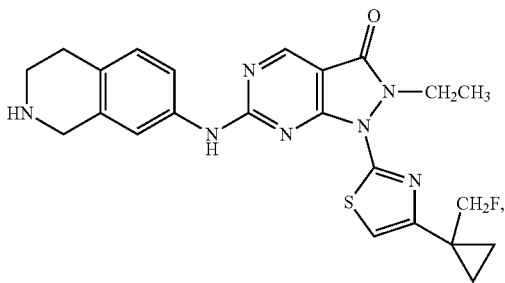
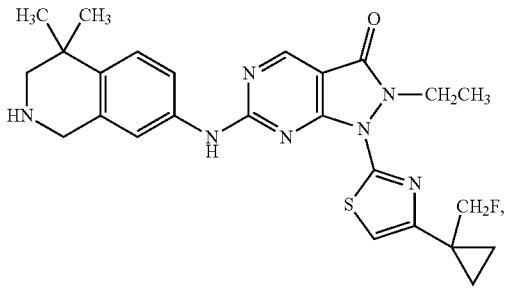

215
-continued
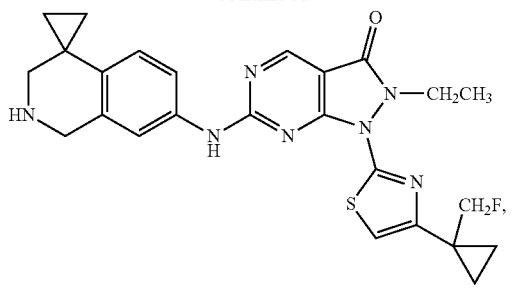
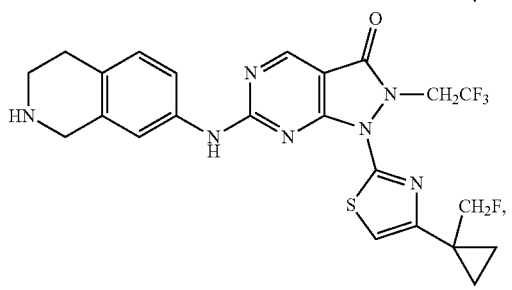
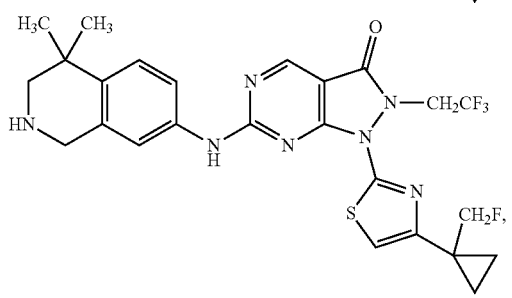
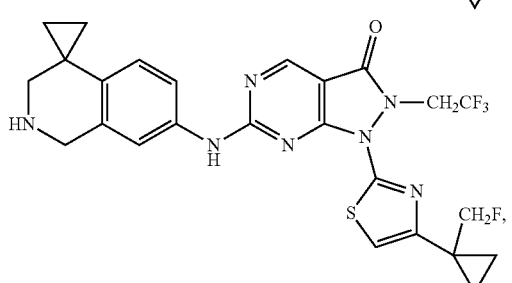
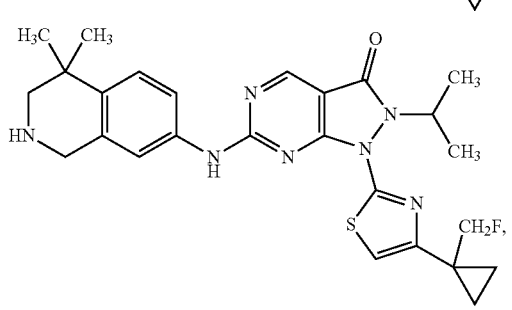
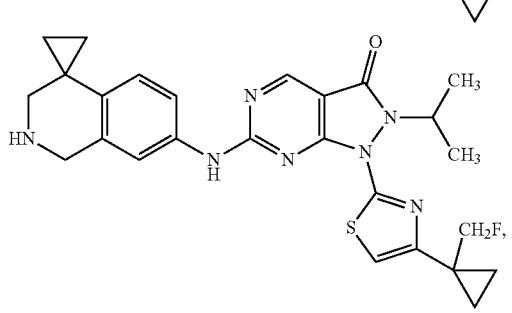
216
-continued
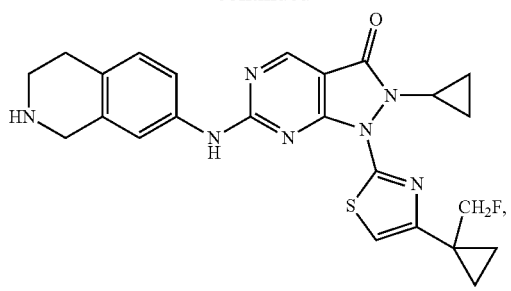
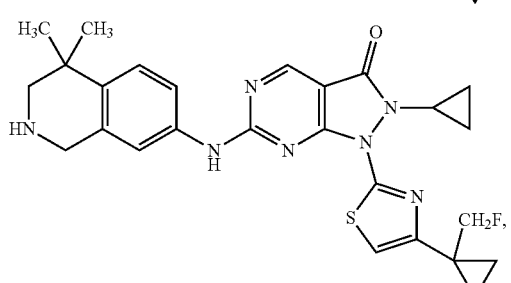
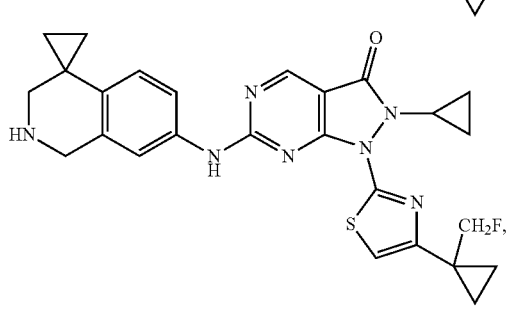
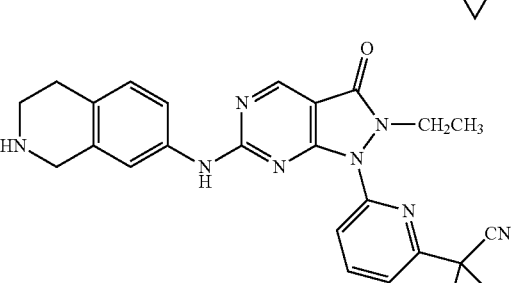
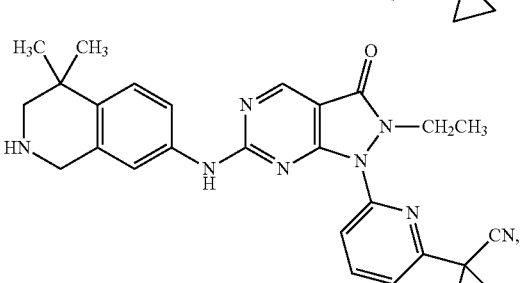
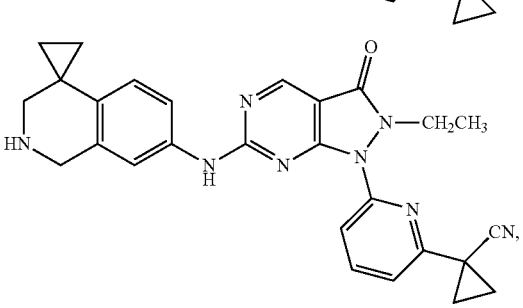

217
-continued
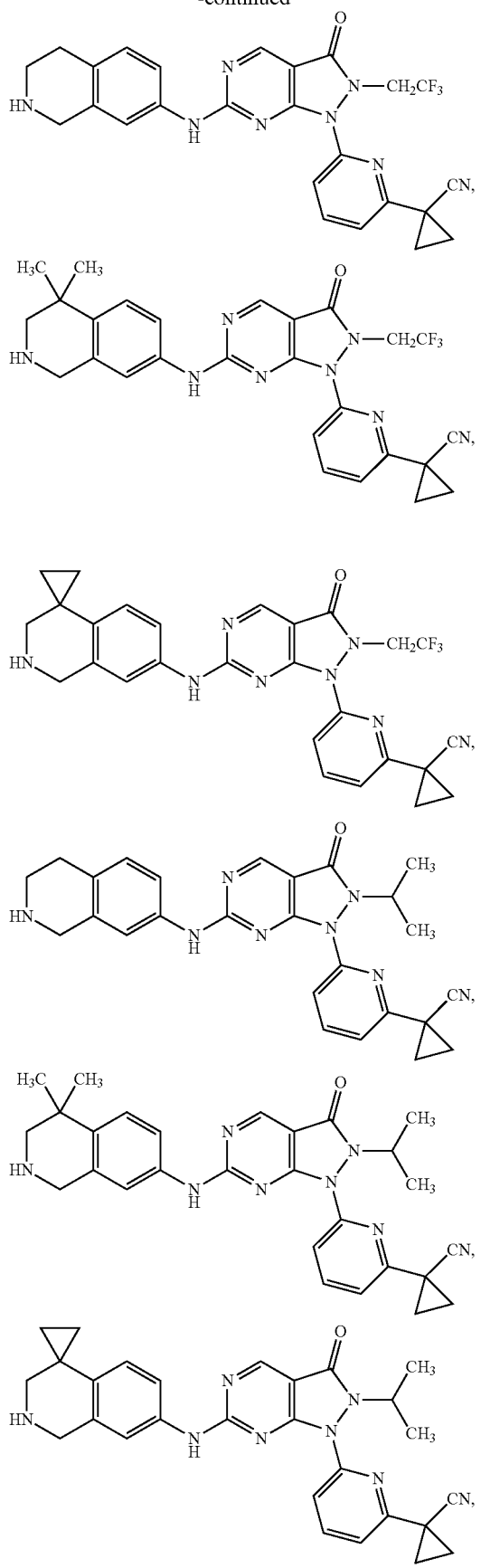
218
-continued
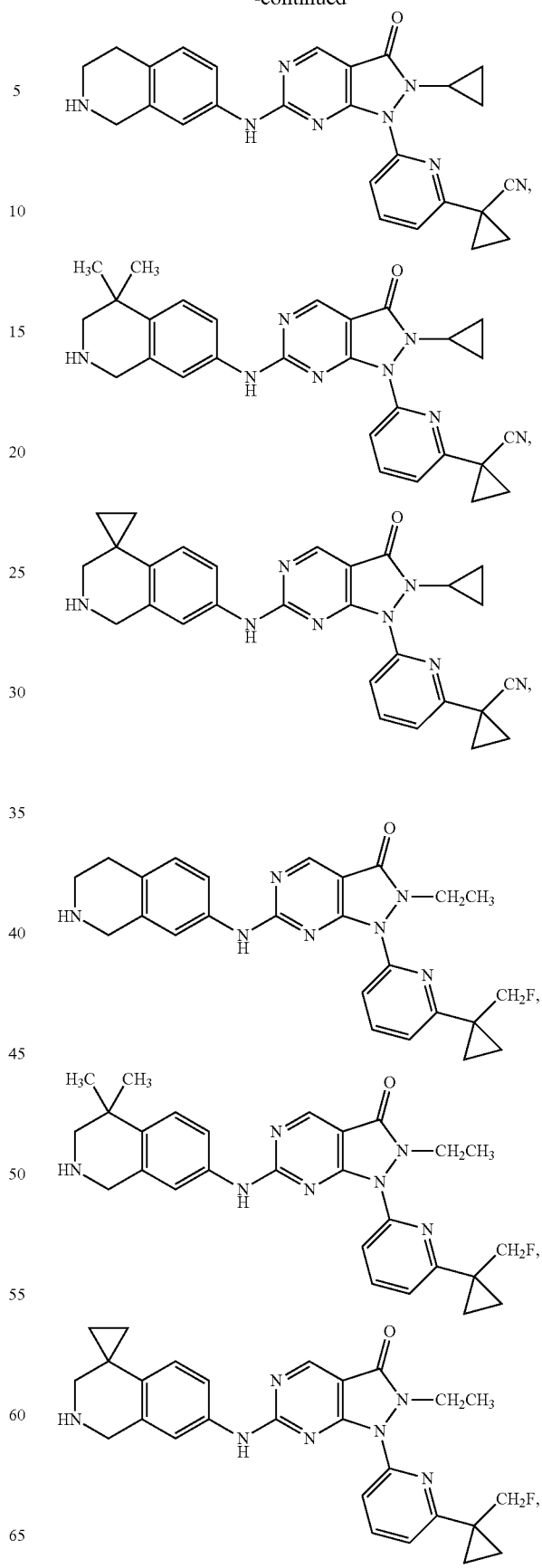

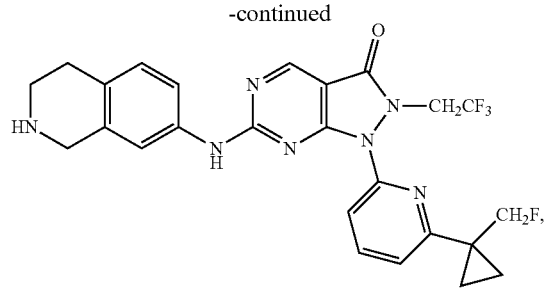
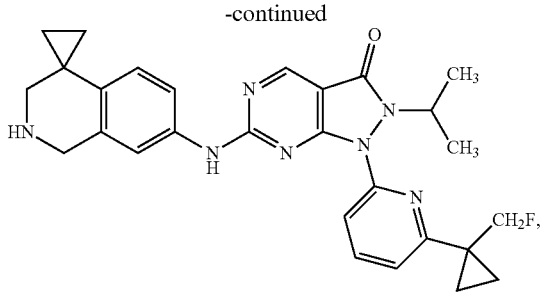
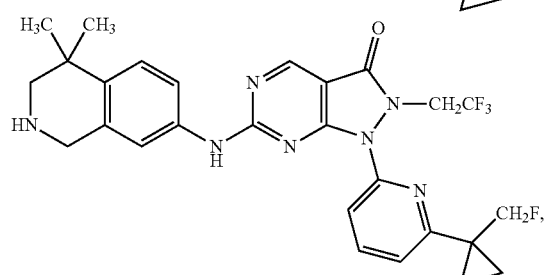
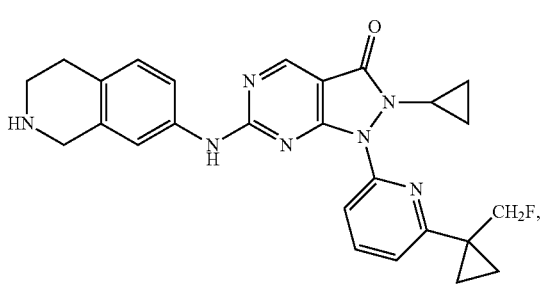
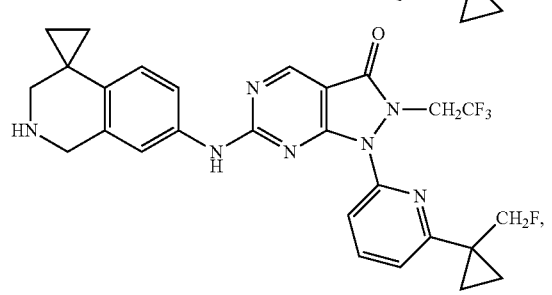
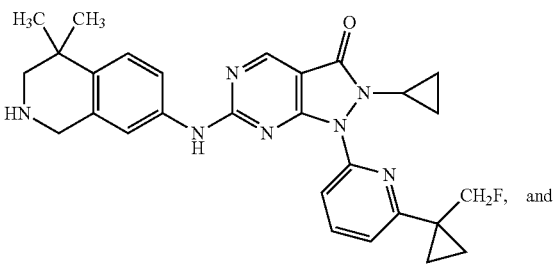
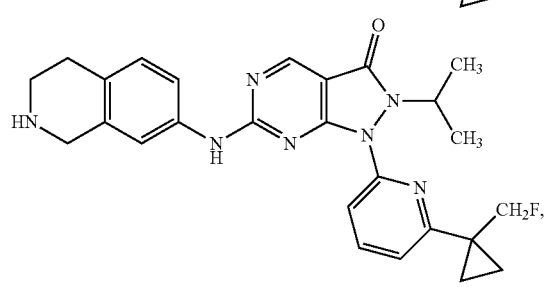
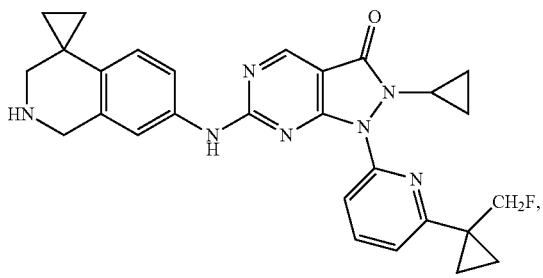
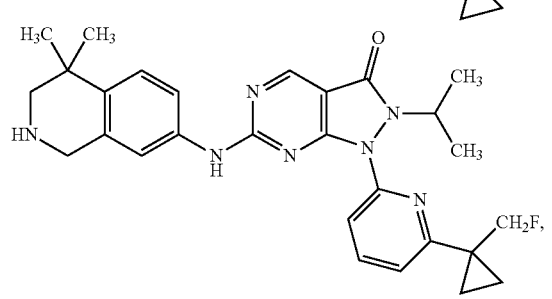
or a pharmaceutically acceptable salt thereof.
* * * * *